US010573818B2

(12) United States Patent
Mujica-Fernaud et al.

(10) Patent No.: US 10,573,818 B2
(45) Date of Patent: Feb. 25, 2020

(54) MATERIALS FOR ORGANIC ELECTROLUMINESCENT DEVICES

(71) Applicant: Merck Patent GmbH, Darmstadt (DE)

(72) Inventors: Teresa Mujica-Fernaud, Darmstadt (DE); Elvira Montenegro, Weinheim (DE); Jochen Pfister, Seeheim-Jugenheim (DE); Irina Martynova, Griesheim (DE); Frank Stieber, Einhausen (DE)

(73) Assignee: Merck Patent GmbH (DE)

( * ) Notice: Subject to any disclaimer, the term of this patent is extended or adjusted under 35 U.S.C. 154(b) by 333 days.

(21) Appl. No.: 15/531,959

(22) PCT Filed: Nov. 5, 2015

(86) PCT No.: PCT/EP2015/002225
§ 371 (c)(1),
(2) Date: May 31, 2017

(87) PCT Pub. No.: WO2016/087017
PCT Pub. Date: Jun. 9, 2016

(65) Prior Publication Data
US 2017/0317283 A1   Nov. 2, 2017

(30) Foreign Application Priority Data

Dec. 1, 2014   (EP) .................................... 14004045

(51) Int. Cl.
| | | |
|---|---|---|
| *H01L 51/00* | (2006.01) | |
| *C07C 211/60* | (2006.01) | |
| *C07C 211/61* | (2006.01) | |
| *C07D 311/96* | (2006.01) | |
| *C07D 333/76* | (2006.01) | |
| *C07D 307/91* | (2006.01) | |
| *C07D 209/86* | (2006.01) | |
| *C07D 335/20* | (2006.01) | |
| *C09K 11/02* | (2006.01) | |
| *H01L 51/50* | (2006.01) | |
| *H01L 51/56* | (2006.01) | |

(52) U.S. Cl.
CPC .......... *H01L 51/006* (2013.01); *C07C 211/60* (2013.01); *C07C 211/61* (2013.01); *C07D 209/86* (2013.01); *C07D 307/91* (2013.01); *C07D 311/96* (2013.01); *C07D 333/76* (2013.01); *C07D 335/20* (2013.01); *C09K 11/02* (2013.01); *H01L 51/0032* (2013.01); *H01L 51/0054* (2013.01); *H01L 51/0061* (2013.01); *H01L 51/0067* (2013.01); *H01L 51/0072* (2013.01); *H01L 51/0073* (2013.01); *H01L 51/0074* (2013.01); *H01L 51/0077* (2013.01); *H01L 51/0085* (2013.01); *C07C 2603/18* (2017.05); *C07C 2603/40* (2017.05); *C07C 2603/94* (2017.05); *H01L 51/0003* (2013.01); *H01L 51/0052* (2013.01); *H01L 51/0056* (2013.01); *H01L 51/0057* (2013.01); *H01L 51/0058* (2013.01); *H01L 51/5012* (2013.01); *H01L 51/5016* (2013.01); *H01L 51/5056* (2013.01); *H01L 51/5088* (2013.01); *H01L 51/5096* (2013.01); *H01L 51/56* (2013.01)

(58) Field of Classification Search
CPC .............. H01L 51/006; H01L 51/0057; H01L 51/0071; H01L 51/0072; H01L 51/0073; H01L 51/0074
See application file for complete search history.

(56) References Cited

U.S. PATENT DOCUMENTS

| | | |
|---|---|---|
| 9,490,432 B2 | 11/2016 | Zeika et al. |
| 2014/0312311 A1 | 10/2014 | Chen et al. |
| 2014/0316134 A1 | 10/2014 | Stoessel et al. |

FOREIGN PATENT DOCUMENTS

| | | | |
|---|---|---|---|
| JP | H08259937 A | 10/1996 | |
| KR | 20120093076 A | 8/2012 | |
| WO | WO-2009003455 A1 | 1/2009 | |
| WO | WO-2013083216 A1 * | 6/2013 | ........... C07D 221/20 |

OTHER PUBLICATIONS

Chen et al., JACS 2006, 128, 10992-10993.*
Chen et al., JACS 2006, 128, 10992-10993 (Supporting Information).*
Jou et al., J. Photonics for Energy 2012, 2, 021208-(1-9).*
SciFinder Searches.*
Chen, C-T., et al., "Doubly Ortho-Linked Quinoxaline/ Diphenylfluorene Hybrids as Bipolar, Fluorescent Chameleons for Optoelectronic Applications", Journal of the American Chemical Society, vol. 128, No. 34, (2006), pp. 10992-10993.
International Search Report for PCT/EP2015/002225 dated Feb. 11, 2016.
Jiang, H., "Organic Ambipolar Conjugated Molecules for Electronics: Synthesis and Structure-Property Relationships", Macromolecular Rapid Communications, vol. 31, No. 23, (2010), pp. 2007-2034.
Wei, Y., et al., "Emission Mechanism of Doubly ortho-Linked Quinoxaline/Diphenylfluorene or cis-Stilbene/Fluorene Hybrid Compounds Based on the Transient Absorption and Emission Measurements during Pulse Radiolysis", Journal of the American Chemical Society, vol. 131, No. 19 , (2009), pp. 6698-6707.
Written Opinion of the International Searching Authority for PCT/ EP2015/002225 dated Feb. 11, 2016.
Chen, C-T., et al., "Spirally configured cis-stilbene/fluorene hybrids as ambipolar, fluorescent materials for organic light emitting diode applications", RSC Advances, 2013, vol. 3, pp. 9381-9390.

* cited by examiner

*Primary Examiner* — Vu A Nguyen
(74) *Attorney, Agent, or Firm* — Drinker Biddle & Reath LLP

(57) ABSTRACT

The present invention relates to compounds of formula (1) which are suitable for use in electronic devices, especially in organic electroluminescent devices.

39 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2015/002225, filed Nov. 5, 2015, which claims benefit; of European Application No. 14004045.2, filed Dec. 1, 2014, both of which are incorporated herein by reference in their entirety.

The present invention relates to tribenzotropone derivatives, especially for use in organic electroluminescent devices. The invention further relates to a process for preparing the inventive compounds and to electronic devices comprising these compounds.

The structure of organic electroluminescent devices (OLEDs) in which organic semiconductors are used as functional materials is described, for example, in U.S. Pat. Nos. 4,539,507, 5,151,629, EP 0676461 and WO 98/27136. Emitting materials used are frequently organometallic complexes which exhibit phosphorescence rather than fluorescence. For quantum-mechanical reasons, up to four times the energy efficiency and power efficiency is possible using organometallic compounds as phosphorescent emitters. In general terms, there is still a need for improvement in OLEDs, especially also in OLEDs which exhibit triplet emission (phosphorescence), for example with regard to efficiency, operating voltage and lifetime.

The properties of phosphorescent OLEDs are not just determined by the triplet emitters used. More particularly, the other materials used, for example matrix materials, are also of particular significance here. Improvements to these materials can thus also lead to distinct improvements in the OLED properties.

According to the prior art, among other materials, indolocarbazole derivatives (for example according to WO 2007/063754 or WO 2008/056746) or indenocarbazole derivatives (for example according to WO 2010/136109 or WO 2011/000455), especially those substituted by electron-deficient heteroaromatics such as triazine, are used as matrix materials for phosphorescent emitters. In addition, for example, bisdibenzofuran derivatives (for example according to EP 2301926) are used as matrix materials for phosphorescent emitters. However, there is still a need for improvement in the case of use of these matrix materials, especially in relation to the efficiency, the lifetime and the operating voltage of the device.

The problem addressed by the present invention is that of providing compounds suitable for use in a fluorescent or phosphorescent OLED, especially a phosphorescent OLED, for example as matrix material or as charge transport material, especially hole transport or electron blocker material. A particular problem addressed by the present invention is that of providing matrix materials which are also suitable for green- and blue-phosphorescing OLEDs, and providing novel charge transport materials.

It has been found that, surprisingly, electroluminescent devices containing compounds of the following formula (1) have improvements over the prior art, especially when used as hole transport and hole injection materials.

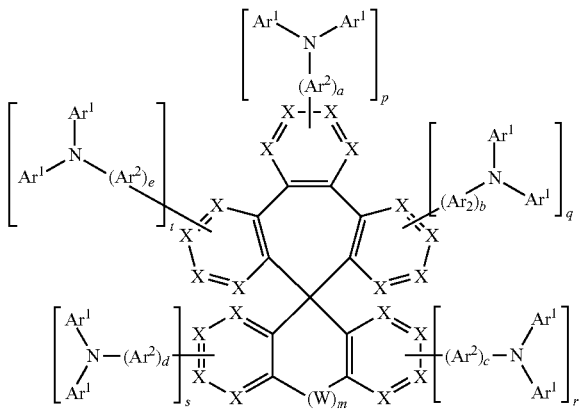

Formula (1)

where the symbols and indices used are as follows:

X is the same or different at each instance and is $CR^1$ or N;

$Ar^2$ is the same or different at each instance and is a bivalent aromatic or heteroaromatic ring system which has 5 to 60 aromatic ring atoms and may be substituted by one or more $R^2$ radicals;

$Ar^1$ is the same or different at each instance and is an aromatic or heteroaromatic ring system which has 5 to 60 aromatic ring atoms and may in each case also be substituted by one or more $R^2$ radicals; where $Ar^1$ and/or $Ar^2$ radicals bonded to the same nitrogen atom may be joined via at least one K group;

K is the same or different at each instance and is a single bond or a bivalent bridge selected from $N(R^2)$, $B(R^2)$, O, C=O, $C(R^2)_2$, $Si(R^2)_2$, $C=C(R^2)_2$, S=O, $P(R^2)$, $P(=O)R^2$ and S;

W is the same or different at each instance and is a single bond or a bivalent bridge selected from $N(R^2)$, $B(R^2)$, O, C=O, $C(R^2)_2$, $Si(R^2)_2$, S and $R^2C=CR^2$;

Ar is the same or different at each instance and is an aromatic or heteroaromatic ring system, preferably an aryl or heteroaryl group, which has 5 to 40 aromatic ring atoms and may be substituted by one or more $R^3$ radicals;

$R^1$ is the same or different at each instance and is H, D, F, Cl, Br, I, C(=O)Ar, $P(=O)Ar_2$, S(=O)Ar, $S(=O)_2Ar$, $CR^2=CR^2Ar$, CN, $NO_2$, $Si(R^2)_3$, $B(OR^2)_2$, $OSO_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by $R^2C=CR^2$, C≡C, $Si(R^2)_2$, C=O, $C=NR^2$, $P(=O)(R^2)$, SO, $SO_2$, $NR^2$, O, S or $CONR^2$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^2$ radicals, or an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals, or a combination of these systems; at the same time, two or more $R^2$ substituents together with the atoms to which they are bonded and also with one another, or two $R^1$ substituents, may form a mono- or polycyclic, aliphatic or aromatic ring system;

$R^2$ is the same or different at each instance and is H, D, F, Cl, Br, I, $N(R^3)_2$, $N(Ar)_2$, $C(=O)Ar$, $P(=O)Ar_2$, $S(=O)Ar$, $S(=O)_2Ar$, $CR^3=CR^3Ar$, CN, $NO_2$, $Si(R^3)_3$, $B(OR^3)_2$, $OSO_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by $R^3C=CR^3$, $C\equiv C$, $Si(R^3)_2$, $C=O$, $C=NR^3$, $P(=O)(R^3)$, SO, $SO_2$, $NR^3$, O, S or $CONR^3$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^3$ radicals, or an aryloxy or heteroaryloxy group which has 5 to 40 aromatic ring atoms and may be substituted by one or more $R^3$ radicals, or an aralkyl or heteroaralkyl group which has 5 to 40 aromatic ring atoms and may be substituted by one or more $R^3$ radicals, or a combination of these systems; at the same time, two or more $R^3$ substituents together with the atoms to which they are bonded and also with one another, or two $R^2$ substituents, may form a mono- or polycyclic, aliphatic or aromatic ring system;

$R^3$ is the same or different at each instance and is H, D, F, Cl, Br, I, $C(=O)Ar$, $P(=O)Ar_2$, $S(=O)Ar$, $S(=O)_2Ar$, $CR^4=CR^4Ar$, CN, $NO_2$, $Si(R^4)_3$, $B(OR^4)_2$, $OSO_2R^4$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^4$ radicals, where one or more nonadjacent $CH_2$ groups may be replaced by $R^4C=CR^4$, $C\equiv C$, $Si(R^4)_2$, $C=O$, $C=NR^4$, $P(=O)(R^4)$, SO, $SO_2$, $NR^4$, O, S or $CONR^4$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^4$ radicals, or an aryloxy or heteroaryloxy group which has 5 to 40 aromatic ring atoms and may be substituted by one or more $R^4$ radicals, or an aralkyl or heteroaralkyl group which has 5 to 40 aromatic ring atoms and may be substituted by one or more $R^4$ radicals, or a combination of these systems; at the same time, two or more $R^4$ substituents together with the atoms to which they are bonded and also with one another, or two $R^3$ substituents, may form a mono- or polycyclic, aliphatic or aromatic ring system;

$R^4$ is the same or different at each instance and is H, D, F or an aliphatic hydrocarbyl radical having 1 to 20 carbon atoms or an aryl or heteroaryl group which has 5 to 40 ring atoms and may be substituted by one or more $R^5$ radicals, or a combination of these groups;

$R^5$ is the same or different at each instance and is H, D, F or an aliphatic hydrocarbyl radical having 1 to 20 carbon atoms;

m is 0 or 1, where m=0 means that no W group is bonded at this position, and the carbon atoms in question that bind to W are each replaced by an X group; and p, q, r, s, t are the same or different at each instance and are 0, 1 or 2;

a, b, c, d, e are the same or different at each instance and are 0, 1 or 2;

where p+q+r+s+t is greater than 1; and, if r is greater than or equal to 1 and s is greater than or equal to 1 and m is equal to 0, and c and d for at least one $(Ar^2)_cN(Ar^1)_2$ group and at least one $(Ar^2)_dN(Ar^1)_2$ group are 0, these $N(Ar^1)_2$ two groups are not arranged in the respective para positions to the quaternary carbon atom of the base skeleton.

The base skeleton in the context of the invention refers to a compound corresponding to the compound of the formula (1) with no radicals. This is a compound of the formula (1) in which p+q+r+s+t=0 and $R^1$ and $R^2$ are each H. The base skeleton is shown in the formula (1b):

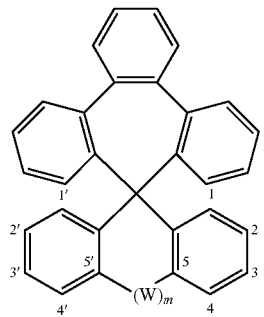

Formula (1b)

where the symbols and indices correspond to the formula (1).

The $(Ar^2)N(Ar^1)_2$ groups are each bonded to the base skeleton in place of $R^1$ in a $CR^1$ unit.

Preferably, the compound is not a compound of the formula (1c):

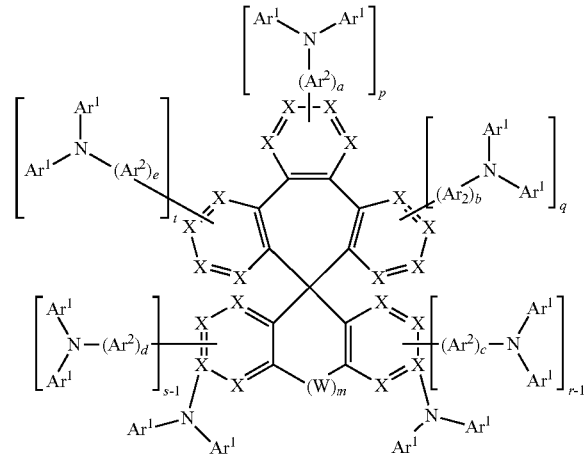

Formula (1c)

where the symbols and indices correspond to the formula (1) and, in addition, r is greater than or equal to 1 and s is greater than or equal to 1.

An aryl group in the context of this invention contains 6 to 60 carbon atoms; a heteroaryl group in the context of this invention contains 2 to 60 carbon atoms and at least one heteroatom, with the proviso that the sum total of carbon atoms and heteroatoms is at least 5. The heteroatoms are preferably selected from N, O and/or S. An aryl group or heteroaryl group is understood here to mean a simple aromatic cycle, i.e. benzene, or a simple heteroaromatic cycle, for example thiophene, etc., or a condensed (fused) aryl or heteroaryl group, for example naphthalene, anthracene, phenanthrene, dibenzofuran, etc. Aromatic systems joined to one another by a single bond, for example biphenyl, by contrast, are not referred to as an aryl or heteroaryl group but as an aromatic ring system.

An aromatic ring system in the context of this invention contains 6 to 80 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention is understood to mean a system which does not necessarily contain only aryl or heteroaryl groups, but in which it is also possible for two or more aryl or heteroaryl groups to be joined by a nonaromatic unit (preferably less than 10% of the atoms other than H), for example a carbon, nitrogen or oxygen atom. For example, systems such as fluorene, 9,9'-spirobifluorene, 9,9-diarylfluorene, triarylamine, diaryl ethers, stilbene, etc. are also to be regarded as aromatic ring systems in the context of this invention, and likewise systems in which two or more aryl groups are joined, for example, by a short alkyl group. In addition, aromatic systems joined to one another by a single bond, for example biphenyl, are referred to as aromatic ring system in the context of this application.

In a preferred embodiment of the invention, the compound does not comprise any further diarylamino groups apart from the diarylamino groups shown in formula (1) or preferred embodiments thereof. This means that preferably heteroaromatic ring systems do not comprise any diarylamino groups. This also includes amines having heteroaryl groups.

An electron-deficient heteroaryl group in the context of present invention is defined as a 5-membered heteroaryl group having at least two heteroatoms, for example imidazole, oxazole, oxadiazole, etc., or as a 6-membered heteroaryl group having at least one heteroatom, for example pyridine, pyrimidine, pyrazine, triazine, etc. It is also possible for further 6-membered aryl or 6-membered heteroaryl groups to be fused onto these groups, as, for example, in benzimidazole or quinoline.

In the context of the present invention, an aliphatic hydrocarbyl radical or an alkyl group or an alkenyl or alkynyl group which may typically contain 1 to 40 or else 1 to 20 carbon atoms and in which individual hydrogen atoms or $CH_2$ groups may also be replaced by the abovementioned groups are preferably understood to mean the methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkenyl, alkynyl, alkoxy or thioalkyl groups according to the present invention may be straight-chain, branched or cyclic, where one or more nonadjacent $CH_2$ groups may be replaced by the abovementioned groups; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5-80 aromatic ring atoms and may also be substituted in each case by the abovementioned radicals and which may be joined to the aromatic or heteroaromatic system via any desired positions is especially understood to mean groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combinations of these systems. These groups may each be substituted by the abovementioned radicals.

An aryloxy group as defined in the present invention is understood to mean an aryl group as defined above bonded via an oxygen atom. An analogous definition applies to heteroaryloxy groups.

An electron-deficient heteroaryl group in the context of present invention is defined as a 5-membered heteroaryl group having at least two heteroatoms, for example imidazole, oxazole, oxadiazole, etc., or as a 6-membered heteroaryl group having at least one heteroatom, for example pyridine, pyrimidine, pyrazine, triazine, etc. It is also possible for further 6-membered aryl or 6-membered heteroaryl groups to be fused onto these groups, as, for example, in benzimidazole or quinoline.

The wording that two or more radicals together may form a ring, in the context of the present description, shall be understood to mean, inter alia, that the two radicals are joined to one another by a chemical bond. This is illustrated by the following scheme:

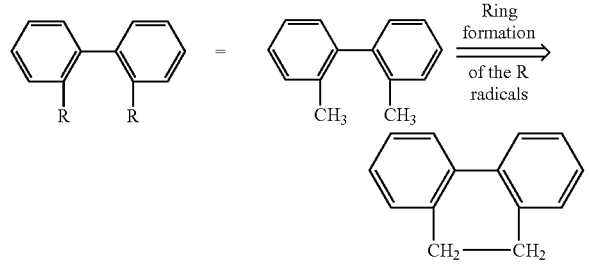

In addition, however, the abovementioned wording shall also be understood to mean that, if one of the two radicals is hydrogen, the second radical binds to the position to which the hydrogen atom was bonded, forming a ring. This shall be illustrated by the following scheme:

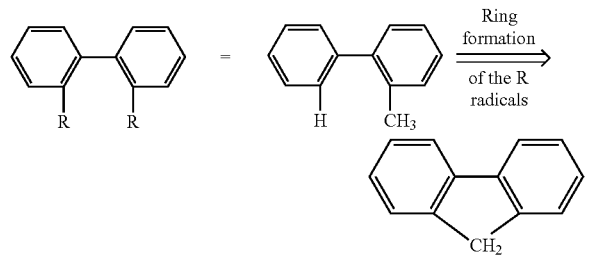

In a further embodiment of the invention, a 6-membered cycle in formula (1) comprises not more than one N as aromatic ring atom, meaning that only one X is N. More preferably, none of the X symbols in formula (1) is N.

A preferred embodiment of the compound of the formula (1) is a compound of the following formula (2):

Formula (2)

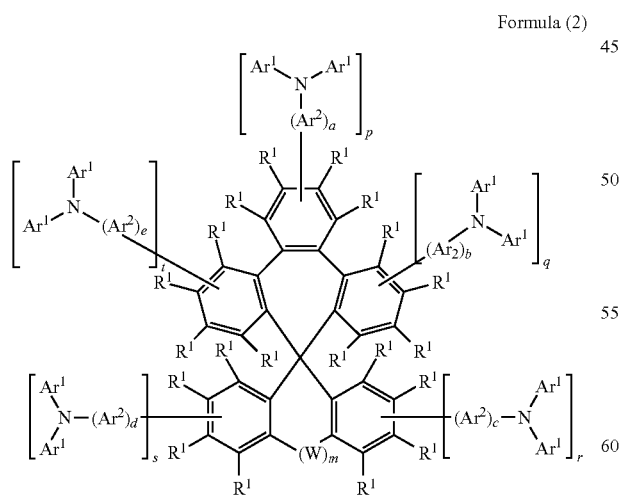

where the symbols and indices used correspond to those of formula (1).

According to the invention, when m is 0, r is greater than or equal to 1, s is greater than or equal to 1 and at least one c is 0 and at least one d is 0, the at least two N(Ar$^1$)$_2$ groups are arranged at the 1, 2, 4, 5, 1', 2', 4' or 5' positions.

In a preferred embodiment of the invention, the compound does not include a compound of the following formula (3):

Formula (3)

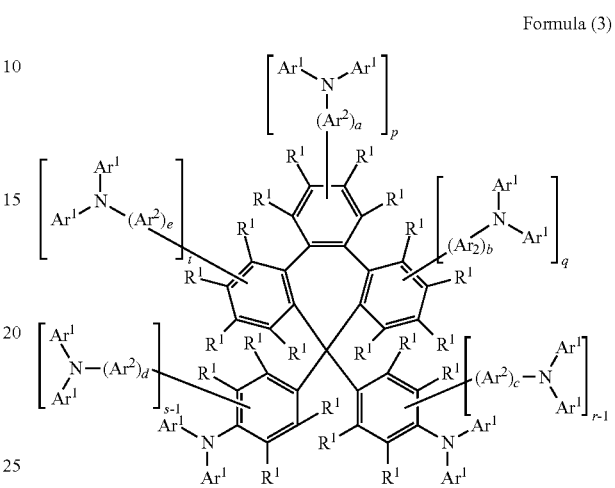

where the symbols and indices used correspond to those of formula (1) and, in addition, r and s are greater than or equal to 1.

In a preferred embodiment of the invention, p+q+r+s+t is a value of 1 to 10, preferably of 1 to 5, more preferably 1 or 2, most preferably 1.

In a further preferred embodiment of the invention, p, q, r, s and t are the same or different at each instance and are 0 or 1.

In a further preferred embodiment of the invention, p is 0.

In a further preferred embodiment, r is 1, and p, q, s and t are each 0. In an alternative preferred embodiment, s is 1, and p, q, r and t are each 0.

Preferably, p, q, r, s and t are the same or different at each instance and are 0 or 1. In this case, one diarylamino group per cycle is attached.

In a preferred embodiment of the invention, the compound is a compound of one of the following formulae (4) and (5):

Formula (4)

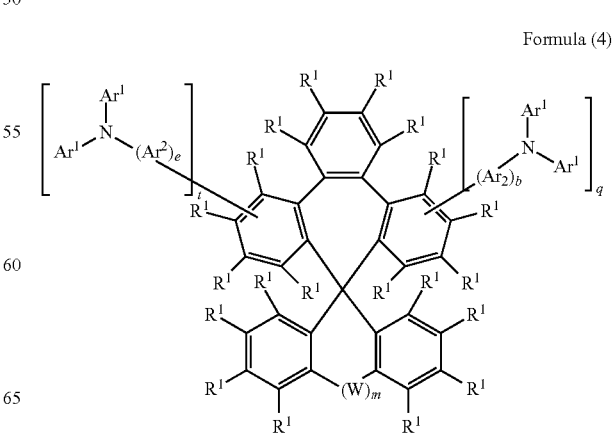

Formula (5)

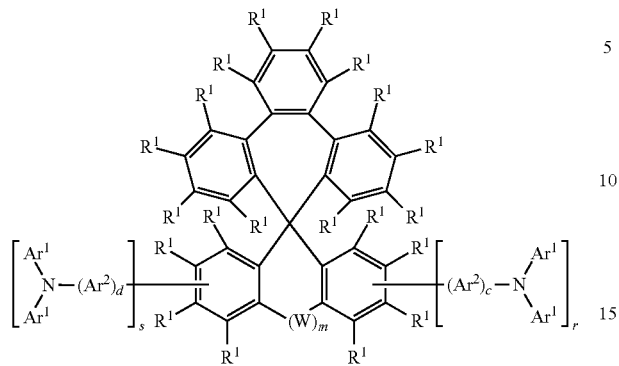

The symbols and indices here correspond to the symbols and indices of the formula (1).

Preferably, the compound according to the invention does not have any further rings condensed or fused onto the base skeleton.

In a preferred embodiment of the invention, W at each instance is O, S or a single bond, more preferably a single bond.

In a further embodiment of the invention, the compound is a compound of one of the following formulae (6) to (11):

Formula (6)

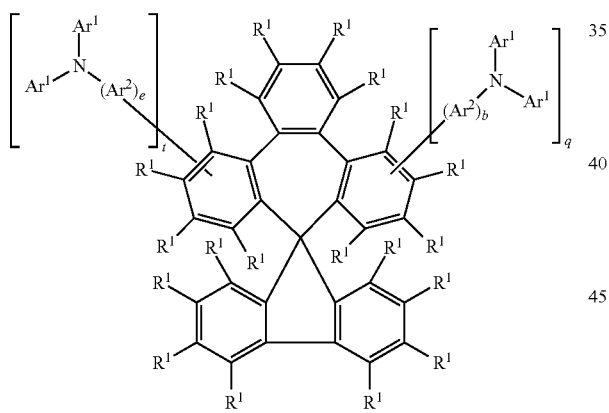

Formula (7)

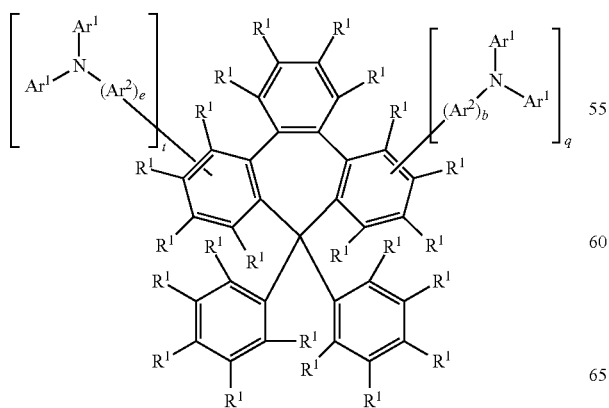

Formula (8)

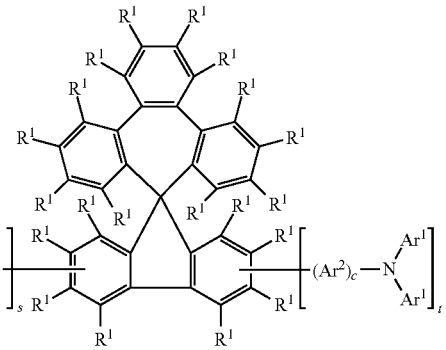

Formula (9)

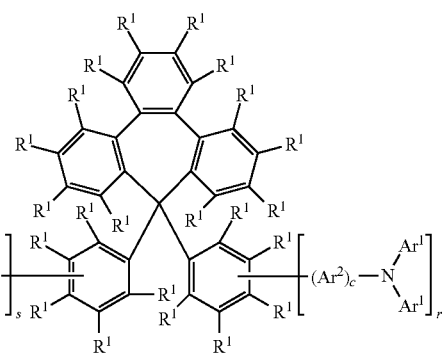

Formula (10)

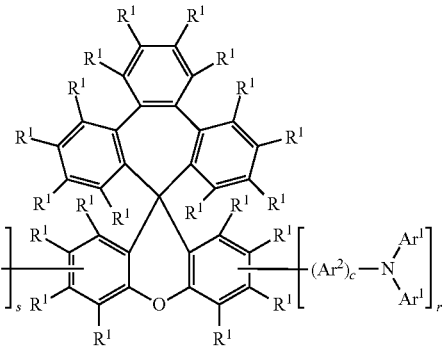

Formula (11)

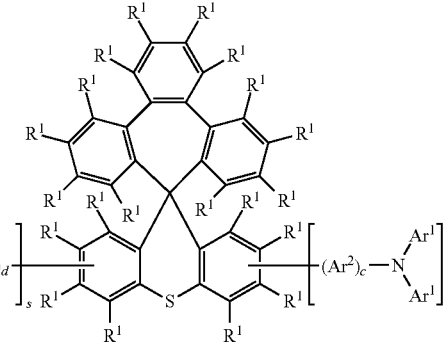

where the symbols and indices correspond to the symbols and indices of formula (1).

In a preferred embodiment, the compound is selected from the compounds of the formulae (8) to (11).

Preferably, in formulae (9), in the case that r is greater than 0 and s is greater than 0, none of the diarylamino groups are arranged para to the quaternary carbon atom of the base skeleton.
In a particularly preferred embodiment of the invention, the compound is a compound of one of the following formulae (8-1) to (11-3):
Formula (8-1)
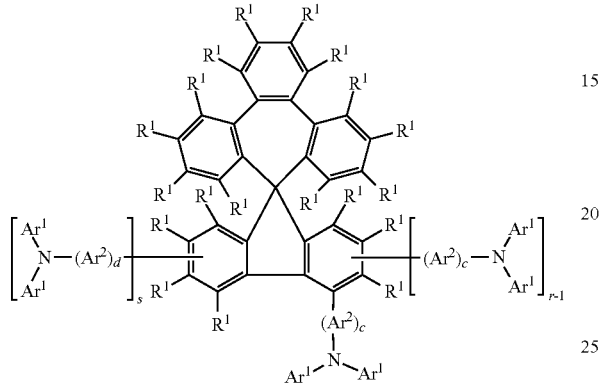
Formula (8-2)
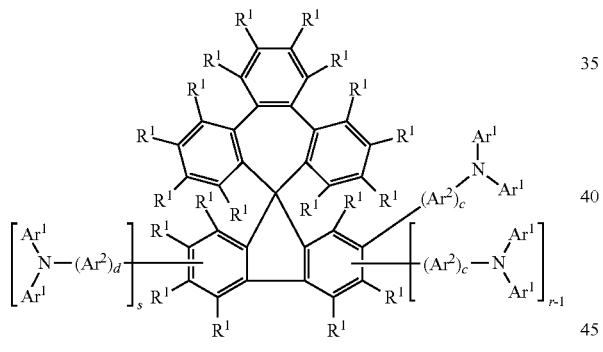
Formula (8-3)
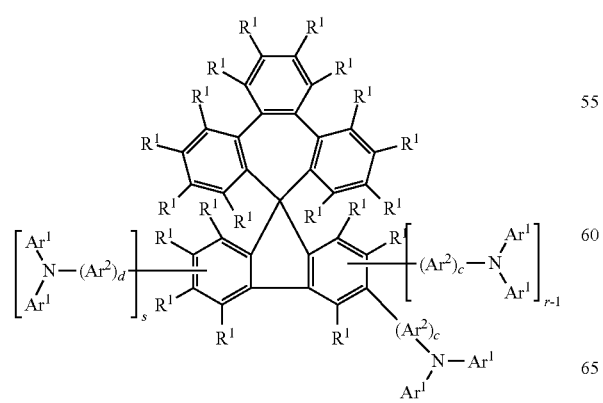
Formula (8-4)
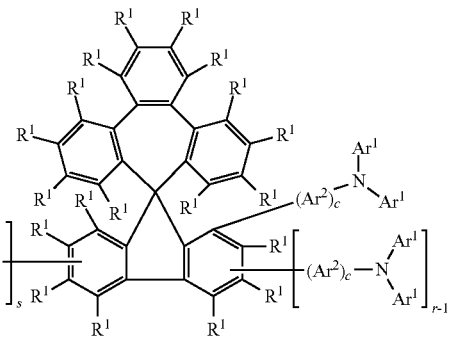
Formula (9-1)
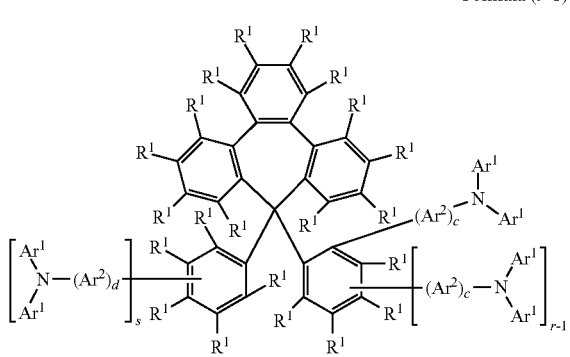
Formula (9-2)
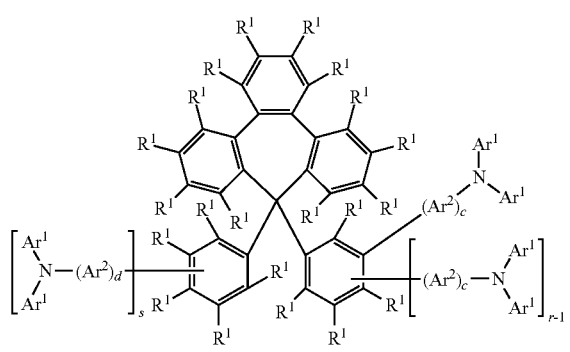
Formula (9-3)
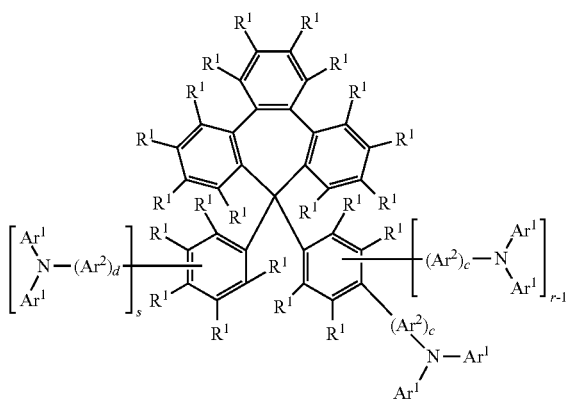

-continued
Formula (10-1)
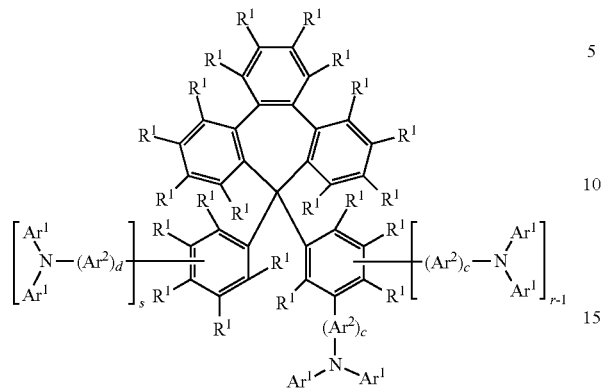
Formula (10-2)
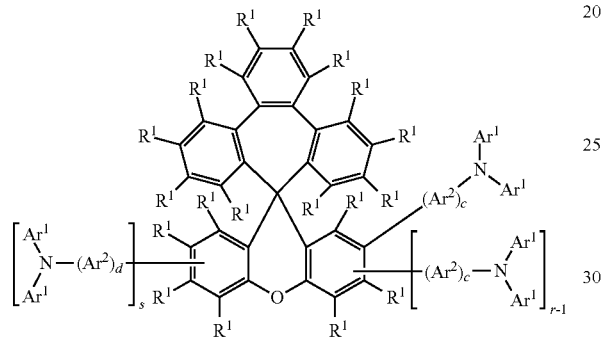
Formula (10-3)
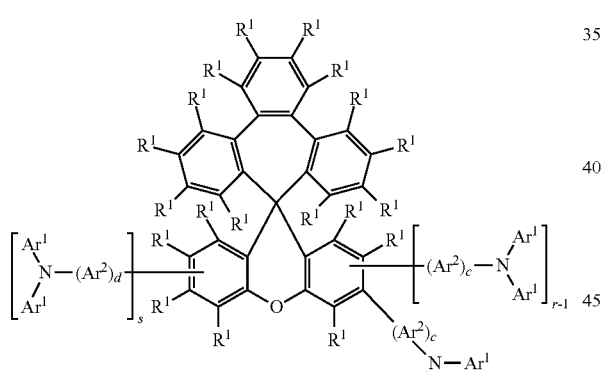
Formula (10-4)
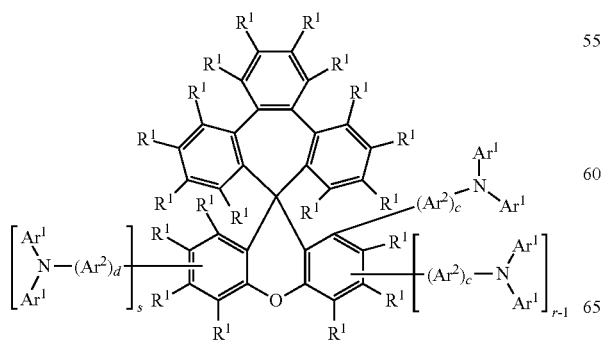
Formula (11-1)
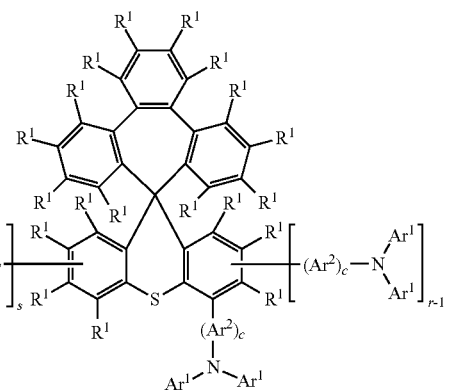
Formula (11-2)
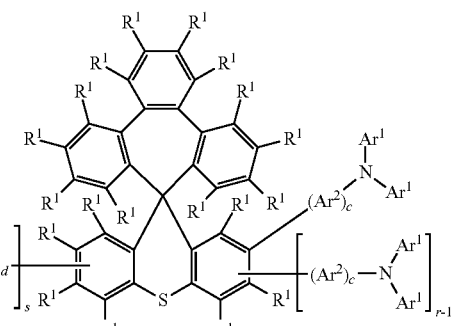
Formula (11-3)
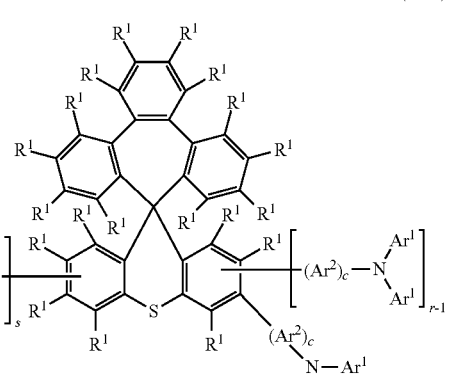
Formula (11-4)
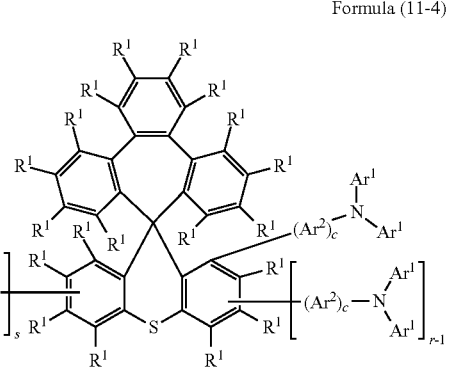
where the symbols and indices correspond to the symbols and indices of formula (1) and, in addition, r is at least 1; and, for the formulae (9-1), (9-2) and (9-3), if s is greater than or equal to 1, no two $N(Ar^1)_2$— groups with c and d=0 are arranged in para positions to the quaternary carbon atom of the base skeleton.

Preferably, in the formulae (8-1) to (11-4), r is 1 and s is 0.

In a further particularly preferred embodiment of the invention, the compound is a compound of one of the following formulae (8-1-1) to (11-4-1):

Formula (8-1-1)

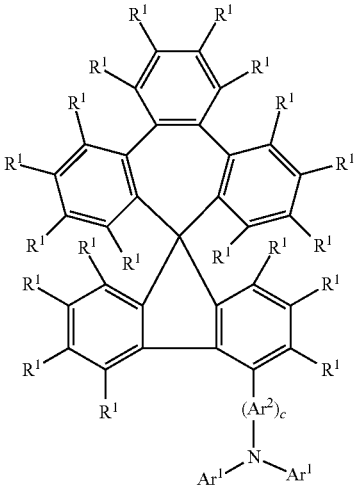

Formula (8-2-1)

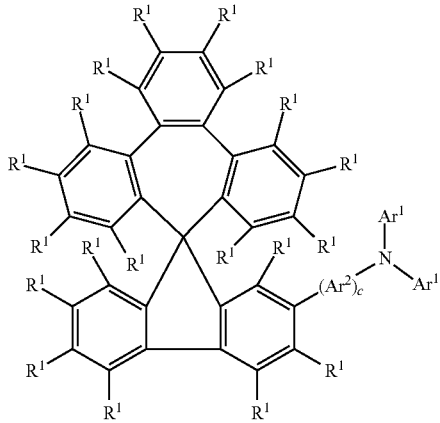

Formula (8-3-1)

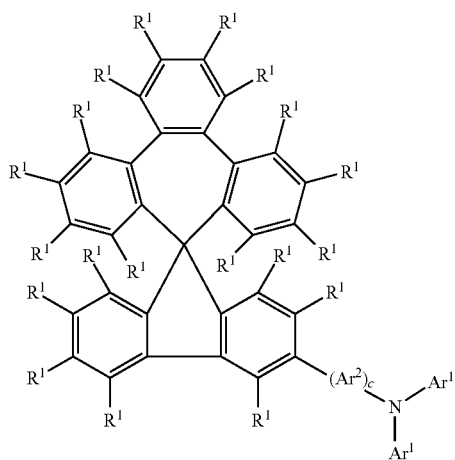

Formula (8-4-1)

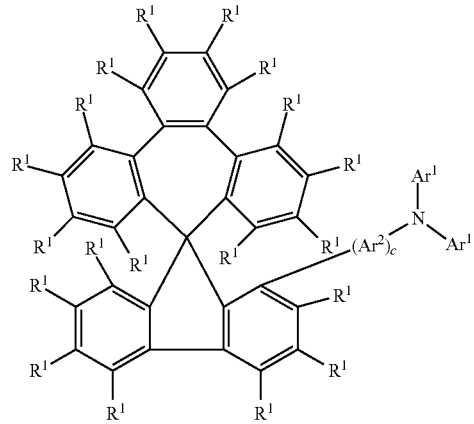

Formula (9-1-1)

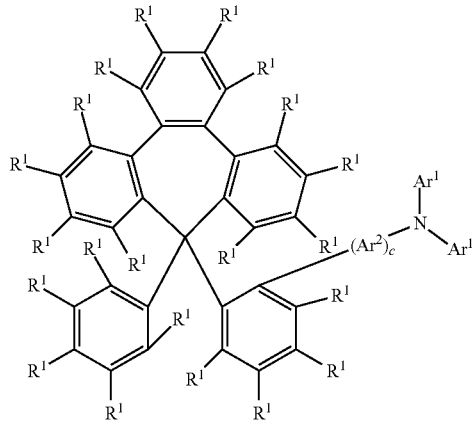

Formula (9-2-1)

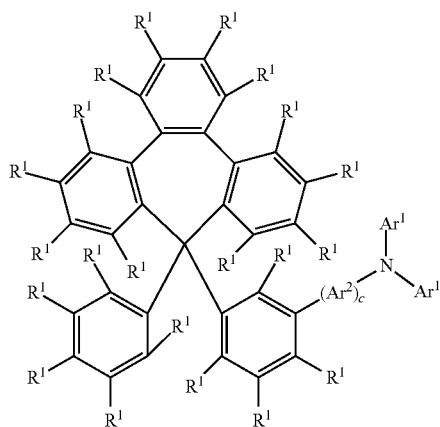

Formula (9-3-1)
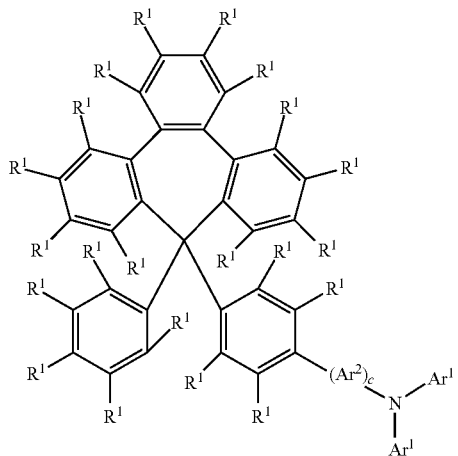
Formula (10-3-1)
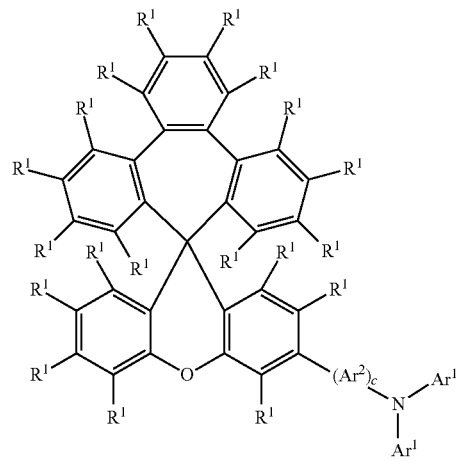
Formula (10-1-1)
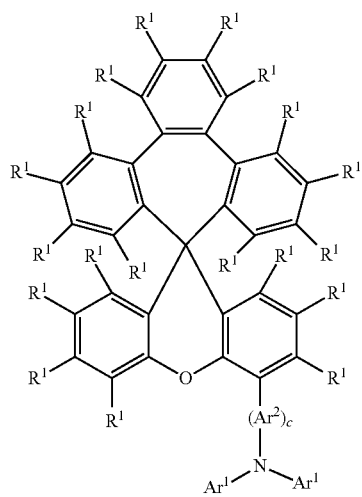
Formula (10-4-1)
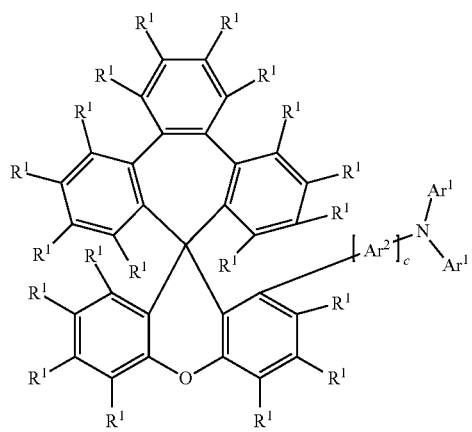
Formula (10-2-1)
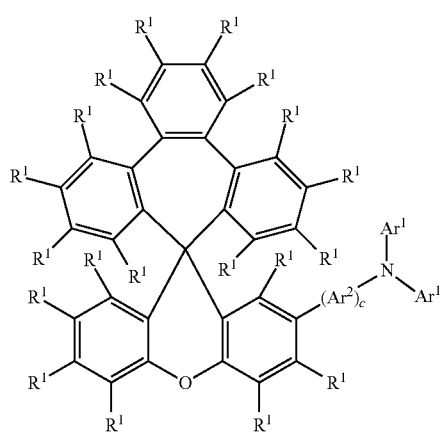
Formula (11-1-1)
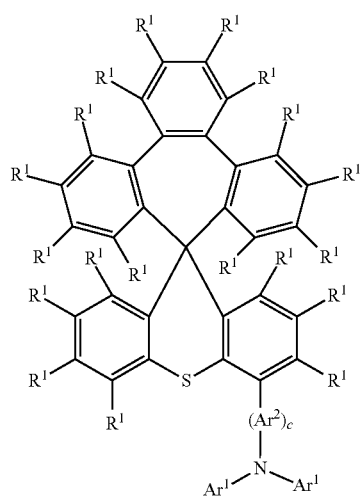

-continued

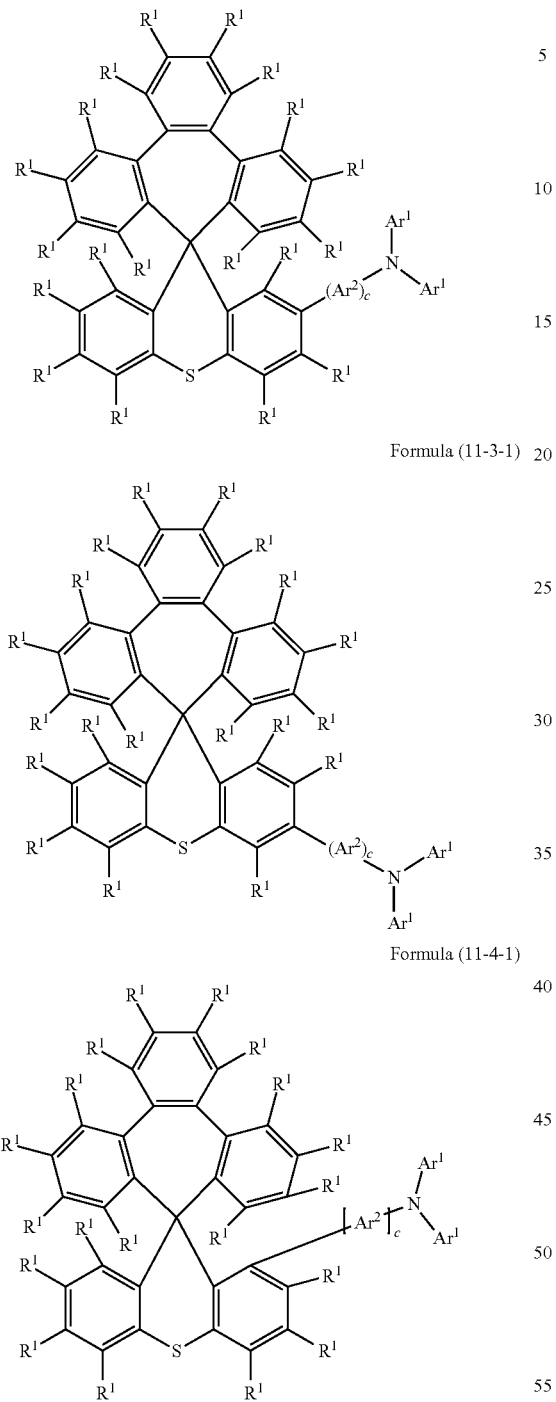

Formula (11-2-1)

Formula (11-3-1)

Formula (11-4-1)

where the symbols and indices correspond to the symbols and indices of formula (1).

In a preferred embodiment of the invention, $R^1$ is the same or different at each instance and is H, D, F or an aliphatic hydrocarbyl radical having 1 to 20 carbon atoms, more preferably H, D or F, most preferably H or D.

In a preferred embodiment of the invention, the $Ar^1$ groups at each instance are selected from the groups having the following formulae (Ar-1) to (Ar-15):

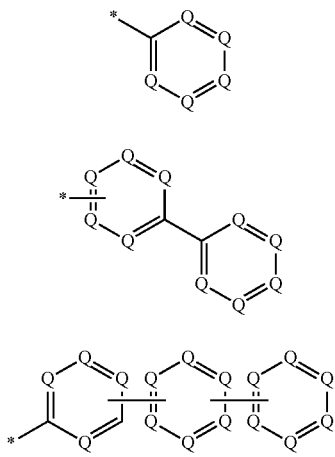

Formula (Ar-1)

Formula (Ar-2)

Formula (Ar-3)

Formula (Ar-4)

Formula (Ar-5)

Formula (Ar-6)

Formula (Ar-7)

Formula (Ar-8)

Formula (Ar-9)

Formula (Ar-10)

Formula (Ar-11)

Formula (Ar-12)

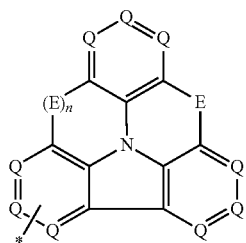

Formula (Ar-16)

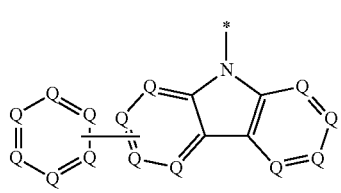

Formula (Ar-13)

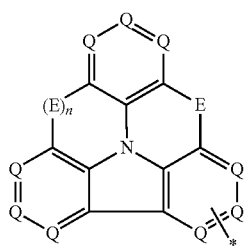

Formula (Ar-17)

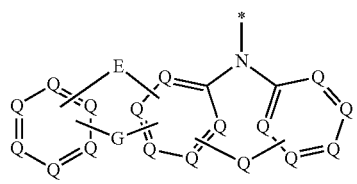

Formula (Ar-14)

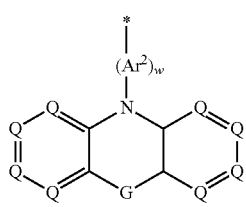

Formula (Ar-18)

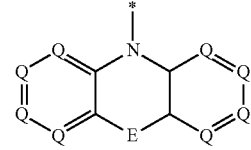

Formula (Ar-15)

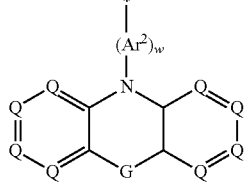

where the symbols and indices correspond to the symbols and indices of formula (1) and, in addition:

Q is the same or different at each instance and is $CR^2$ or N, where not more than 3 Q symbols per cycle are N;

E is the same or different at each instance and is $(CR^2)_2$, $NR^2$, O, S, $Si(R^2)_2$ or C=O;

G at each instance is a single bond, $(CR^2)_2$, $NR^2$, O, S, $Si(R^2)_2$, or C=O;

w is 1, 2, 3 or 4;

n is 0 or 1, where n=0 means that no E group is bonded at this position and $R^2$ radicals are bonded to the corresponding carbon atoms instead; and

* represents the bond to the nitrogen atom.

If the $Ar^1$ groups are bonded to a K group, the $N(Ar^1)_2$ group is preferably selected from the following formulae (Ar-15) to (Ar-18):

Formula (Ar-15)

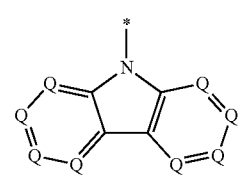

where the symbols and indices correspond to the symbols and indices of formula (1) and, in addition, for the formulae (Ar-15) to (Ar-18):

Q is the same or different at each instance and is $CR^2$ or N, where not more than 2 Q symbols per cycle are N;

E is the same or different at each instance and is $(CR^2)_2$, $NR^2$, O, S, $Si(R^2)_2$ or C=O;

G at each instance is a single bond, $(CR^2)_2$, $Si(R^2)_2$, $NR^2$, O, S or C=O;

* represents the bond to the base skeleton or, if present, to $Ar^2$.

If $Ar^1$ and $Ar^2$ radicals bonded to the same nitrogen atom are bonded via at least one K group, the $Ar^2N(Ar^1)_2$ groups are selected from the structures of the formulae (Ar-5) to (Ar-14) where:

Q is the same or different at each instance and is $CR^2$ or N, where not more than 3 Q symbols per cycle are N;

E is the same or different at each instance and is $NAr^1$ at one instance and $(CR^2)_2$, $Si(R^2)_2$, $NR^2$, O, S or C=O at every further instance;

G at each instance is a single bond, $(CR^2)_2$, $Si(R^2)_2$, $NR^2$, O, S or C=O;

n is 0 or 1, where n=0 means that no E group is bonded at this position and $R^2$ radicals are bonded to the corresponding carbon atoms instead; and

* represents the bond to the base skeleton or, if present, to $Ar^2$.

In this case, the $Ar^1$ group is preferably selected from the formulae (Ar-1) to (Ar-15).

In a further preferred embodiment, in the formula (Ar-1), 0, 1, 2 or 3 Q symbols are N.

Preferred embodiments of the formula (Ar-8) are shown by the following formulae (Ar-8-1) to (Ar-8-7):

Formula (Ar-8-1)
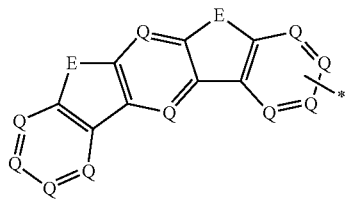

Formula (Ar-8-2)
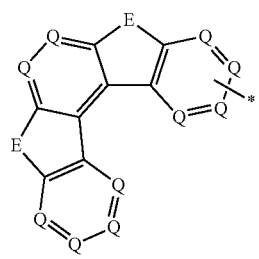

Formula (Ar-8-3)
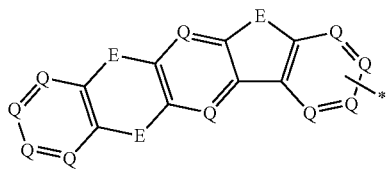

Formula (Ar-8-4)
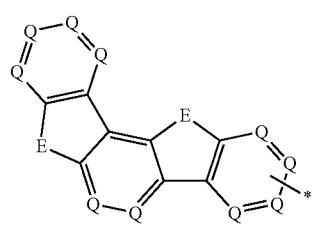

Formula (Ar-8-5)
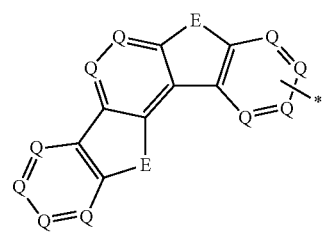

Formula (Ar-8-6)
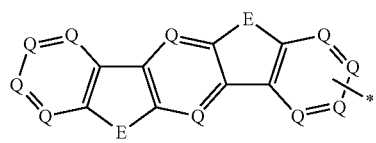

Formula (Ar-8-7)
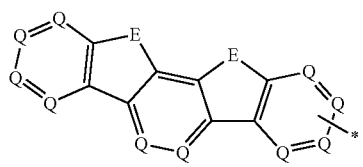

Formula (Ar-8-8)
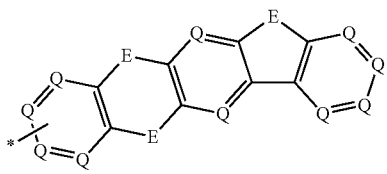

where the symbols correspond to the symbols of the formula (Ar-8). More preferably, Q is always $CR^2$.

In a further preferred embodiment, the $Ar^1$ group is the same or different at each instance and is selected from the groups having the structures of formulae (Ar-1) to (Ar-14), where the general formulae are replaced by the respective particularly preferred embodiments of the following formulae (Ar-1-1) to (Ar-14-1) (for example, formula (Ar-1) is replaced by one of the formulae (Ar-1-1) to (Ar-1-12)):

Formula (Ar-1-1)
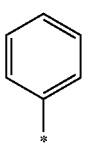

Formula (Ar-1-2)
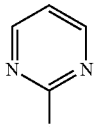

Formula (Ar-1-3)
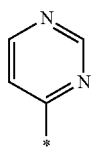

Formula (Ar-1-4)
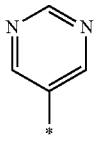

Formula (Ar-1-5)
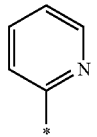

Formula (Ar-1-6)
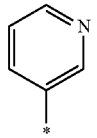

Formula (Ar-1-7)
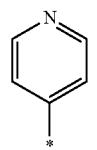

Formula (Ar-1-8)

Formula (Ar-1-9)

Formula (Ar-1-10)

Formula (Ar-1-11)

Formula (Ar-1-12)

Formula (Ar-2-1)

Formula (Ar-2-2)

Formula (Ar-2-3)

Formula (Ar-3-1)

Formula (Ar-3-2)

Formula (Ar-3-3)

Formula (Ar-3-4)

Formula (Ar-3-5)

Formula (Ar-3-6)

Formula (Ar-3-7)

Formula (Ar-3-8)
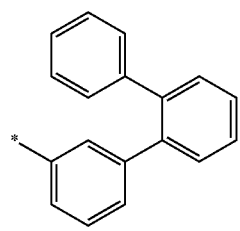
Formula (Ar-3-9)
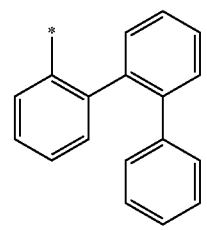
Formula (Ar-4-1)
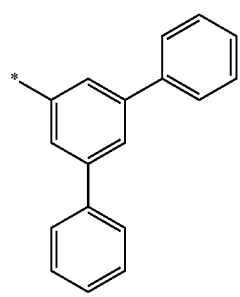
Formula (Ar-4-2)
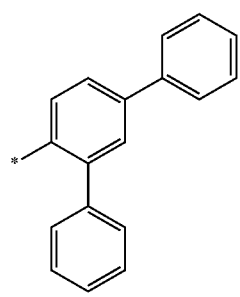
Formula (Ar-4-3)
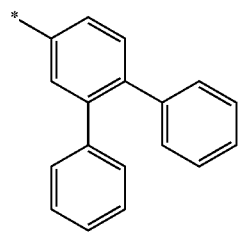
Formula (Ar-5-1)
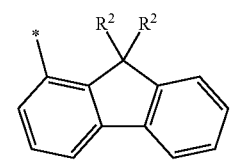
Formula (Ar-5-2)
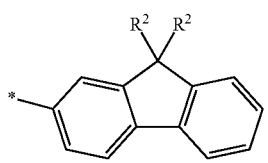
Formula (Ar-5-3)
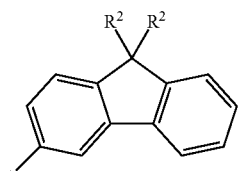
Formula (Ar-5-4)
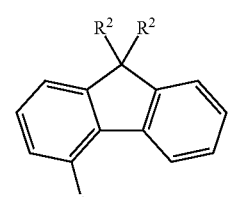
Formula (Ar-5-5)
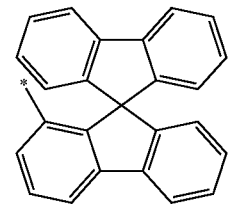
Formula (Ar-5-6)
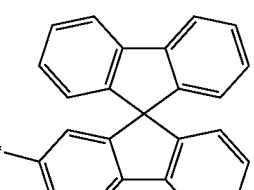
Formula (Ar-5-7)
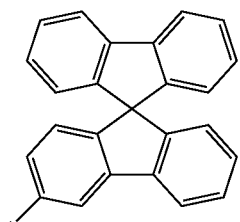
Formula (Ar-5-8)
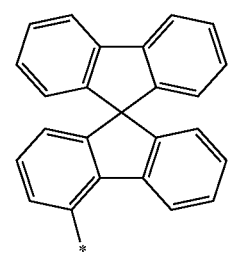
Formula (Ar-5-9)
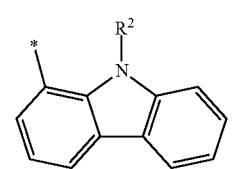

-continued
Formula (Ar-5-10)
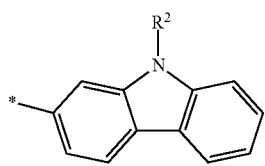
Formula (Ar-5-11)
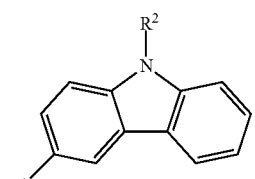
Formula (Ar-5-12)
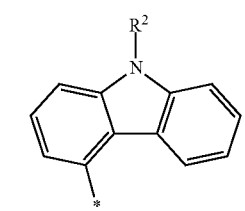
Formula (Ar-5-13)
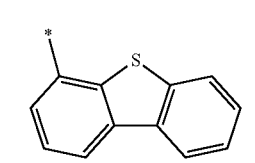
Formula (Ar-5-14)
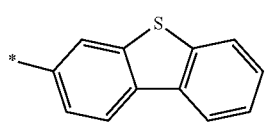
Formula (Ar-5-15)
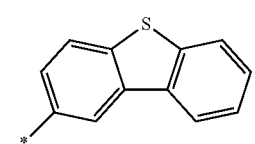
Formula (Ar-5-16)
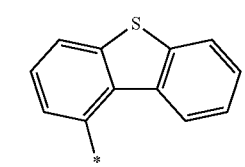
Formula (Ar-5-17)
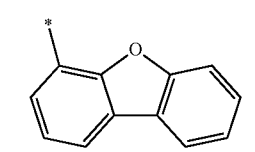
Formula (Ar-5-18)
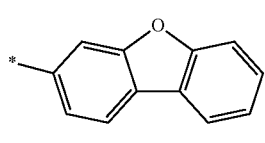
Formula (Ar-5-19)
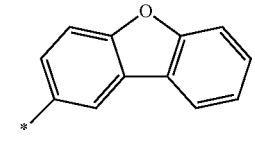
-continued
Formula (Ar-5-20)
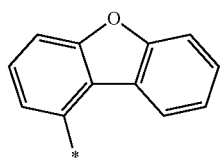
Formula (Ar-6-1)
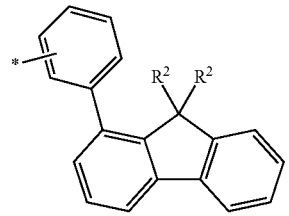
Formula (Ar-6-2)
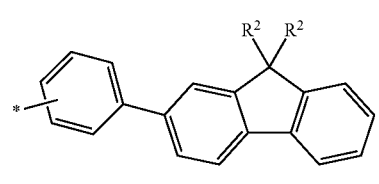
Formula (Ar-6-3)
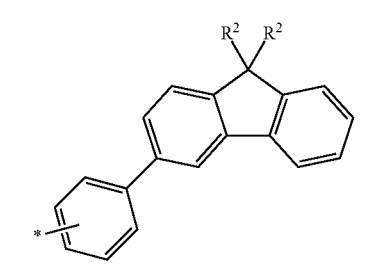
Formula (Ar-6-4)
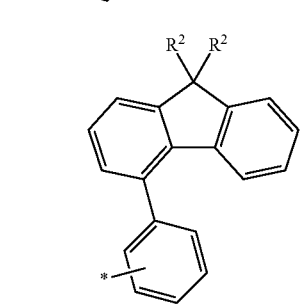
Formula (Ar-6-5)
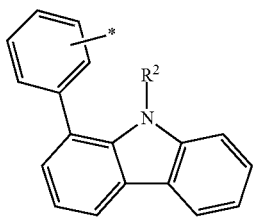
Formula (Ar-6-6)
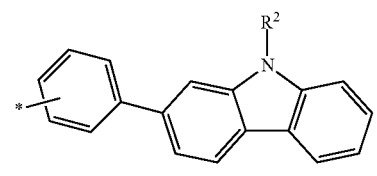

Formula (Ar-6-7)
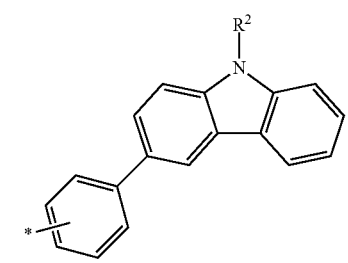
Formula (Ar-6-8)
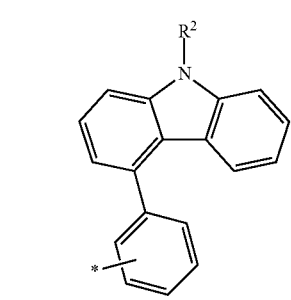
Formula (Ar-6-9)
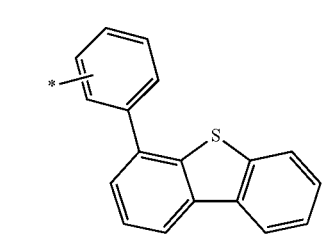
Formula (Ar-6-10)
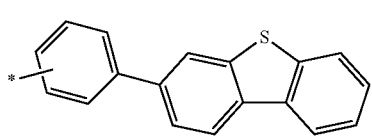
Formula (Ar-6-11)
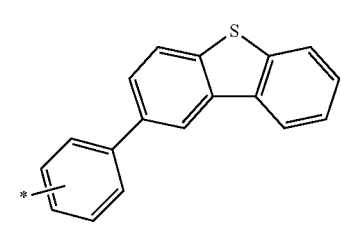
Formula (Ar-6-12)
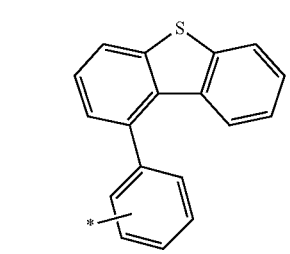
Formula (Ar-6-13)
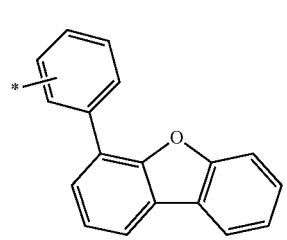
Formula (Ar-6-14)
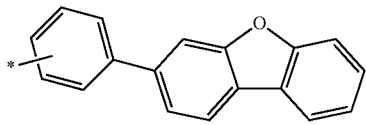
Formula (Ar-6-15)
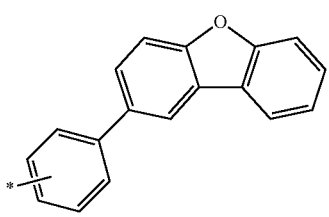
Formula (Ar-6-16)
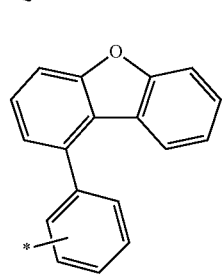
Formula (Ar-8-1-1)
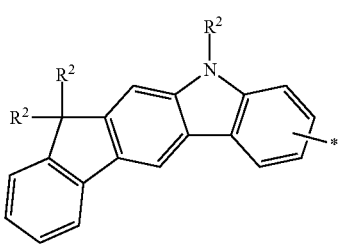
Formula (Ar-8-1-2)
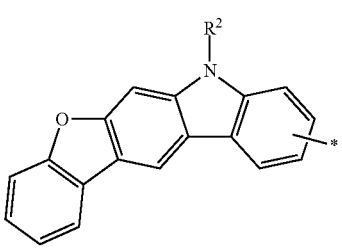
Formula (Ar-8-1-3)
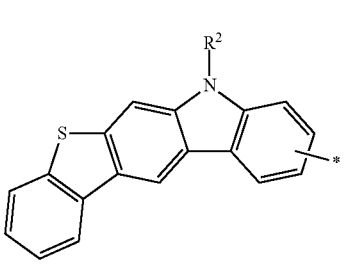
Formula (Ar-8-1-4)
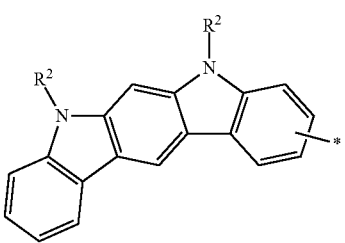

Formula (Ar-8-1-5)
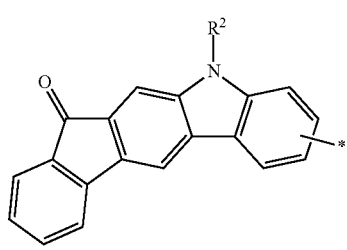
Formula (Ar-8-1-6)
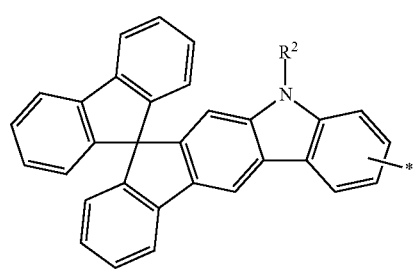
Formula (Ar-8-2-1)
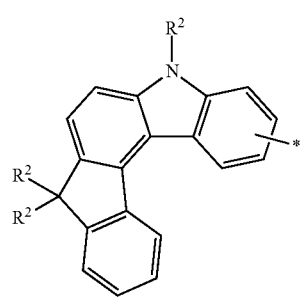
Formula (Ar-8-2-2)
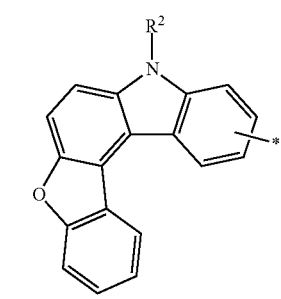
Formula (Ar-8-2-3)
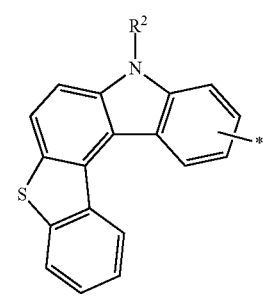
Formula (Ar-8-2-4)
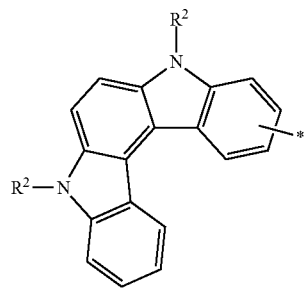
Formula (Ar-8-2-5)
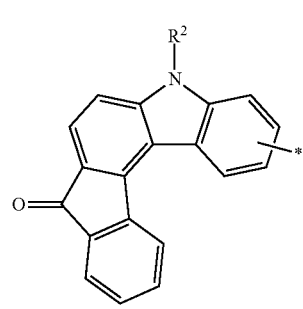
Formula (Ar-8-2-6)
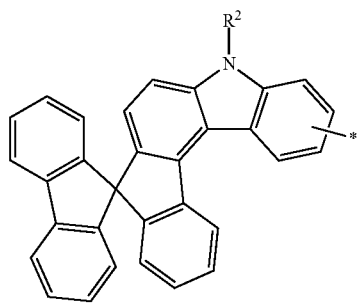
Formula (Ar-8-3-1)
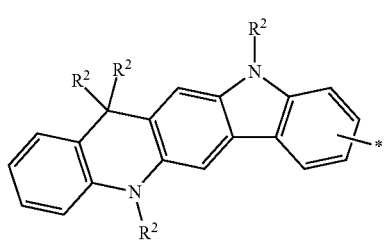
Formula (Ar-8-3-2)
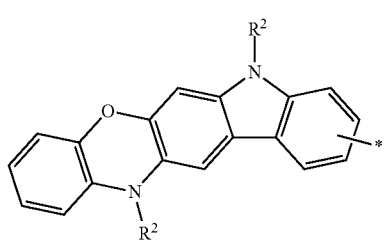

Formula (Ar-8-3-3)
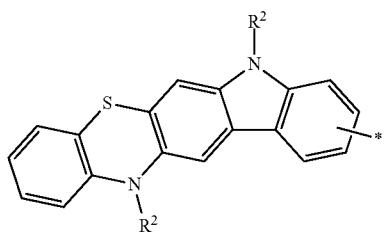
Formula (Ar-8-3-4)
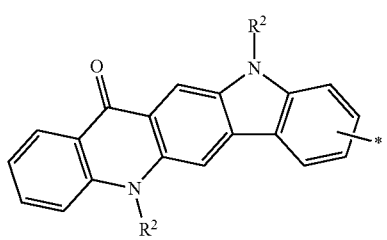
Formula (Ar-8-4-1)

Formula (Ar-8-4-2)
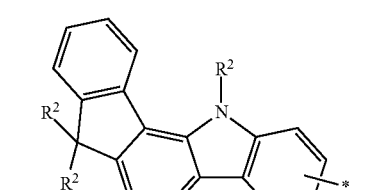
Formula (Ar-8-4-3)
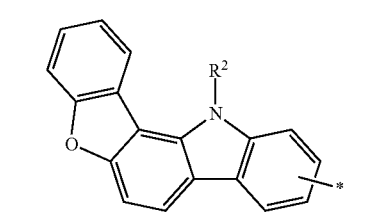
Formula (Ar-8-4-4)
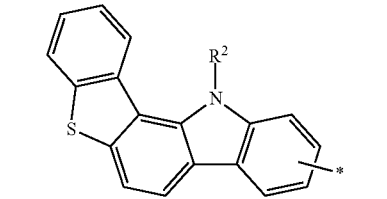
Formula (Ar-8-4-5)
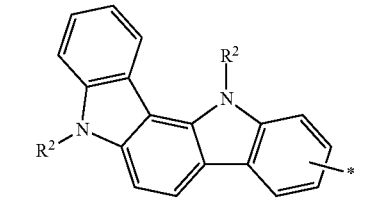
Formula (Ar-8-4-6)
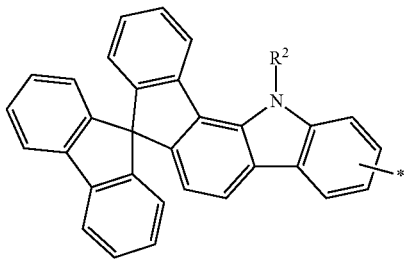
Formula (Ar-8-5-1)
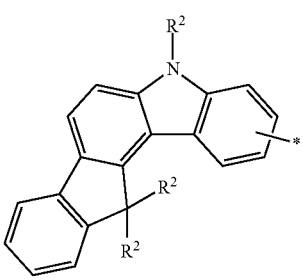
Formula (Ar-8-5-2)
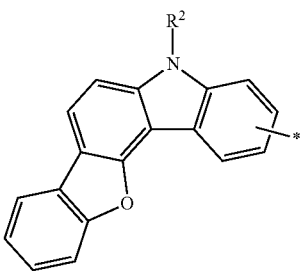
Formula (Ar-8-5-3)
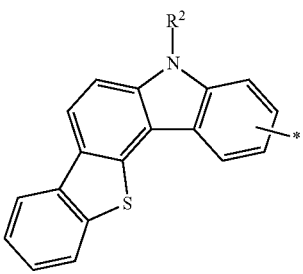
Formula (Ar-8-5-4)
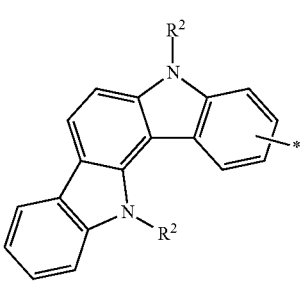

Formula (Ar-8-5-5)
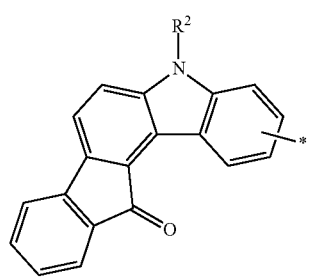
Formula (Ar-8-5-6)
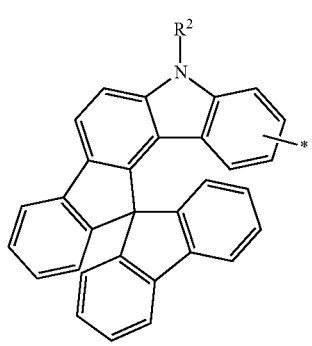
Formula (Ar-8-6-1)
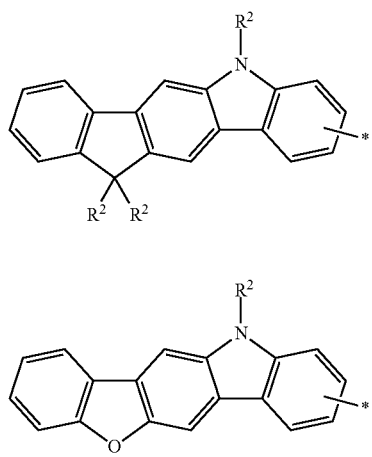
Formula (Ar-8-6-2)
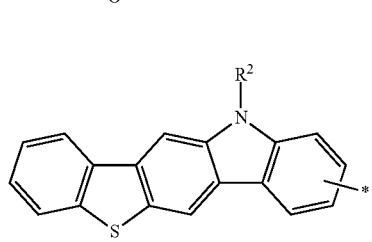
Formula (Ar-8-6-3)
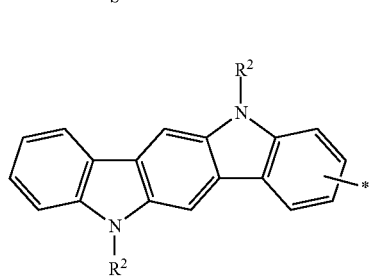
Formula (Ar-8-6-4)
Formula (Ar-8-6-5)
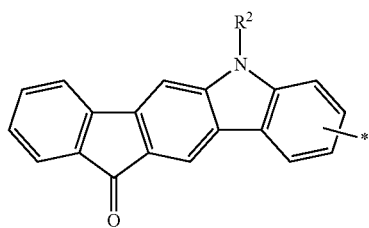
Formula (Ar-8-6-6)
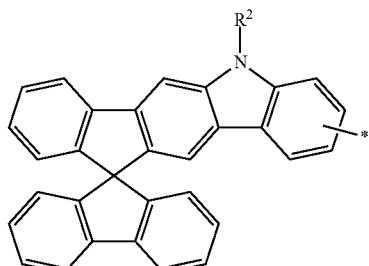
Formula (Ar-8-7-1)
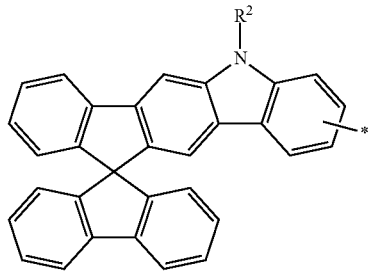
Formula (Ar-8-7-2)
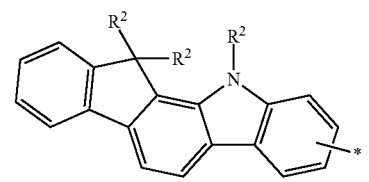
Formula (Ar-8-7-3)
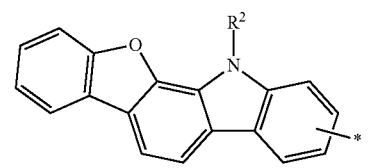
Formula (Ar-8-7-4)
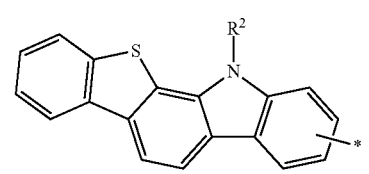
Formula (Ar-8-7-5)
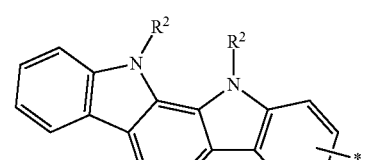

-continued

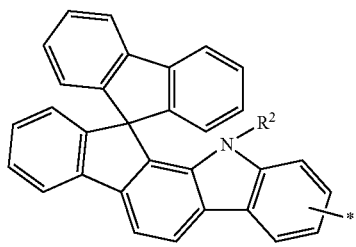
Formula (Ar-8-7-6)

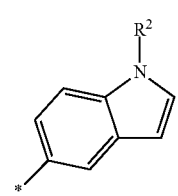
Formula (Ar-9-1)

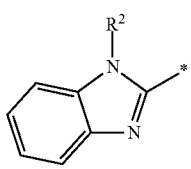
Formula (Ar-10-1)

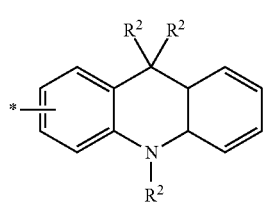
Formula (Ar-11-1)

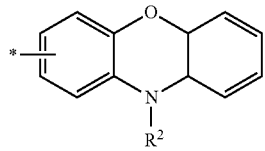
Formula (Ar-11-2)

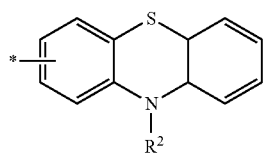
Formula (Ar-11-3)

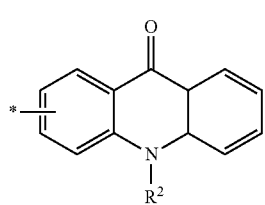
Formula (Ar-11-4)

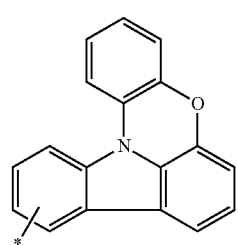
Formula (Ar-13-1)

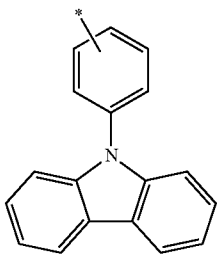
Formula (Ar-14-1)

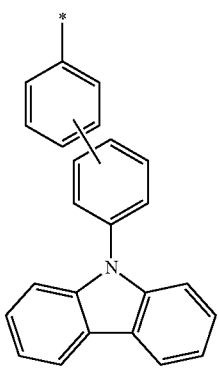
Formula (Ar-14-2)

where the symbols correspond to the symbols in the formulae (Ar-1) to (Ar-14). The formulae may be substituted by $R^2$ at the free positions.

In a further embodiment of the invention, if the $Ar^1$ groups are bonded to a K group, the $N(Ar^1)_2$ group is preferably selected from the formulae (Ar-15) to (Ar-18), where these are replaced in each case by the preferred embodiments of the following formulae (Ar-15-1) to (Ar-18-6):

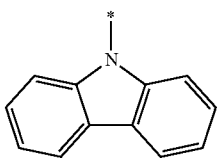
Formula (Ar-15-1)

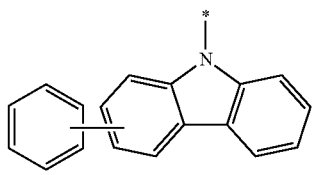
Formula (Ar-16-1)

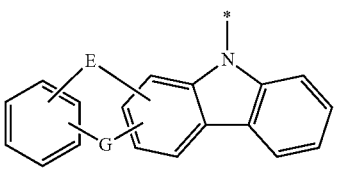
Formula (Ar-17-1)

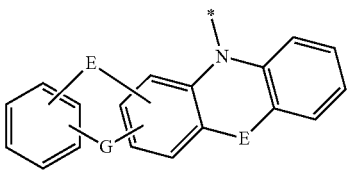
Formula (Ar-17-2)

Formula (Ar-18-1)

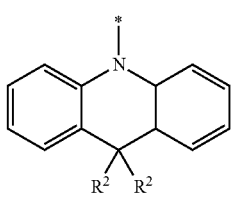

Formula (Ar-8-1-1a)

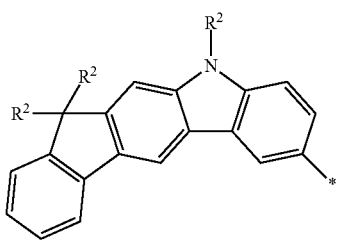

Formula (Ar-18-2)

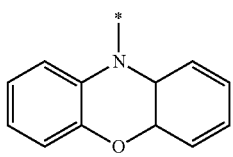

Formula (Ar-8-1-2a)

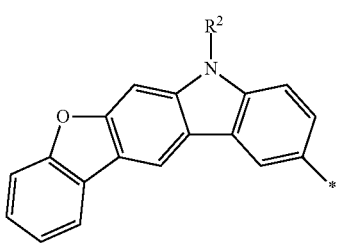

Formula (Ar-18-3)

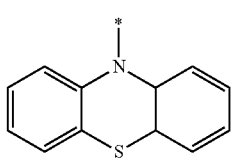

Formula (Ar-8-1-3a)

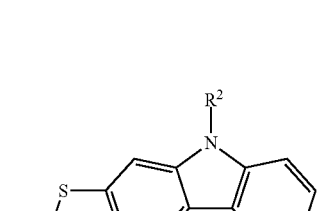

Formula (Ar-18-4)

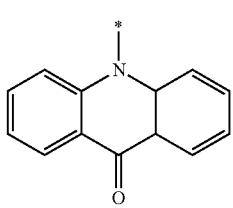

Formula (Ar-8-1-4a)

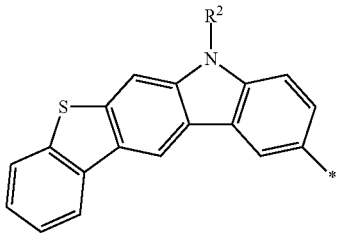

Formula (Ar-18-5)

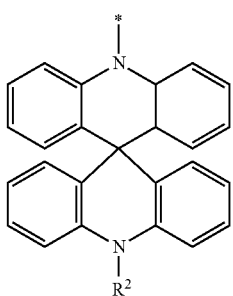

Formula (Ar-8-1-5a)

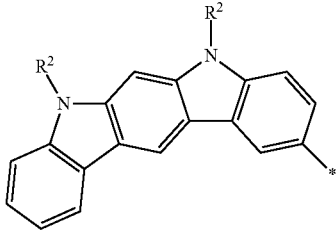

Formula (Ar-18-6)

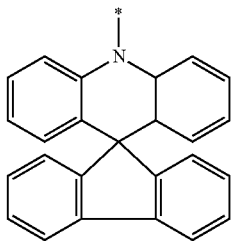

Formula (Ar-8-1-6a)

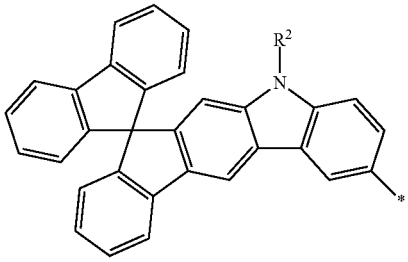

where the symbols correspond to the symbols in the formulae (Ar-15) to (Ar-18). The formulae may be substituted by $R^2$ at the free positions.

In a further embodiment of the invention, the groups of formula (Ar-8) or preferred embodiments thereof are selected from the groups of one of the formulae (Ar-8-1-1a) to (Ar-8-7-6a):

Formula (Ar-8-2-1a)
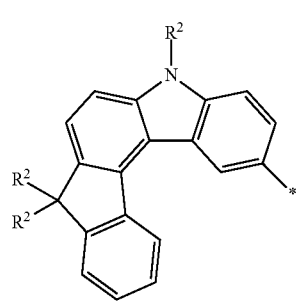
Formula (Ar-8-2-2a)
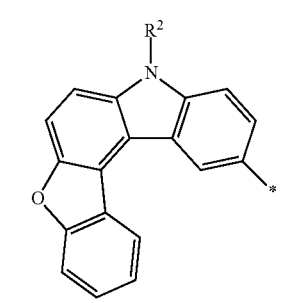
Formula (Ar-8-2-3a)
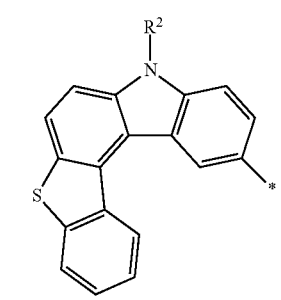
Formula (Ar-8-2-4a)
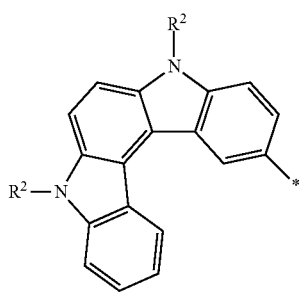
Formula (Ar-8-2-5a)
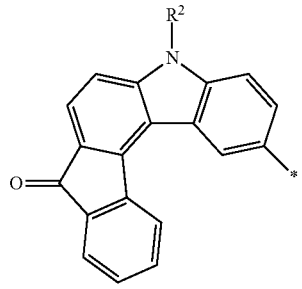
Formula (Ar-8-2-6a)
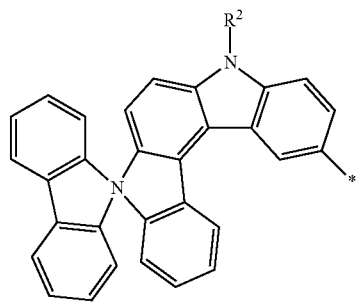
Formula (Ar-8-3-1a)
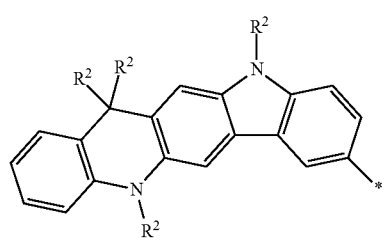
Formula (Ar-8-3-2a)
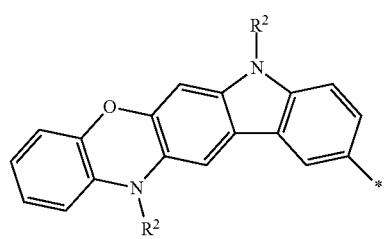
Formula (Ar-8-3-3a)
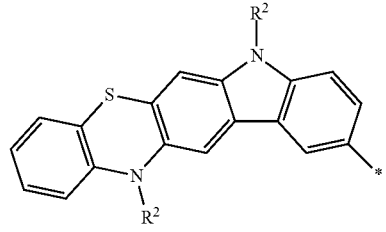
Formula (Ar-8-3-4a)
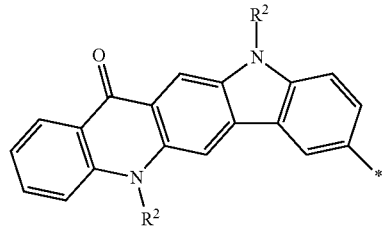
Formula (Ar-8-4-1a)
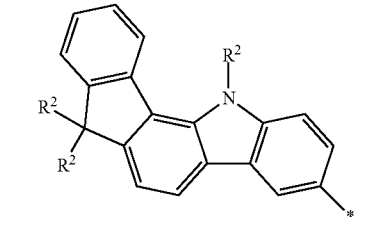

Formula (Ar-8-4-2a)
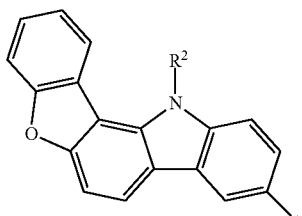
Formula (Ar-8-4-3a)
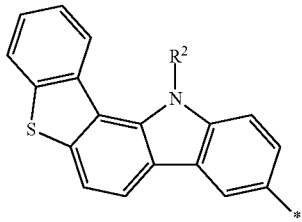
Formula (Ar-8-4-4a)
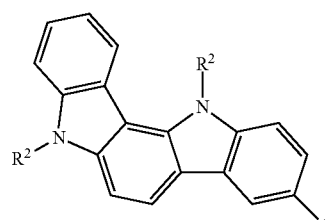
Formula (Ar-8-4-5a)
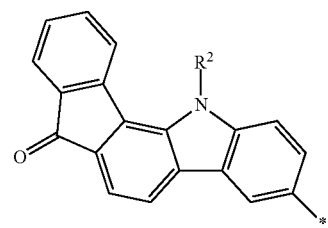
Formula (Ar-8-4-6a)
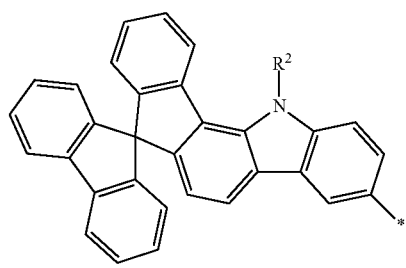
Formula (Ar-8-5-1a)
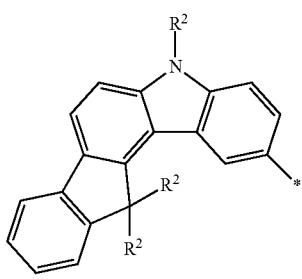
Formula (Ar-8-5-2a)
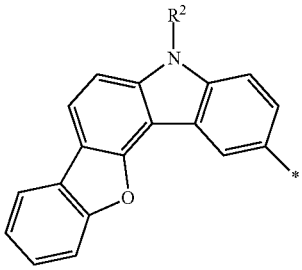
Formula (Ar-8-5-3a)
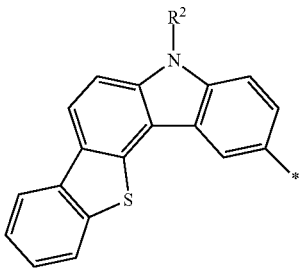
Formula (Ar-8-5-4a)
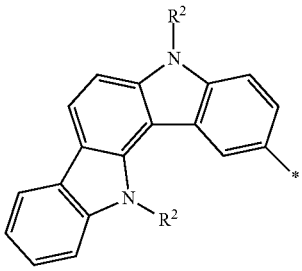
Formula (Ar-8-5-5a)
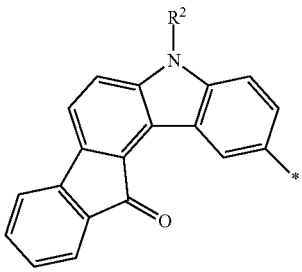
Formula (Ar-8-5-6a)
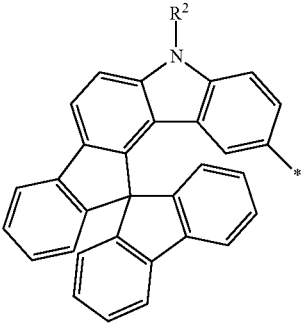

Formula (Ar-8-6-1a)
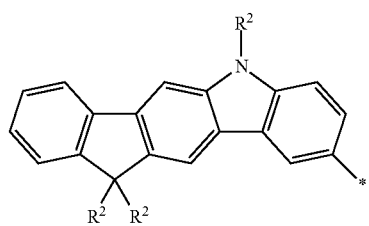

Formula (Ar-8-6-2a)
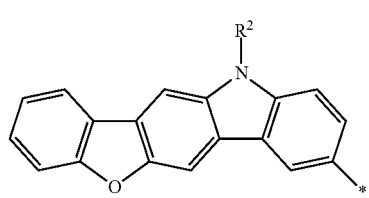

Formula (Ar-8-6-3a)
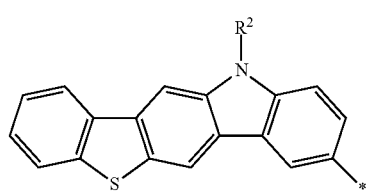

Formula (Ar-8-6-4a)
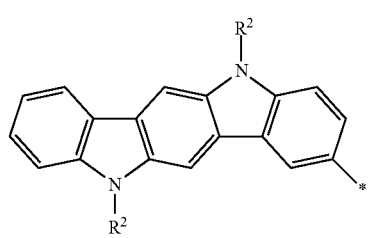

Formula (Ar-8-6-5a)
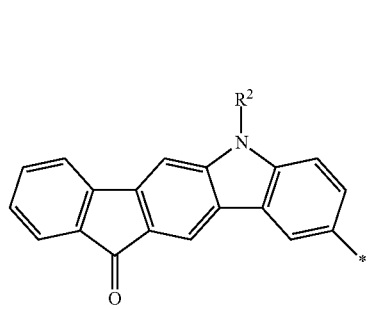

Formula (Ar-8-6-6a)
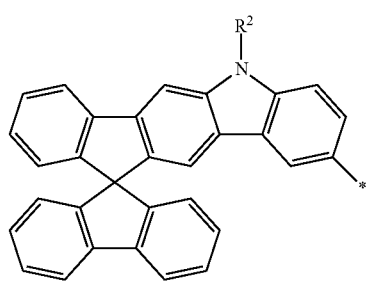

Formula (Ar-8-7-1a)
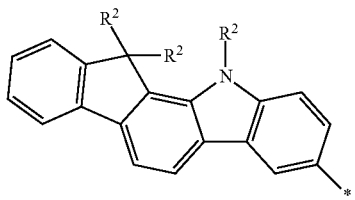

Formula (Ar-8-7-2a)
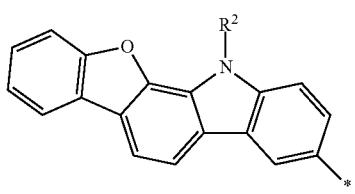

Formula (Ar-8-7-3a)
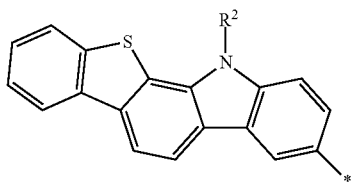

Formula (Ar-8-7-4a)
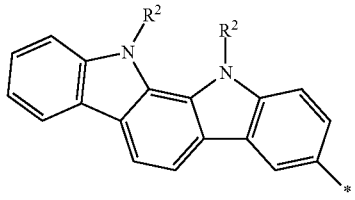

Formula (Ar-8-7-5a)
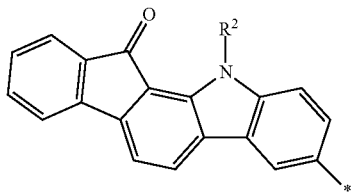

Formula (Ar-8-7-6a)
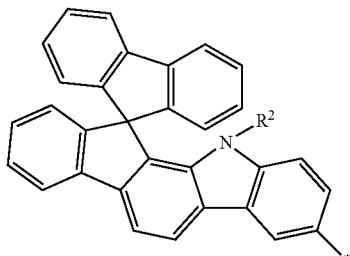

where the symbols correspond to the symbols in formula (Ar-8), The formulae may be substituted by $R^2$ at the free positions.

When one or more $Ar^2$ groups are present, they are preferably a bivalent aromatic or heteroaromatic ring system having 6 to 24 aromatic ring atoms. Preferred $Ar^2$ groups are the same or different and are selected from the group consisting of ortho-, meta- or para-benzene, ortho-, meta- or para-biphenyl, terphenyl, especially ortho-, meta- or para-terphenyl, quaterphenyl, especially ortho-, meta- or para-quaterphenyl, fluorene, 9,9'-spirobifluorene, furan, benzofuran, dibenzofuran, dibenzothiophene, pyrrole, indole or carbazole. These groups may be substituted by one or more $R^2$ radicals, but are preferably unsubstituted.

In a further embodiment of the invention, the $Ar^2$ group is the same or different at each instance and is selected from the formulae (Ar2-1) to (Ar2-13):

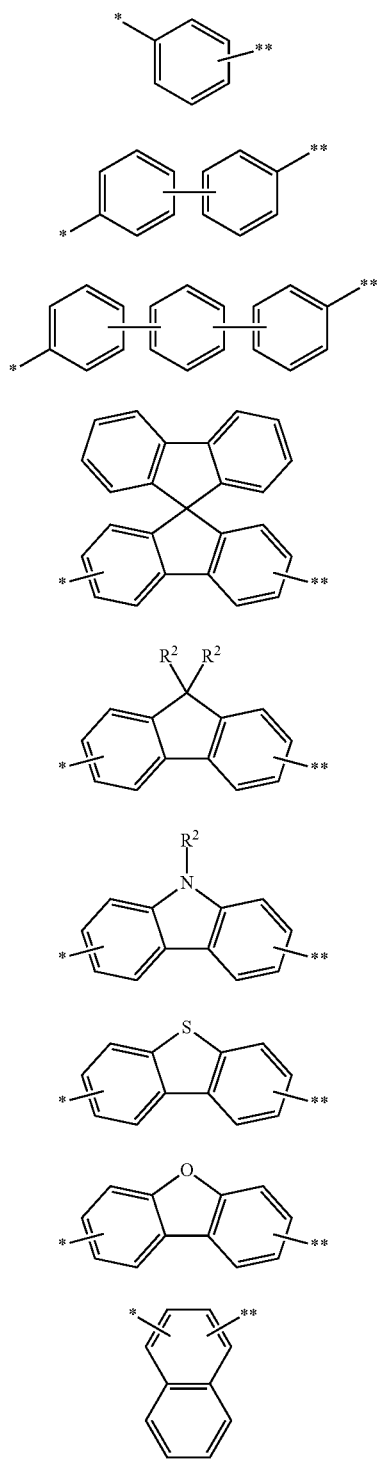

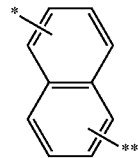

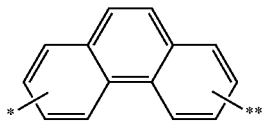

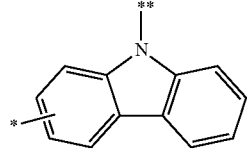

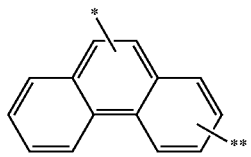

where the symbols used for formula (1) have the definitions given and the bonds identified by * and ** represent the two bonds of the bivalent aromatic or heteroaromatic ring system to the adjacent groups. The bond is preferably a C—C, C—N or N—C bond. The groups may be substituted by $R^2$ at the free positions. They are preferably unsubstituted.

In a further embodiment of the invention, the $Ar^1$ groups are the same or different at each instance and are selected from the formulae (Ar-1) to (Ar-15) or preferred embodiments thereof, and the $Ar^2$ groups, if present, are the same or different and are selected from the formulae (Ar2-1) to (Ar2-13).

In a preferred embodiment of the invention, $R^2$ is the same or different at each instance and is selected from the group consisting of H, D, F, $Si(R^3)_3$, CN, a straight-chain alkyl or alkoxy group having 1 to 10 carbon atoms or a branched or cyclic alkyl or alkoxy group having 3 to 10 carbon atoms, each of which may be substituted by one or more $R^3$ radicals, where one or more nonadjacent $CH_2$ groups may be replaced by O and where one or more hydrogen atoms may be replaced by D or F, an aromatic or heteroaromatic ring system which has 6 to 60 aromatic ring atoms and may be substituted in each case by one or more $R^3$ radicals, where two or more adjacent $R^2$ substituents may optionally form a mono- or polycyclic aliphatic ring system which may be substituted by one or more $R^3$ radicals.

In a particularly preferred embodiment of the invention, $R^2$ is the same or different at each instance and is selected from the group consisting of H, D, F, a straight-chain alkyl group having 1 to 10 carbon atoms or a branched or cyclic alkyl group having 3 to 10 carbon atoms, each of which may be substituted by one or more $R^3$ radicals, an aromatic or heteroaromatic ring system which has 6 to 60 carbon atoms and may be substituted in each case by one or more $R^3$ radicals, where two or more adjacent $R^2$ substituents may optionally form a mono- or polycyclic aliphatic ring system which may be substituted by one or more $R^3$ radicals.

In a further preferred embodiment, $R^2$ which binds to a carbon bridge in an aromatic or heteroaromatic ring system, as, for example, in the formulae (Ar-5-1), (Ar-5-2), (Ar-5-3), (Ar-5-4), (Ar-6-1), (Ar-6-2), (Ar-6-3), (Ar-6-4), (Ar-8-3-1), (Ar-11-1), (Ar-18-1) or (Ar2-2), is the same or different at each instance and is selected from the group consisting of a straight-chain alkyl group having 1 to 10 carbon atoms, a branched or cyclic alkyl group having 3 to 10 carbon atoms or an aromatic ring system having 6 to 30 carbon atoms which is as defined above and which may be substituted by one or more $R^3$ radicals. In this case, the two $R^2$ groups may also form a ring system with one another, which may be aliphatic or, in addition to the definition of $R^2$ given above, may also be aromatic. Ring formation forms a spiro system.

In a further preferred embodiment, $R^2$ which binds to a nitrogen atom is selected from the group consisting of a straight-chain alkyl group having 1 to 10 carbon atoms, a branched or cyclic alkyl group having 3 to 10 carbon atoms or an aromatic ring system having 6 to 30 carbon atoms, especially an aromatic ring system having 6 to 24 carbon atoms which is as defined above and which may be substituted by one or more $R^3$ radicals.

In a further preferred embodiment, $R^2$, when it is an aromatic or heteroaromatic ring system, is selected from the formulae (Ar-1) to (Ar-15) or $N(Ar)_2$.

The abovementioned embodiments may be combined with one another as desired. More particularly, it is preferable to combine the preferred embodiments detailed above with one another.

Examples of preferred compounds of the above-detailed embodiments or compounds as usable with preference in organic electronic devices are the following compounds:

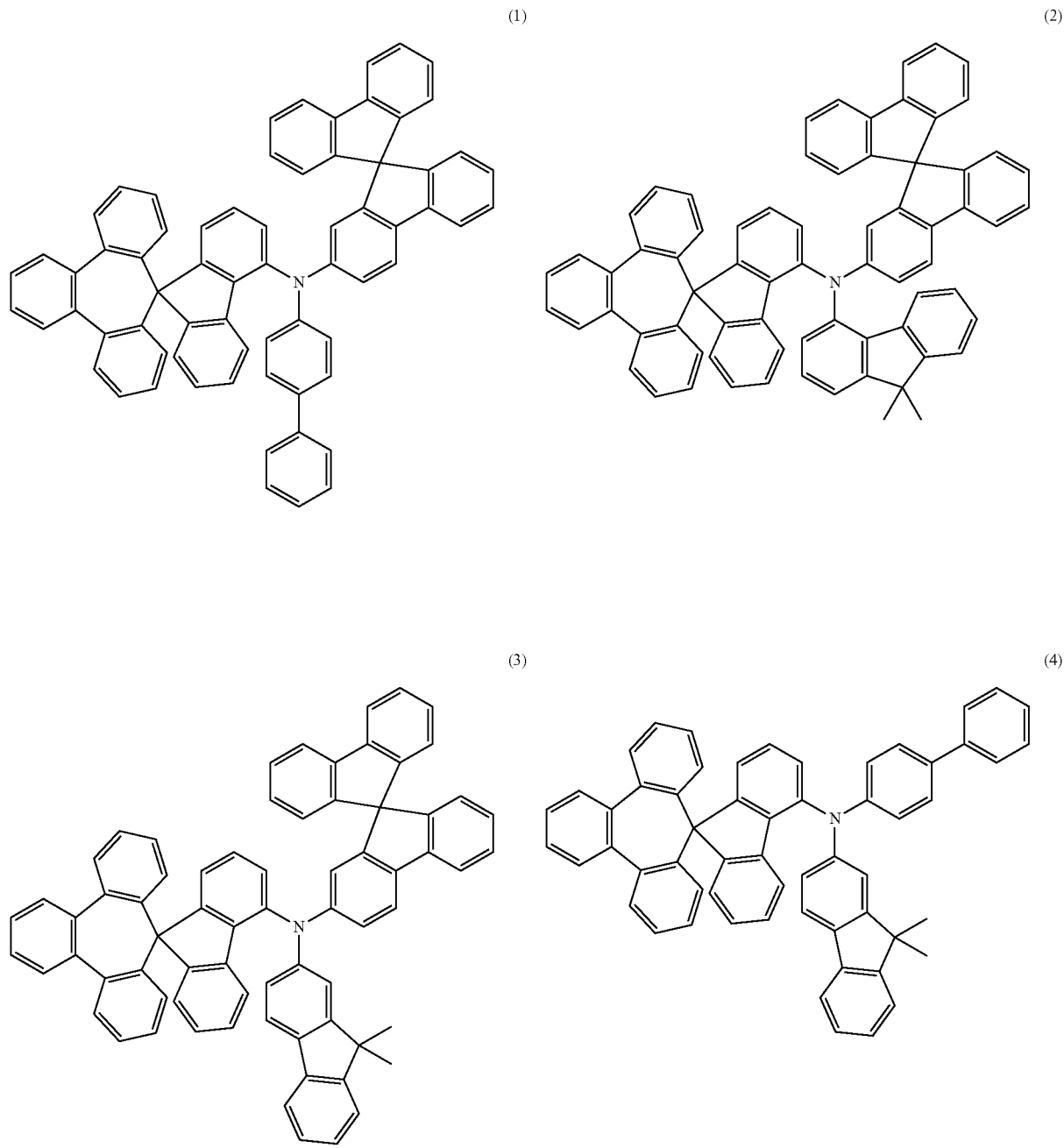

-continued
(5)
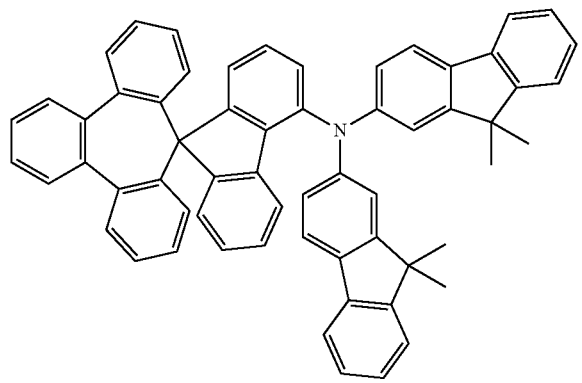
(6)
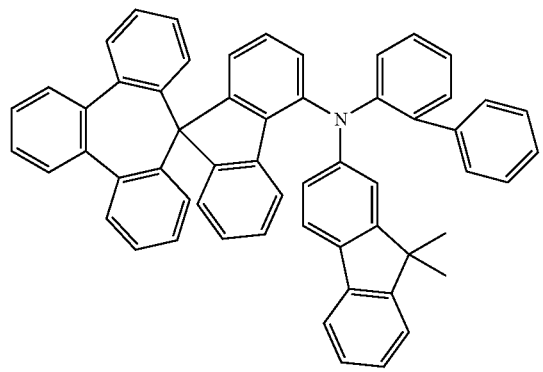
(7)
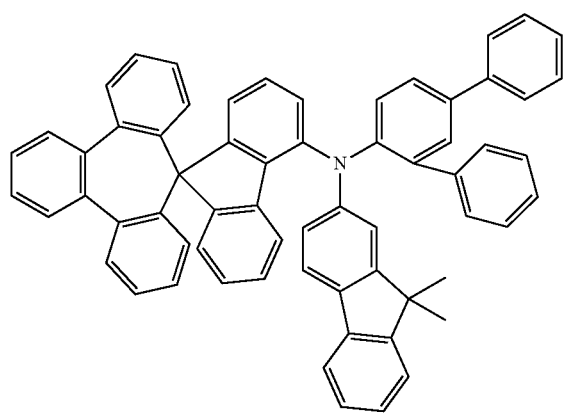
(8)
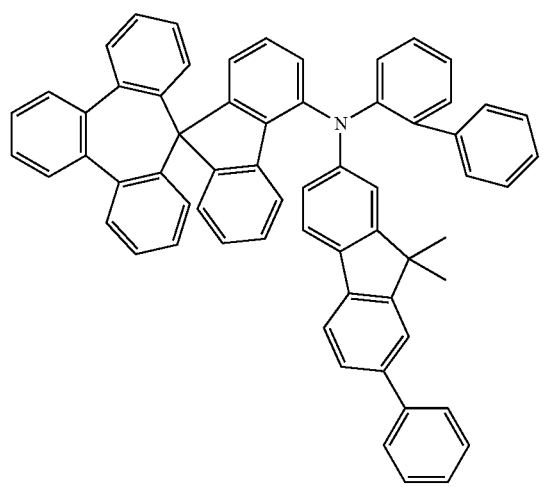
(9)
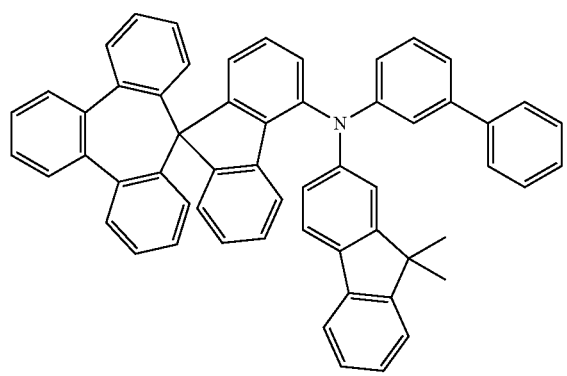
(10)
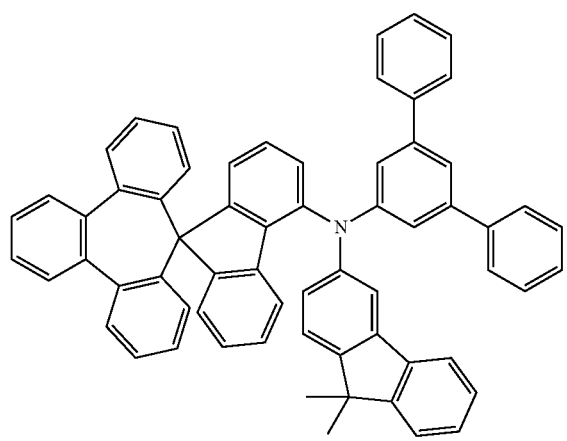

-continued
(11)
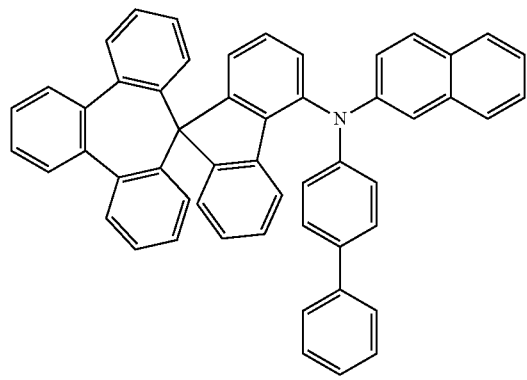
(12)
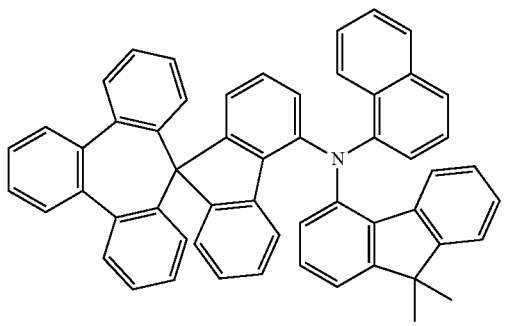
(13)
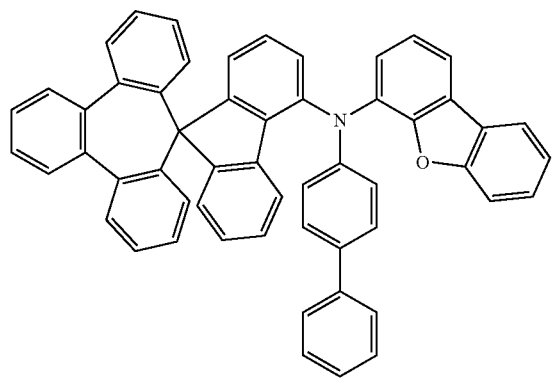
(14)
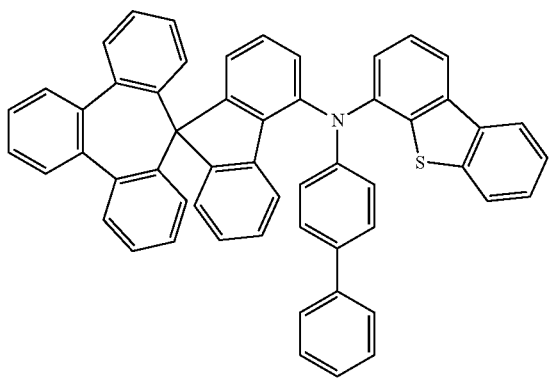
(15)
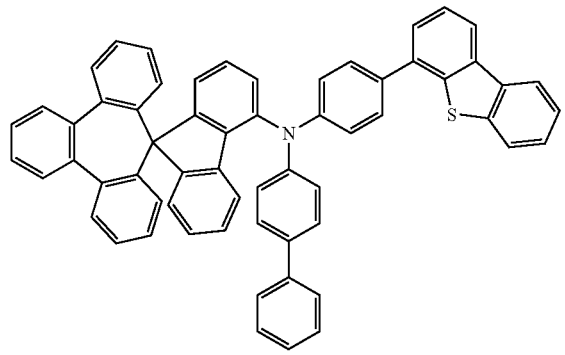
(16)
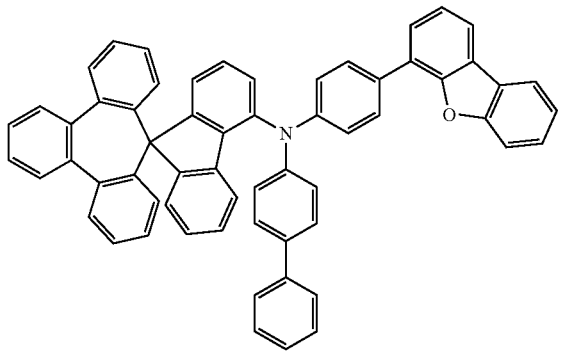
(17)
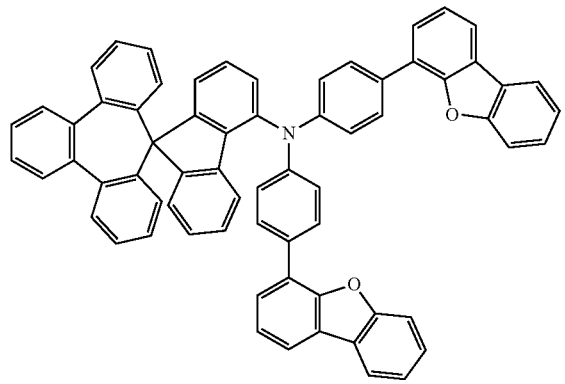
(18)
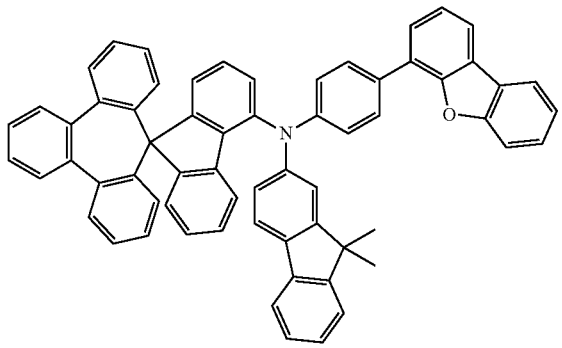

(19) 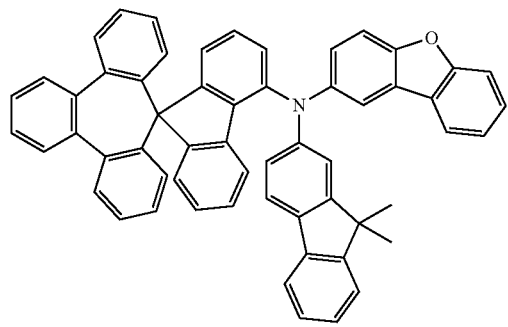
(20) 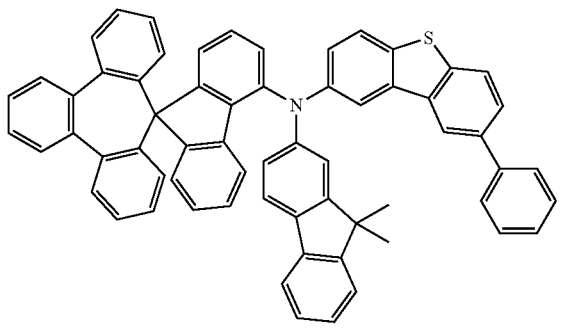
(21) 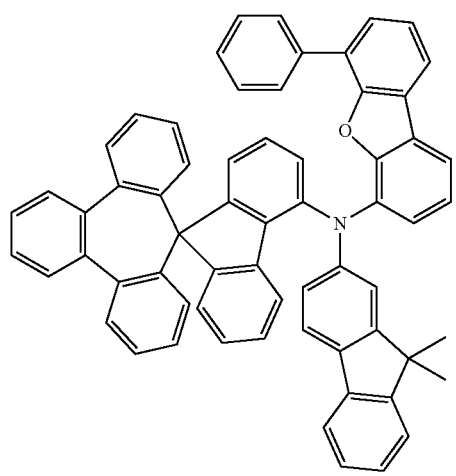
(22) 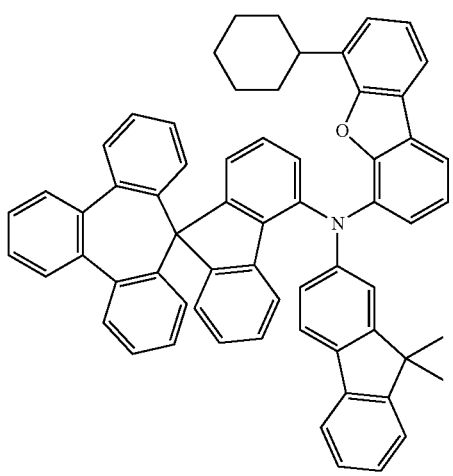
(23) 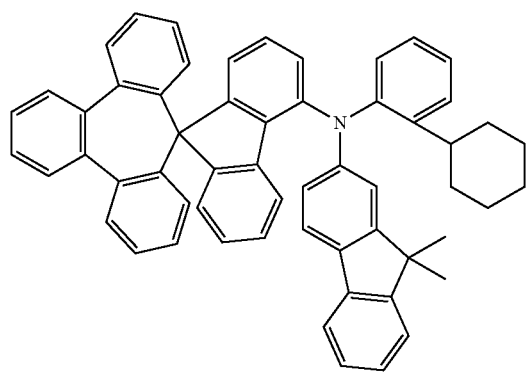
(24) 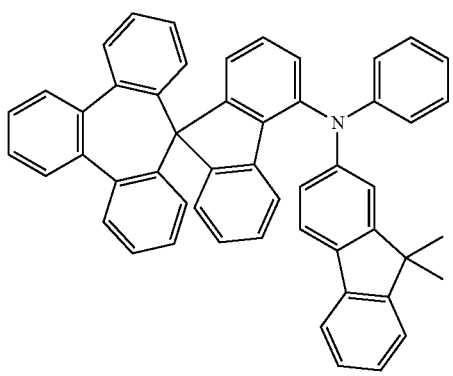

-continued
(25)
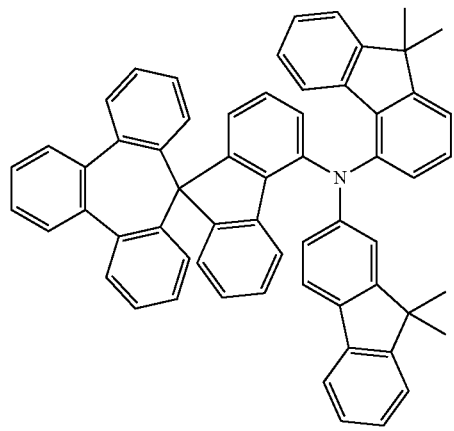
(26)
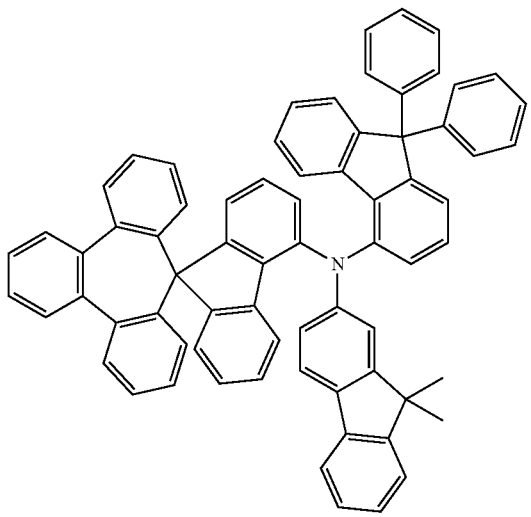
(27)
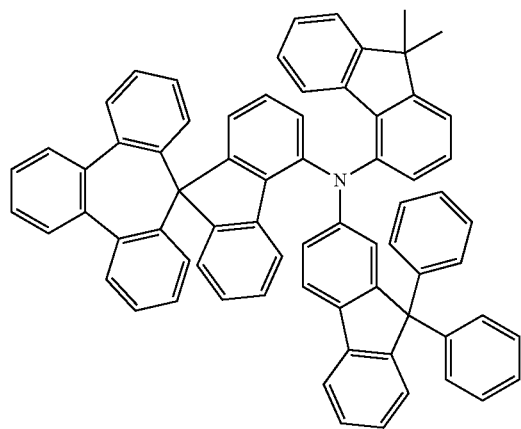
(28)
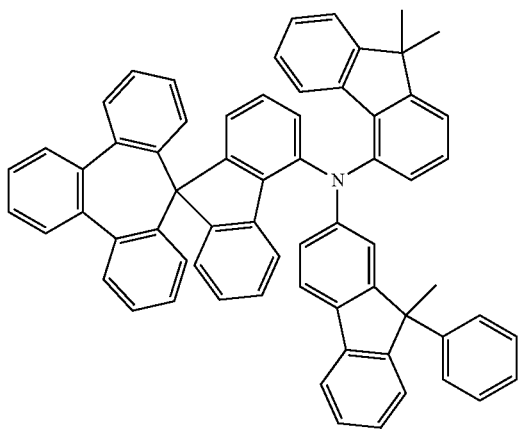
(29)
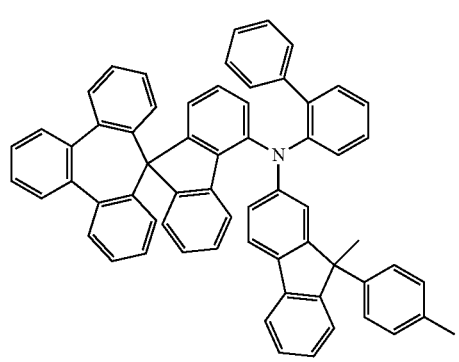
(30)
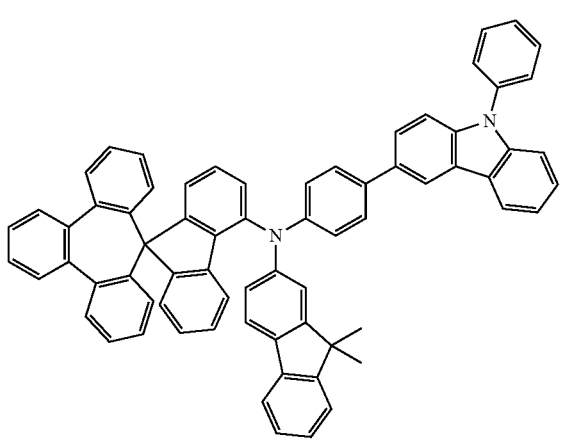

-continued
(31)
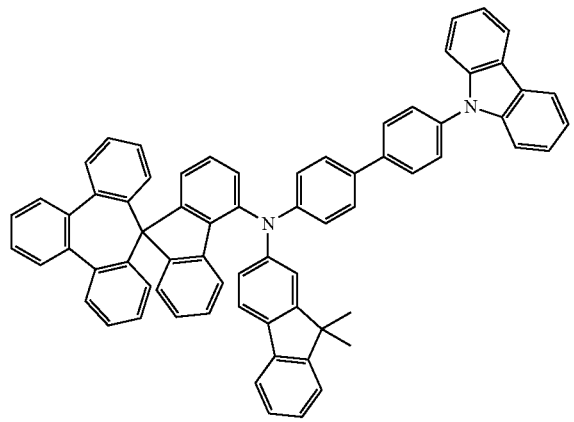
(32)
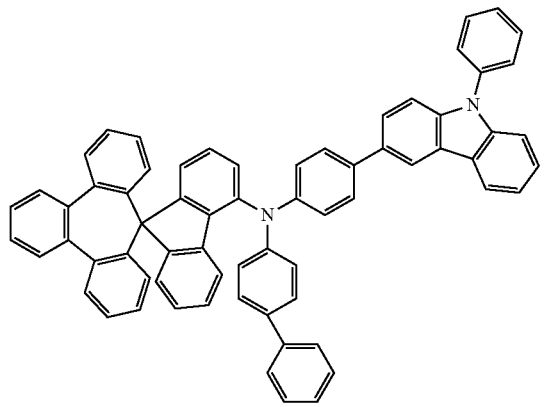
(33)
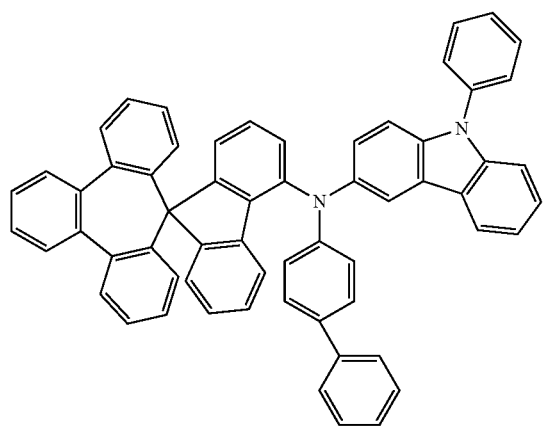
(34)
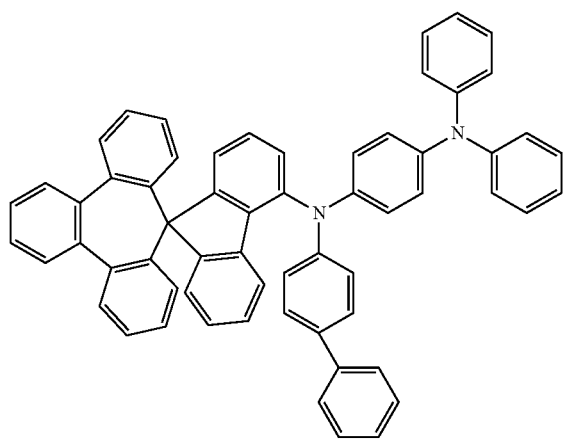
(35)
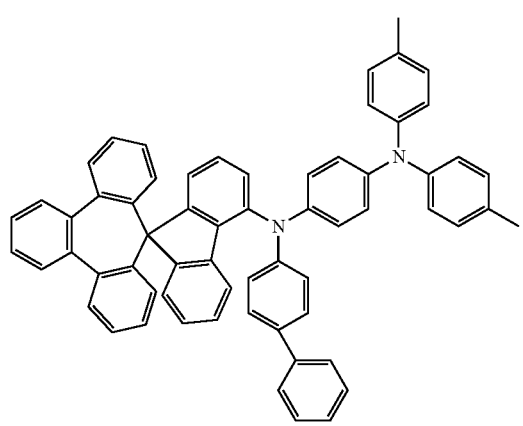
(36)
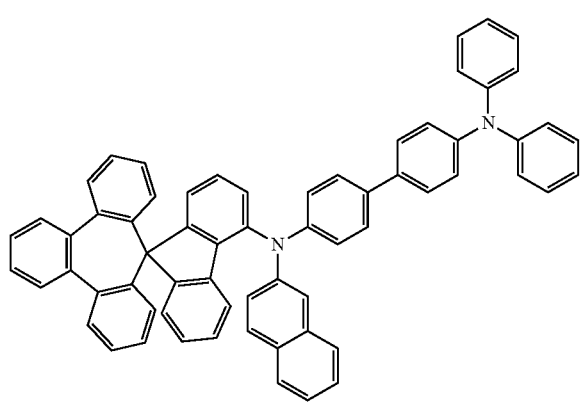
(37)
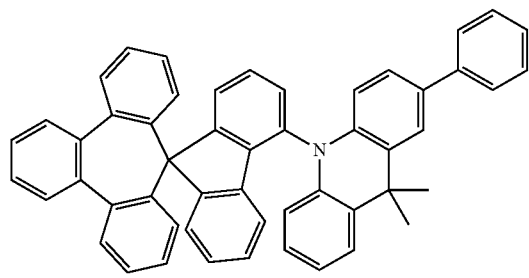
(38)
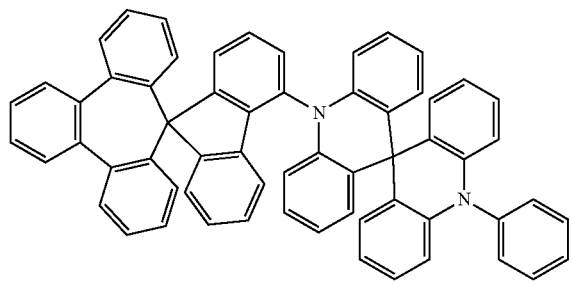

-continued
(39)
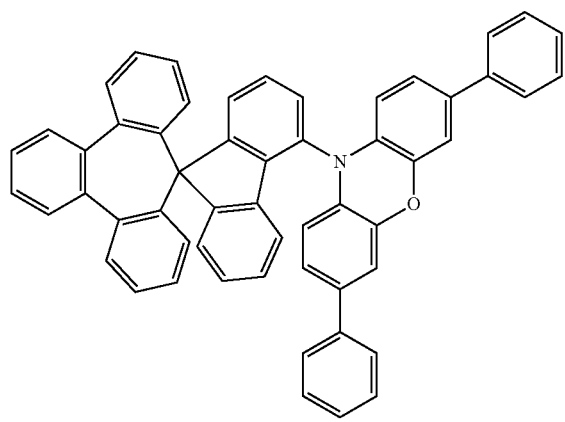
(40)
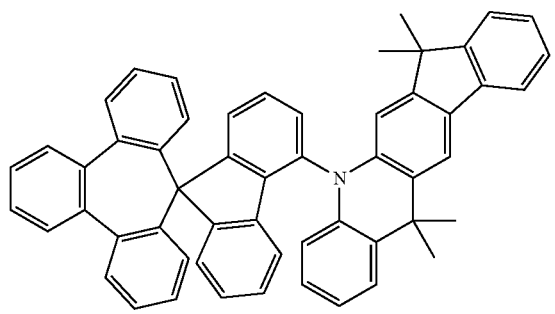
(41)
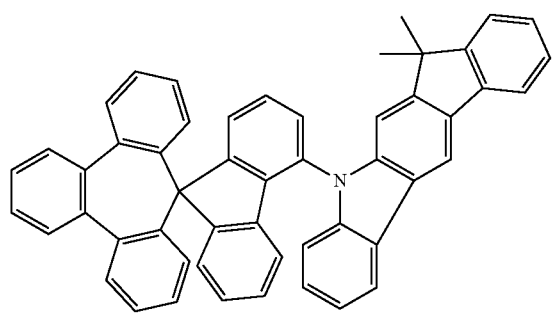
(42)
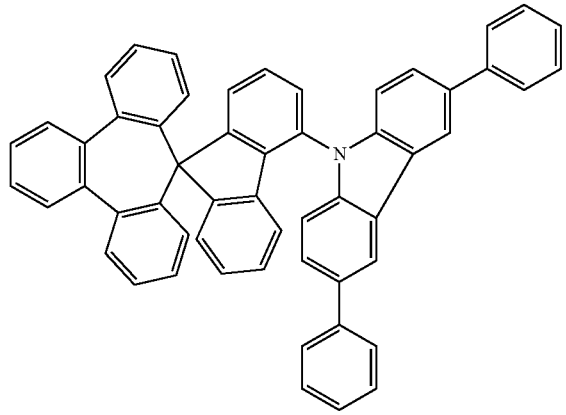
(43)
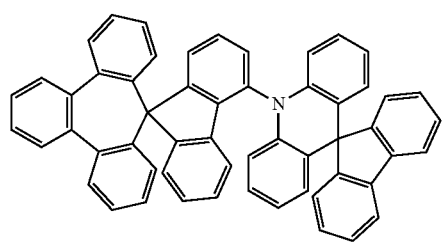
(44)
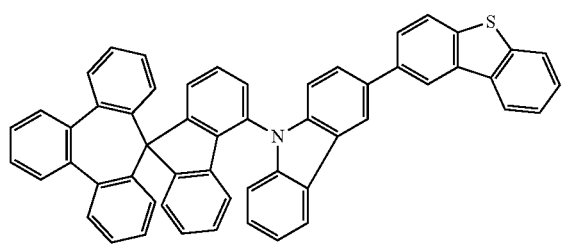
(45)
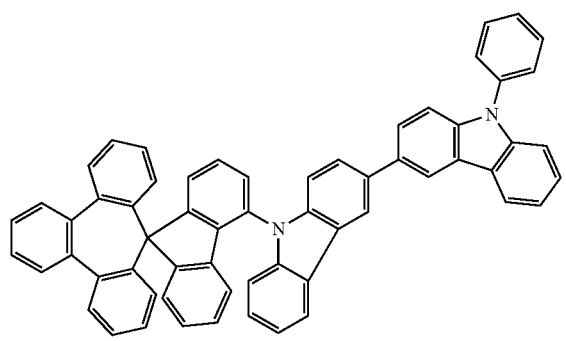
(46)
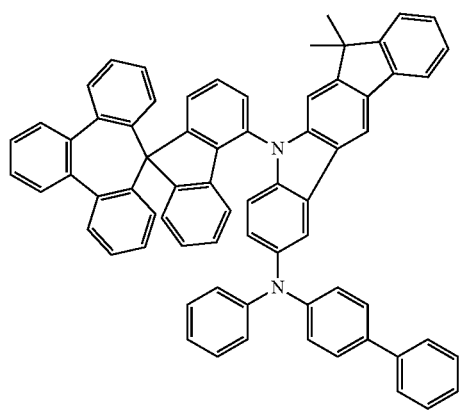

-continued
(47)
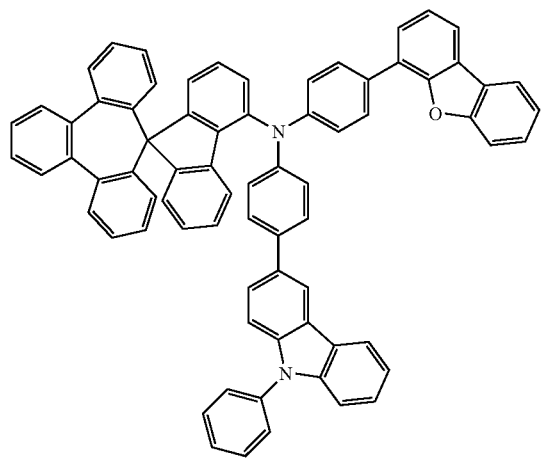
(48)
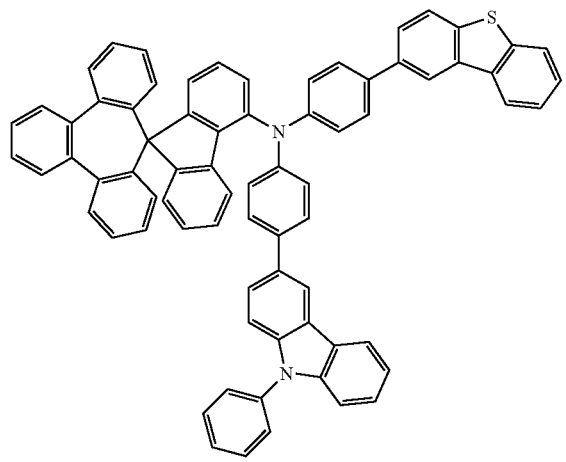
(49)
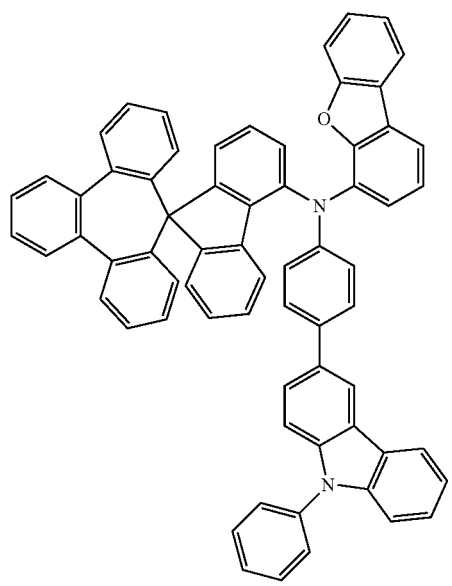
(50)
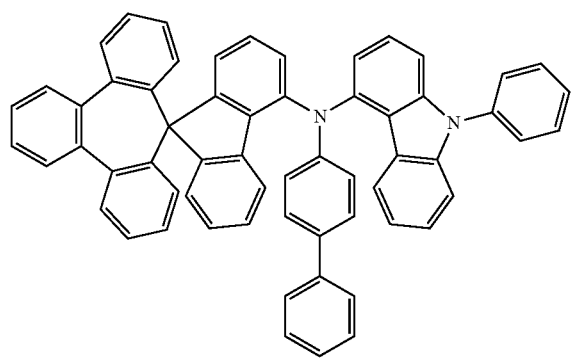
(51)
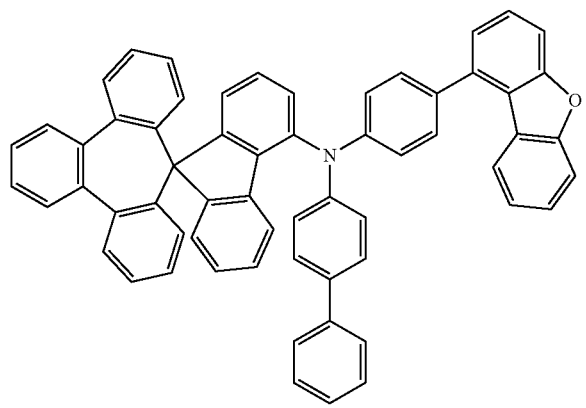
(52)
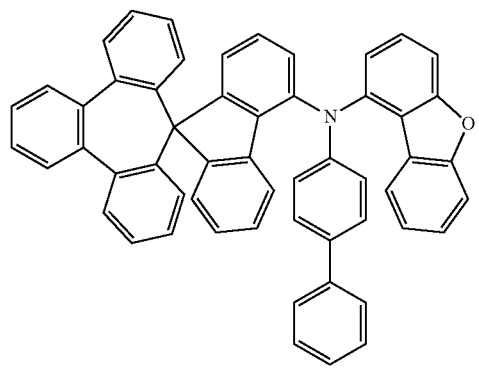

-continued
(53)
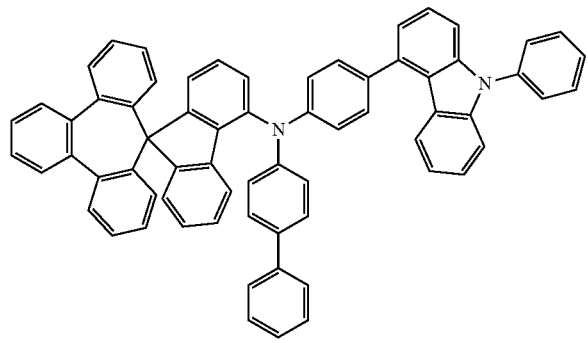
(54)
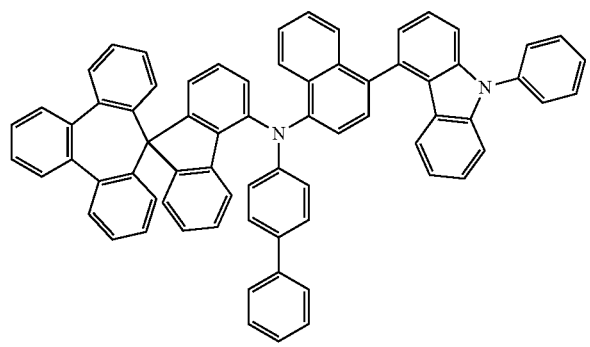
(55)
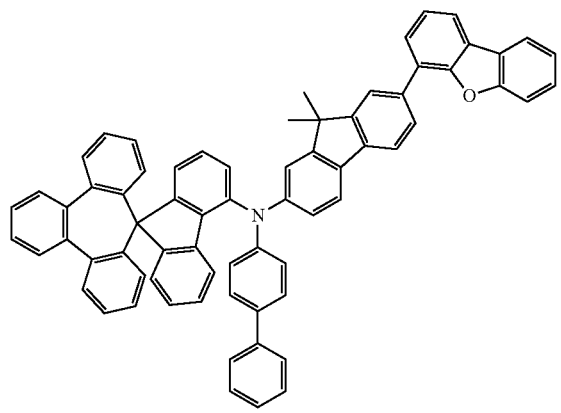
(56)
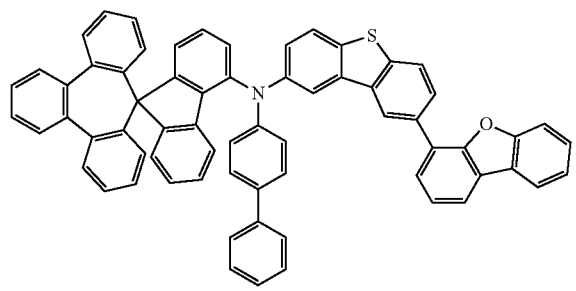
(57)
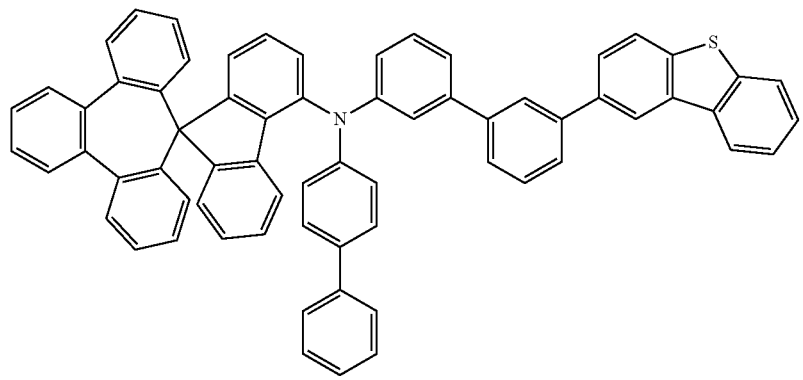
(58)
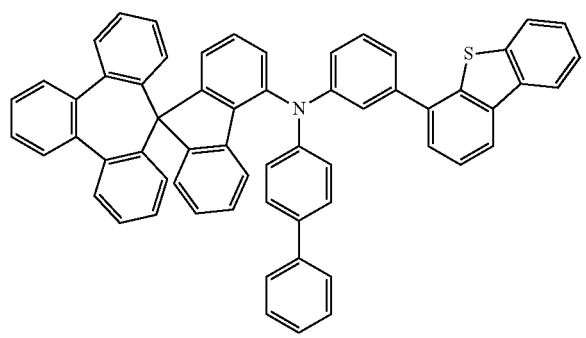
(59)
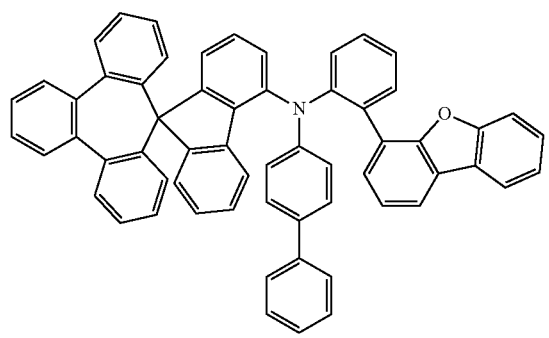

-continued
(60)
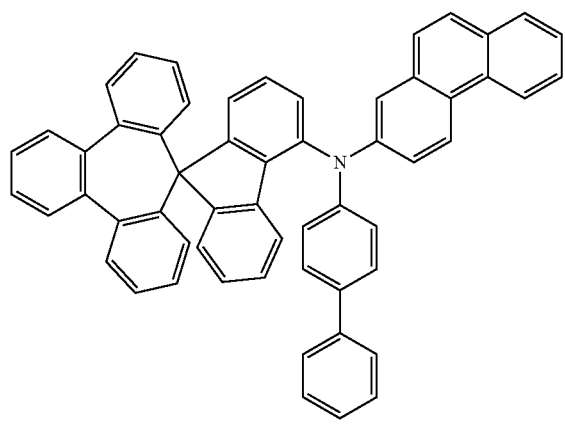
(61)
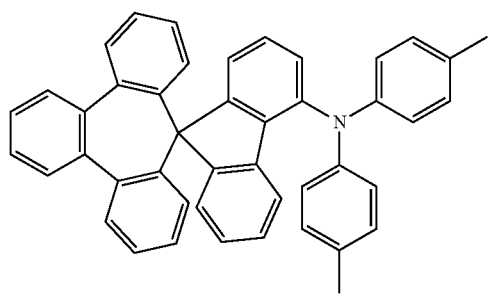
(62)
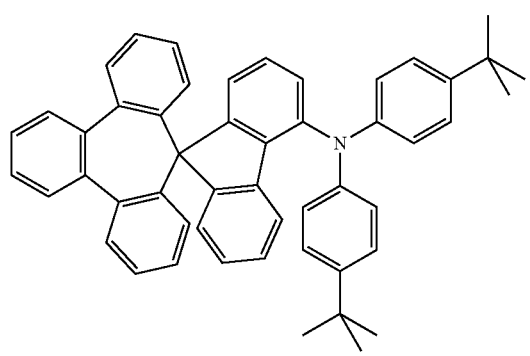
(63)
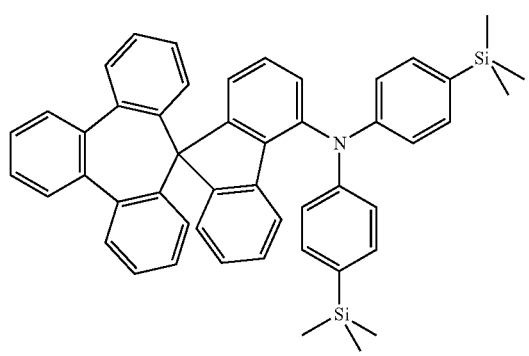
(64)
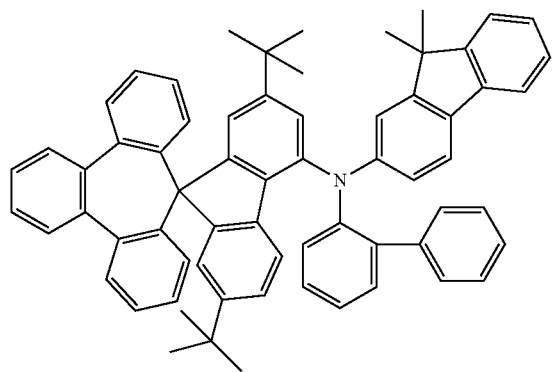
(65)
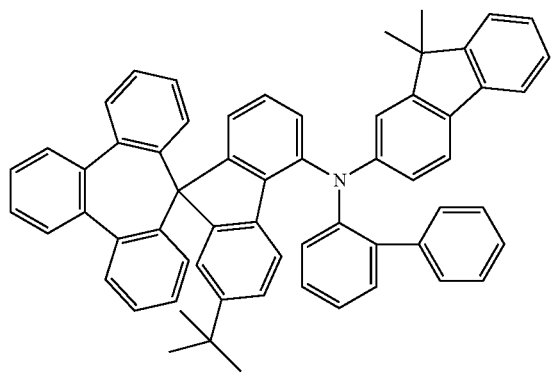

-continued
(66)
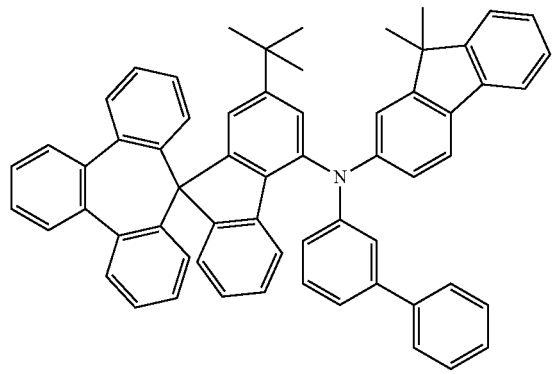
(67)
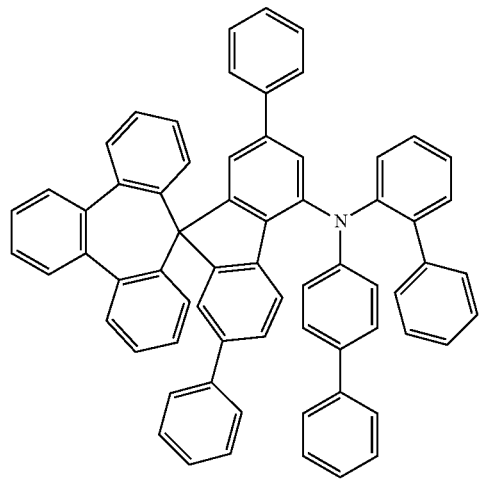
(68)
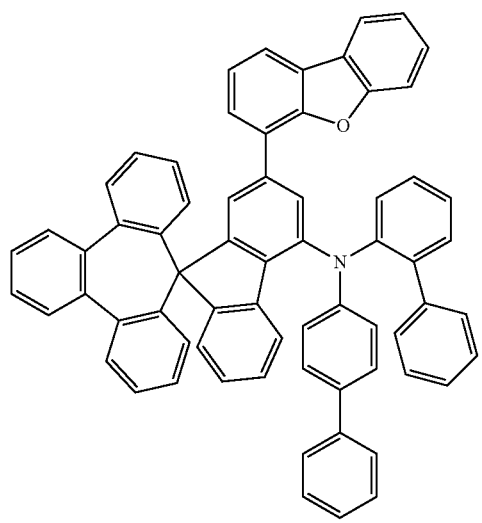
(69)
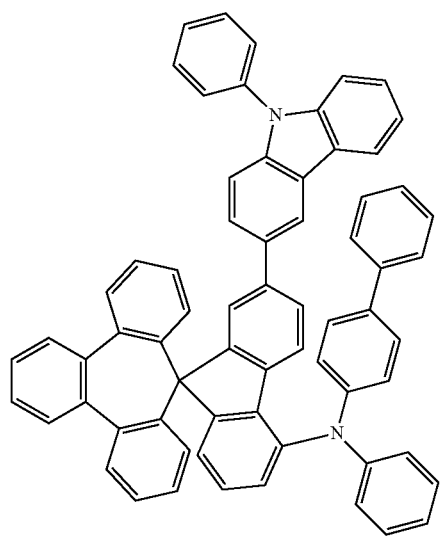
(70)
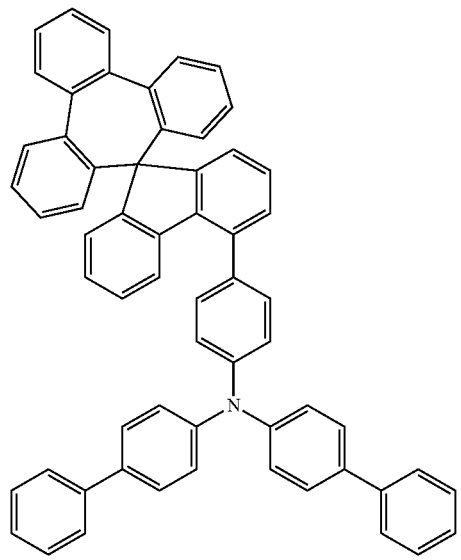
(71)
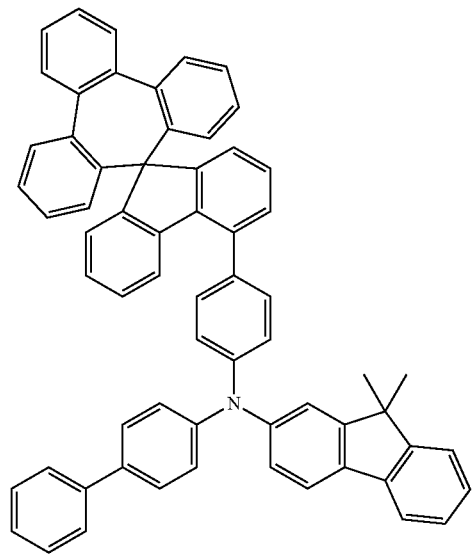

(72)
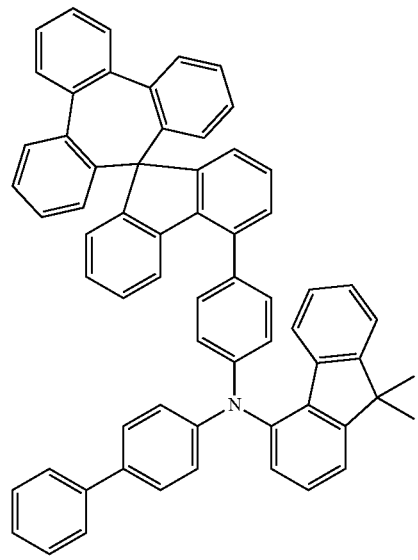
(73)
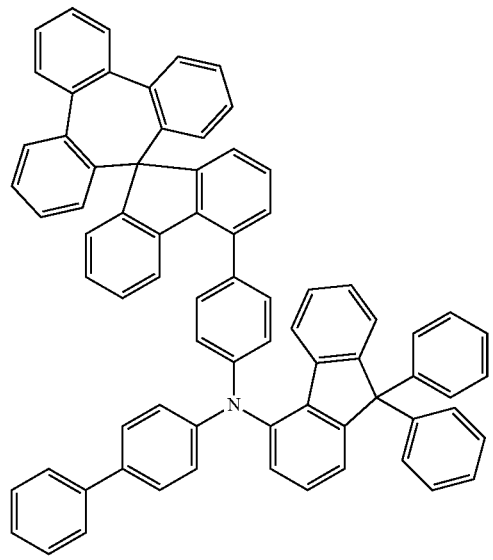
(74)
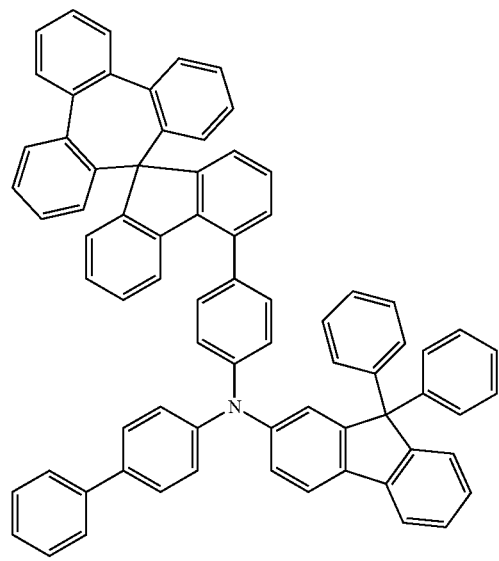
(75)
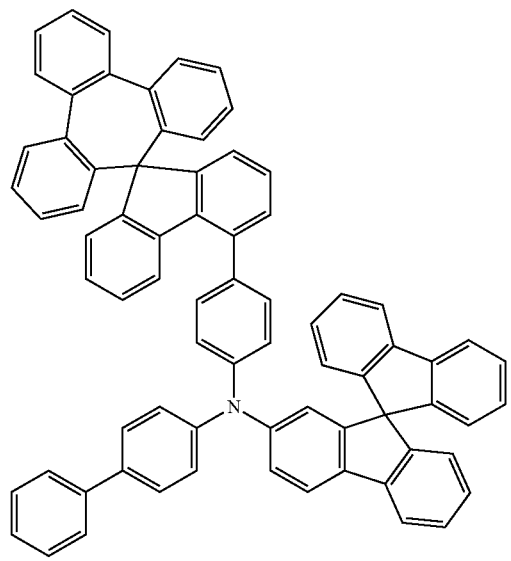

-continued
(76)
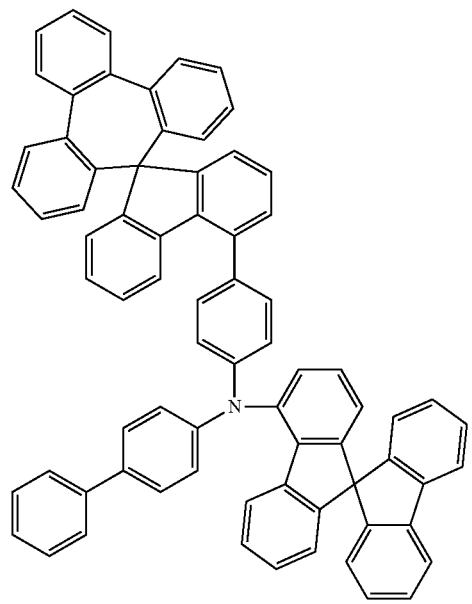
(77)
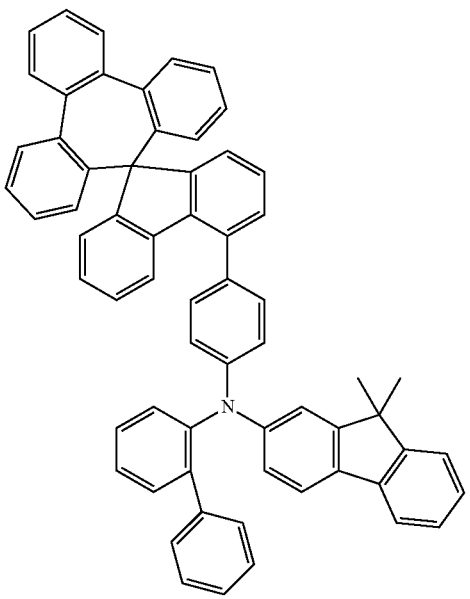
(78)
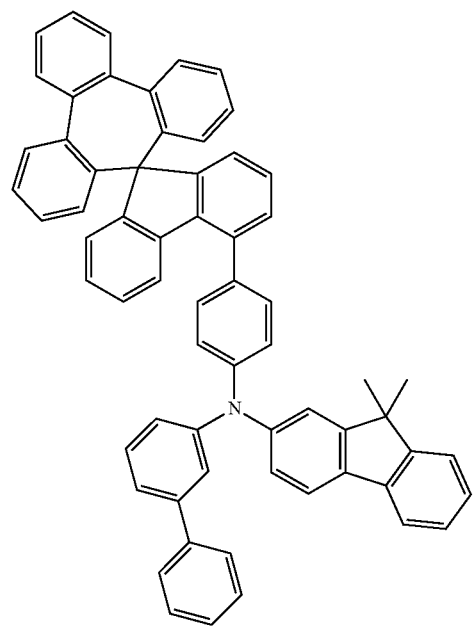
(79)
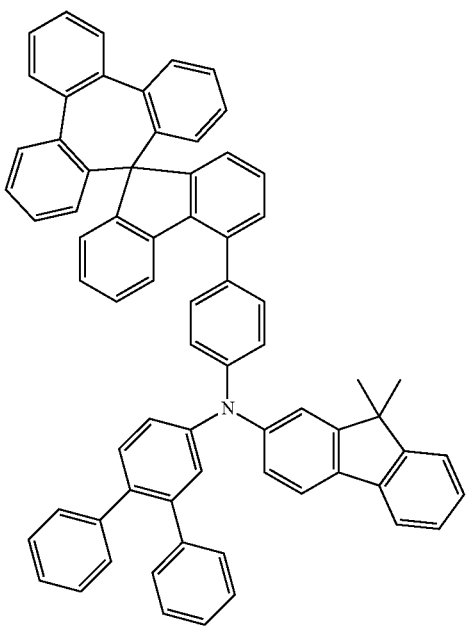

-continued
(80)
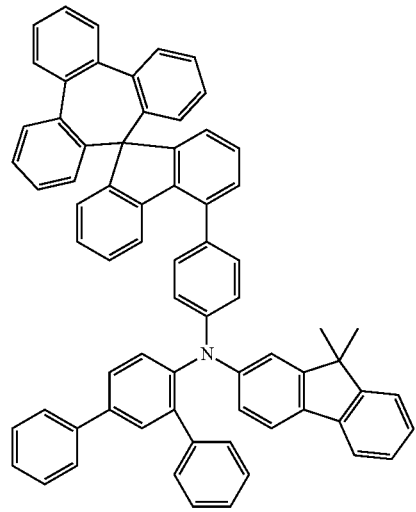
(81)
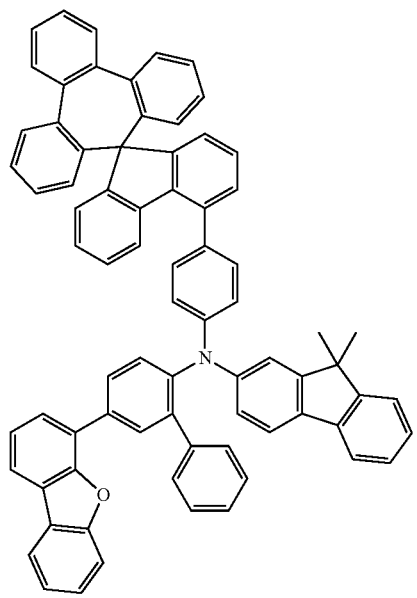
(82)
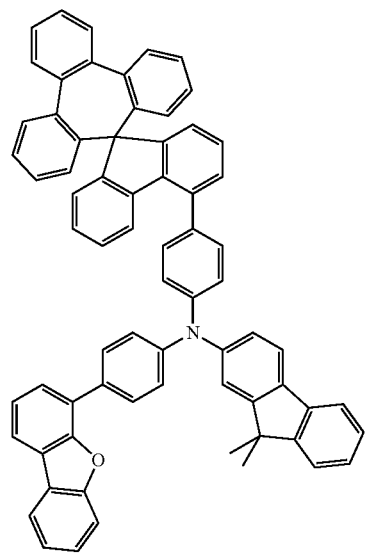
(83)
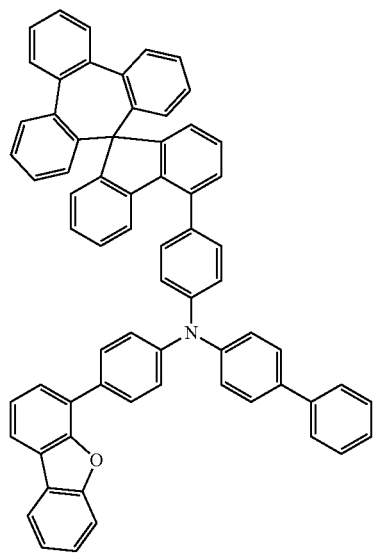

-continued
(84)
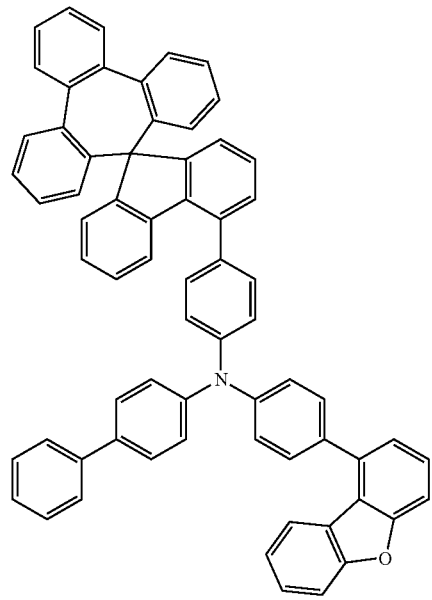
(85)
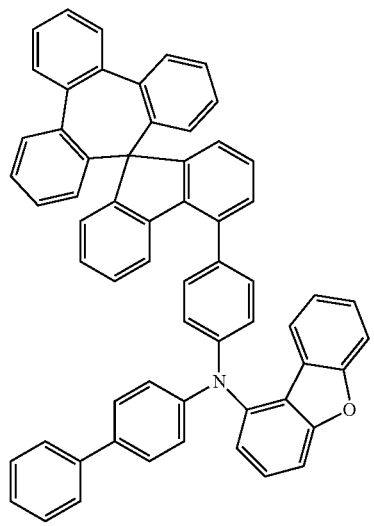
(86)
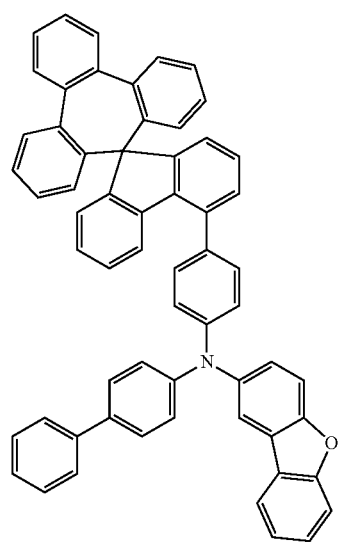
(87)
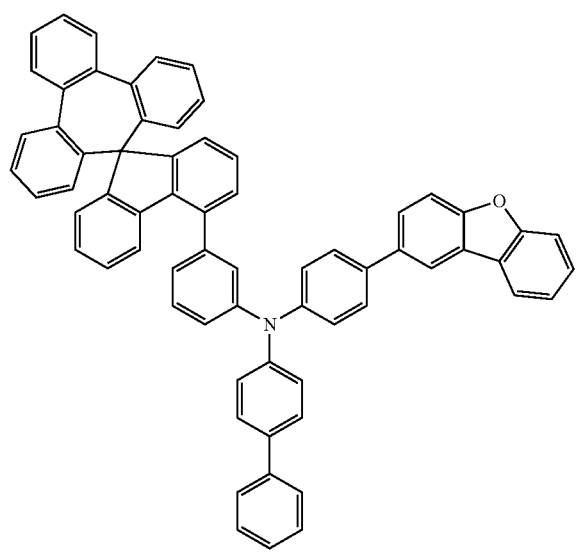

-continued
(88)
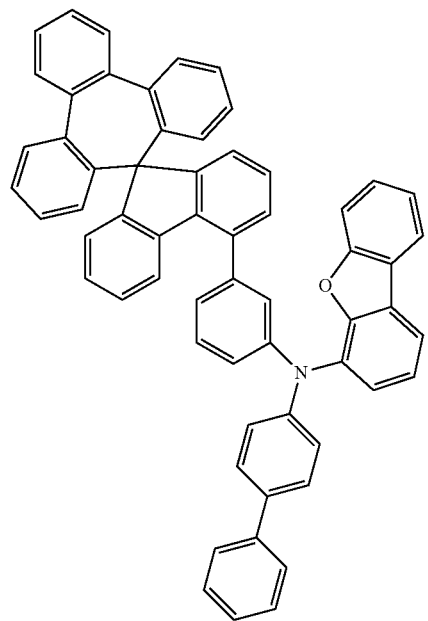
(89)
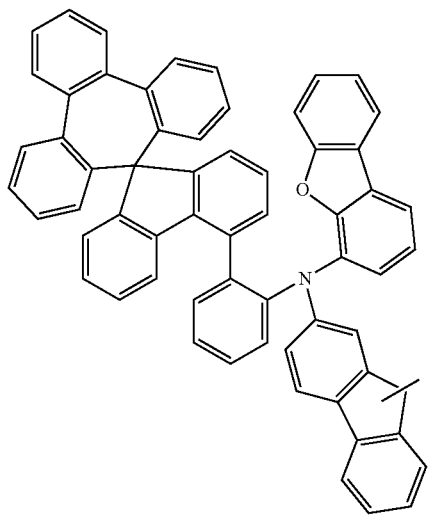
(90)
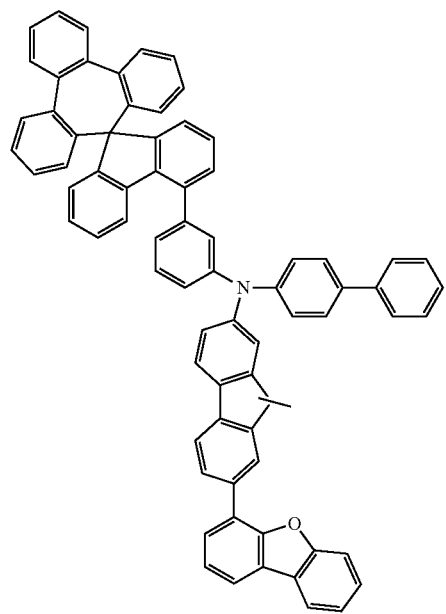
(91)
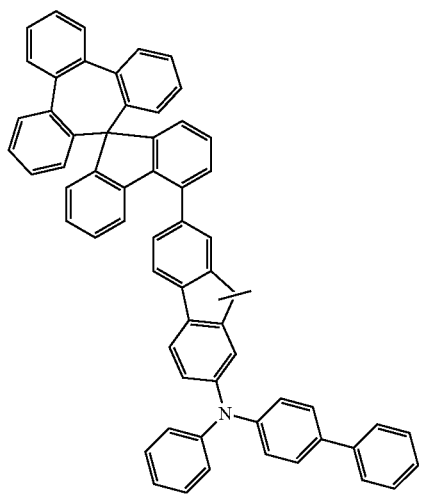

(92)
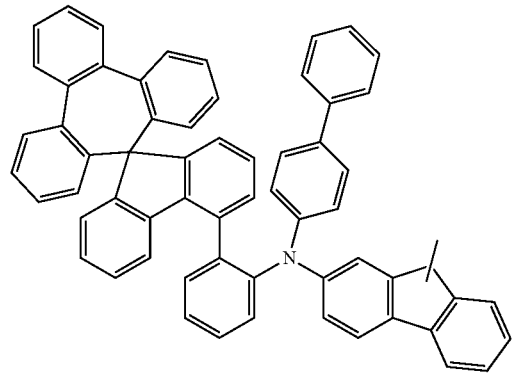
(93)
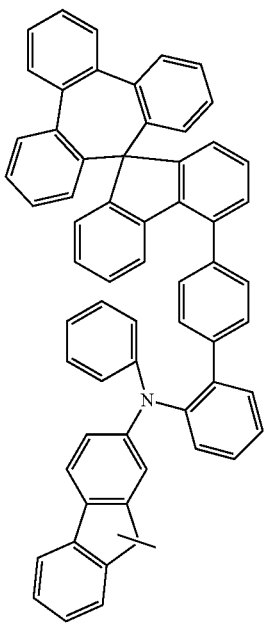
(94)
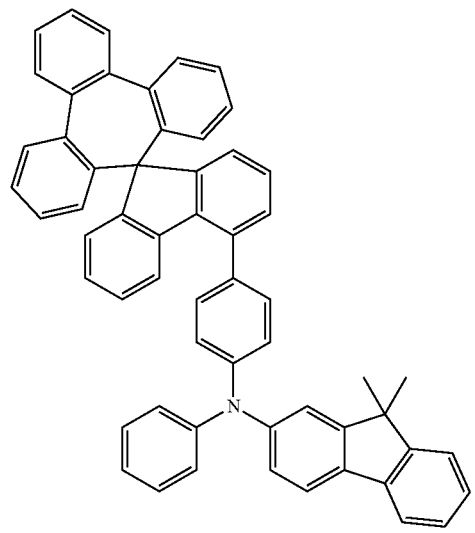
(95)
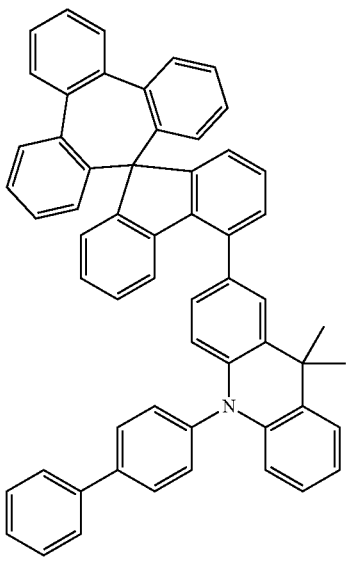

-continued
(96)
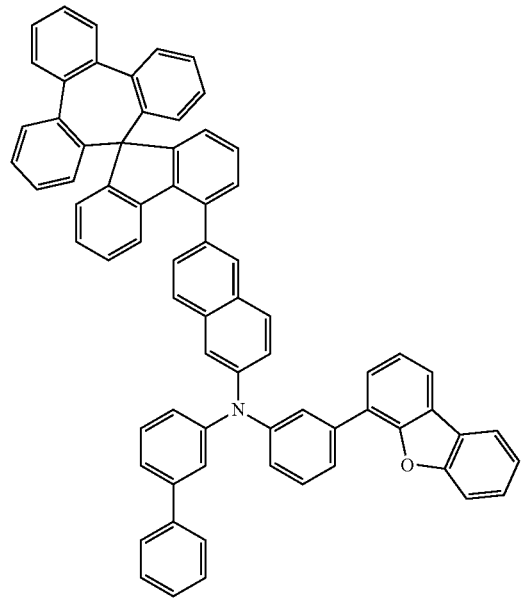
(97)
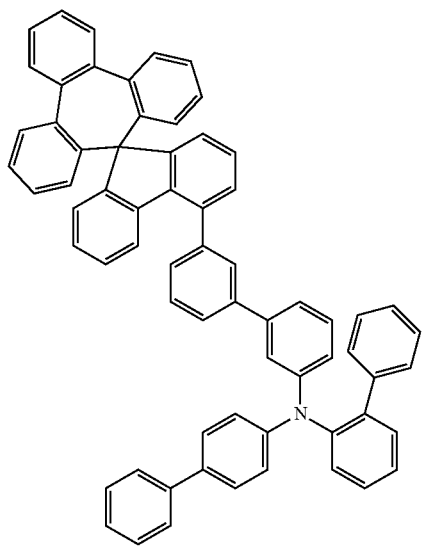
(98)
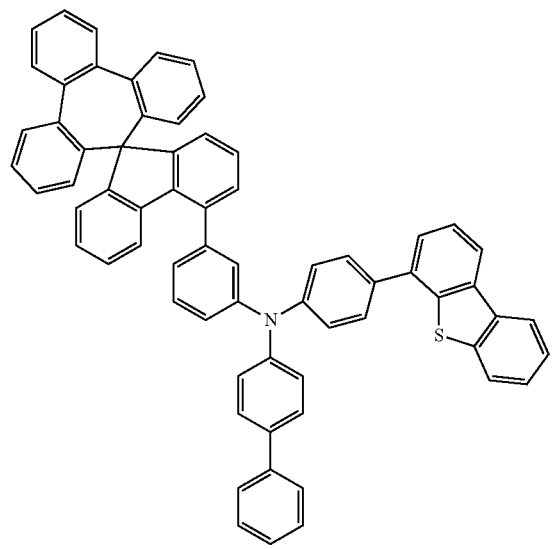
(99)
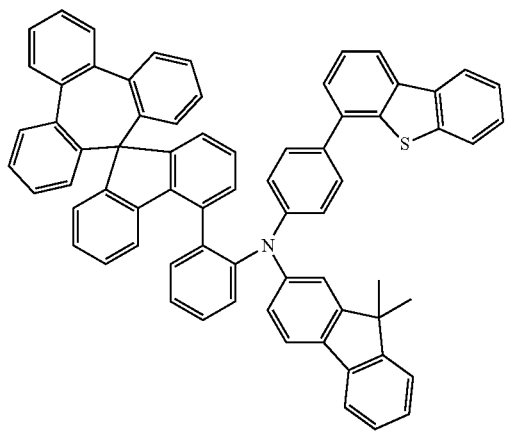

(100)
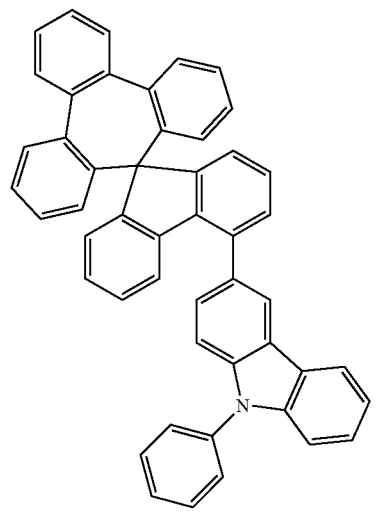
(101)
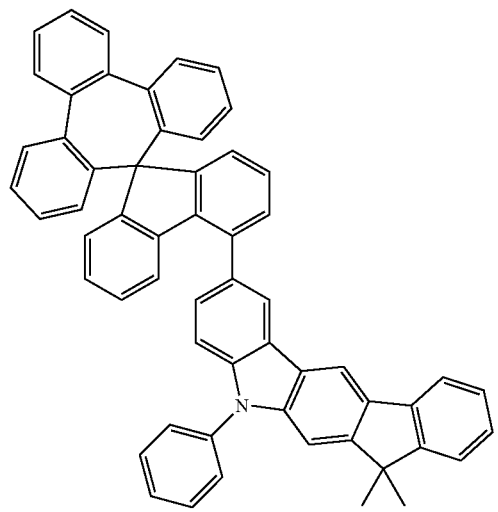
(102)
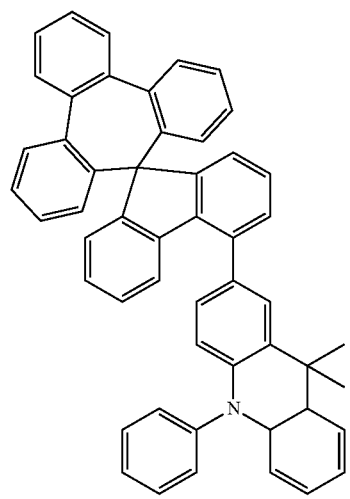
(103)
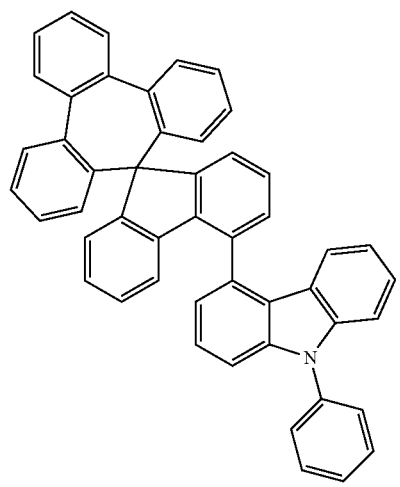
(104)
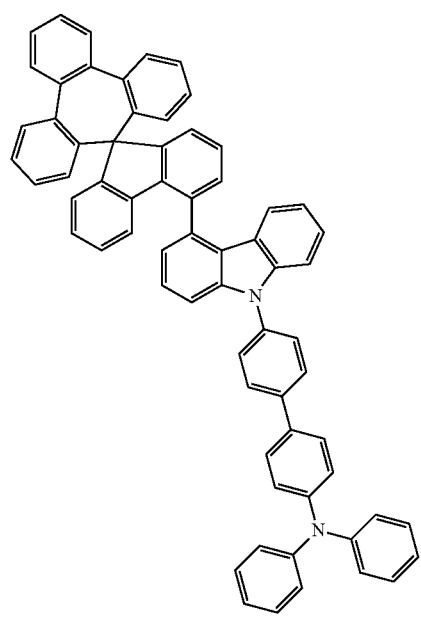
(105)
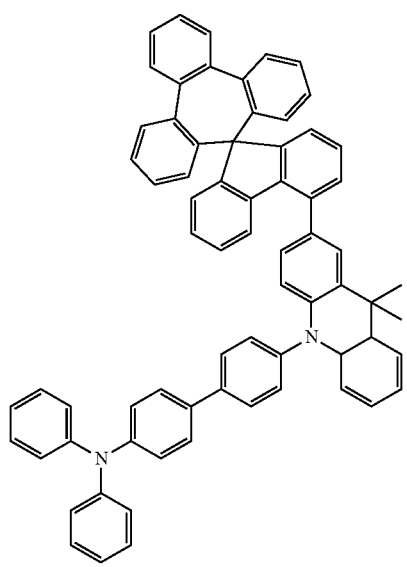

-continued
(106)
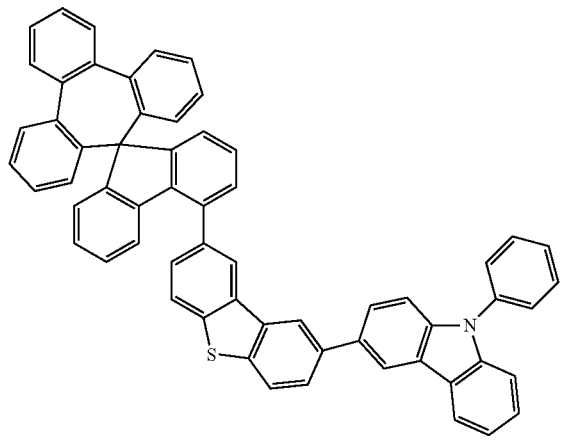
(107)
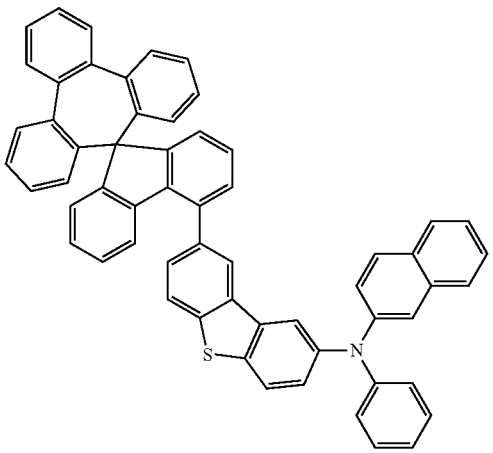
(108)
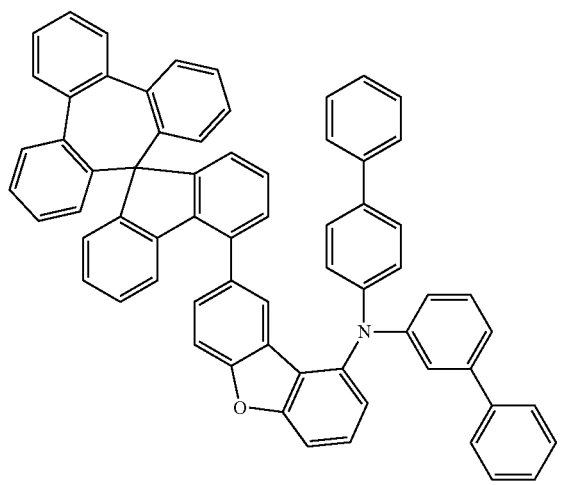
(109)
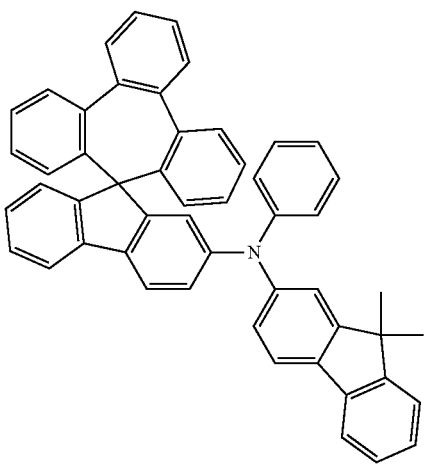
(110)
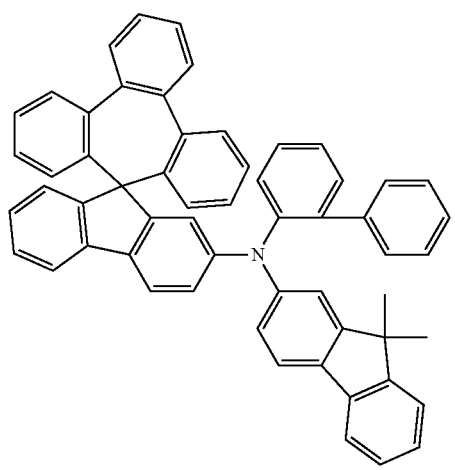
(111)
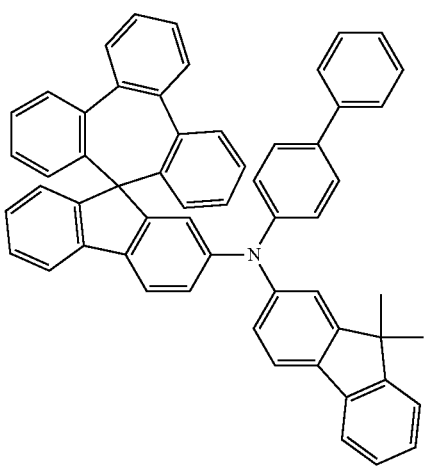

-continued
(112)
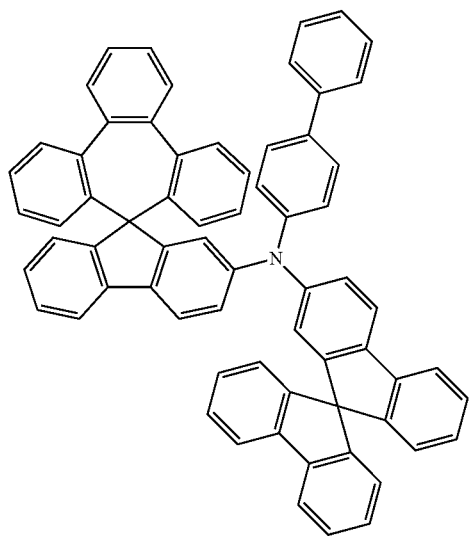
(113)
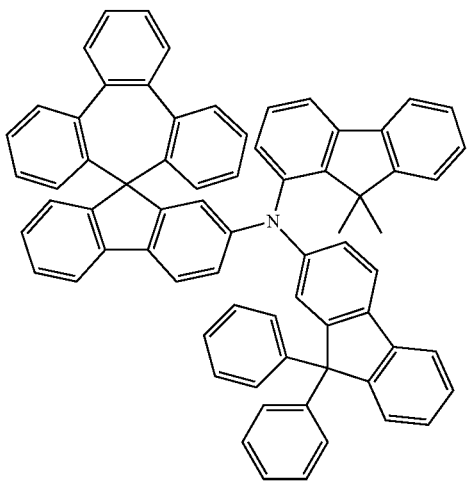
(114)
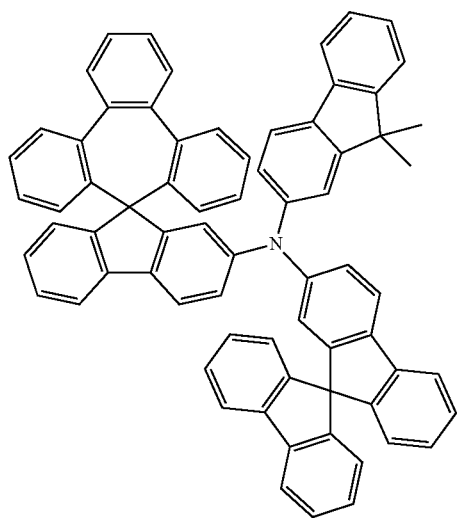
(115)
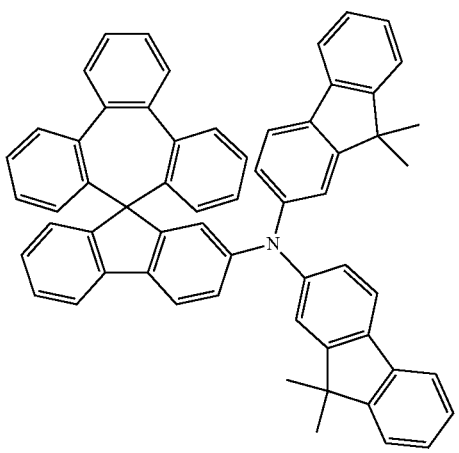
(116)
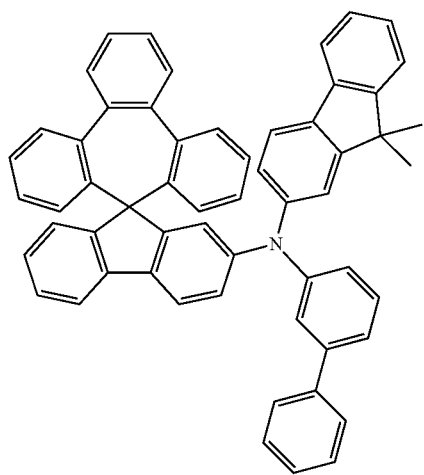
(117)
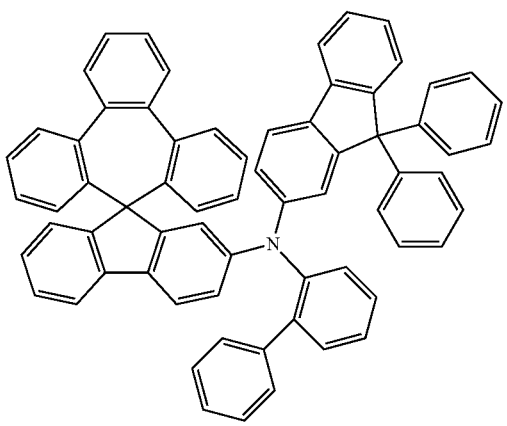

-continued
(118)
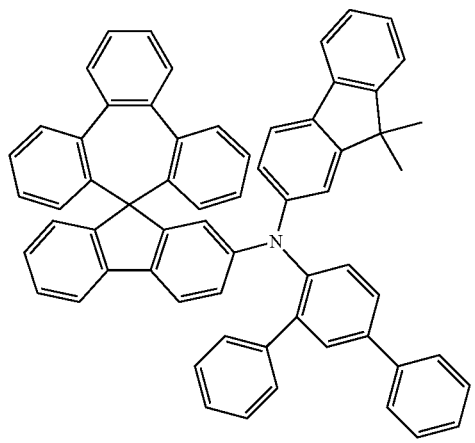
(119)
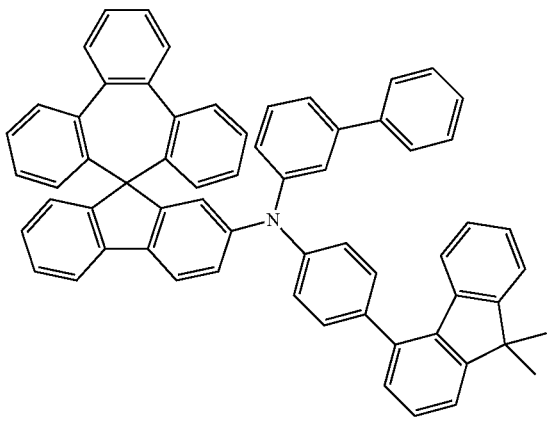
(120)
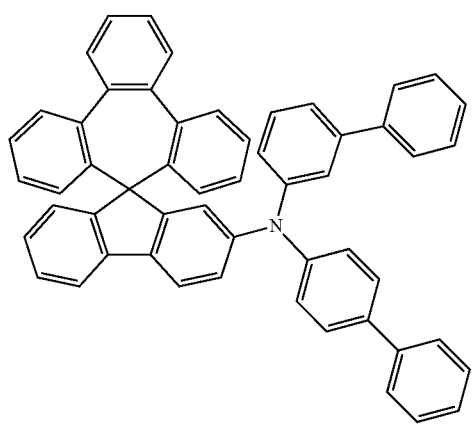
(121)
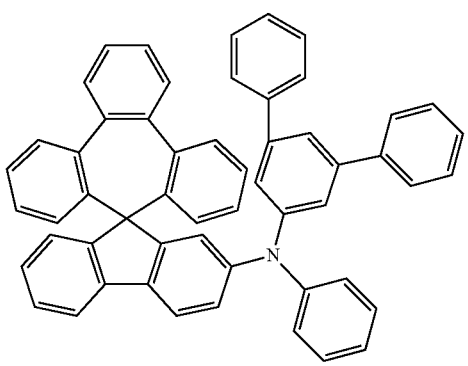
(122)
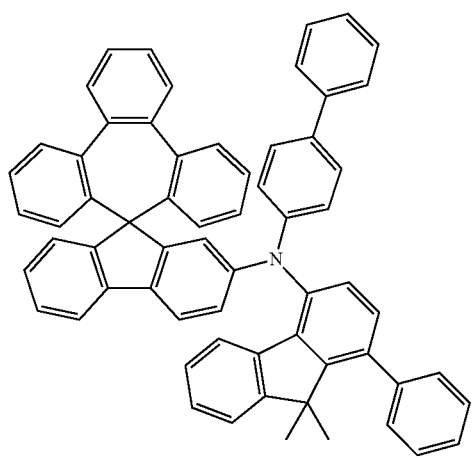
(123)
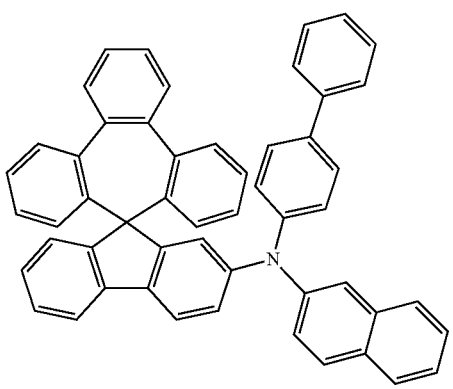

-continued
(124)
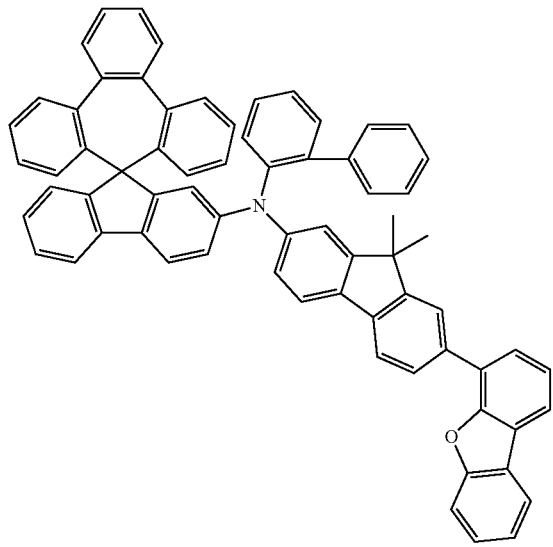
(125)
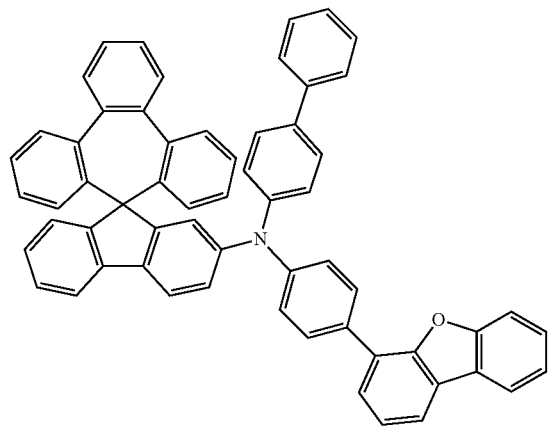
(126)
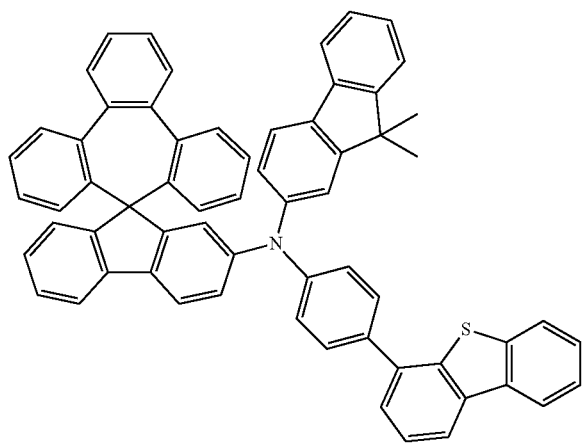
(127)
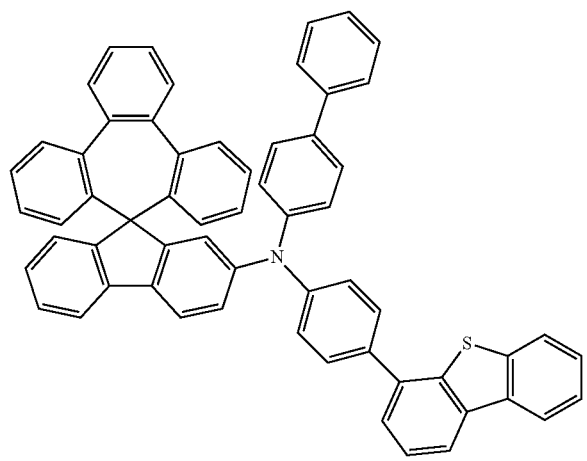
(128)
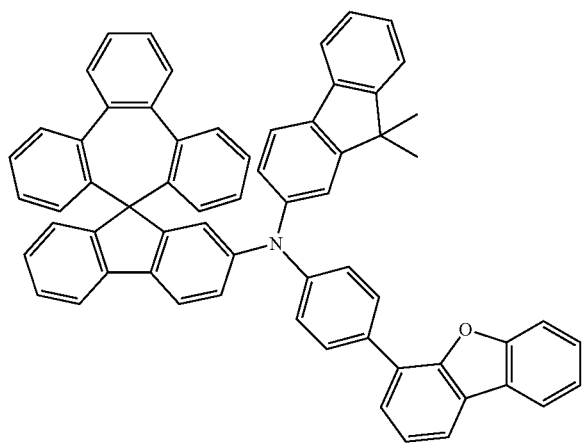
(129)
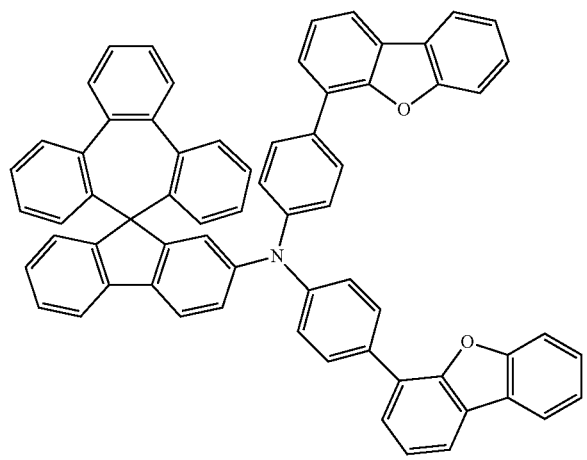

-continued
(130)
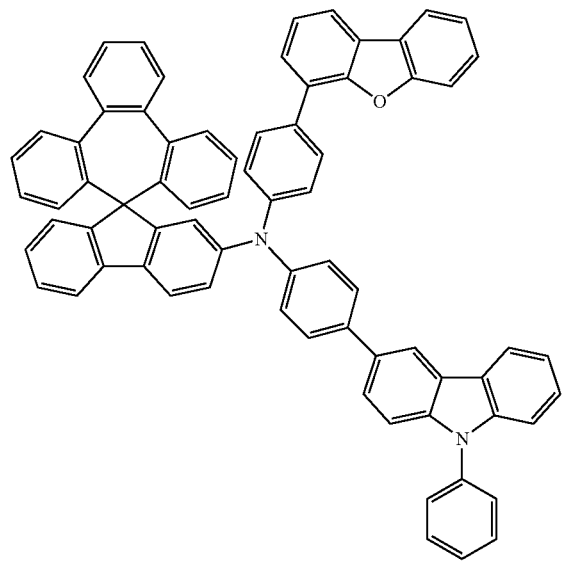
(131)
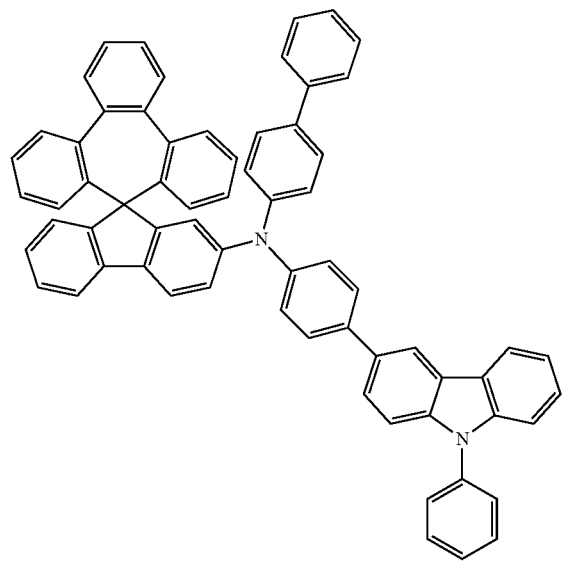
(132)
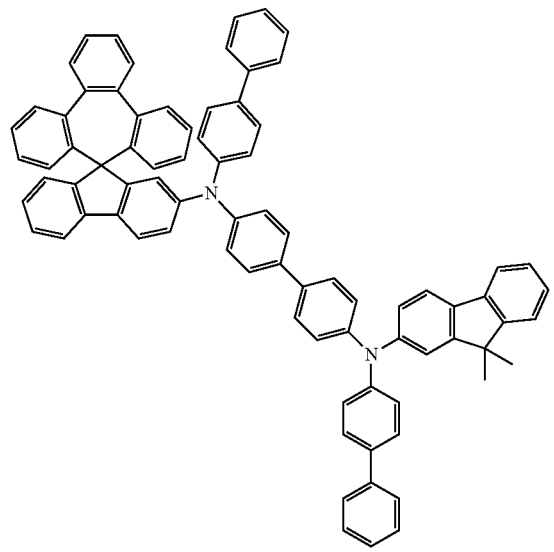
(133)
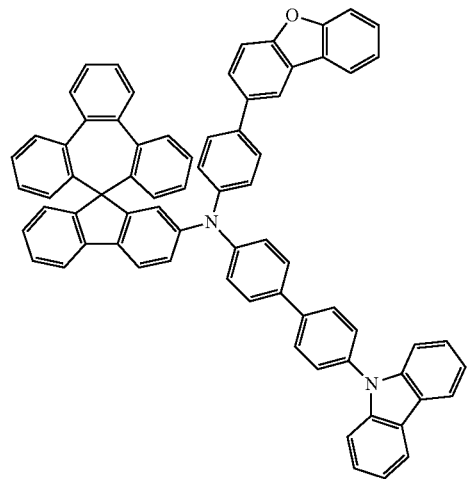
(134)
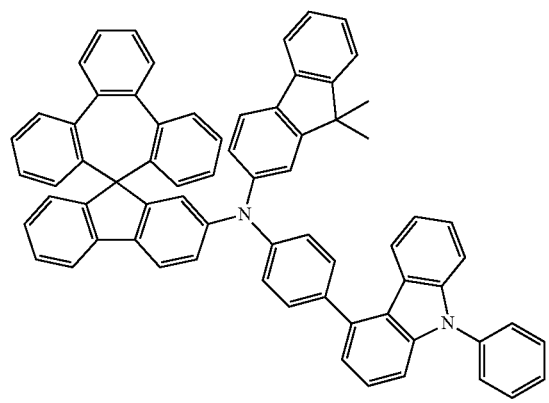
(135)
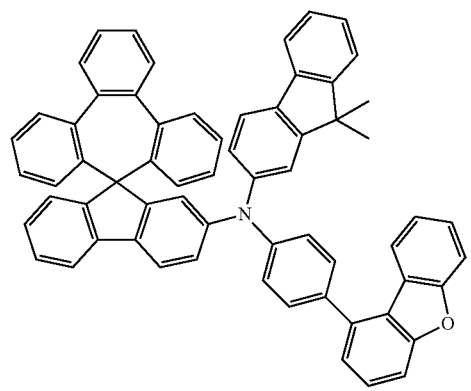

-continued
(136)
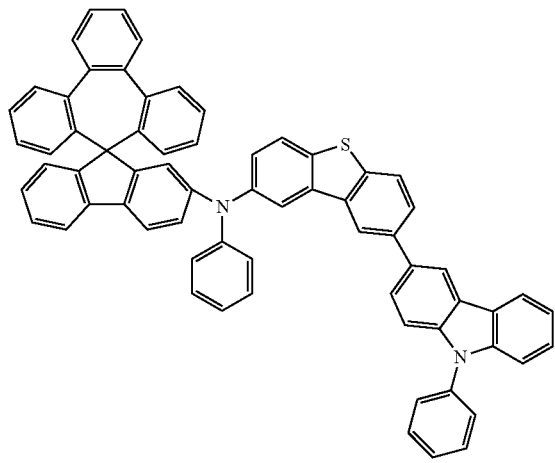
(137)
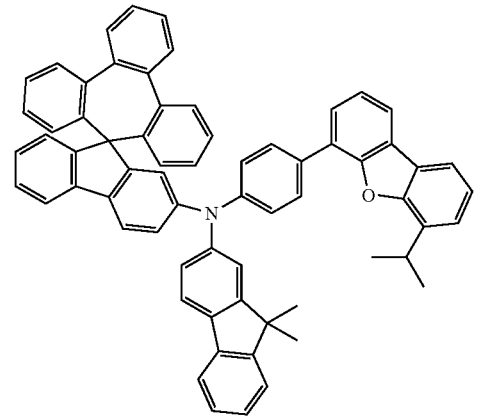
(138)
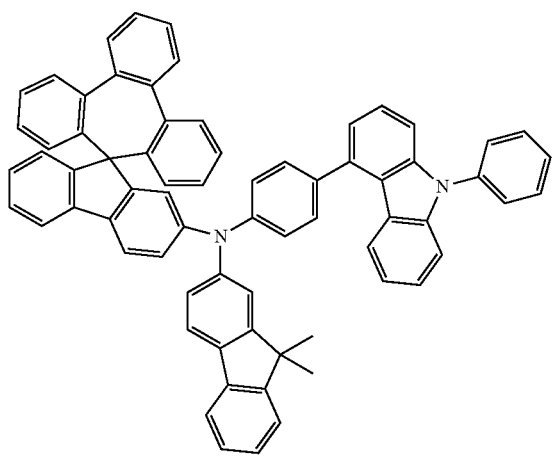
(139)
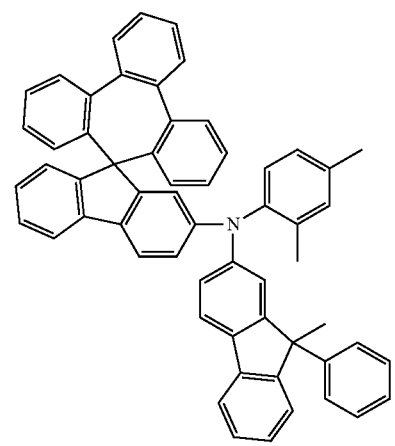
(140)
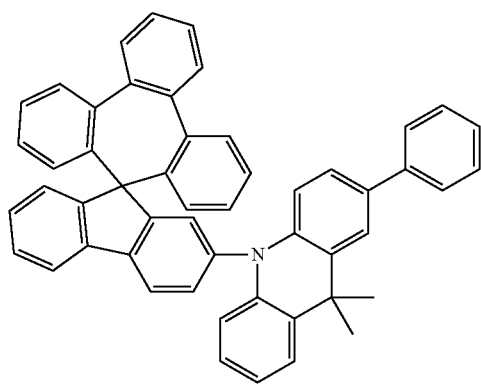
(141)
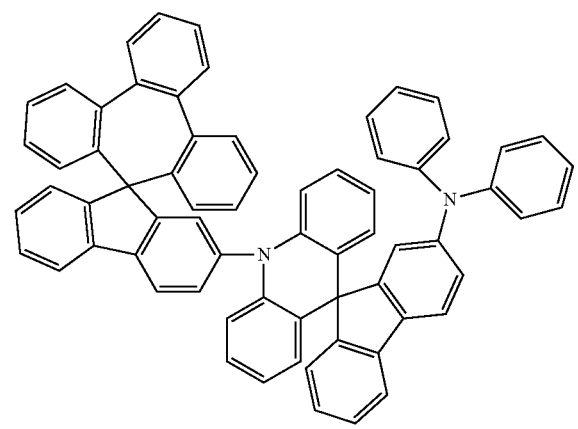

-continued
(142)
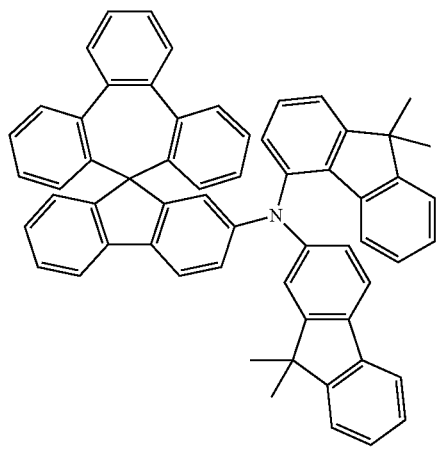
(143)
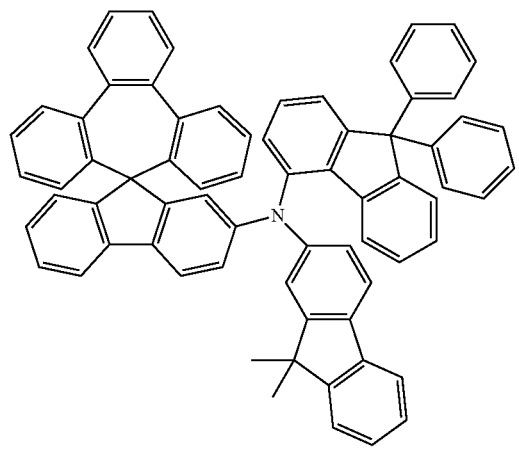
(144)
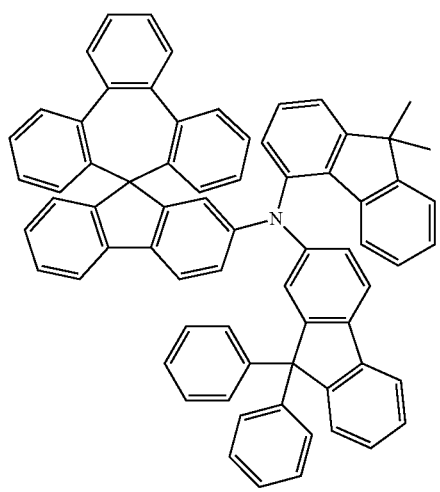
(145)
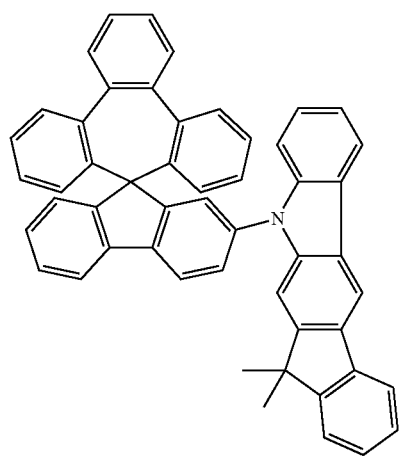
(146)
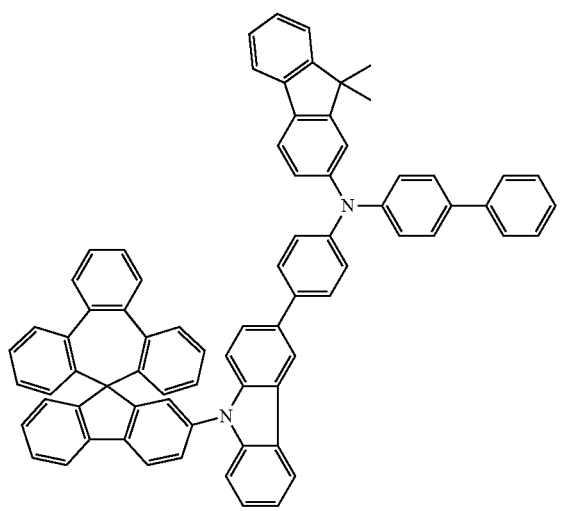
(147)
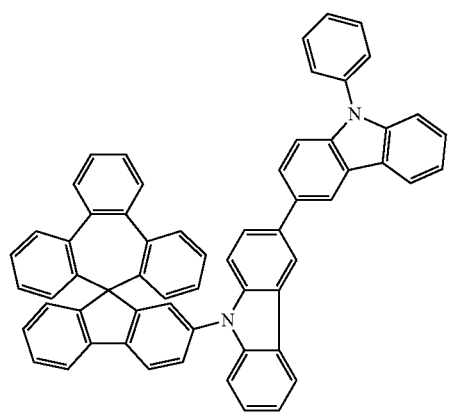

-continued
(148)
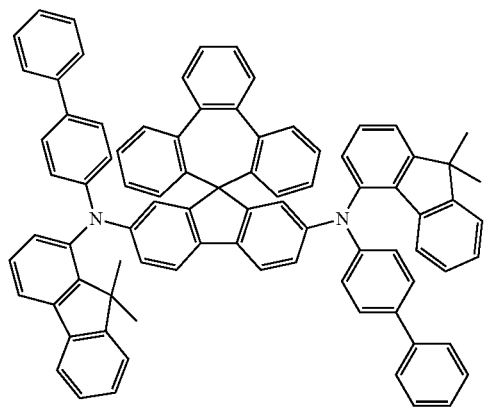
(149)
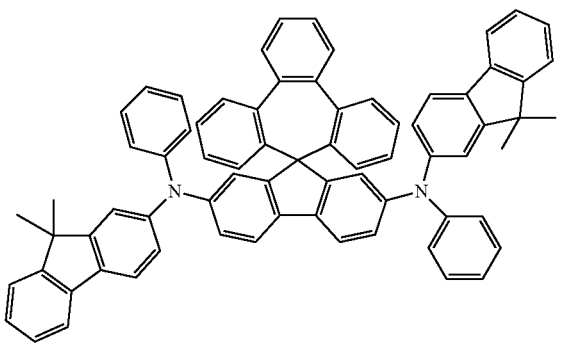
(150)
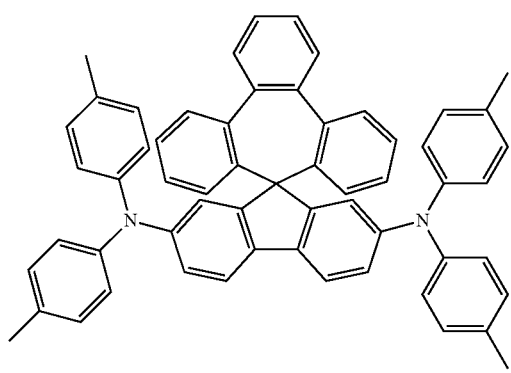
(151)
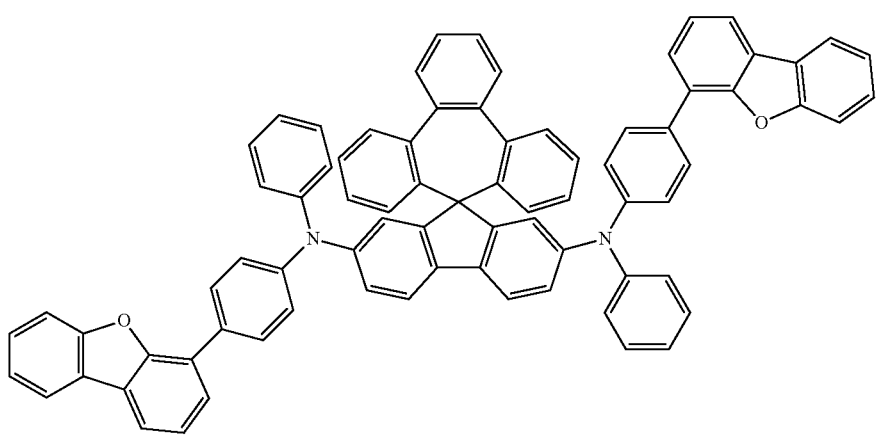
(152)
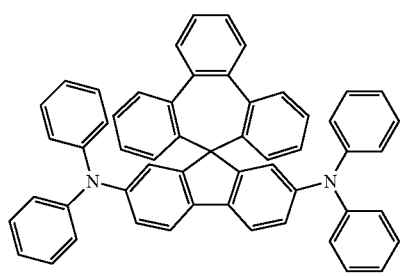
(153)
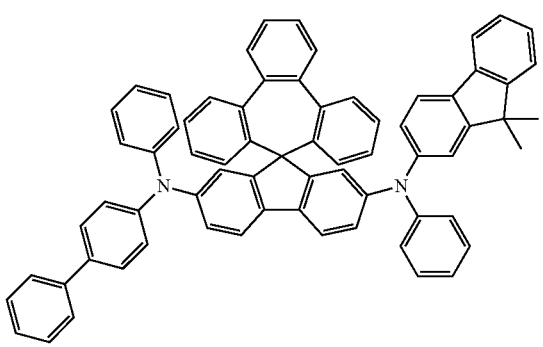

-continued
(154)
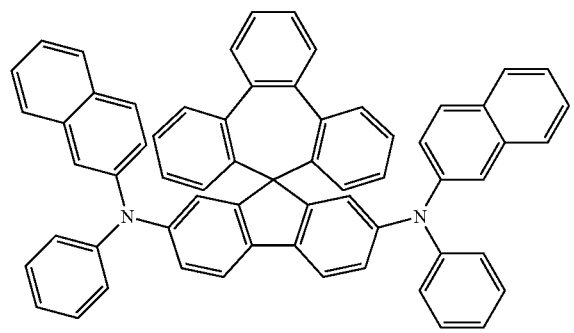
(155)
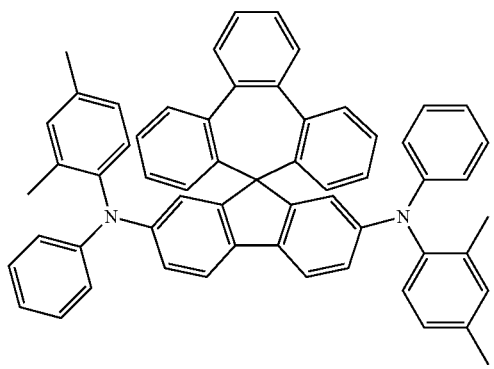
(156)
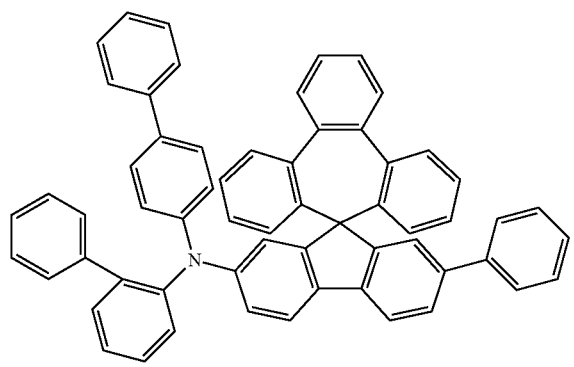
(157)
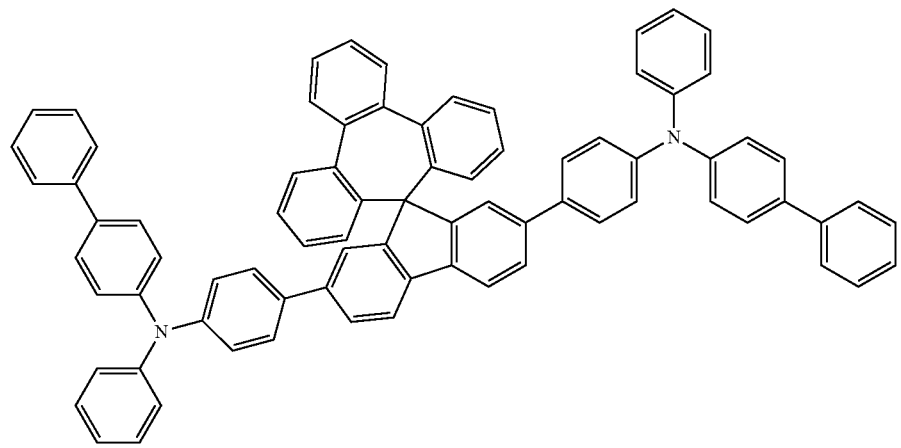
(158)
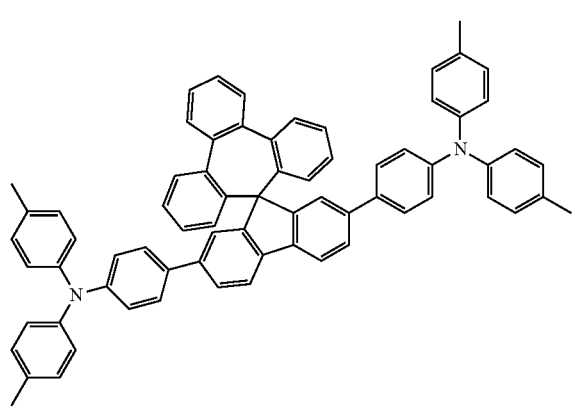
(159)
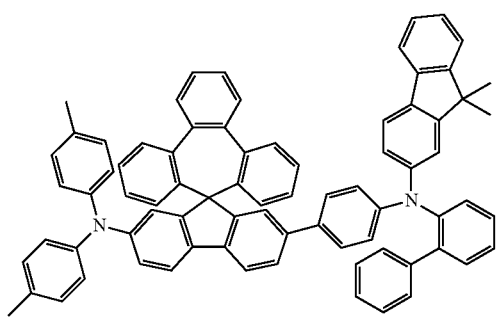

-continued
(160)
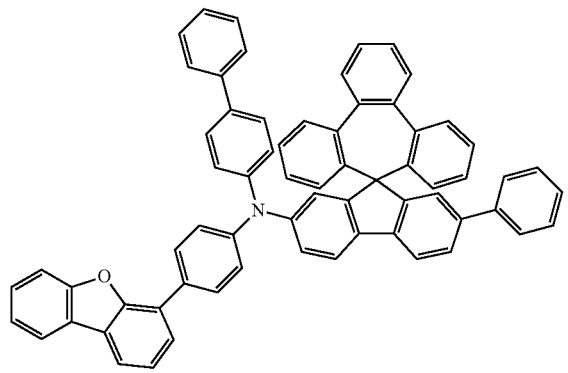
(161)
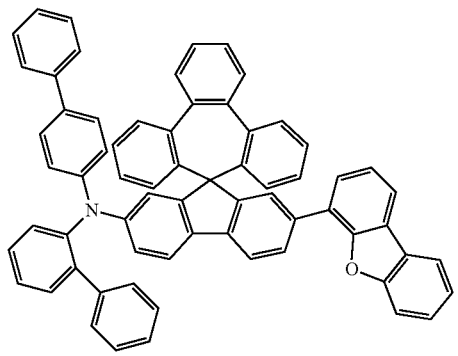
(162)
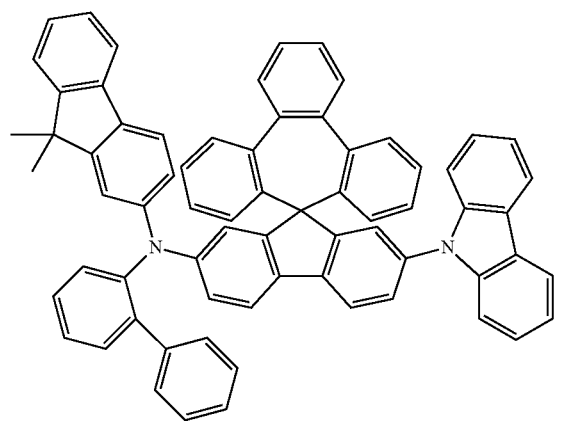
(163)
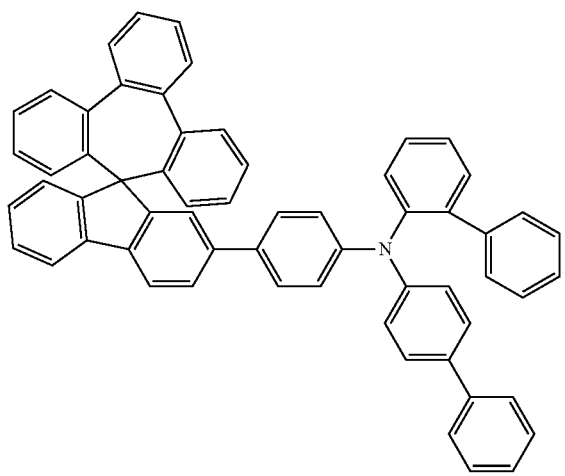
(164)
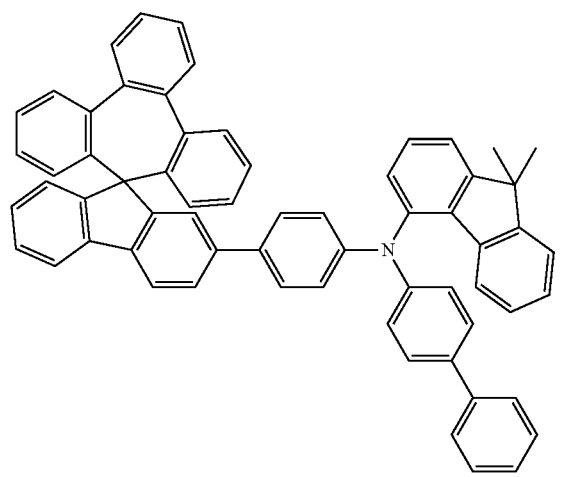
(165)
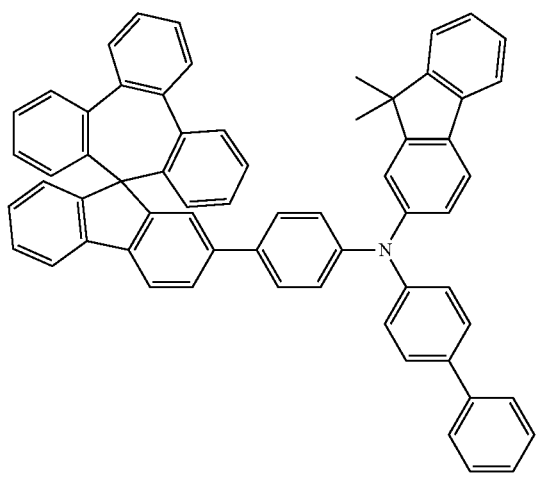

(166)
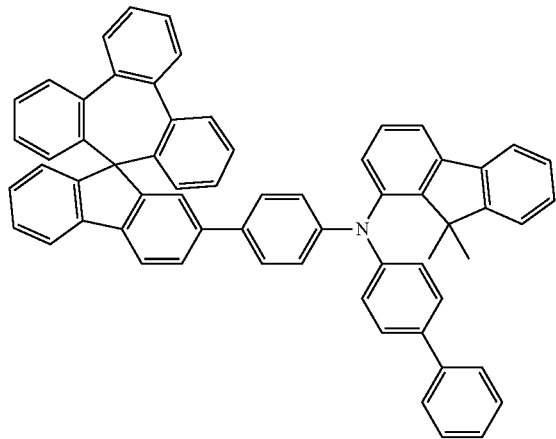
(167)
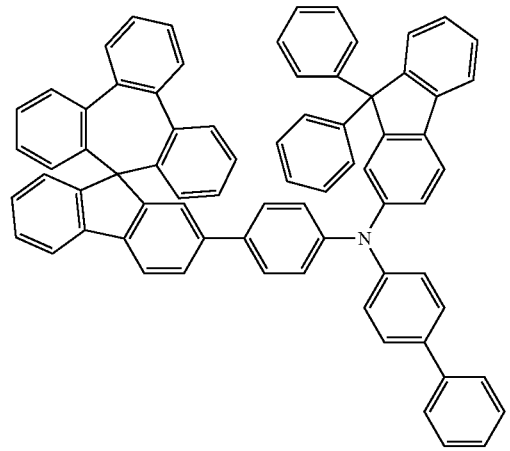
(168)
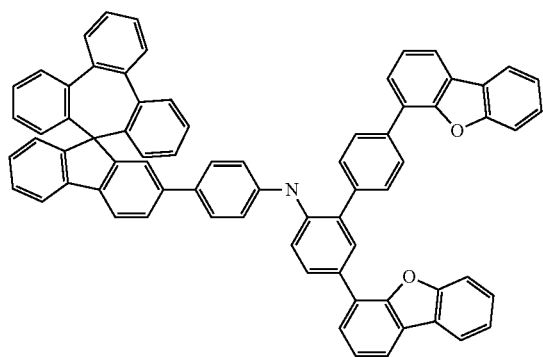
(169)
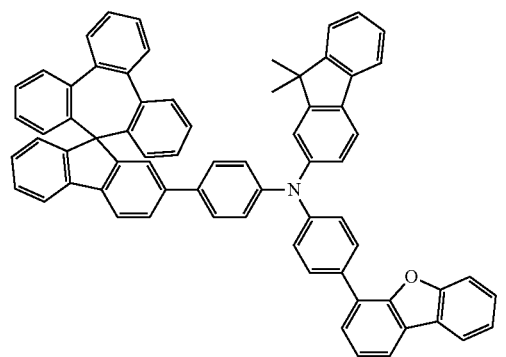
(170)
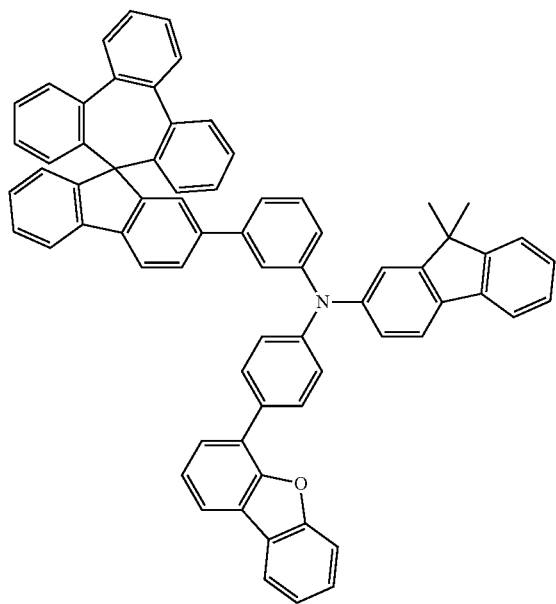
(171)
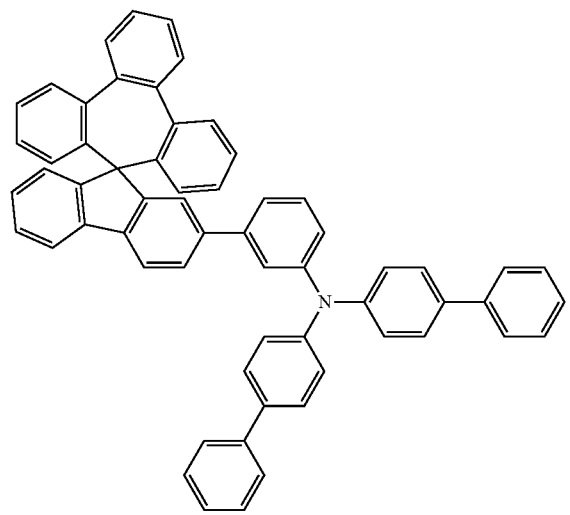

-continued
(172)
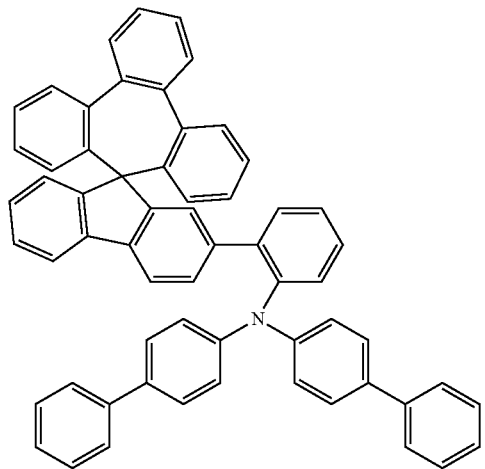
(173)
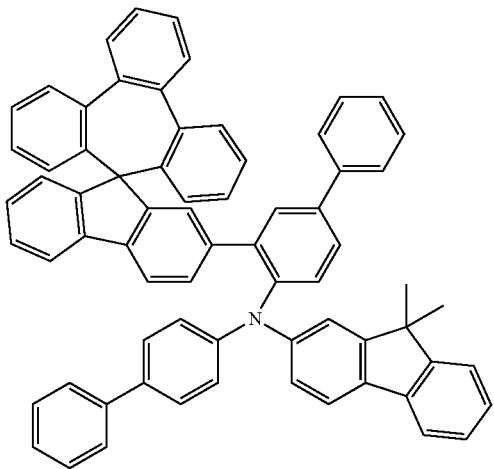
(174)
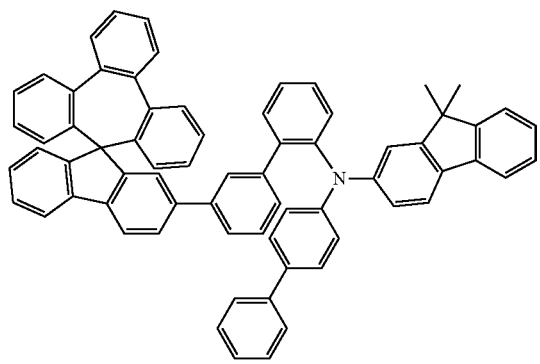
(175)
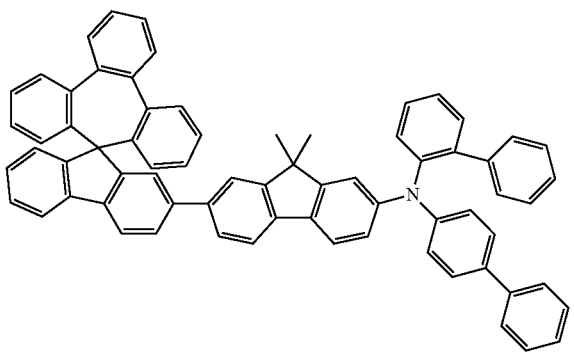
(176)
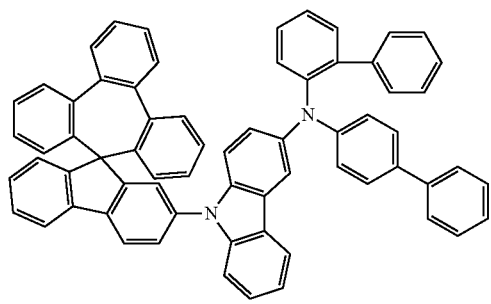
(177)
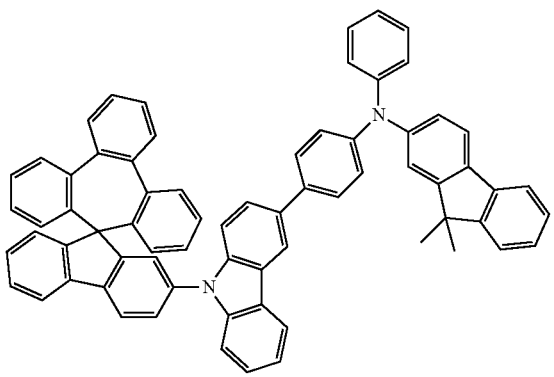

-continued
(178)
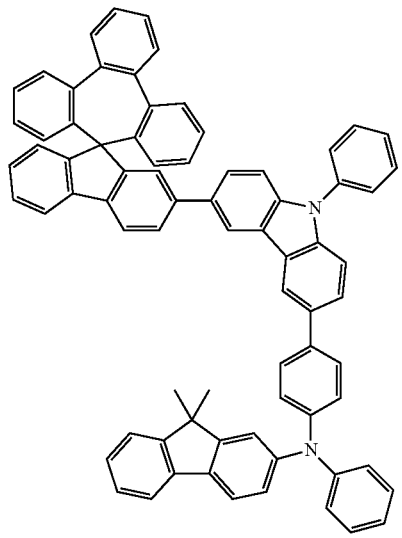
(179)
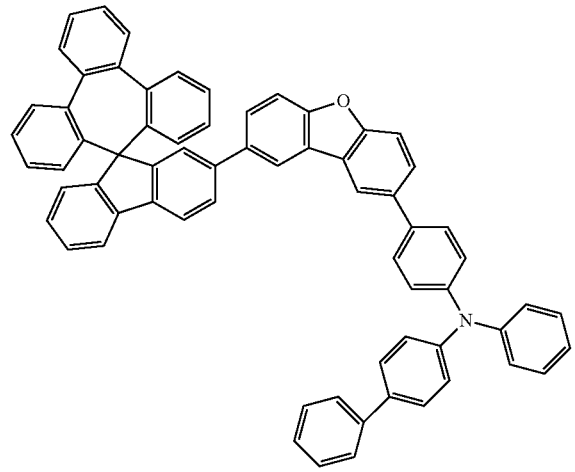
(180)
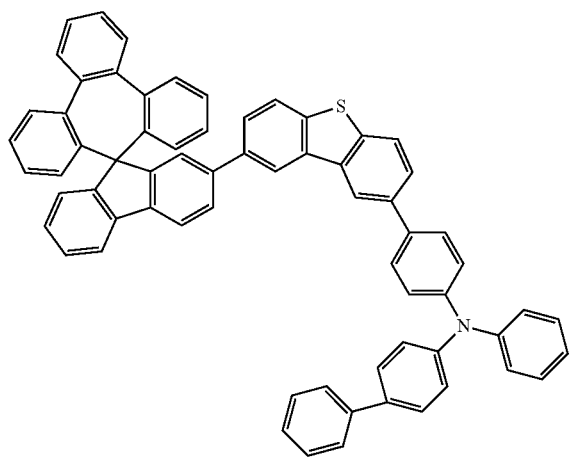
(181)
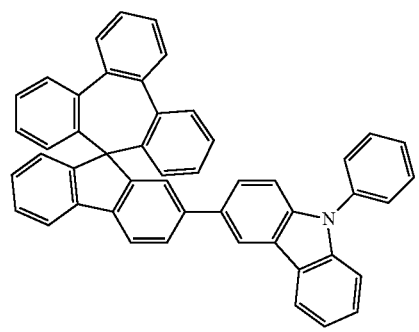
(182)
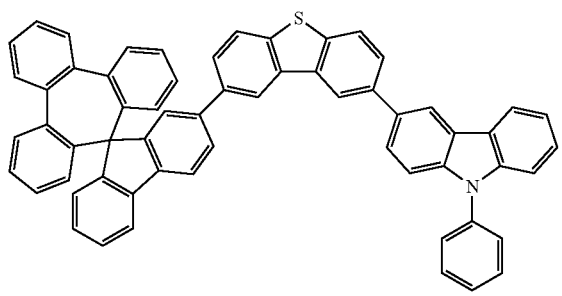
(183)
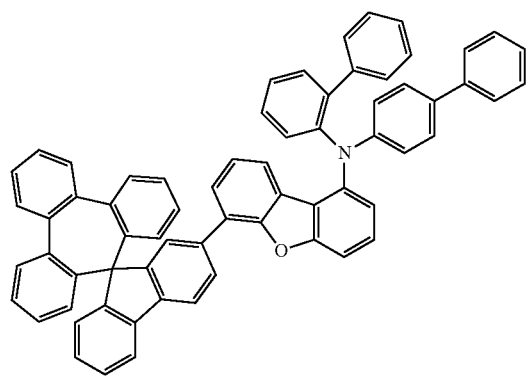

-continued
(184)
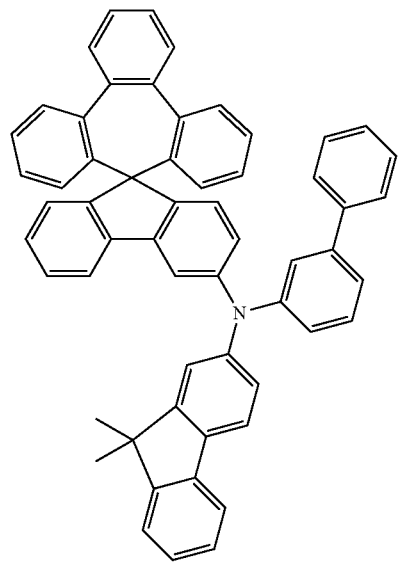
(185)
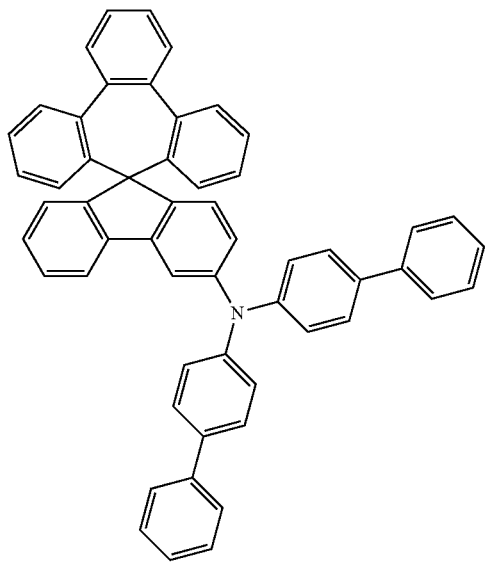
(186)
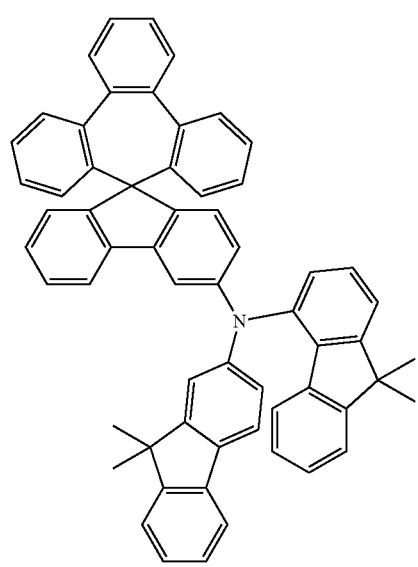
(187)
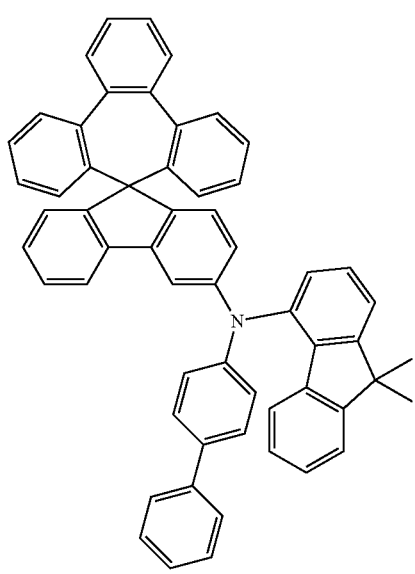

-continued
(188)
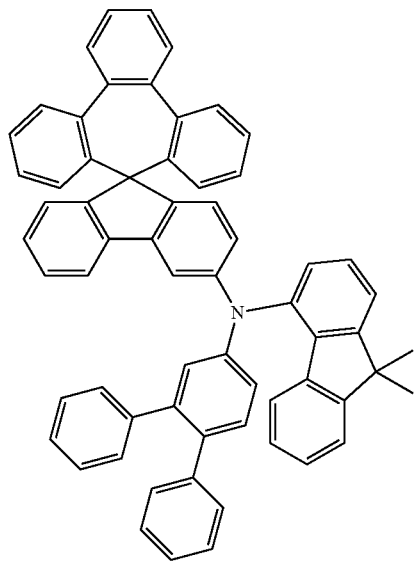
(189)
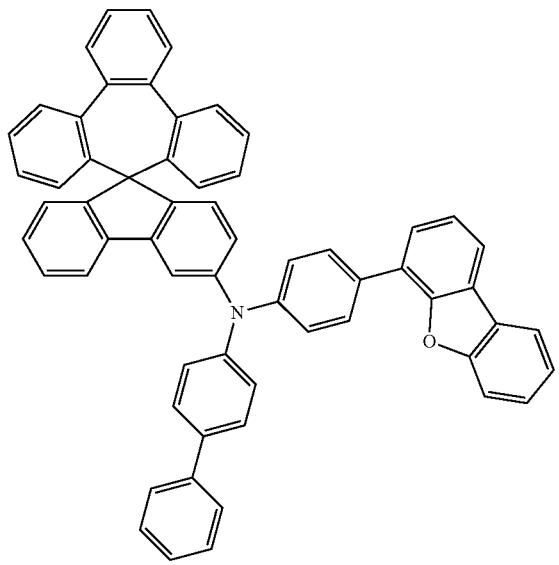
(190)
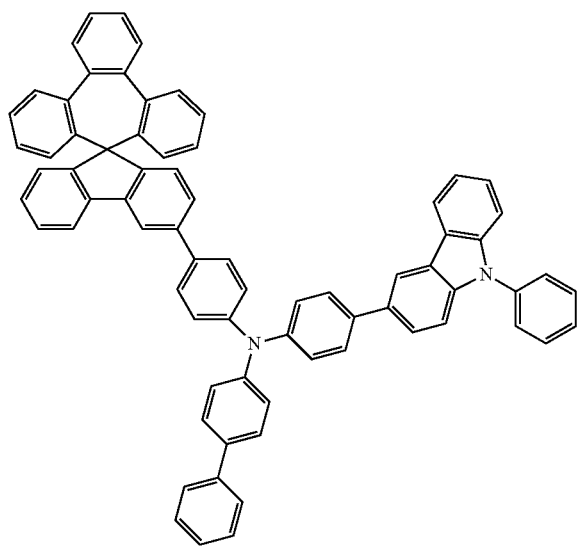
(191)
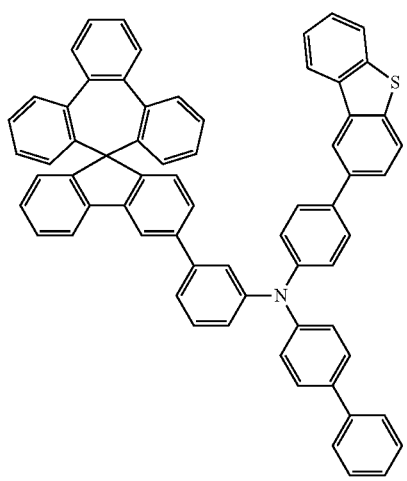
(192)
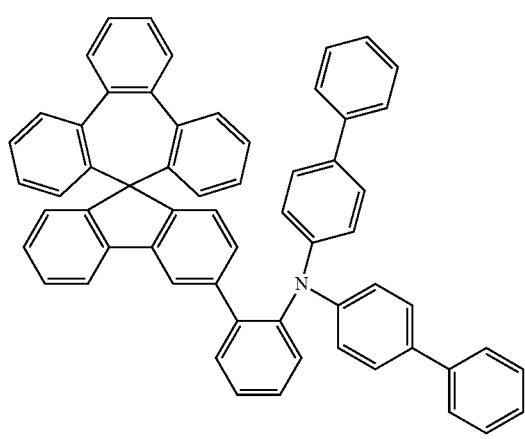
(193)
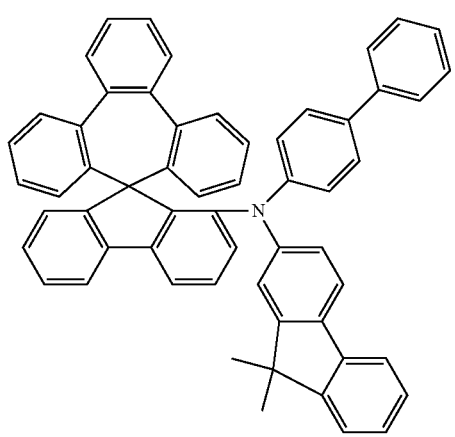

-continued
(194)
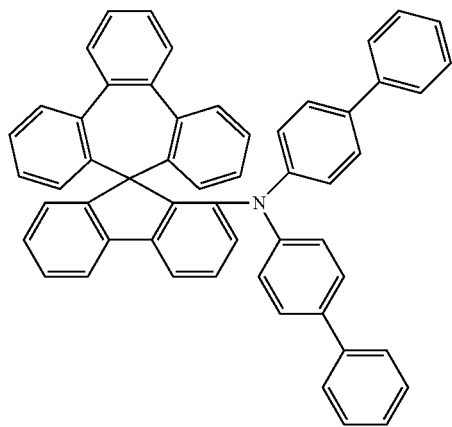
(195)
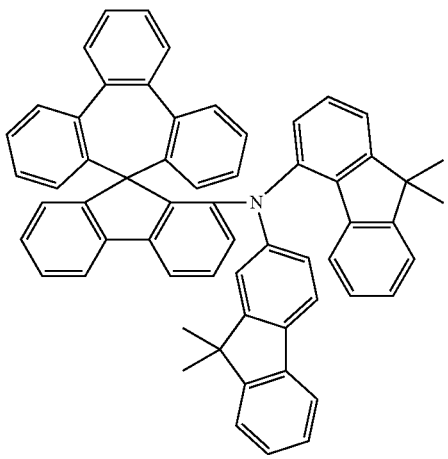
(196)
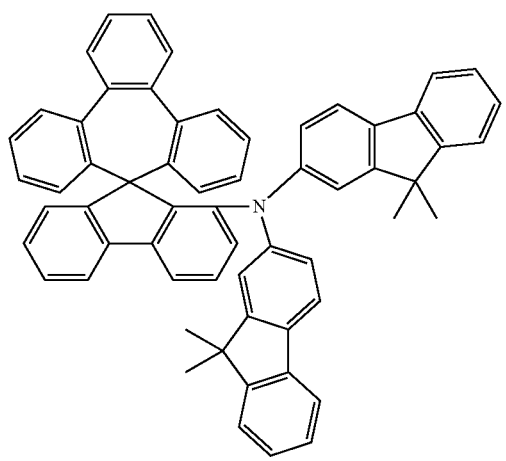
(197)
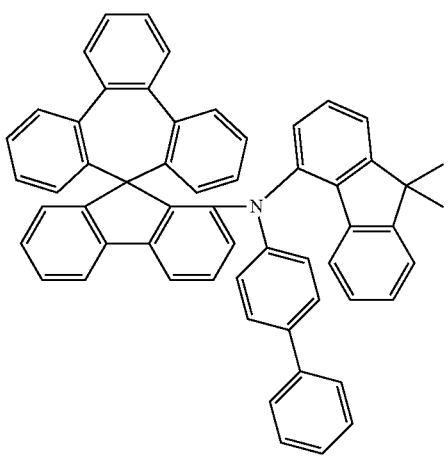
(198)
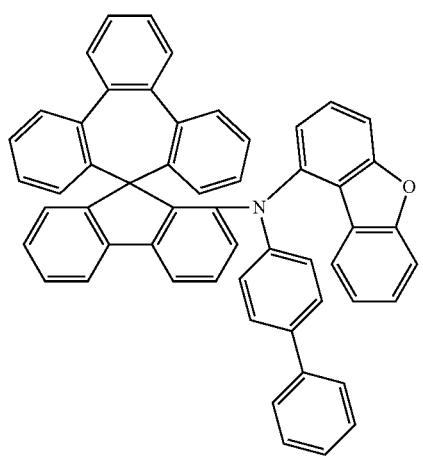
(199)
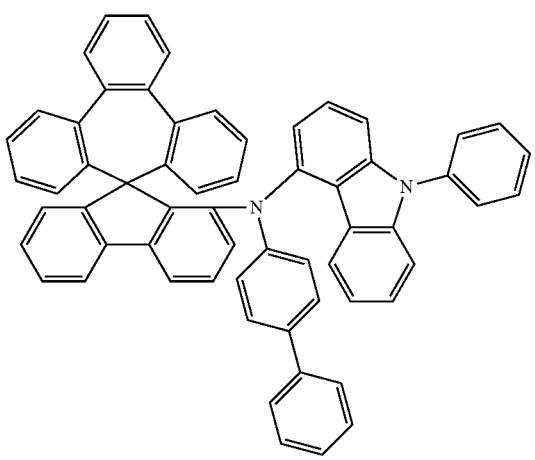

(200)
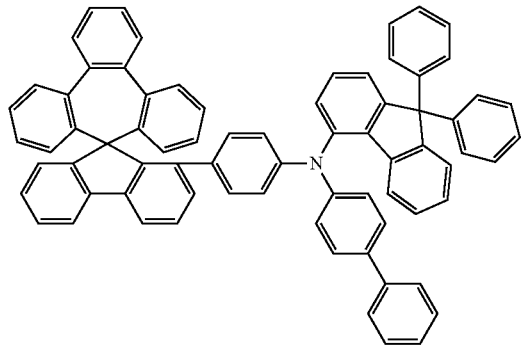
(201)
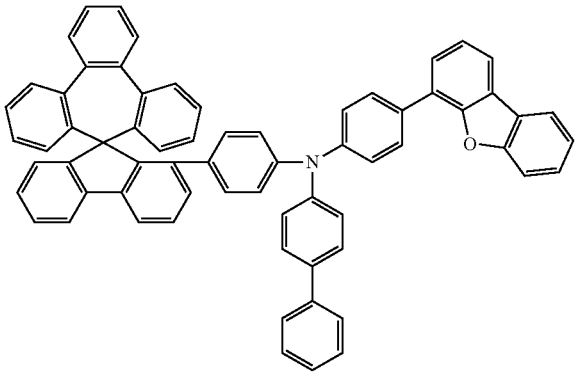
(202)
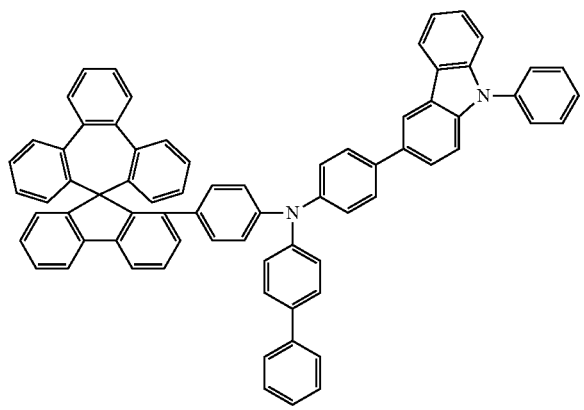
(203)
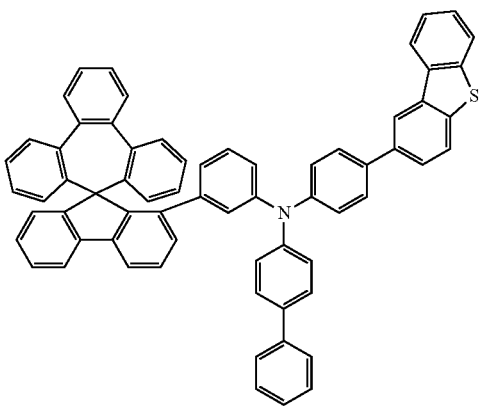
(204)
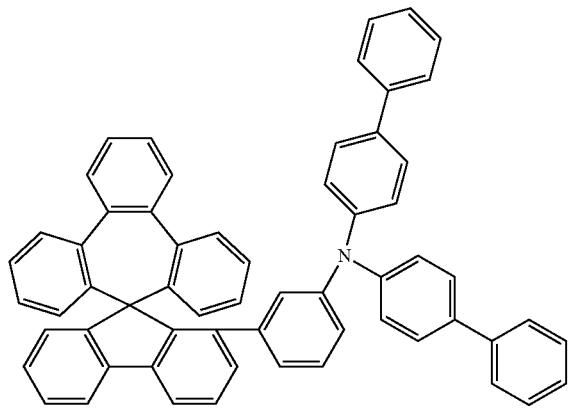
(205)
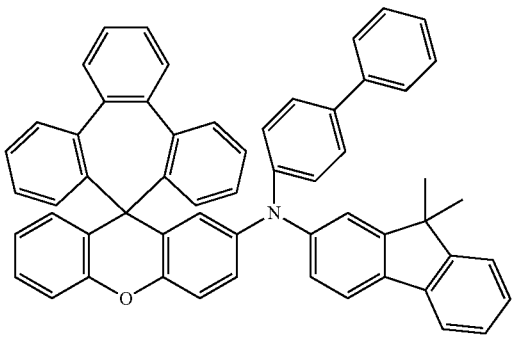
(206)
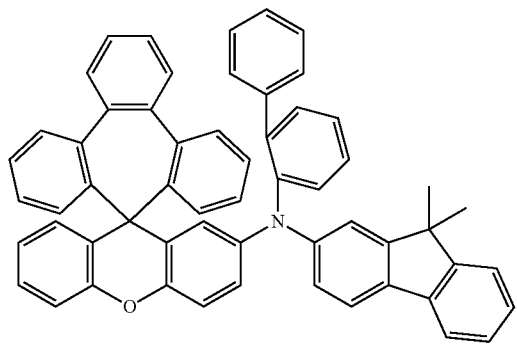
(207)
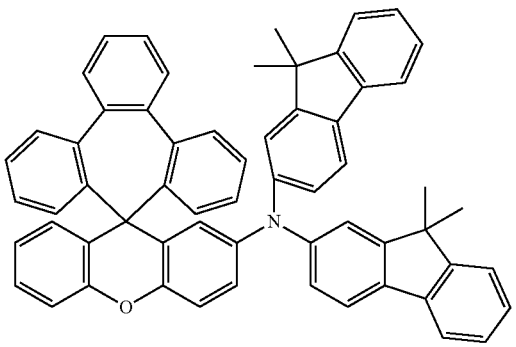

-continued
(208)
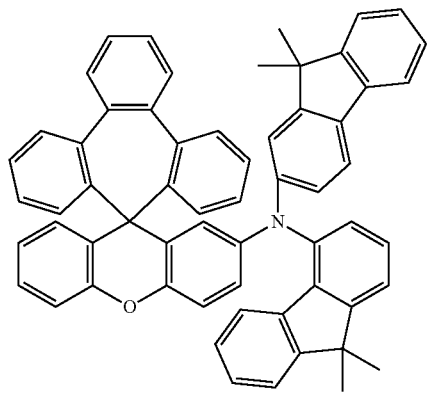
(209)
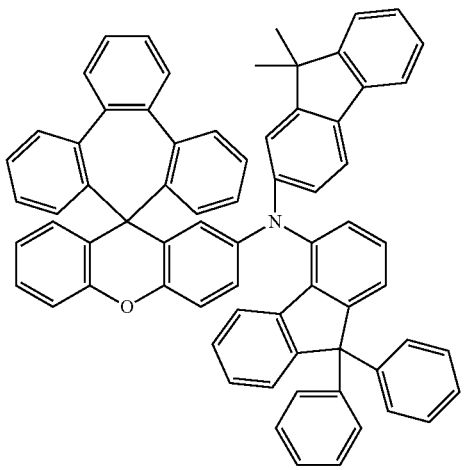
(210)
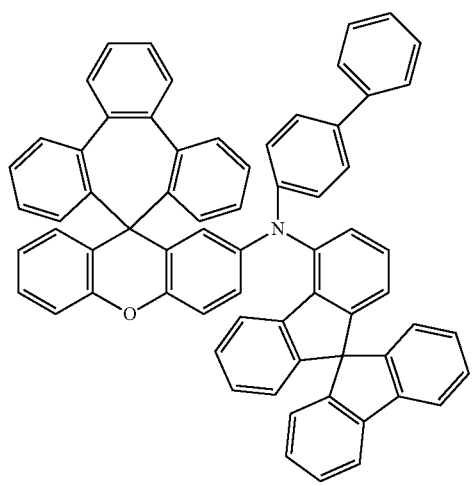
(211)
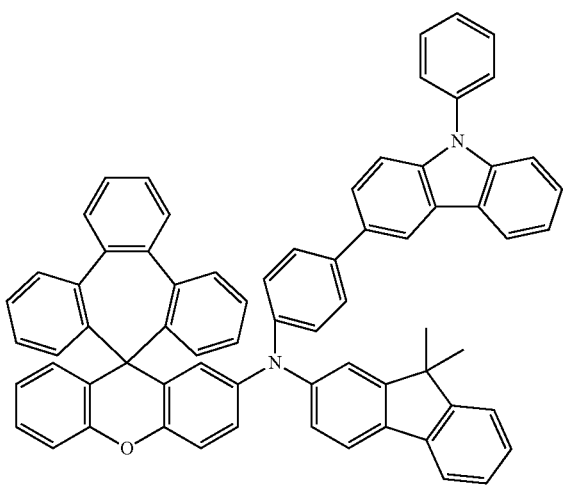
(212)
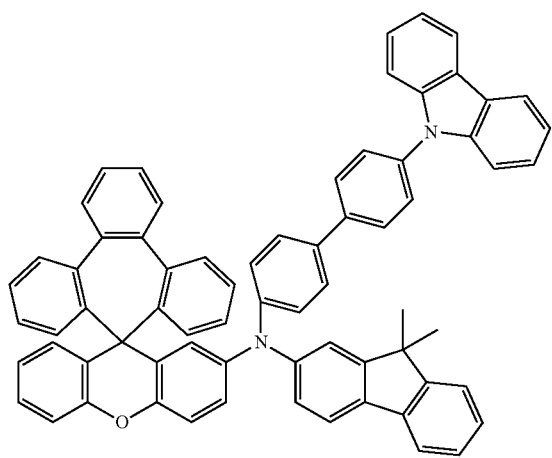
(213)
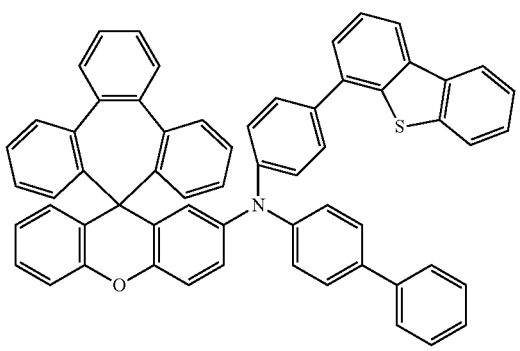

-continued
(214)
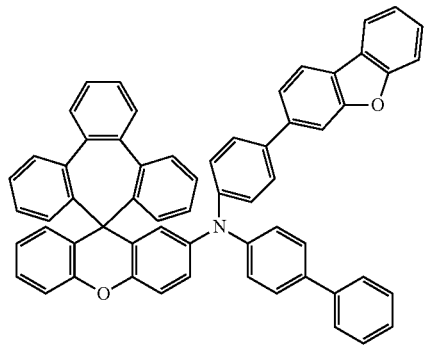
(215)
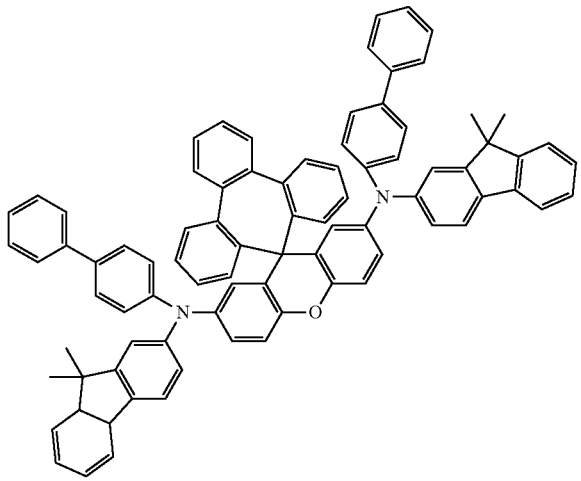
(216)
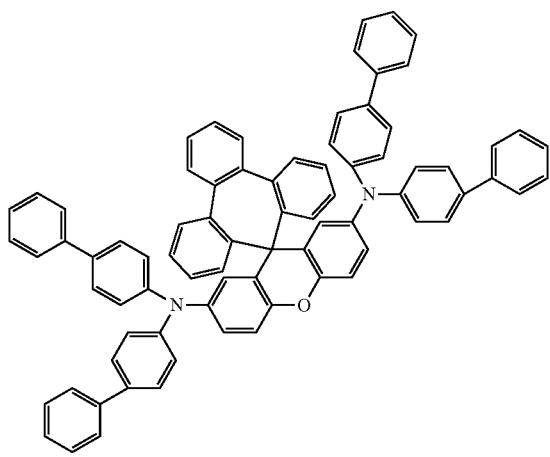
(217)
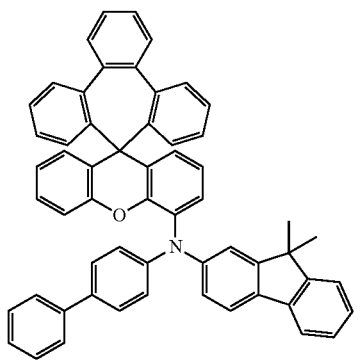
(218)
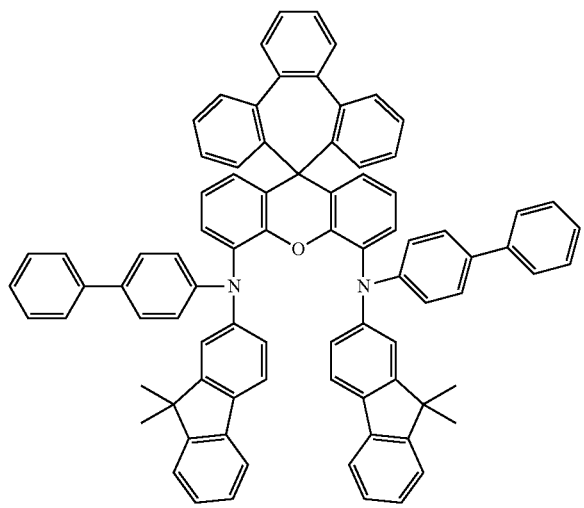
(219)
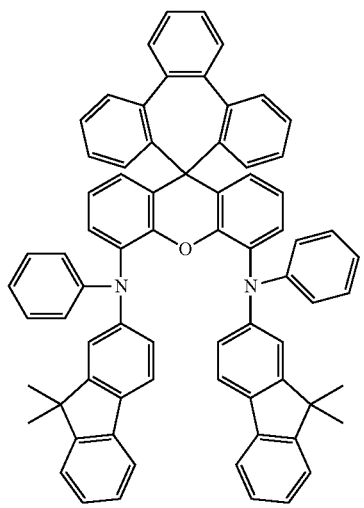

-continued
(220)
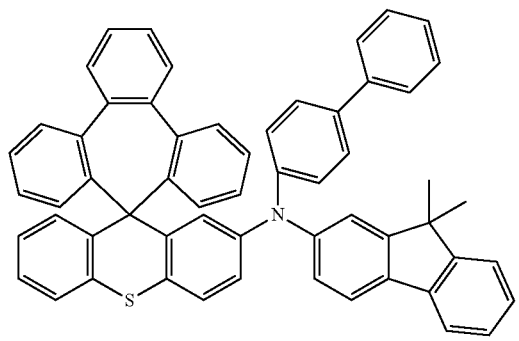
(221)
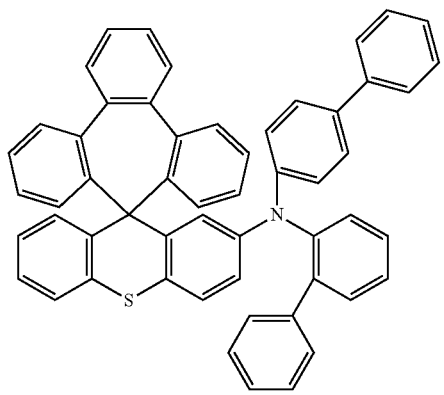
(222)
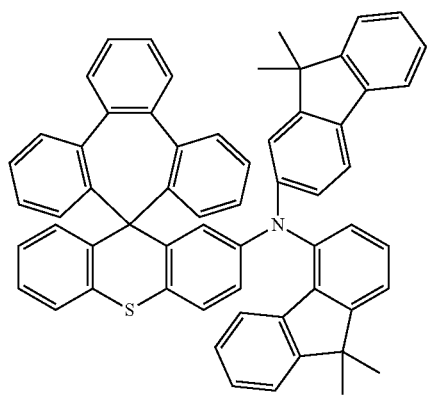
(223)
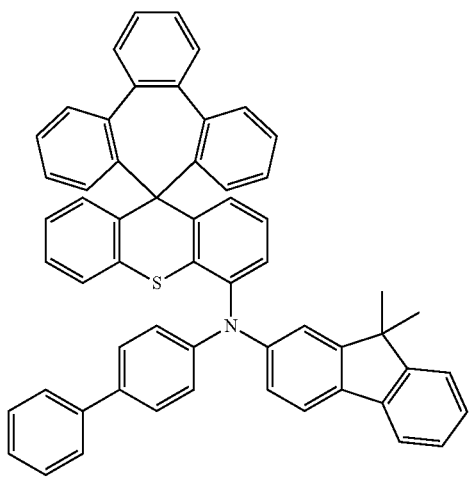
(224)
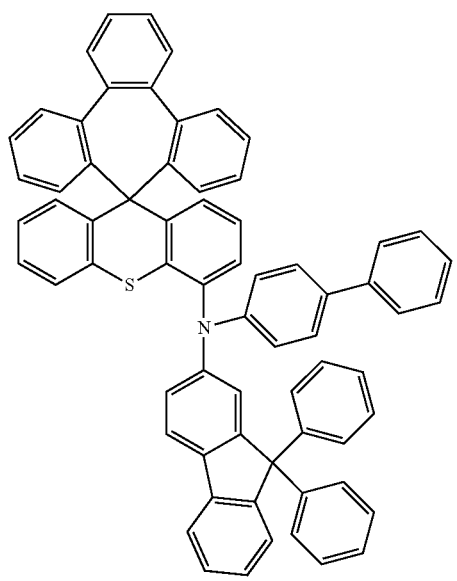
(225)
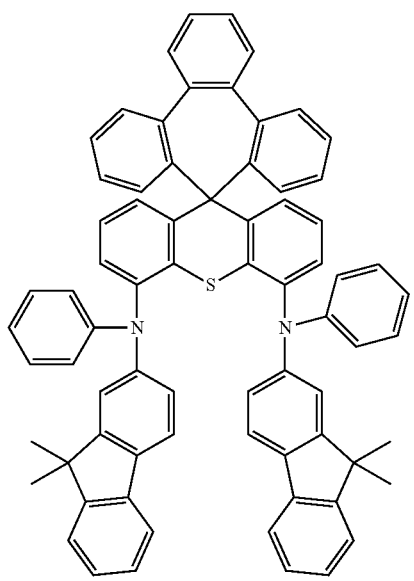

-continued
(226)
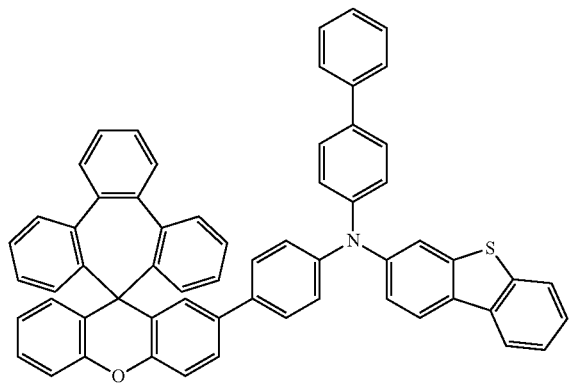
(227)
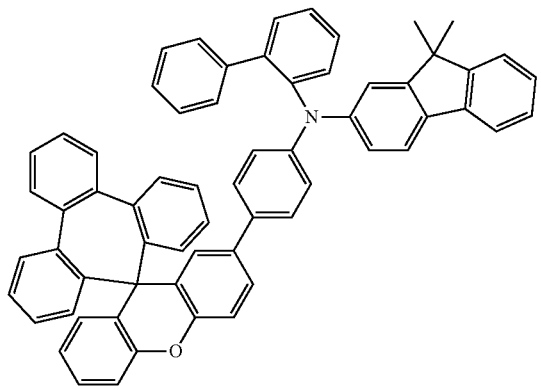
(228)
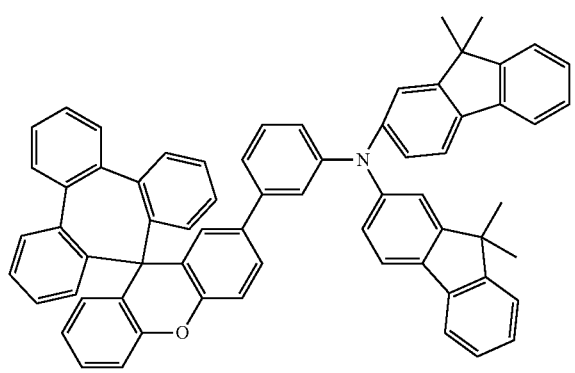
(229)
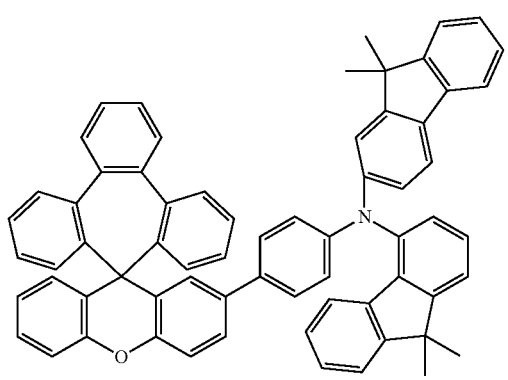
(230)
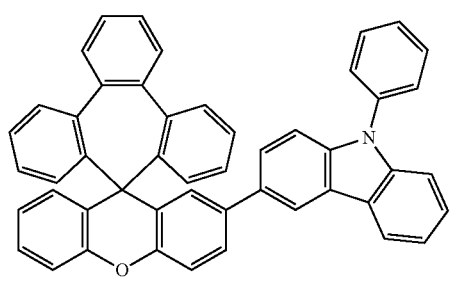
(231)
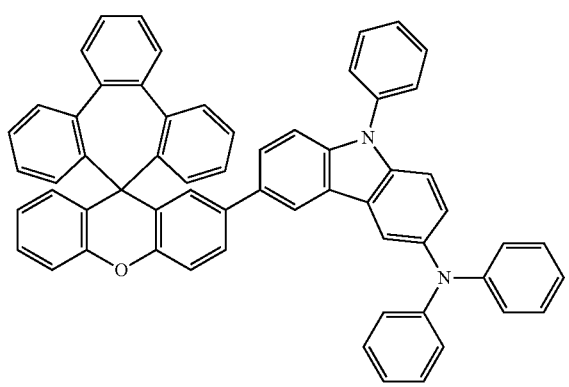

-continued
(232)
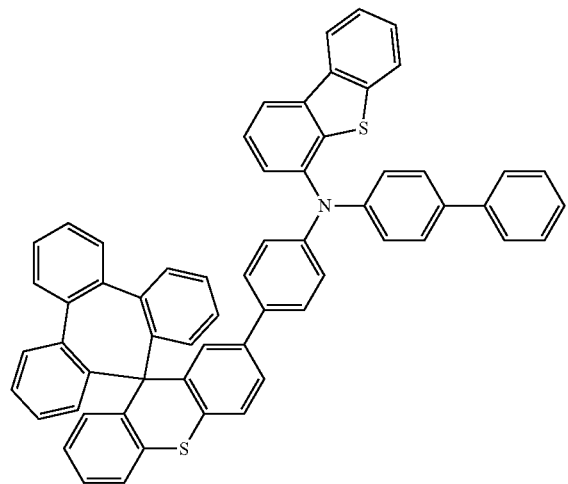
(233)
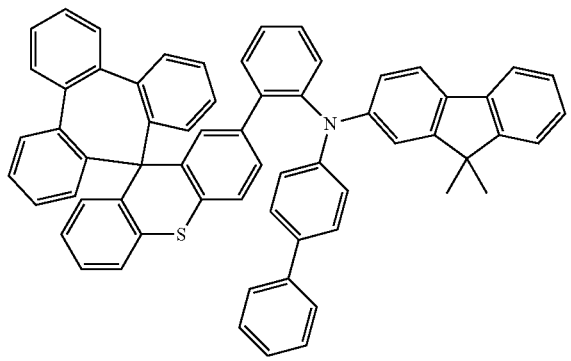
(234)
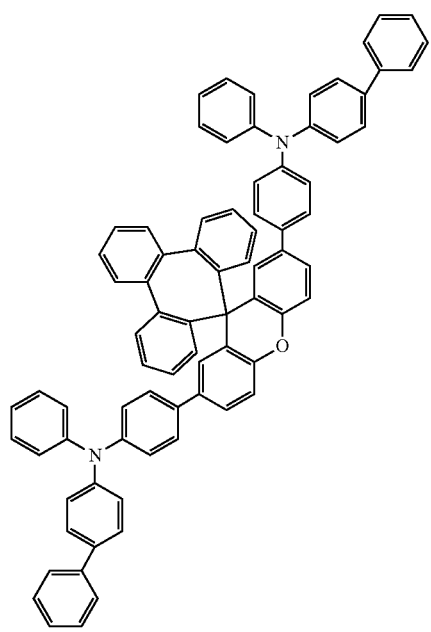
(235)
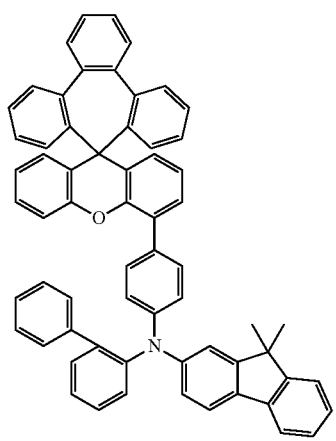

-continued
(236)
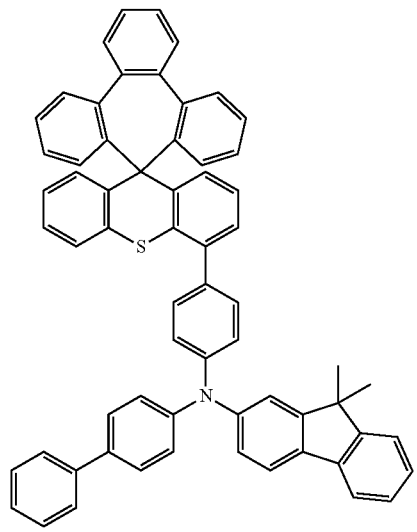
(237)
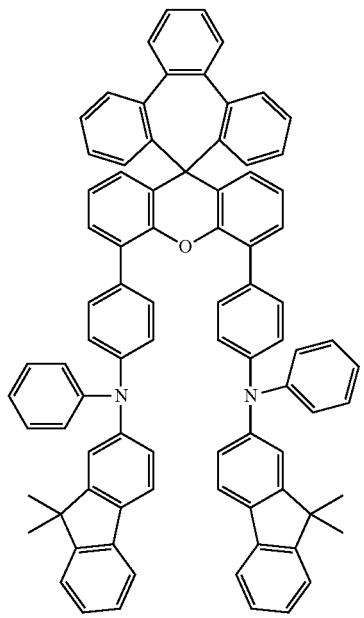
(238)
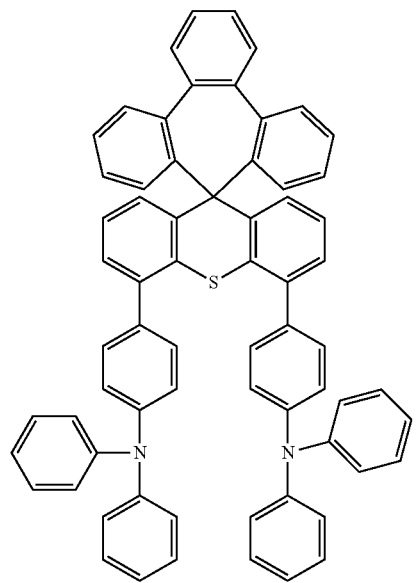
(239)
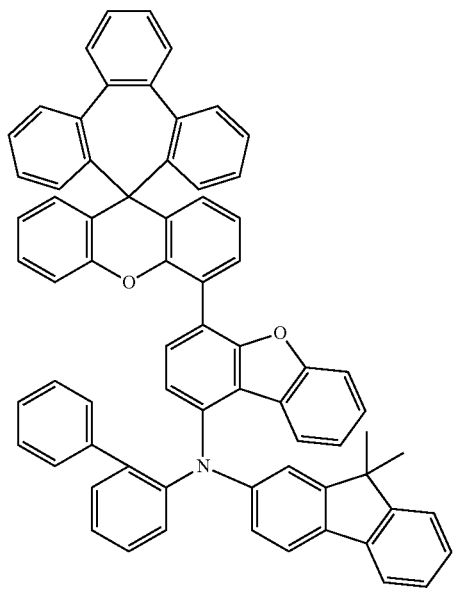

(240)
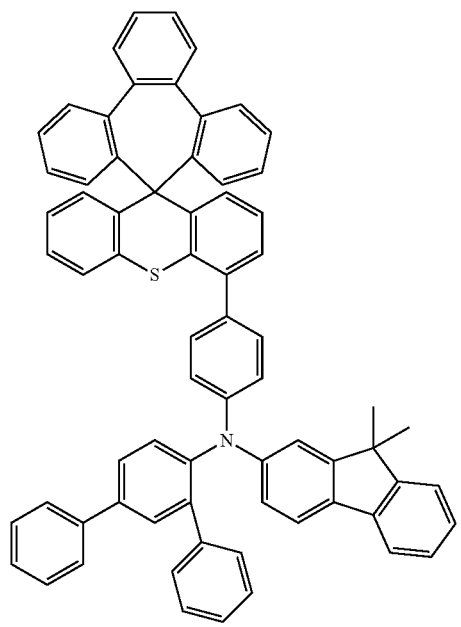
(241)
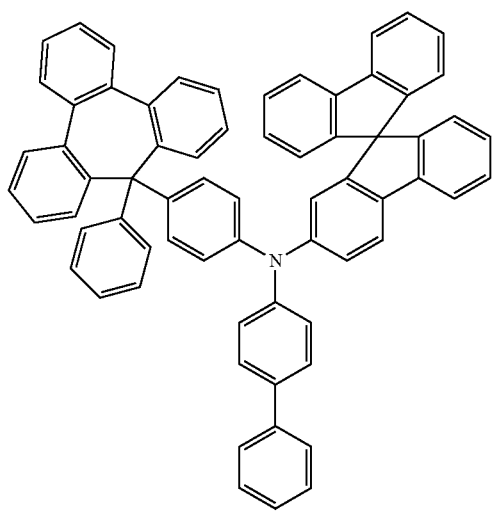
(242)
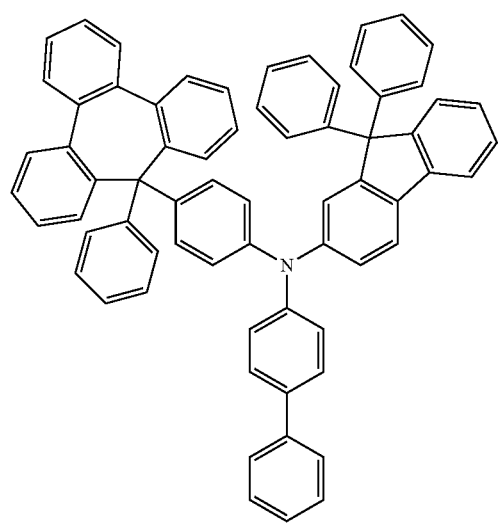
(243)
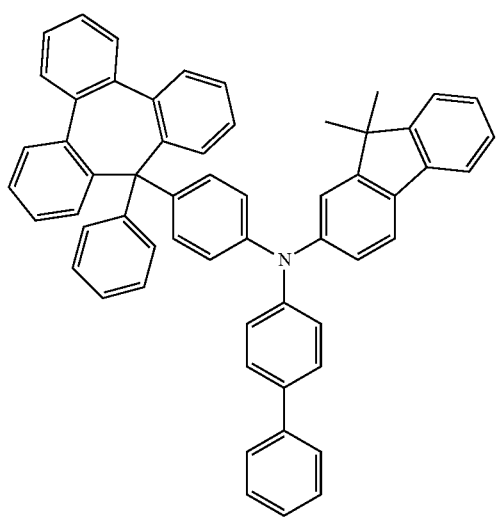
(244)
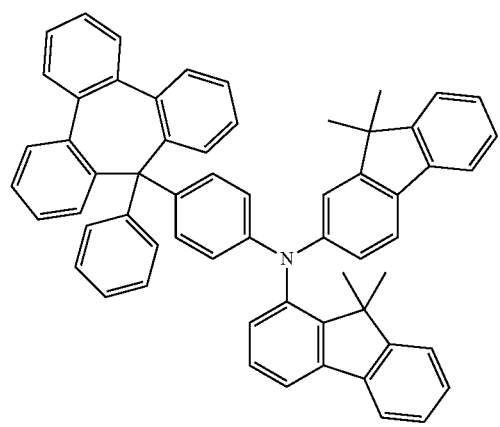
(245)
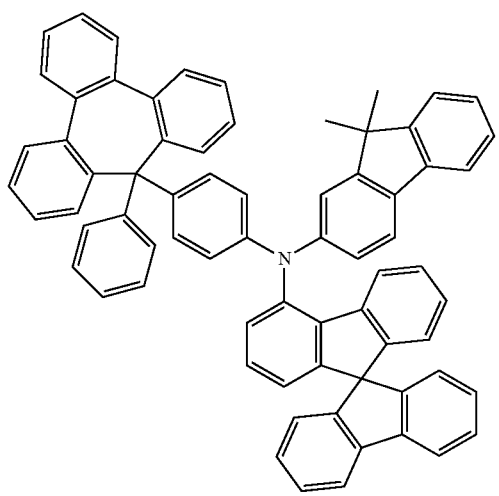

-continued
(246)
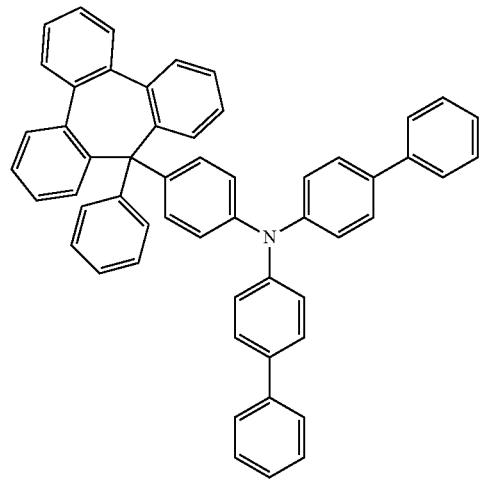
(247)
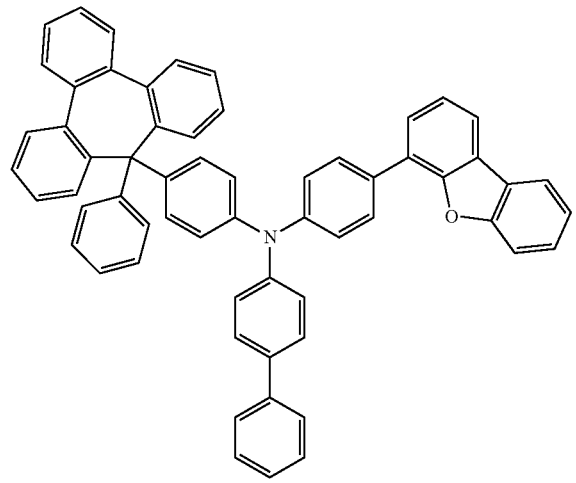
(248)
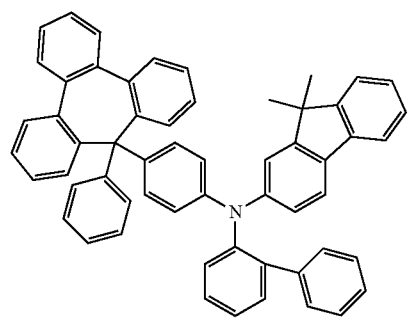
(249)
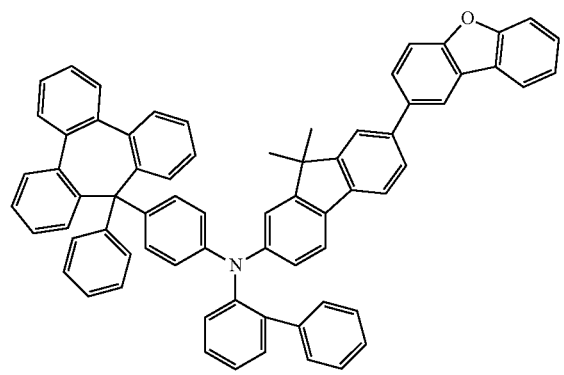
(250)
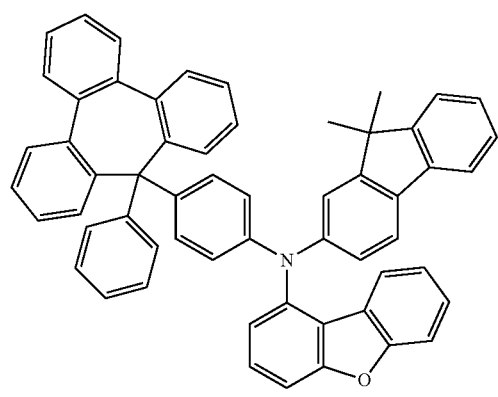
(251)
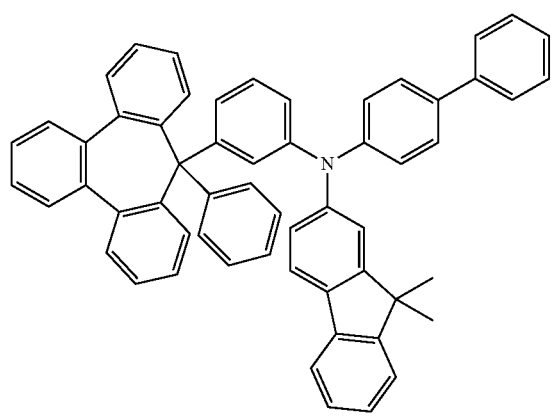

-continued
(252)
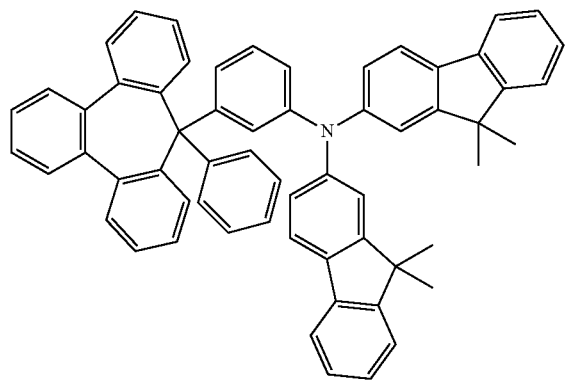
(253)
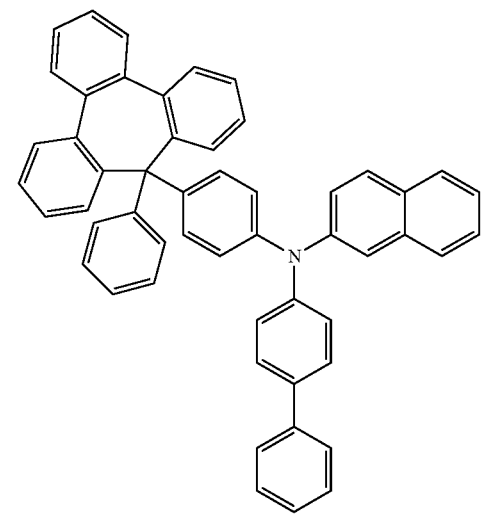
(254)
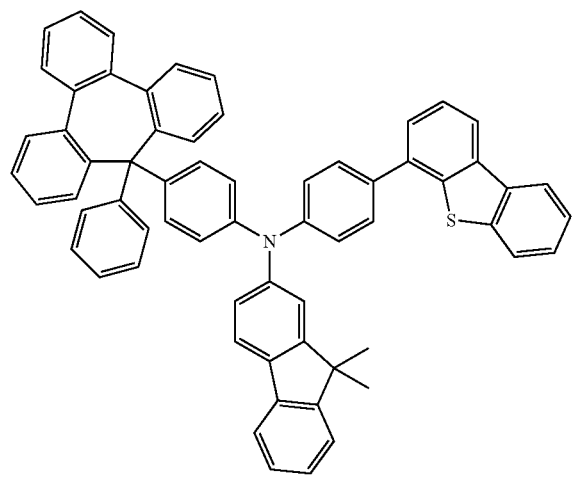
(255)
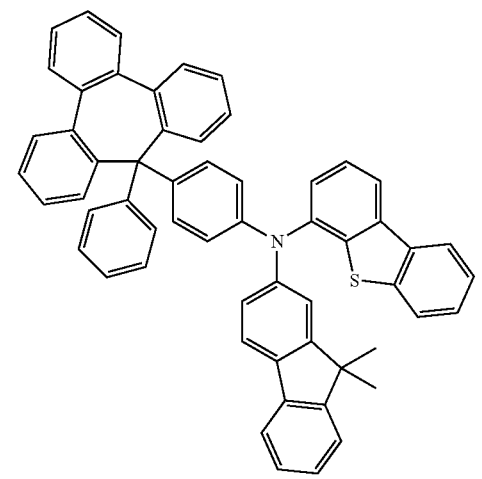
(256)
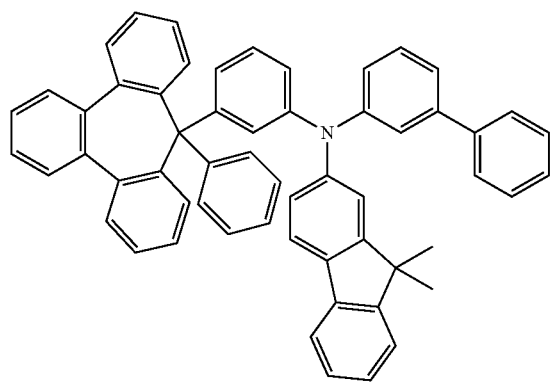
(257)
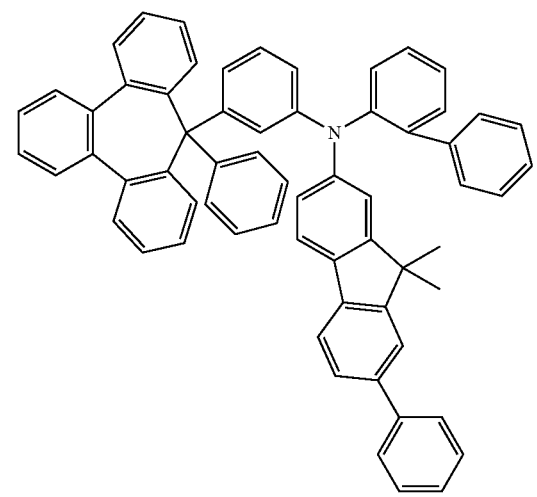

-continued
(258)
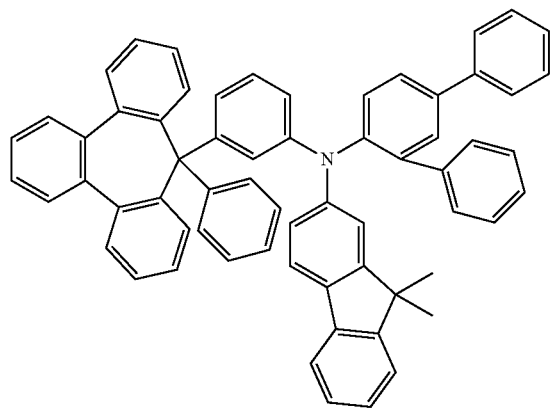
(259)
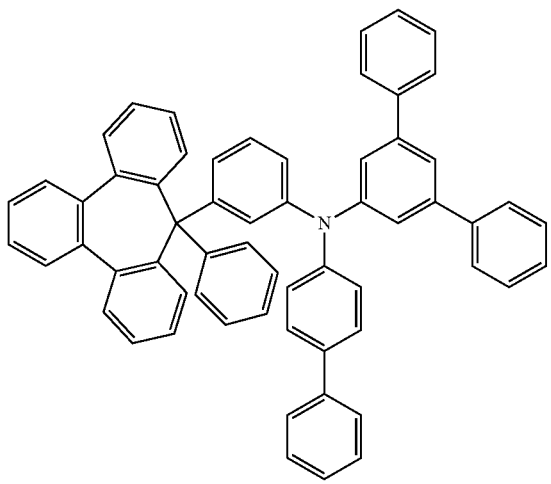
(260)
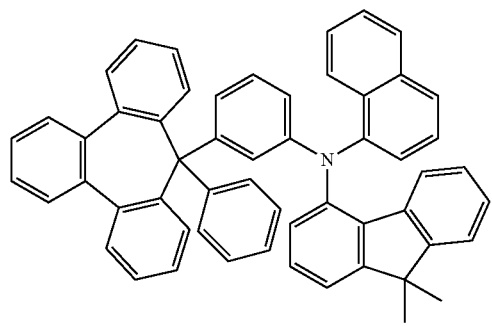
(261)
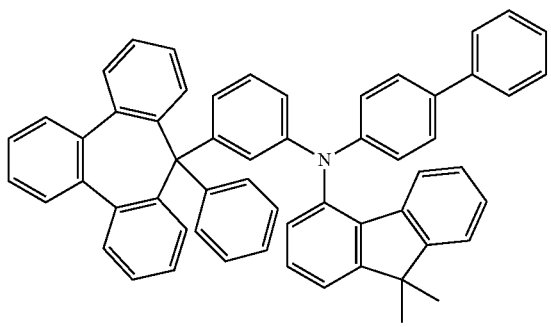
(262)
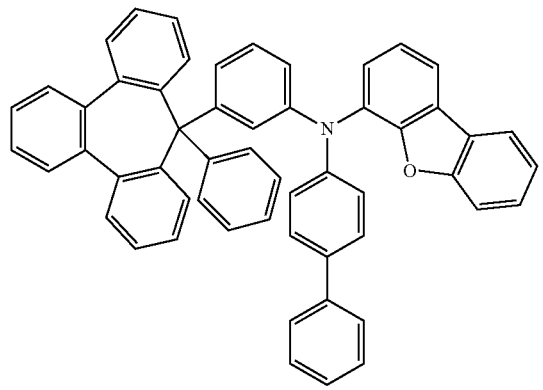
(263)
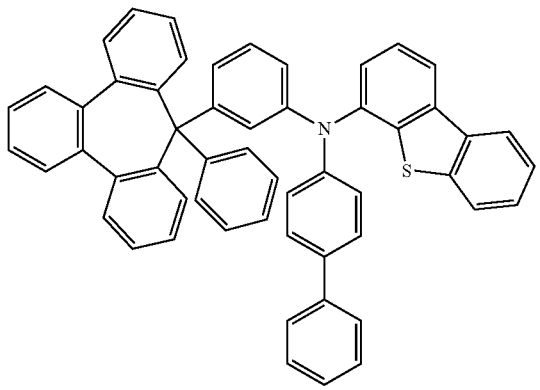
(264)
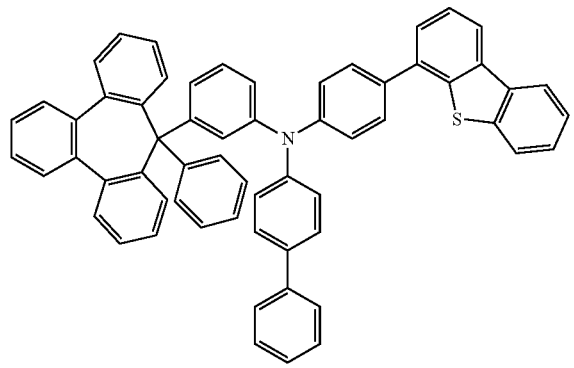
(265)
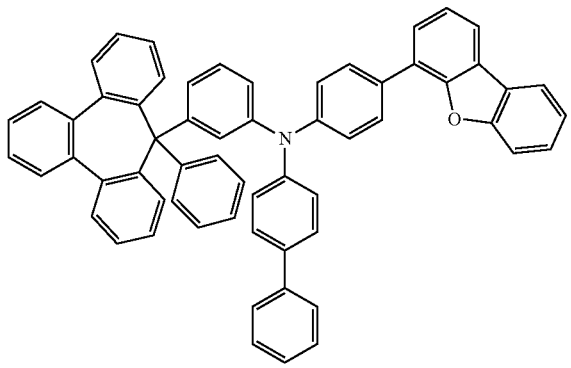

-continued
(266)
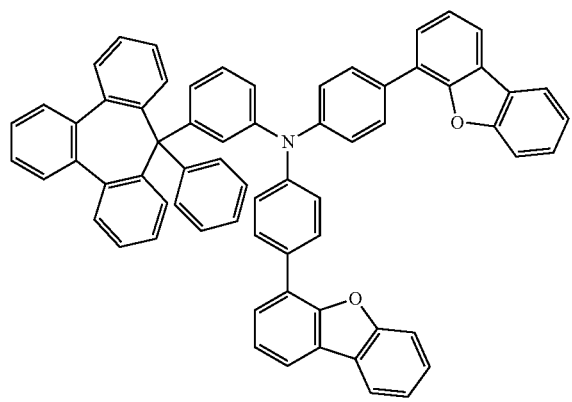
(267)
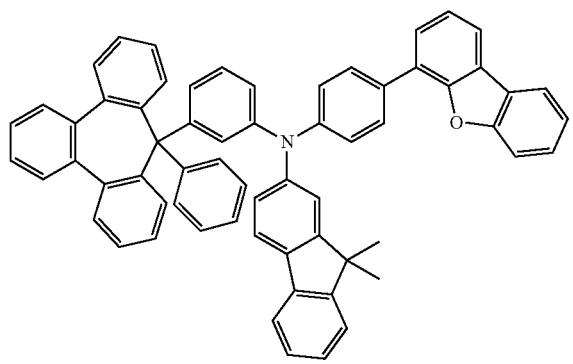
(268)
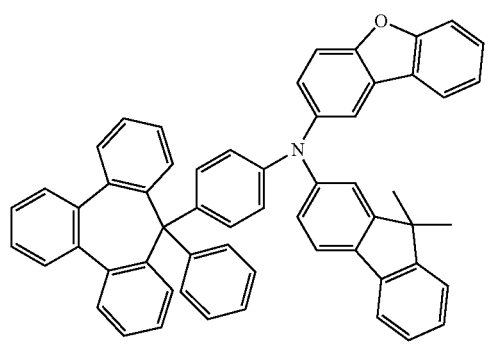
(269)
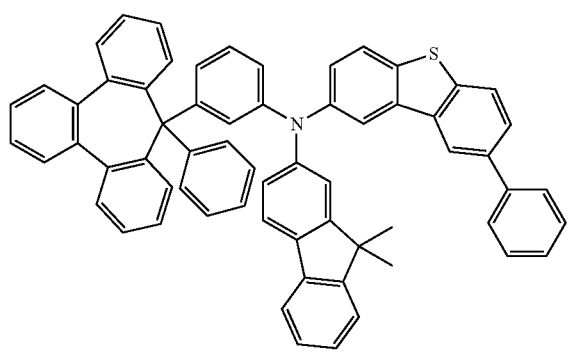
(270)
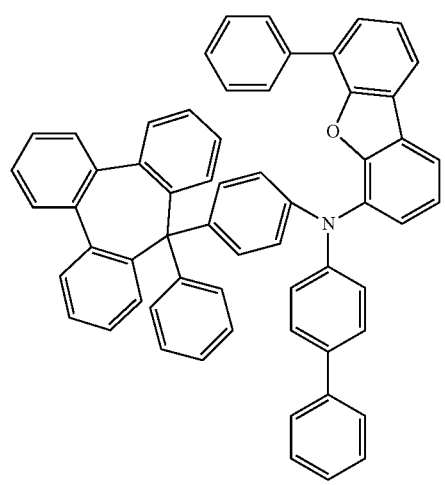
(271)
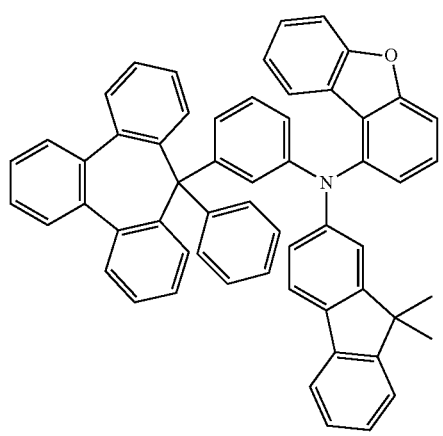

-continued
(272)
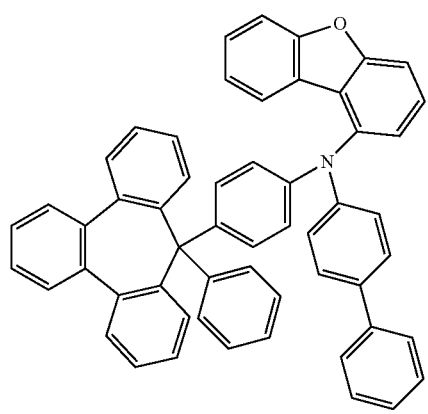
(273)
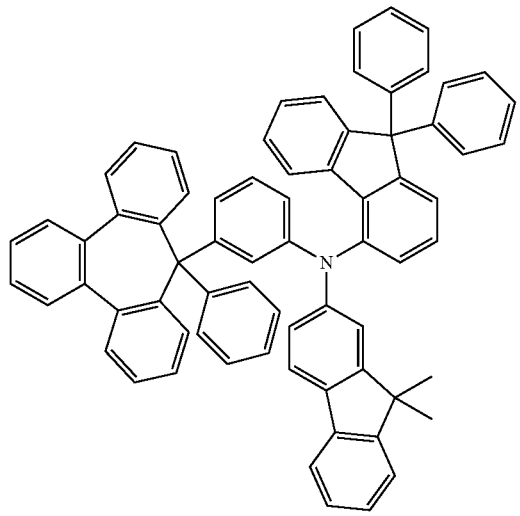
(274)
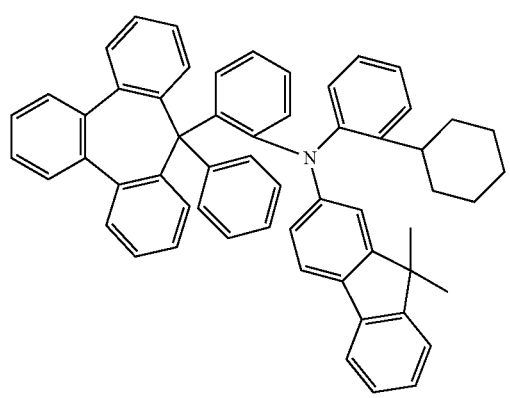
(275)
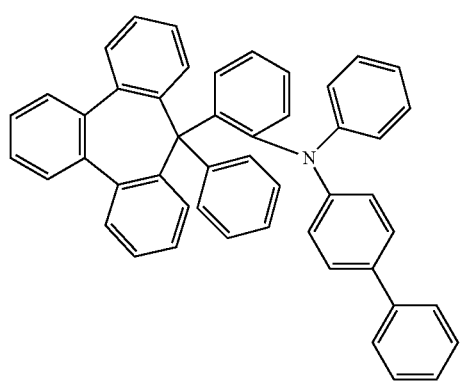
(276)
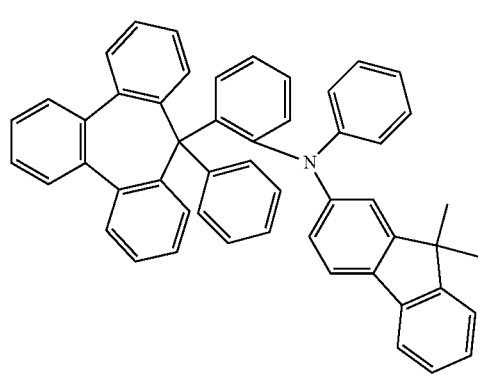
(277)
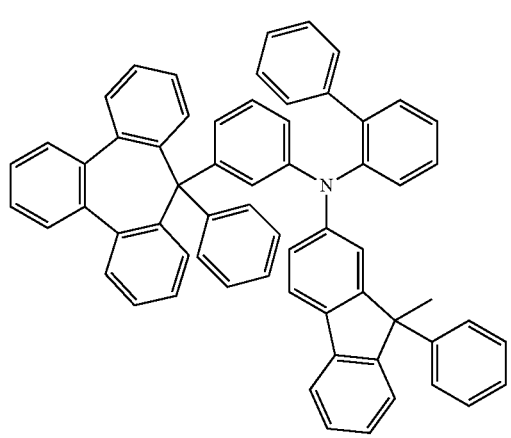

-continued
(278)
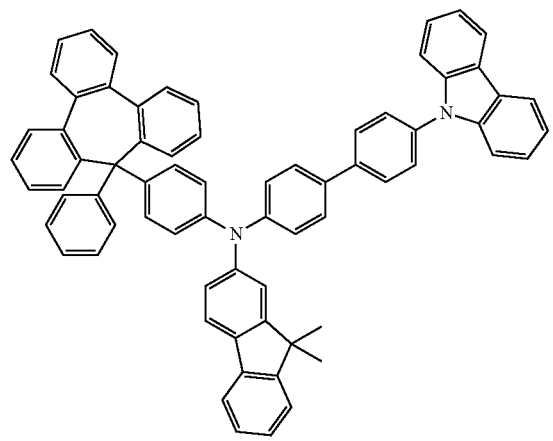
(279)
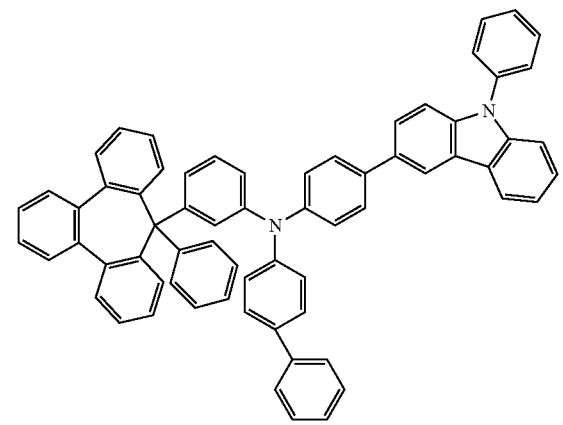
(280)
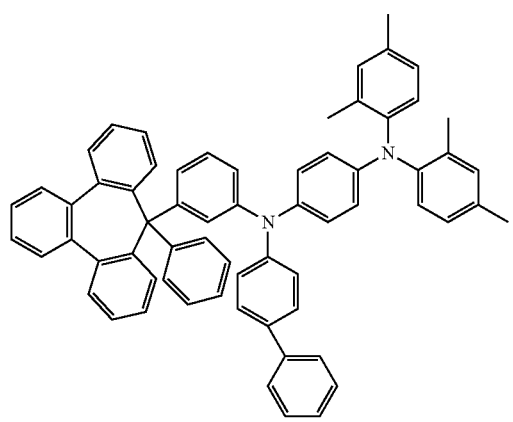
(281)
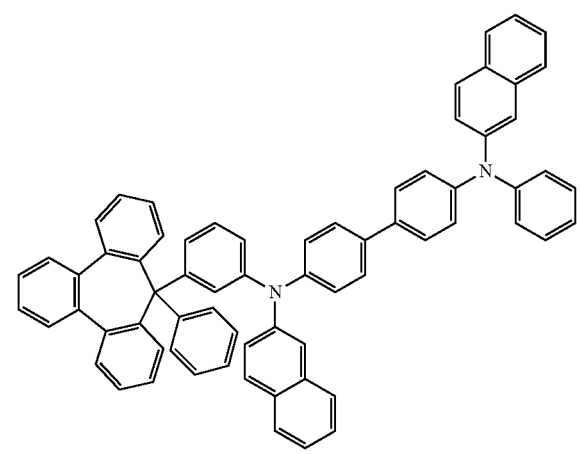
(282)
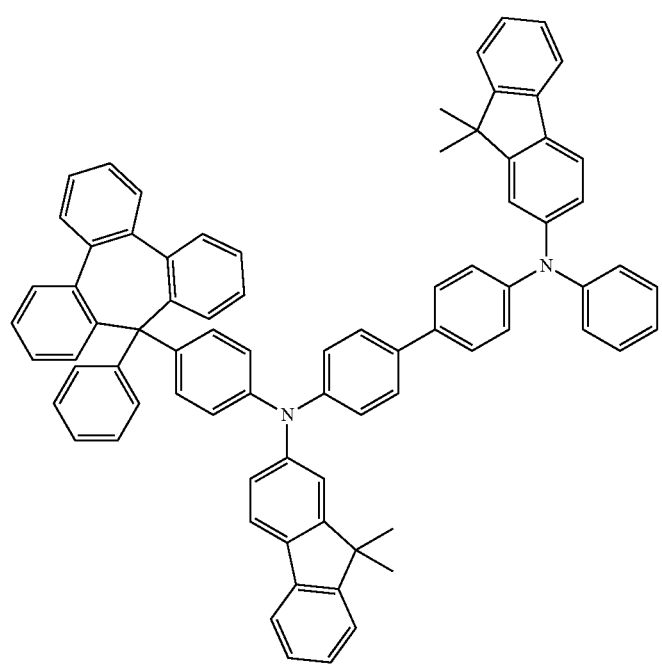

(283)
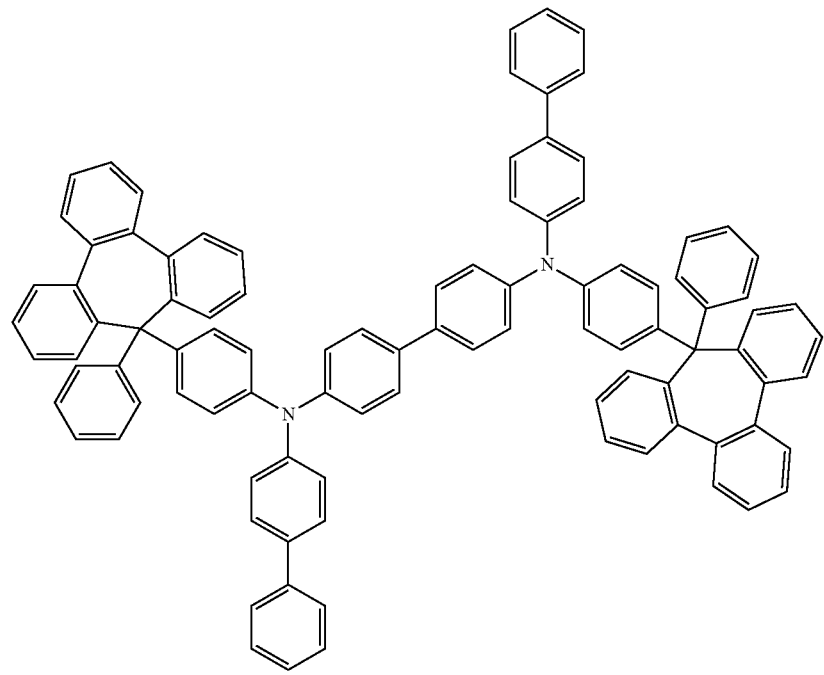
(284)
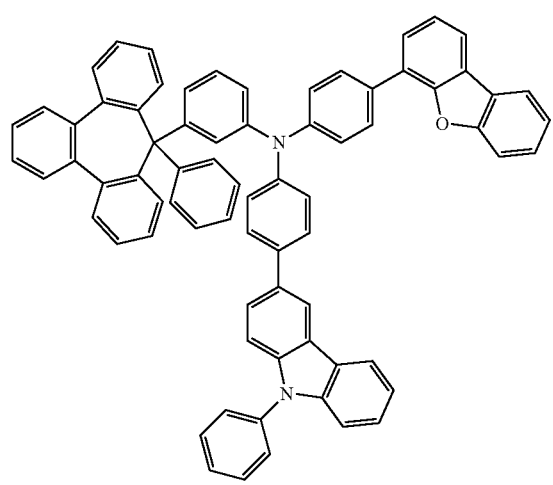
(285)
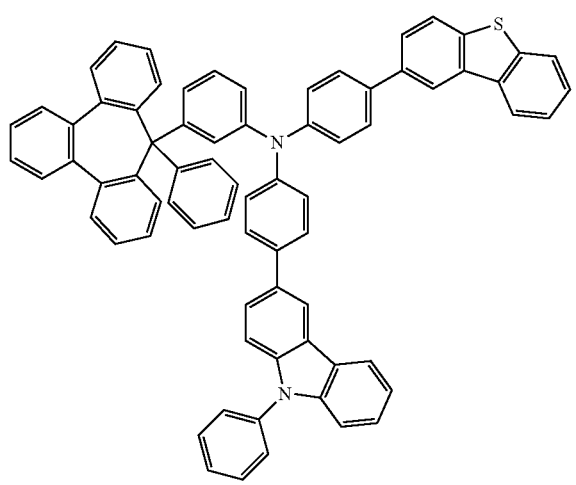

-continued
(286)
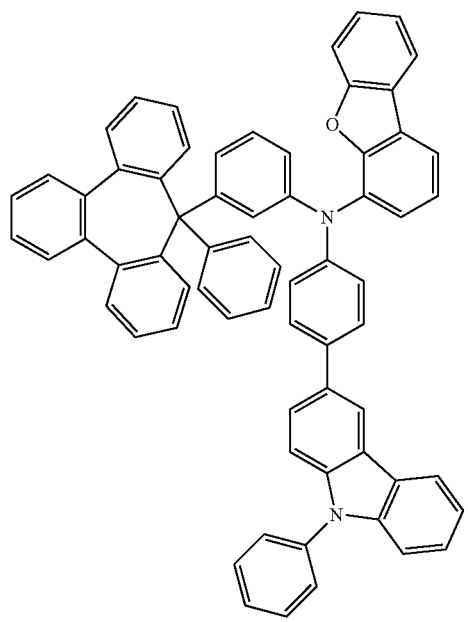
(287)
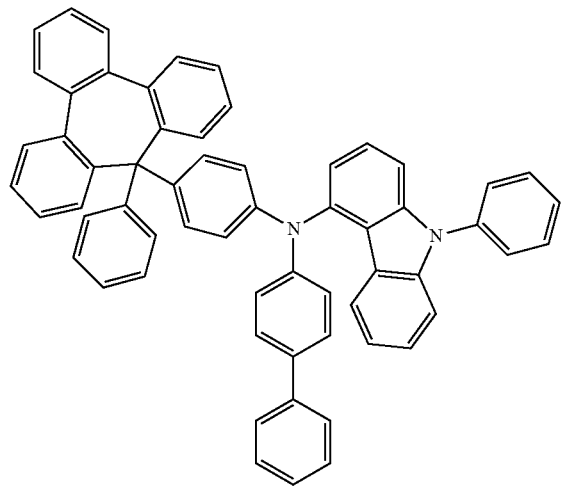
(288)
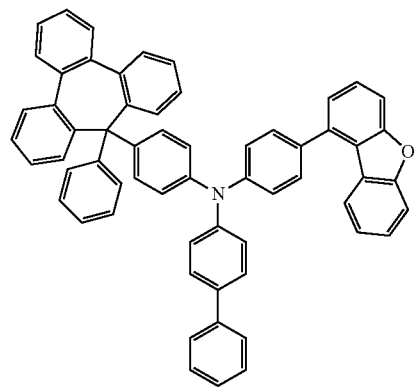
(289)
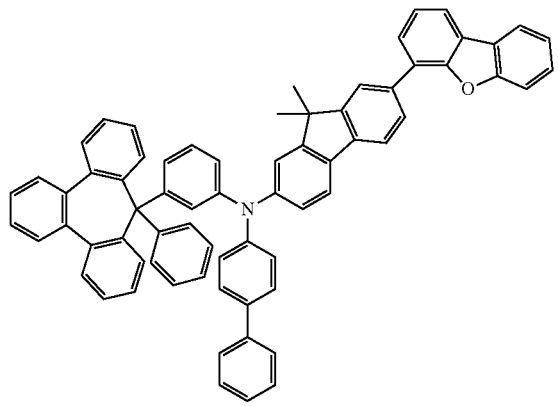
(290)
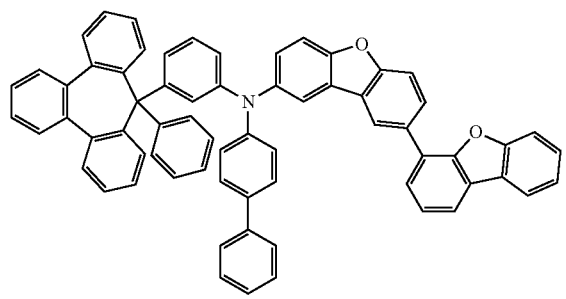
(291)
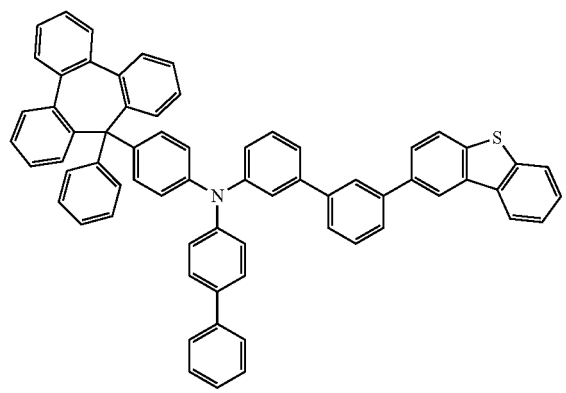

-continued
(292)
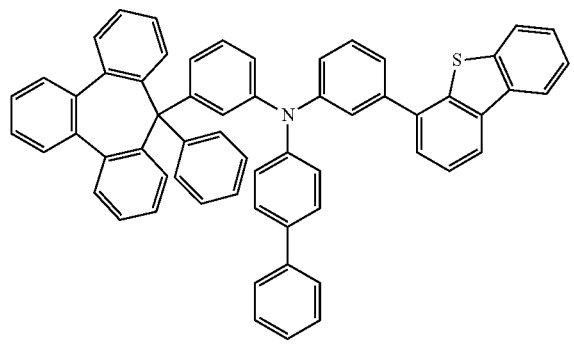
(293)
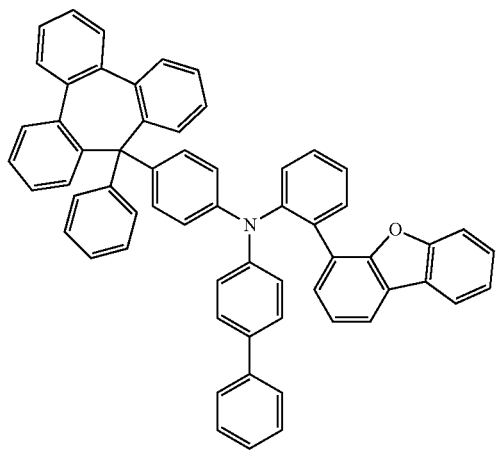
(294)
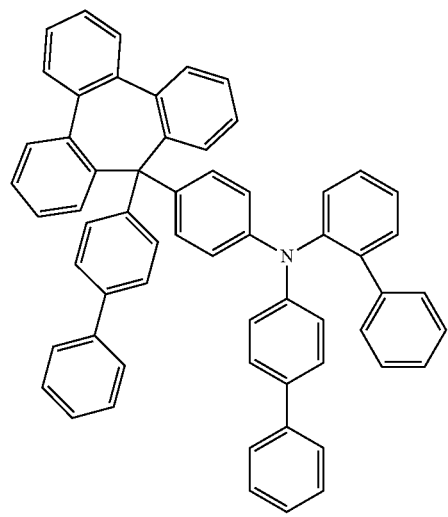
(295)
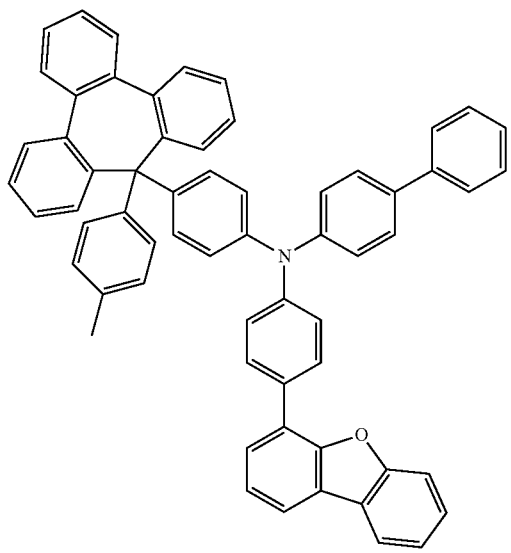
(296)
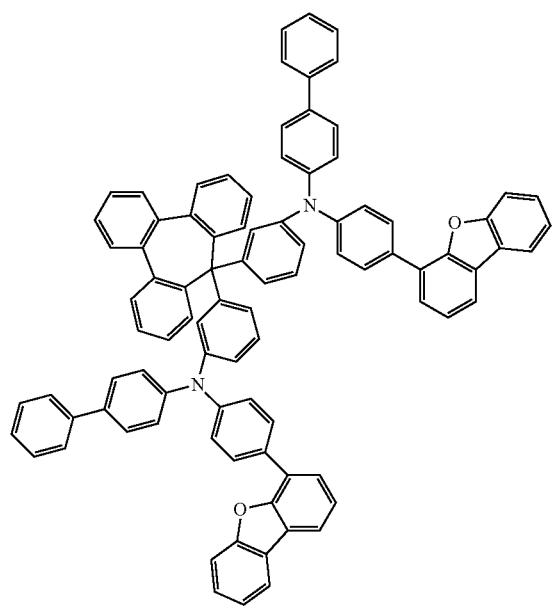
(297)
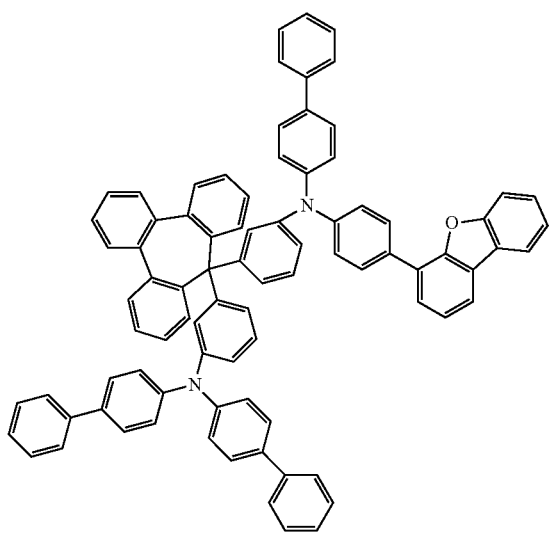

-continued
(298)
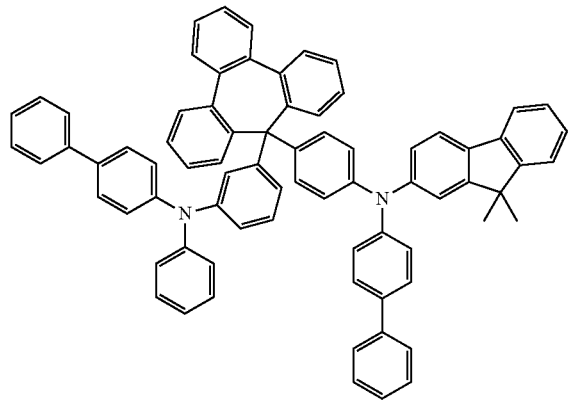
(299)
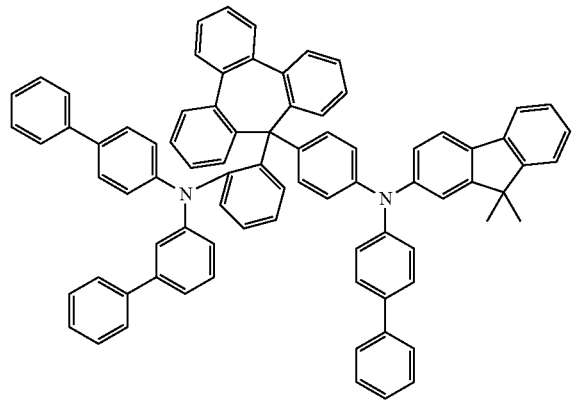
(300)
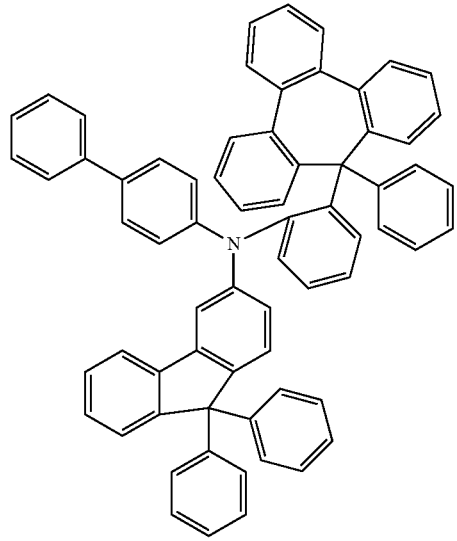
(301)
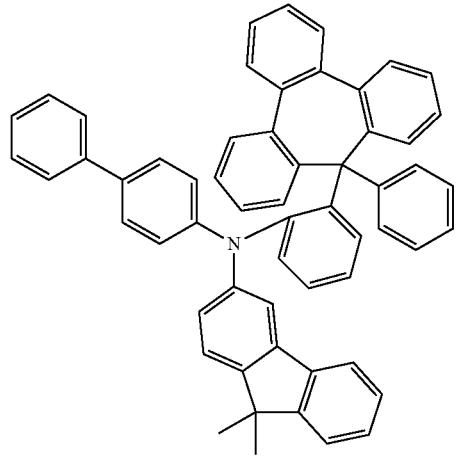
(302)
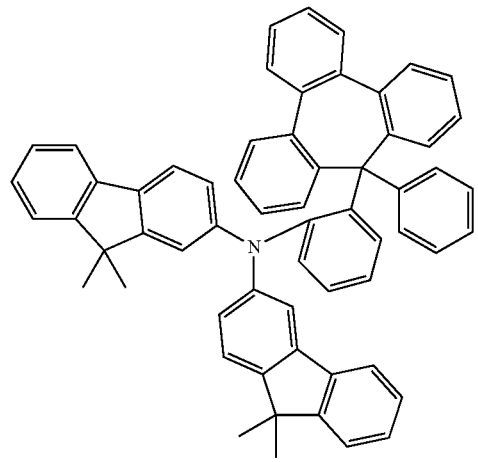
(303)
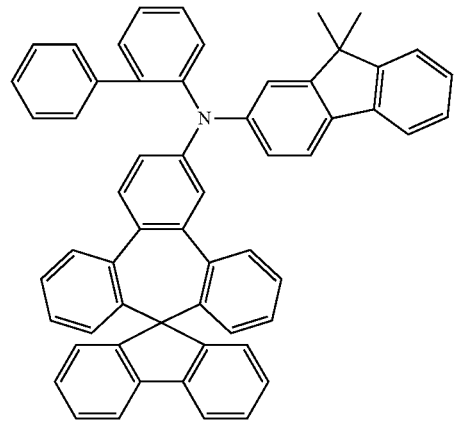

-continued
(304)
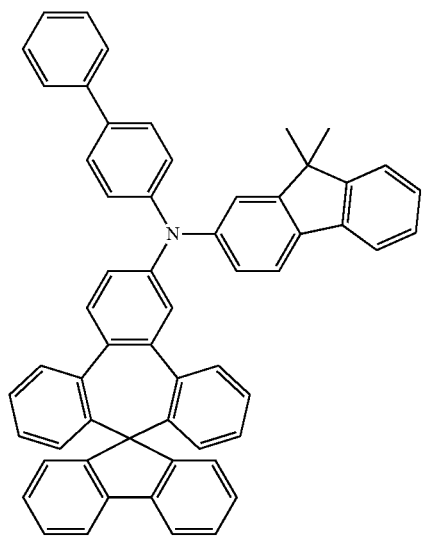
(305)
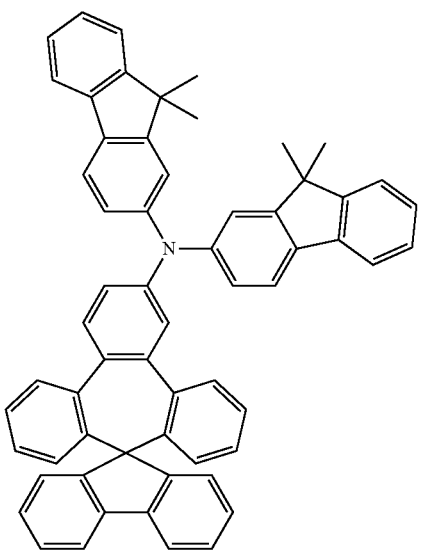
(306)
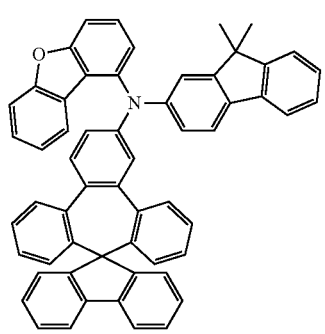
(307)
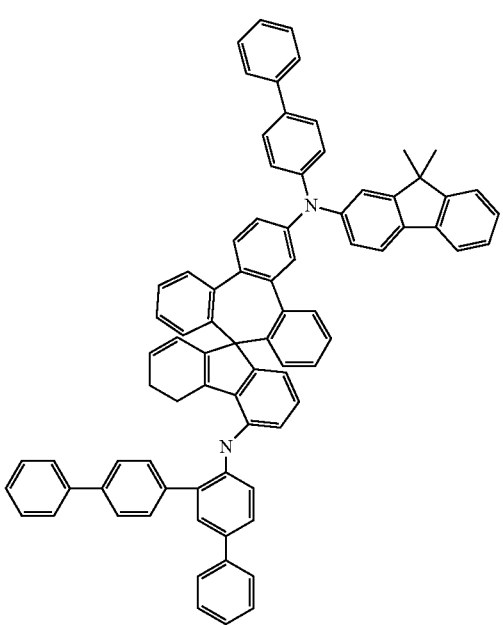

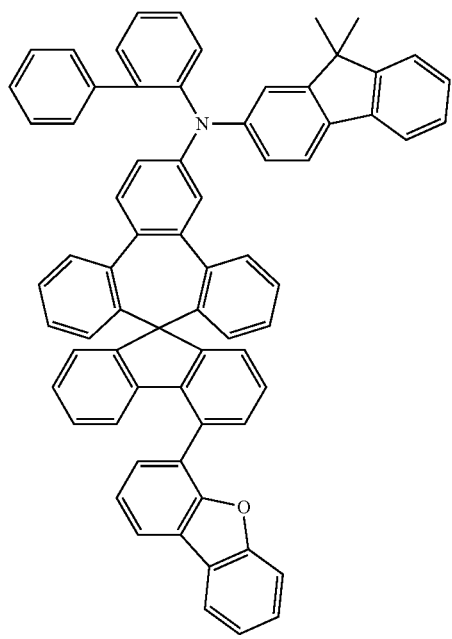

(308)

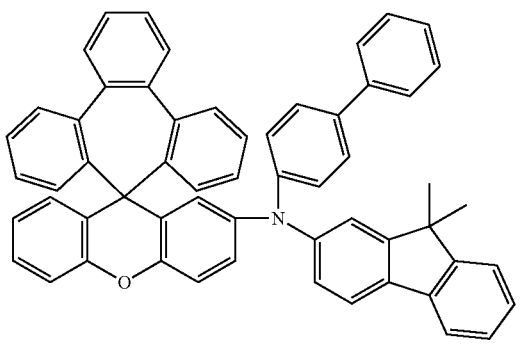

(309)

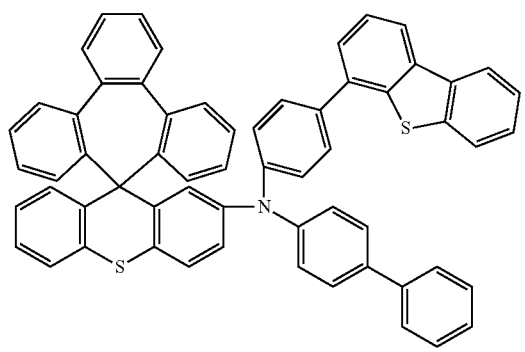

(310)

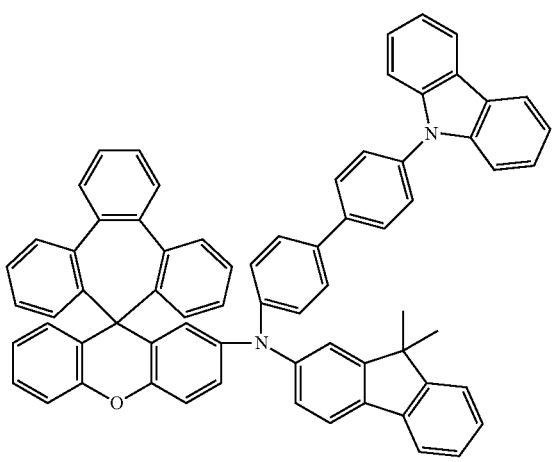

(311)

The inventive compounds can be prepared by synthesis steps known to those skilled in the art, for example bromination, Suzuki coupling, Ullmann coupling, Hartwig-Buchwald coupling, etc.

The synthesis of the inventive compounds proceeds, for example, from tribenzotropone derivatives (9H-tribenzo[a,c,e]cyclohepten-9-one (CAS No.: 68089-73-6)). The reaction with the keto group with appropriately substituted aromatic or heteroaromatic systems can build up the base skeleton. Preference is given here to nucleophilic attack by lithiated aromatics on the keto group. This can also be used to form the spiro centre when m is 1. The reaction forms the quaternary carbon atom of the base skeleton in place of the keto group.

The base skeleton can be functionalized by further coupling reactions, for example by reactive leaving groups, to give compounds of the formula (1). Especially suitable for this purpose are transition metal-catalysed coupling reactions (e.g. Suzuki coupling, Hartwig-Buchwald coupling or Stille coupling). For this purpose, the group to be coupled also has to have a correspondingly suitable leaving group, especially chlorine, bromine, iodine, triflate or a boronic acid derivative, especially boronic acid or a boronic ester.

The present invention therefore further provides a process for preparing a compound of formula (1) wherein the compound of the formula (1) is formed by one or more coupling reactions and/or cyclizations.

The present invention therefore further provides a process for preparing a compound of formula (1) by coupling the base skeleton substituted by a reactive leaving group with
  a) a primary amine, followed by coupling with a further aromatic group substituted by a reactive leaving group, or
  b) with a secondary amine, or
  c) with a triarylamine derivative.

The reactive leaving group here is preferably selected from Cl, Br, I, triflate or tosylate or, for a Suzuki coupling, also boronic acid, or a boronic acid derivative, especially a boronic ester.

The synthesis methods shown above are of illustrative character and can be modified in a suitable manner by the person skilled in the art in the field of organic synthesis if this is advantageous for the synthesis of particular embodiments of inventive compounds.

The above-described inventive compounds, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (1), wherein the bond(s) to the polymer, oligomer or dendrimer, may be localized at any free positions in formula (1). According to the linkage of the inventive compound, the compound is part of a side chain of the oligomer or polymer or part of the main chain.

An oligomer in the context of this invention is understood to mean a compound formed from at least three monomer units. A polymer in the context of this invention is understood to mean a compound formed from at least ten monomer units.

The inventive polymers, oligomers and dendrimers may be conjugated, partly conjugated or nonconjugated. The inventive oligomers or polymers may be linear, branched or dendritic.

In the structures having linear linkage, the units of formula (1) or embodiments thereof may be joined directly to one another, or they may be joined to one another via a bivalent group, for example via a substituted or unsubstituted alkylene group, via a heteroatom or via a bivalent aromatic or heteroaromatic group.

In branched and dendritic structures, it is possible, for example, for 3, 5 or more units of formula (1) or embodiments thereof to be joined by a trivalent or higher-valency group, for example via a trivalent or higher-valency aromatic or heteroaromatic group, to give a branched or dendritic oligomer or polymer.

For the repeat units of formula (1) in oligomers, dendrimers and polymers, the same preferences apply as described above for the inventive compounds.

For preparation of the oligomers or polymers, the monomers of the invention are homopolymerized or copolymerized with further monomers. Suitable and preferred comonomers are chosen from fluorenes (for example according to EP 842208 or WO 2000/22026), spirobifluorenes (for example according to EP 707020, EP 894107 or WO 2006/061181), paraphenylenes (for example according to WO 1992/18552), carbazoles (for example according to WO 2004/070772 or WO 2004/113468), thiophenes (for example according to EP 1028136), dihydrophenanthrenes (for example according to WO 2005/014689 or WO 2007/006383), cis- and trans-indenofluorenes (for example according to WO 2004/041901 or WO 2004/113412), ketones (for example according to WO2005/040302), phenanthrenes (for example according to WO 2005/104264 or WO 2007/017066) or else a plurality of these units. The polymers, oligomers and dendrimers typically contain still further units, for example emitting (fluorescent or phosphorescent) units, for example vinyltriarylamines (for example according to WO 2007/068325) or phosphorescent metal complexes (for example according to WO 2006/003000), and/or charge transport units, especially those based on triarylamines.

The inventive polymers, oligomers and dendrimers have advantageous properties, especially high lifetimes, high efficiencies and good color coordinates.

The inventive polymers and oligomers are generally prepared by polymerization of one or more monomer types, of which at least one monomer leads to repeat units of the formula (1) in the polymer. Suitable polymerization reactions are known to those skilled in the art and are described in the literature. Particularly suitable and preferred polymerization reactions which lead to C—C and C—N bonds are as follows:

(A) SUZUKI polymerization
(B) YAMAMOTO polymerization
(C) STILLE polymerization and
(D) HARTWIG-BUCHWALD polymerization.

How the polymerization can be conducted by these methods and how the polymers can then be separated from the reaction medium and purified is known to those skilled in the art and is described in detail in the literature, for example in WO 2003/048225, WO 2004/037887 and WO 2004/037887.

The present invention thus also provides a process for preparing the inventive polymers, oligomers and dendrimers, which is characterized in that they are prepared by polymerization according to SUZUKI, polymerization according to YAMAMOTO, polymerization according to STILLE or polymerization according to HARTWIG-BUCHWALD. The inventive dendrimers can be prepared by processes known to those skilled in the art or in analogy thereto. Suitable processes are described in the literature, for example in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the inventive compounds from the liquid phase, for example by spin-coating or by printing methods, formulations of the inventive compounds are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentyl benzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of formula (1) or embodiments thereof or at least one polymer, oligomer or dendrimer containing at least one unit of formula (1) or embodiments thereof and at least one solvent, preferably an organic solvent. The way in which such solutions can be prepared is known to those skilled in the art and is described, for example, in WO 2002/072714, WO 2003/019694 and the literature cited therein.

The present invention further provides mixtures comprising at least one inventive compound and at least one further compound. The further compound may, for example, be a fluorescent or phosphorescent dopant when the inventive compound is used as matrix material, especially a phosphorescent dopant. Suitable dopants are detailed below in connection with the organic electroluminescent devices and are also preferred for the inventive mixtures.

The inventive compounds and mixtures are suitable for use in an electronic device. An electronic device is understood to mean a device containing at least one layer containing at least one organic compound. This component may also contain inorganic materials or else layers formed entirely from inorganic materials.

The present invention therefore further provides for the use of the inventive compounds or mixtures in an electronic device, especially in an organic electroluminescent device.

The present invention still further provides an electronic device comprising at least one of the above-detailed inventive compounds or mixtures. In this case, the preferences detailed above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitized solar cells, organic optical detectors, organic photoreceptors, organic field-quench devices (O-FQDs), light-emitting electrochemical cells (LECs), organic laser diodes (O-lasers) and organic plasmon emitting devices (D. M. Koller et al., *Nature Photonics* 2008, 1-4), preferably organic electroluminescent devices (OLEDs, PLEDs), especially phosphorescent OLEDs.

The organic electroluminescent device comprises cathode, anode and at least one emitting layer. Apart from these layers, it may comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily each of these layers need be present. In this case, it is possible for the organic electroluminescent device to contain an emitting layer, or for it to contain a plurality of emitting layers. If a plurality of emission layers are present, these preferably have several emission maxima between 380 nm and 750 mm overall, such that the overall result is white emission; in other words, various emitting compounds which may fluoresce or phosphoresce are used in the emitting layers. Especially preferred are systems having three emitting layers, where the three layers show blue, green and orange or red emission (for the basic construction see, for example, WO 2005/011013). These may be fluorescent or phosphorescent emission layers or else hybrid systems in which fluorescent and phosphorescent emission layers are combined with one another.

The inventive compound according to the above-detailed embodiments may be used in different layers, according to the exact structure. Preference is given to an organic electroluminescent device containing a compound of formula (1) or according to the preferred embodiments as matrix material for fluorescent or phosphorescent emitters, especially for phosphorescent emitters, and/or in an electron-blocking or exciton-blocking layer and/or in a hole transport layer and/or in a hole injection layer, according to the exact substitution. In this context, the above-detailed preferred embodiments also apply to the use of the materials in organic electronic devices.

In a preferred embodiment of the invention, the compound of formula (1) or according to the preferred embodiments is used as hole transport material and/or hole injection material.

If the compound of formula (1) or according to the preferred embodiments is used as hole transport material in a hole transport layer, a hole injection layer or an electron blocker layer, the compound can be used as pure material, i.e. in a proportion of 100%, in the hole transport layer, or it can be used in combination with one or more further compounds. In a preferred embodiment, the organic layer containing the compound of the formula (1) then additionally contains one or more p-dopants. p-dopants used according to the present invention are preferably those organic electron acceptor compounds capable of oxidizing one or more of the other compounds in the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600, WO 2012/095143 and DE 102012209523.

Particularly preferred p-dopants are quinodimethane compounds, azaindenofluorenediones, azaphenalenes, azatriphenylenes, $I_2$, metal halides, preferably transition metal halides, metal oxides, preferably metal oxides containing at least one transition metal or a metal of main group 3, and transition metal complexes, preferably complexes of Cu, Co, Ni, Pd and Pt with ligands containing at least one oxygen atom as bonding site. Preference is further given to transition metal oxides as dopants, preferably oxides of rhenium, molybdenum and tungsten, more preferably $Re_2O_7$, $MoO_3$, $WO_3$ and $ReO_3$. Preference is further given to bismuth complexes having electron-deficient carboxylate ligands, preferably fluorinated carboxylate ligands.

The p-dopants are preferably in substantially homogeneous distribution in the p-doped layers. This can be achieved, for example, by coevaporation of the p-dopant and the hole transport material matrix.

Preferred p-dopants are especially the following compounds:

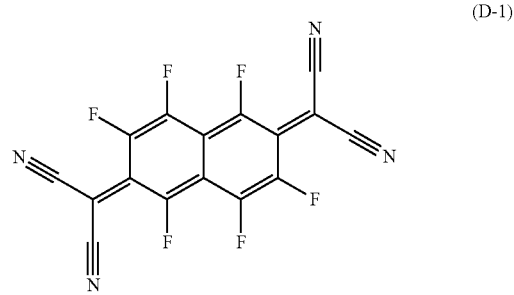

(D-1)

(D-2) 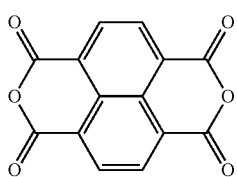
(D-3) 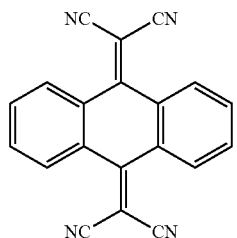
(D-4) 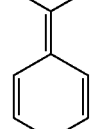
(D-5) 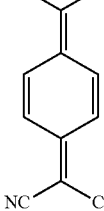
(D-6) 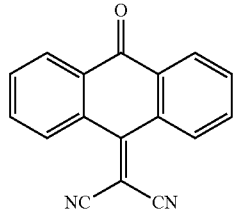
(D-7) 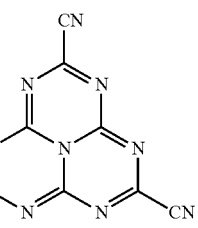
(D-7) 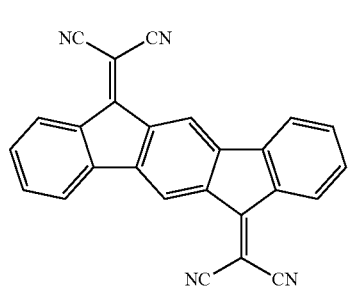
(D-8) 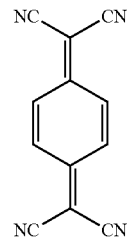
(D-9) 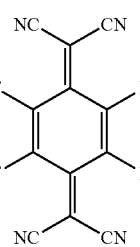
(D-10) 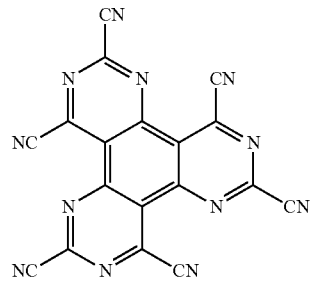
(D-11) 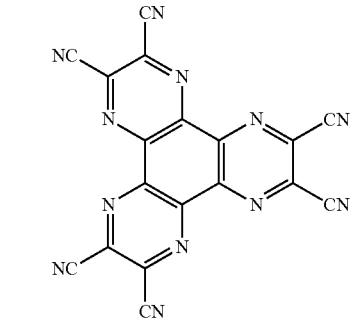
(D-12) 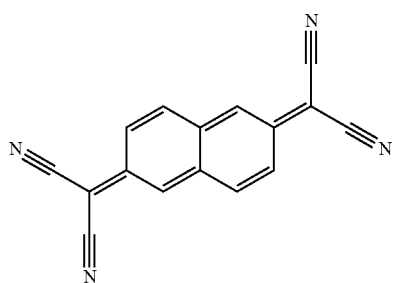

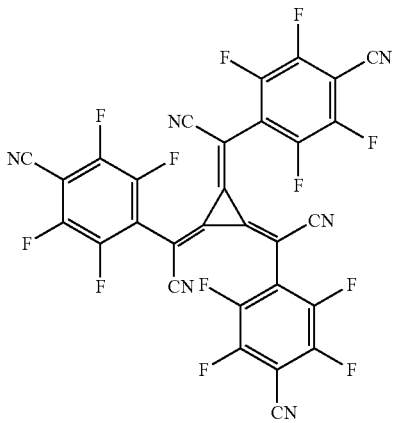

(D-13)

In a preferred embodiment of the invention, the compound of formula (1) or according to the preferred embodiments is used as matrix material for a fluorescent or phosphorescent compound, especially for a phosphorescent compound, in an emitting layer. In this case, the organic electroluminescent device may contain an emitting layer, or it may contain a plurality of emitting layers, where at least one emitting layer contains at least one inventive compound as matrix material.

A further preferred embodiment of the present invention is the use of the compound of formula (1) or according to the preferred embodiments as matrix material for a phosphorescent emitter in combination with a further matrix material. Particularly suitable matrix materials which can be used in combination with the compounds of formula (1) or according to the preferred embodiments are aromatic ketones, aromatic phosphine oxides or aromatic sulphoxides or sulphones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109 and WO 2011/000455, azacarbazole derivatives, for example according to EP 1617710, EP 1617711, EP 1731584, JP 2005/347160, bipolar matrix materials, for example according to WO 2007/137725, silanes, for example according to WO 005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or according to the unpublished application EP 11003232.3, triphenylene derivatives, for example according to WO 2012/048781, or lactams, for example according to WO 2011/116865 or WO 2011/137951. It is likewise possible for a further phosphorescent emitter which emits at a shorter wavelength than the actual emitter to be present as co-host in the mixture.

The mixture of the compound of formula (1) or according to the preferred embodiments and the emitting compound contains between 99% and 1% by volume, preferably between 98% and 10% by volume, more preferably between 97% and 60% by volume and especially between 95% and 80% by volume of the compound of formula (1) or according to the preferred embodiments, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

The term "phosphorescent dopants (emitters)" typically encompasses compounds where the emission of light is effected through a spin-forbidden transition, for example a transition from an excited triplet state or a state having a higher spin quantum number, for example a quintet state.

Suitable phosphorescent dopants are especially compounds which, when suitably excited, emit light, preferably in the visible region, and also contain at least one atom of atomic number greater than 20, preferably greater than 38, and less than 84, more preferably greater than 56 and less than 80. Preferred phosphorescent dopants are compounds containing copper, molybdenum, tungsten, rhenium, ruthenium, osmium, rhodium, iridium, palladium, platinum, silver, gold or europium, especially compounds containing iridium, platinum or copper.

In the context of the present invention, all luminescent iridium, platinum or copper complexes are considered to be phosphorescent compounds.

Examples of phosphorescent dopants can be found in applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used for phosphorescent OLEDs according to the prior art and as known to those skilled in the art in the field of organic electroluminescent devices are suitable for use in the inventive devices. It is also possible for the person skilled in the art, without exercising inventive skill, to use further phosphorescent complexes in combination with the inventive compounds in OLEDs.

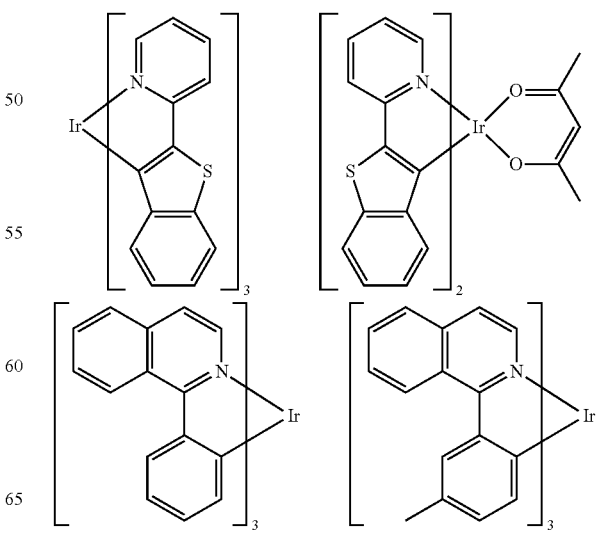

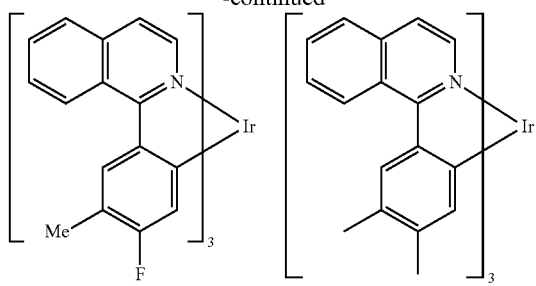
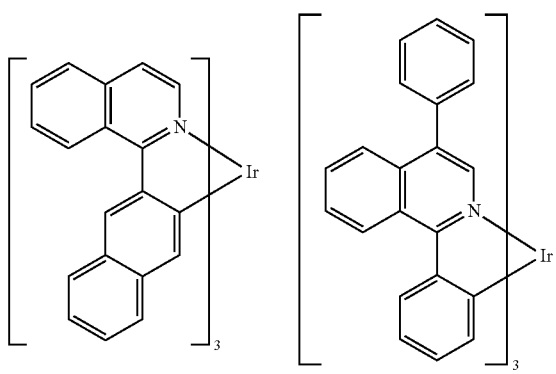
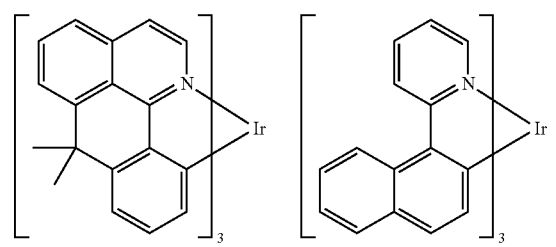
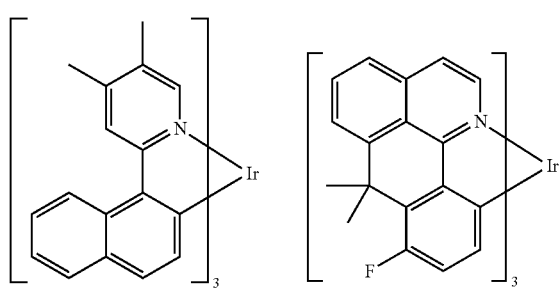
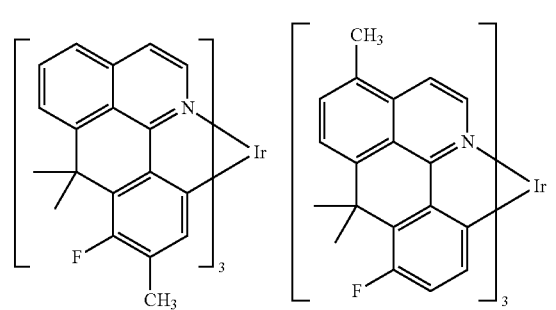
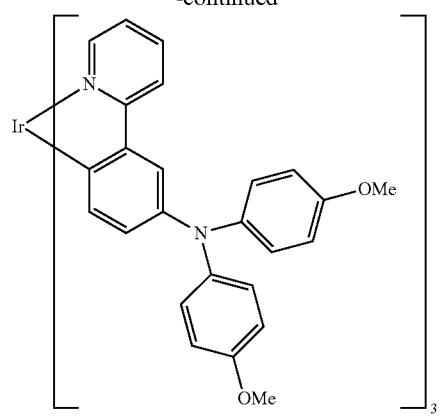
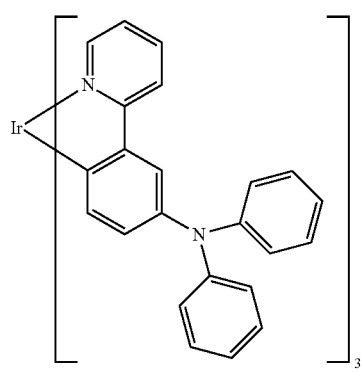
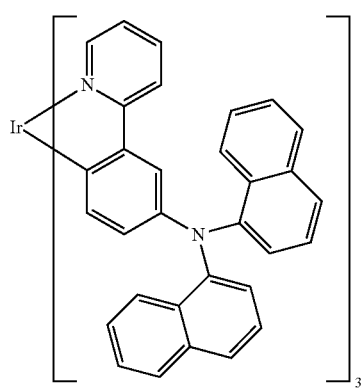
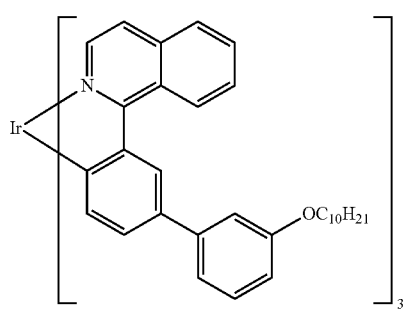

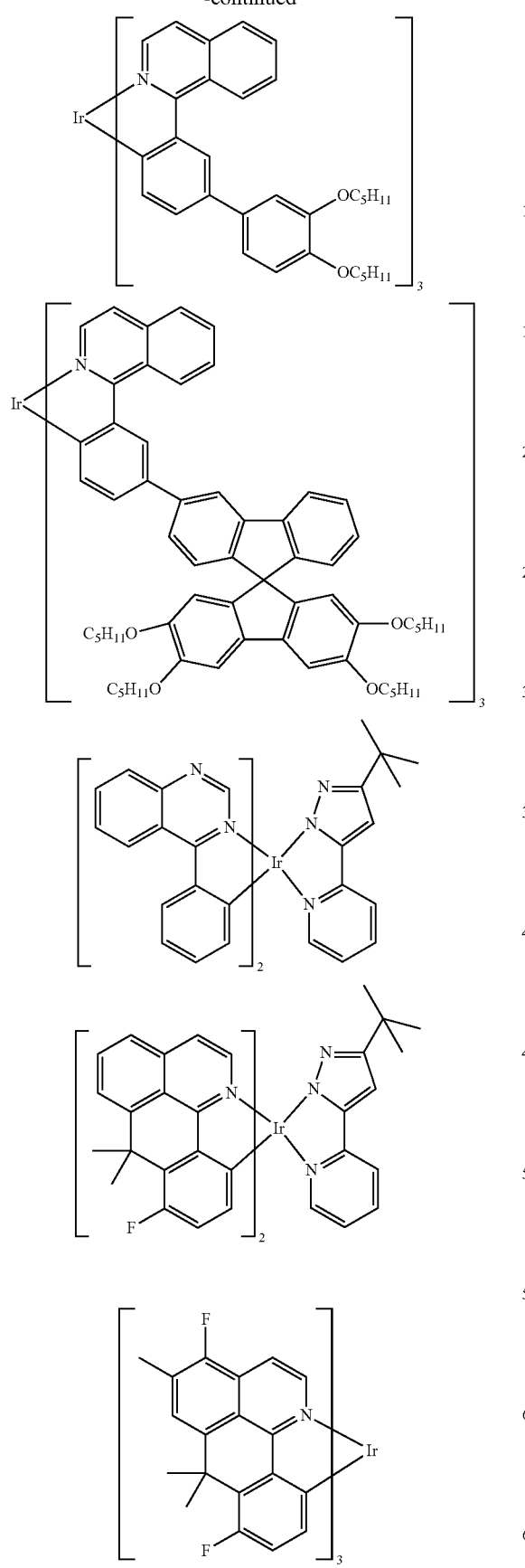
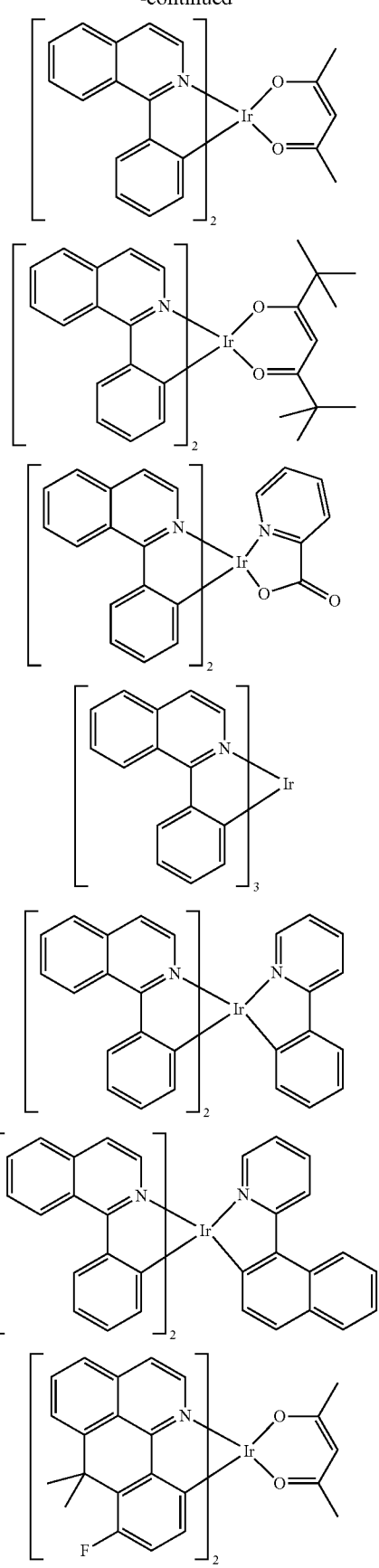

173
-continued
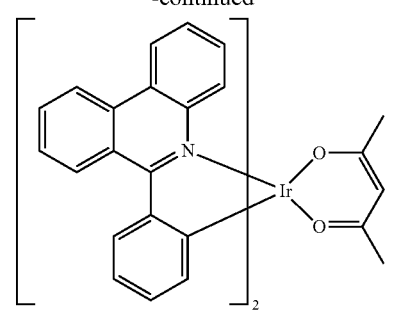
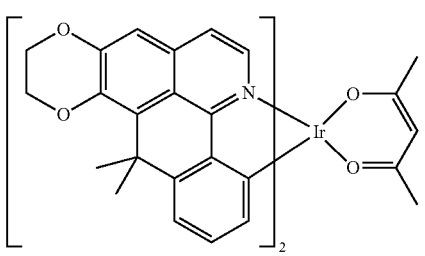
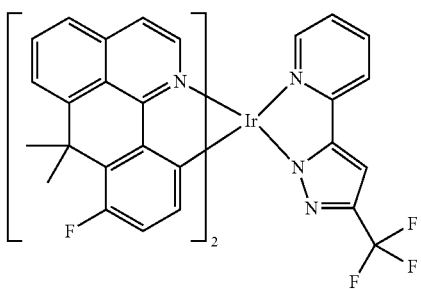
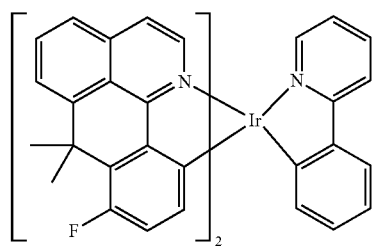
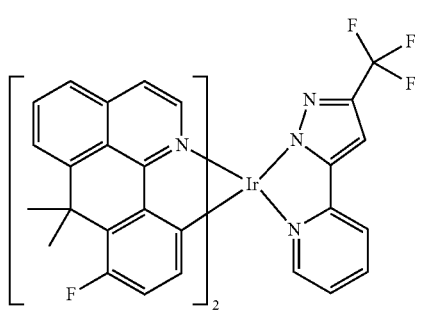
174
-continued
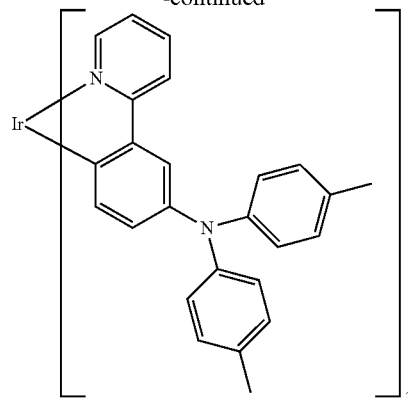
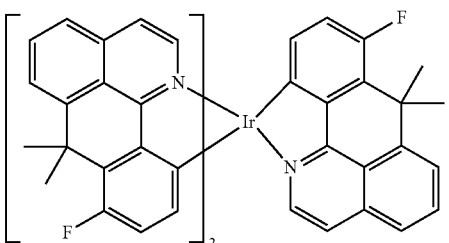
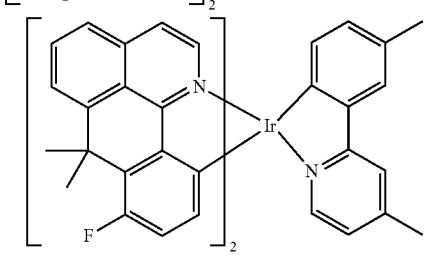
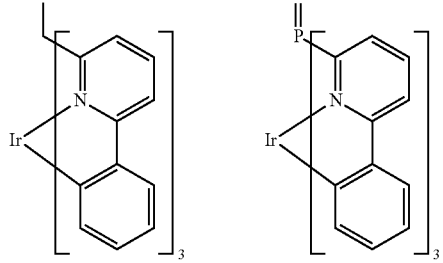
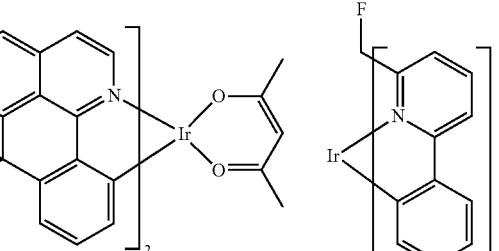
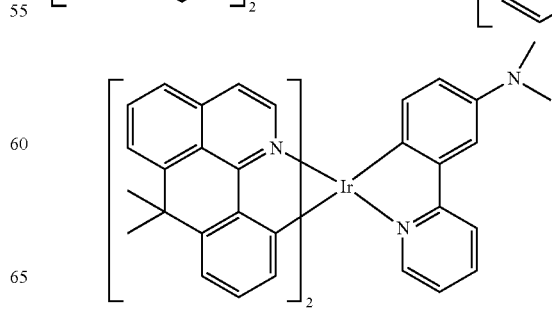

-continued
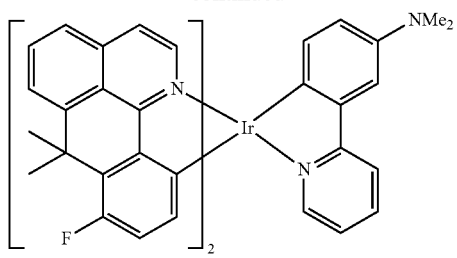
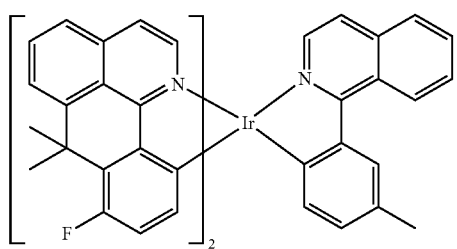
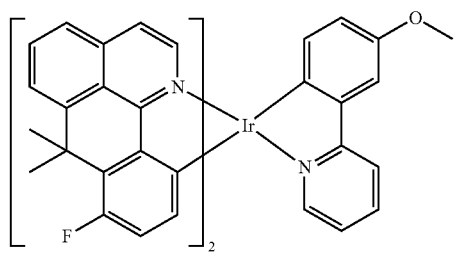
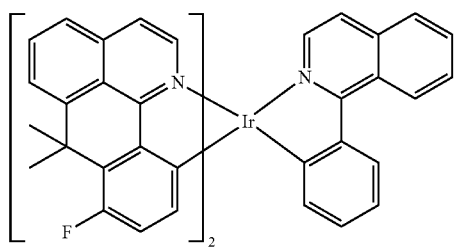
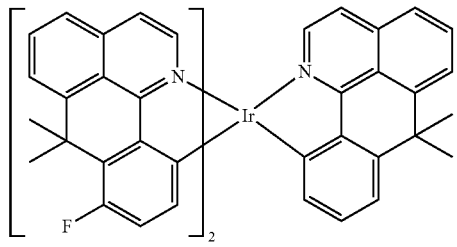
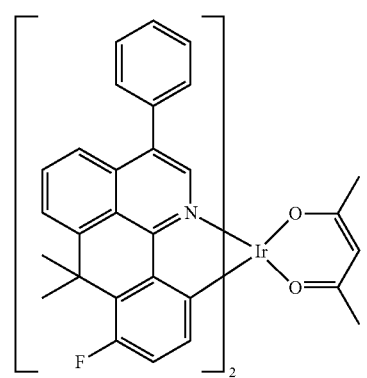
-continued
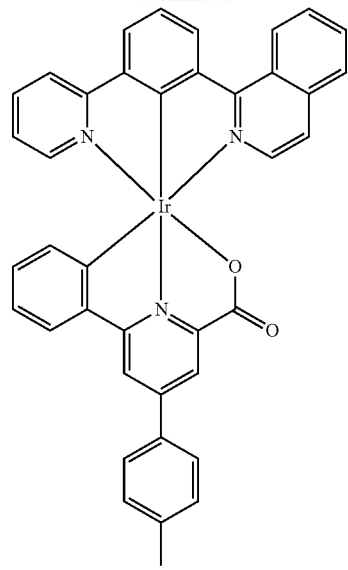
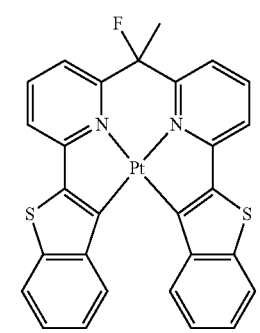
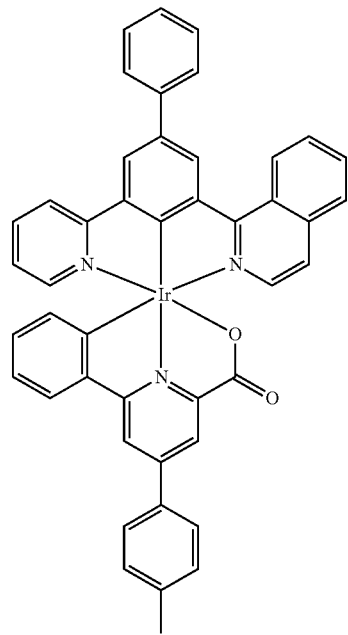

177
-continued
178
-continued
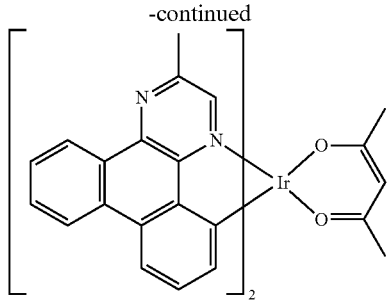
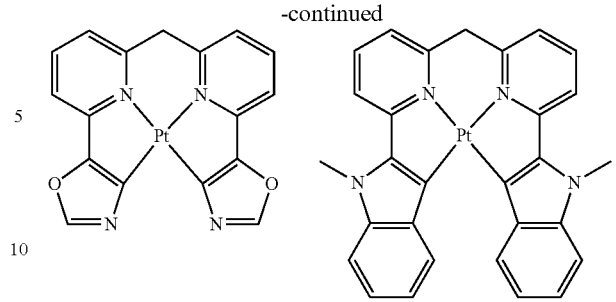
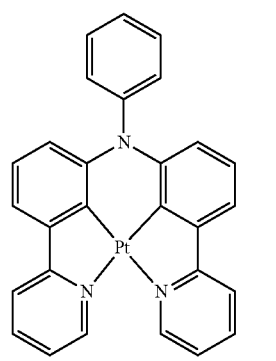
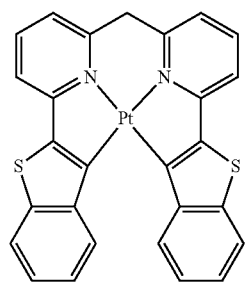
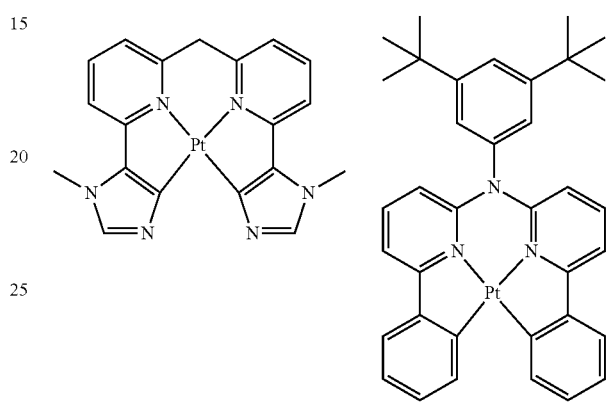
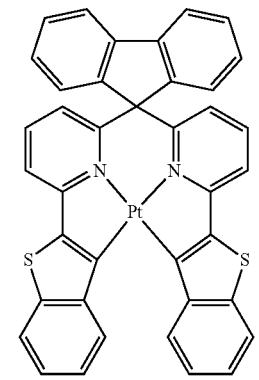
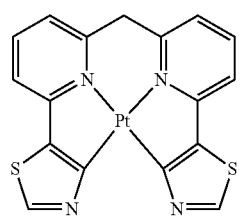
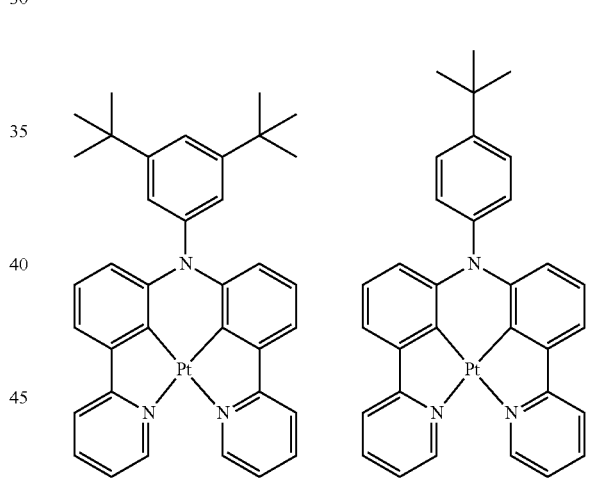
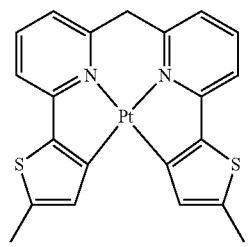
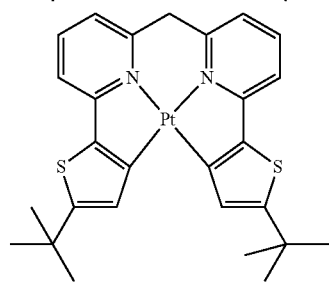
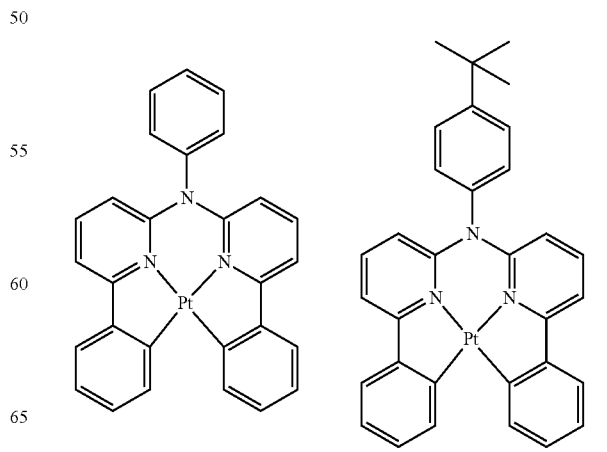

179
-continued
180
-continued
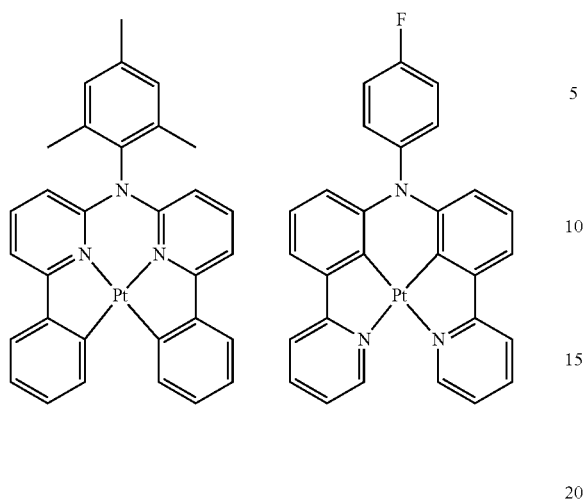
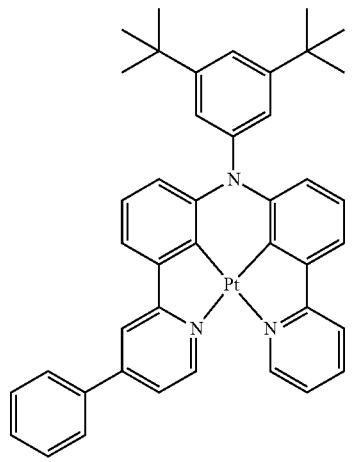
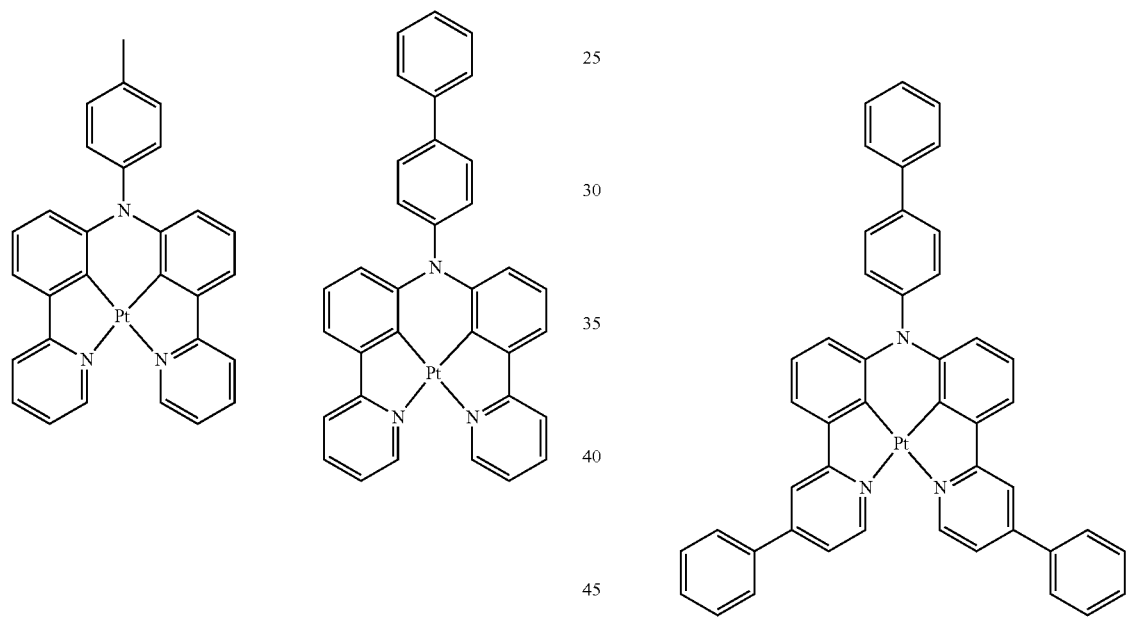
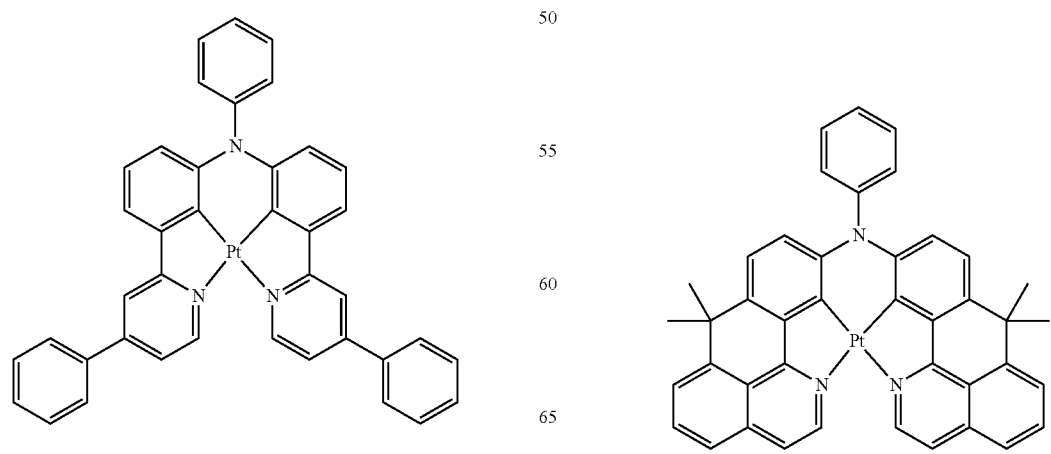

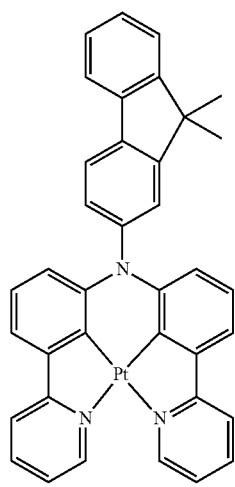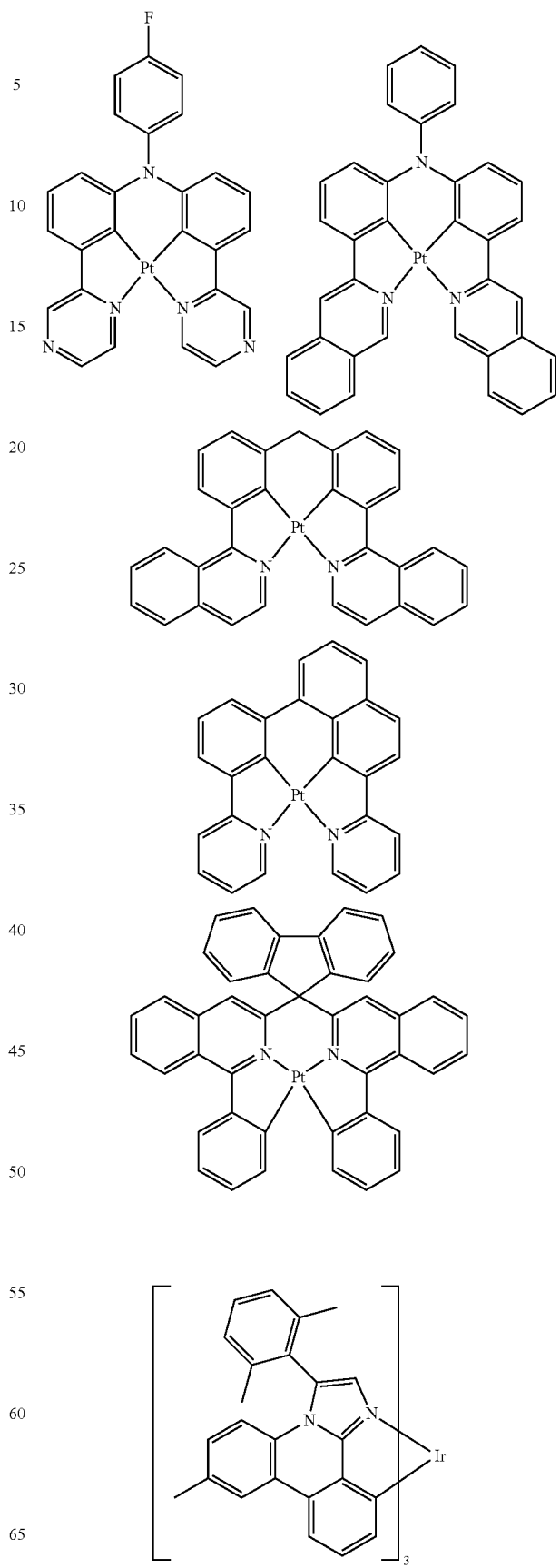

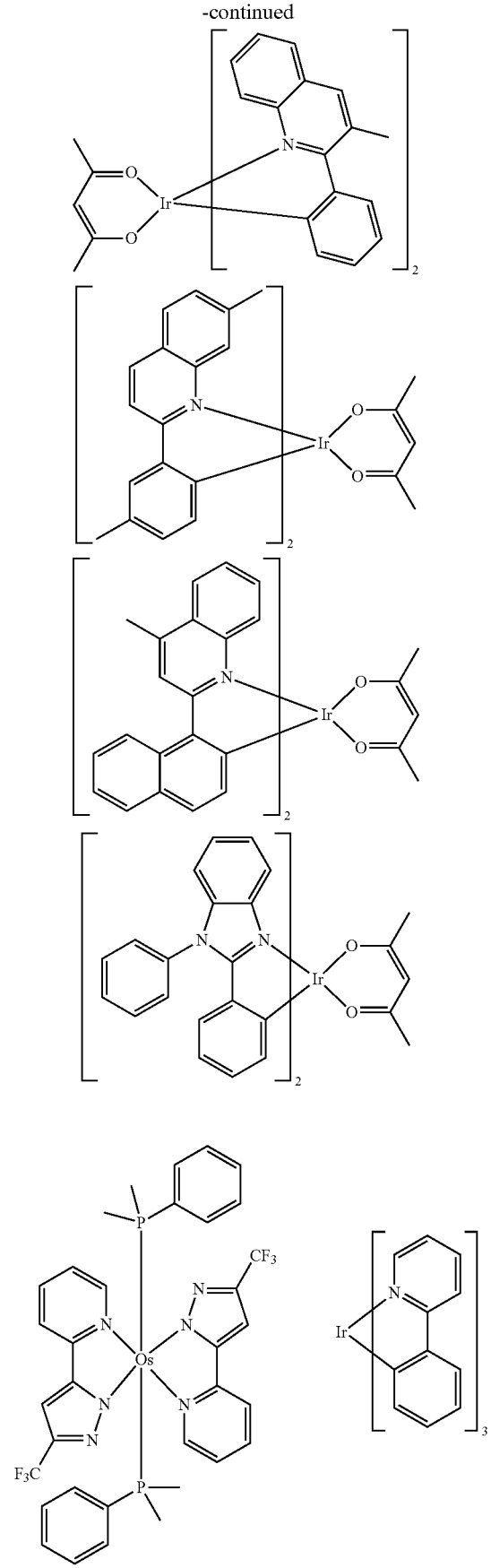
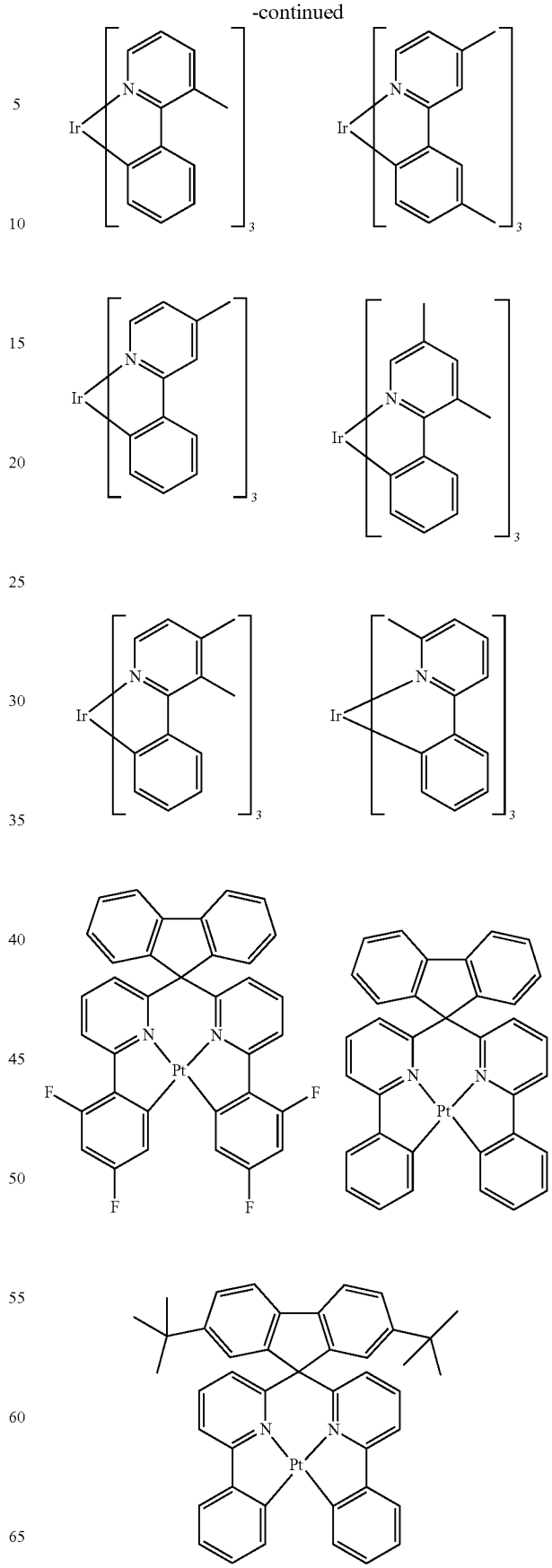

185
-continued
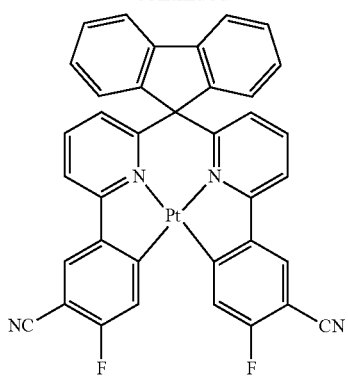
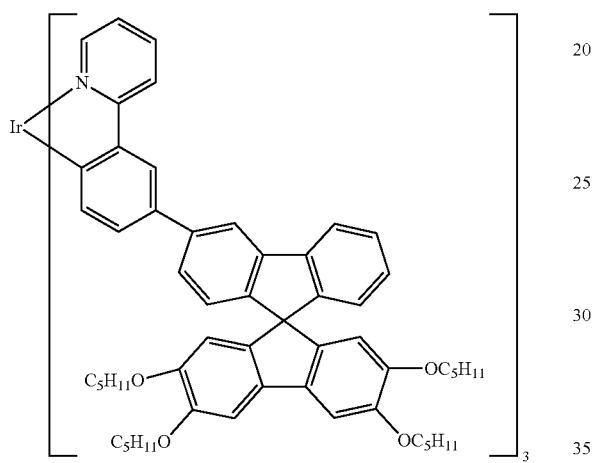
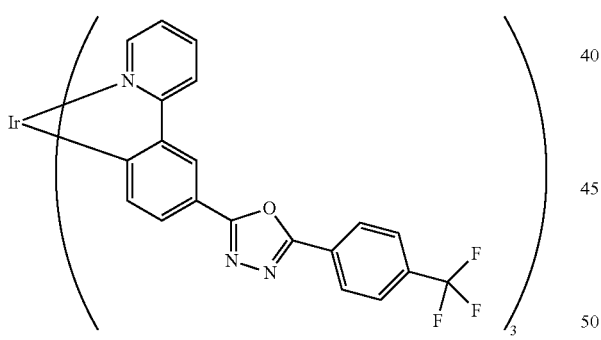
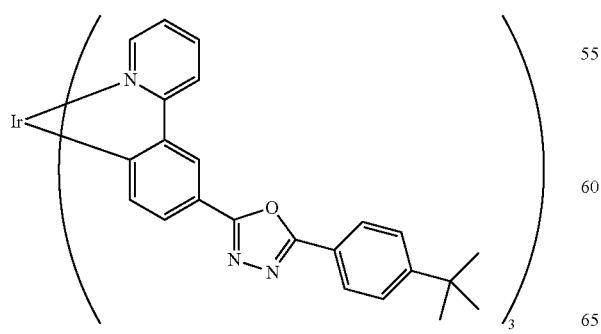
186
-continued
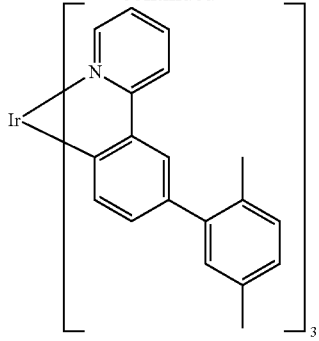
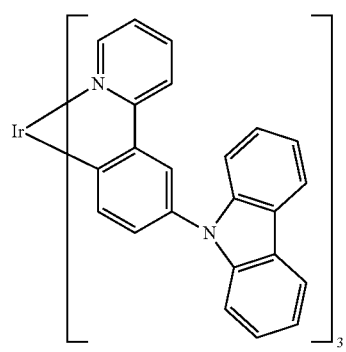
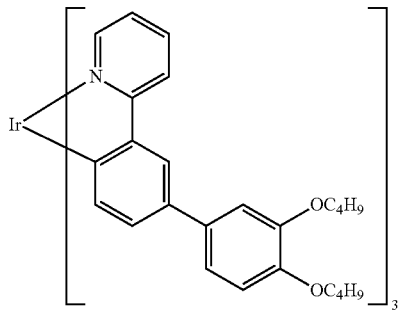
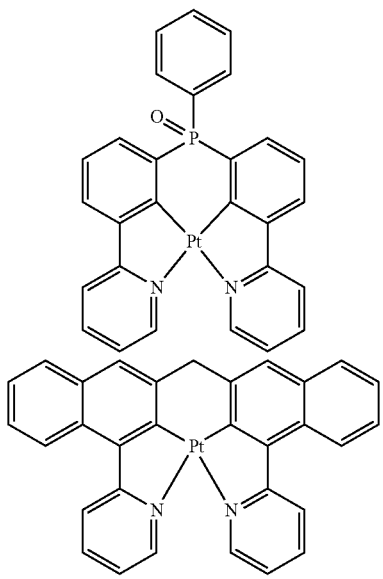

187
-continued
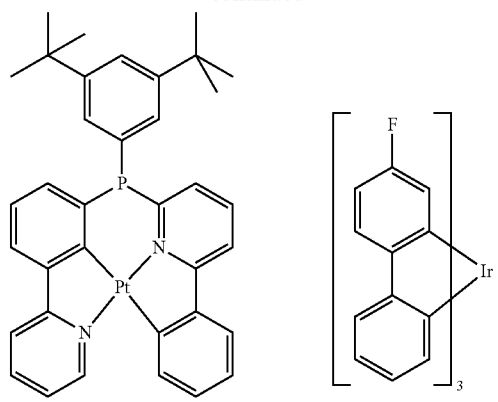
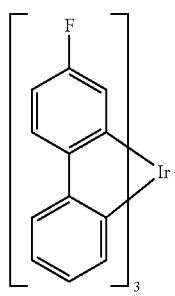
188
-continued
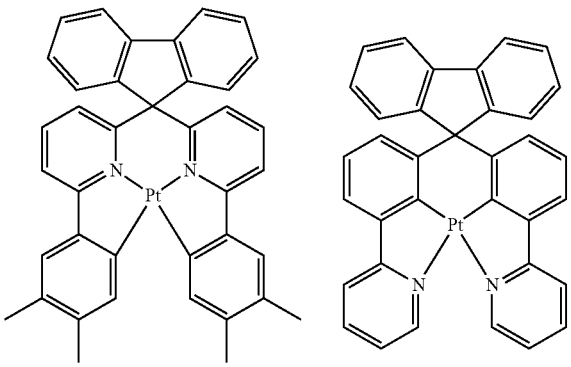
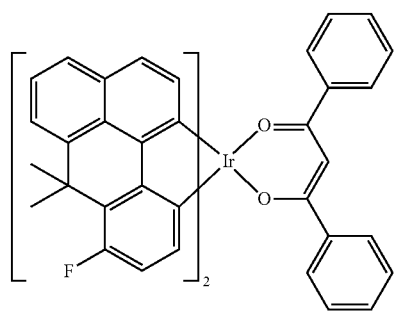
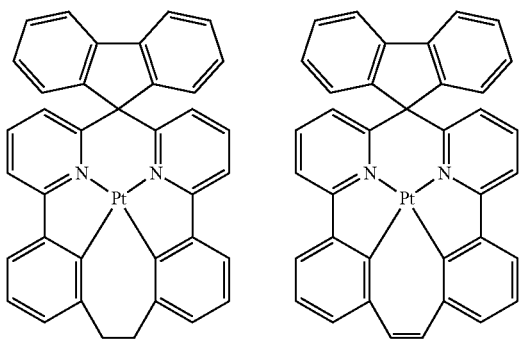
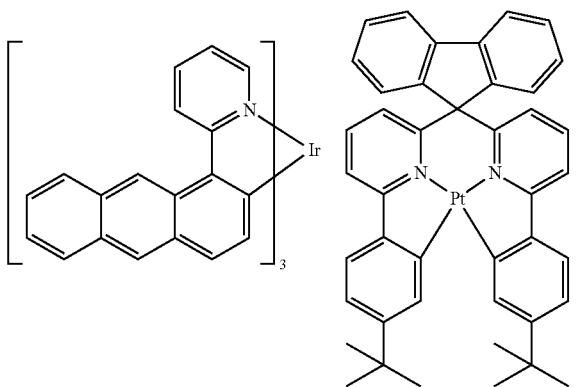
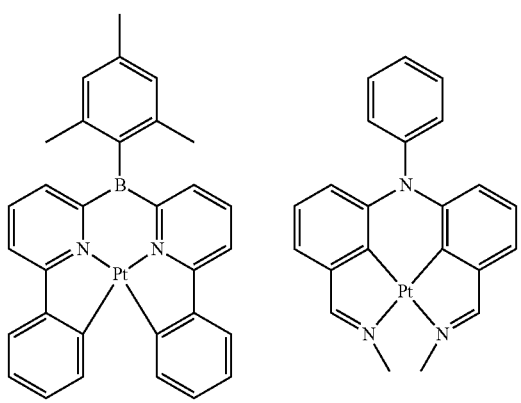
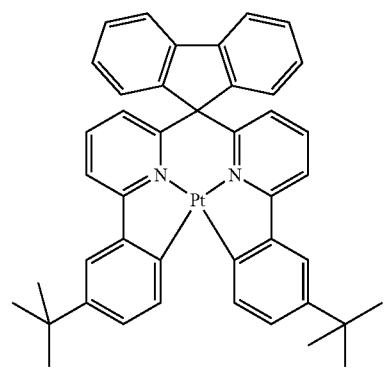
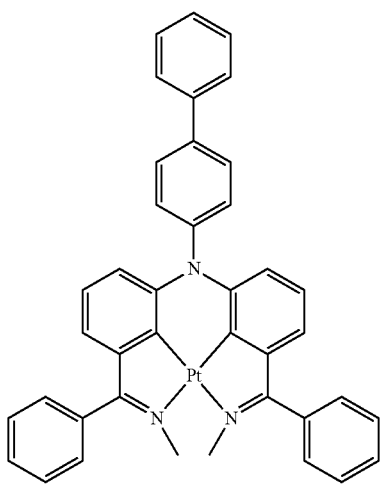

189
-continued
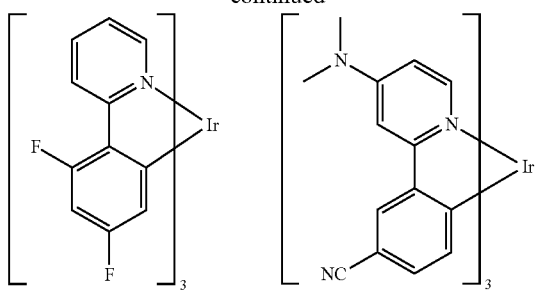
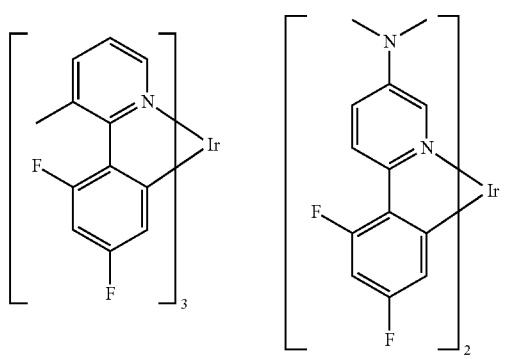
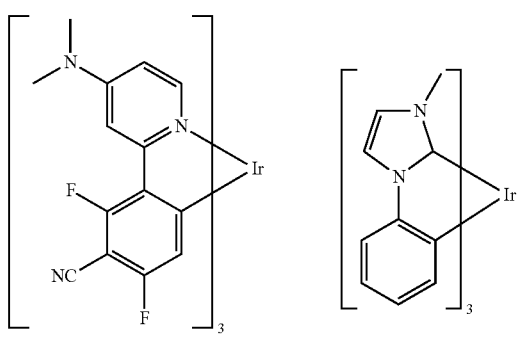
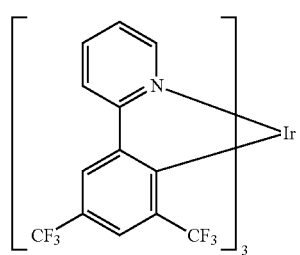
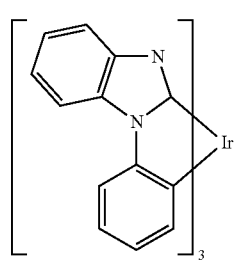
190
-continued
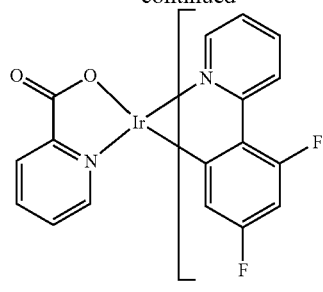
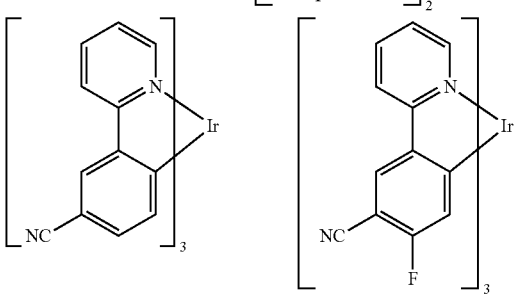
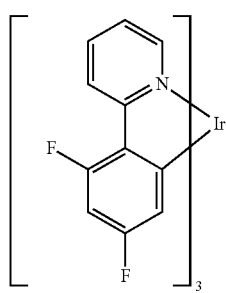
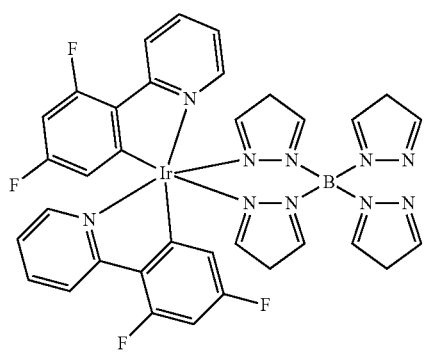
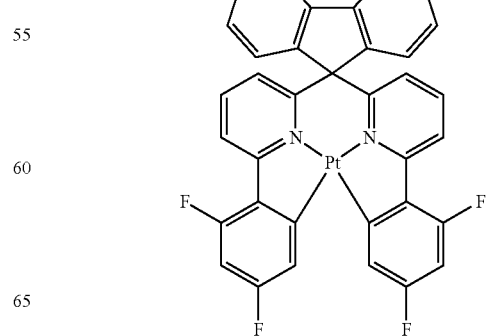

191
-continued
192
-continued
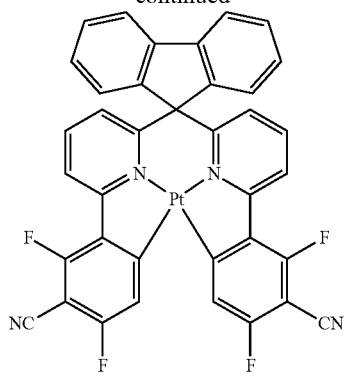
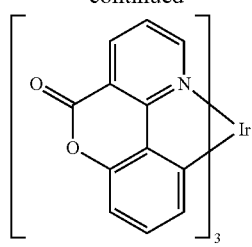
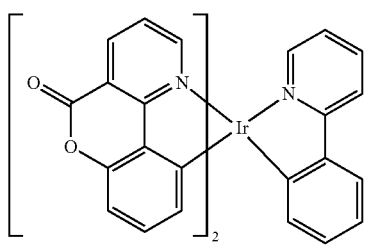
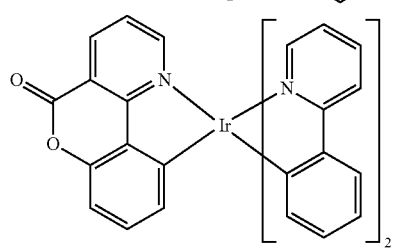
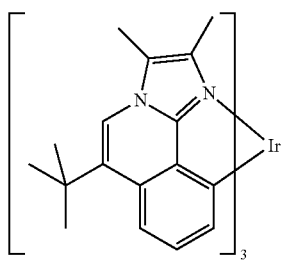
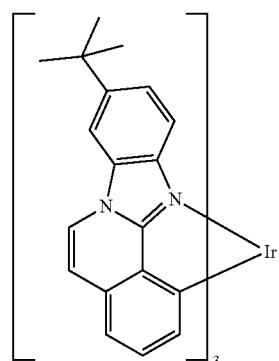
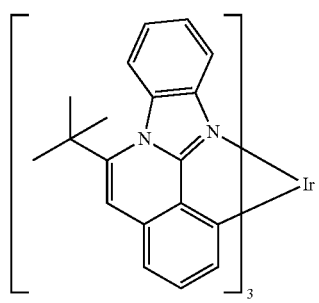

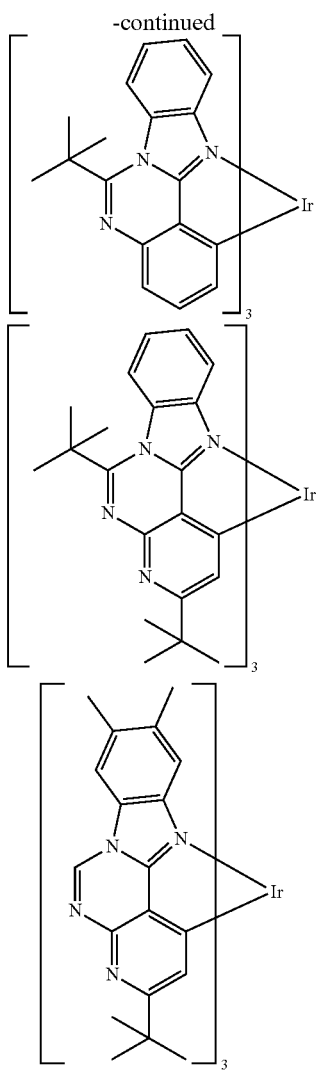

In a further embodiment of the invention, the inventive organic electroluminescent device does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

It is additionally possible to use the inventive compounds in a hole transport layer or in a hole injection layer or in an exciton or electron blocker layer.

In the further layers of the inventive organic electroluminescent device, it is possible to use any materials as typically used according to the prior art. The person skilled in the art is therefore able, without exercising inventive skill, to use any materials known for organic electroluminescent devices in combination with the inventive compounds of formula (1) or according to the preferred embodiments.

Additionally preferred is an organic electroluminescent device, characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. It is also possible that the initial pressure is even lower or higher, for example less than $10^{-7}$ mbar.

Preference is likewise given to an organic electroluminescent device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example, M. S. Arnold et al., Appl. Phys. Lett. 2008, 92, 053301).

Preference is additionally given to an organic electroluminescent device, characterized in that one or more layers are produced from solution, for example by spin-coating, or by any printing method, for example inkjet printing, LITI (light-induced thermal imaging, thermal transfer printing), screen printing, flexographic printing, offset printing or nozzle printing. For this purpose, soluble compounds are needed, which are obtained, for example, through suitable substitution. These methods are especially also suitable for oligomers, dendrimers and polymers.

In addition, hybrid methods are possible, in which, for example, one or more layers are applied from solution and one or more further layers are applied by vapour deposition. For example, it is possible to apply the emitting layer from solution and to apply the electron transport layer by vapour deposition.

These methods are known in general terms to those skilled in the art and can be applied without exercising inventive skill to organic electroluminescent devices comprising the inventive compounds.

The inventive compounds, when used in organic electroluminescent devices, have one or more of the following surprising advantages over the prior art:

1. Higher power efficiency of corresponding devices compared to systems according to the prior art.
2. Higher stability of corresponding devices compared to systems according to the prior art, which is manifested particularly in a much longer lifetime.
3. The inventive organic electroluminescent devices have a reduced operating voltage.
4. When the inventive compounds are used as matrix material for phosphorescent emitters, it is already possible to achieve very good results with only a low emitter concentration in the region of less than 10% by volume.
5. The inventive compounds have a very good thermal stability.
6. The inventive compounds have a low sublimation temperature.

The invention is now illustrated in detail by the examples which follow, without any intention of restricting it thereby.

WORKING EXAMPLES

The tribenzocycloheptene-fluorene spiro base skeleton is preferably formed analogously to the conventional spiro synthesis. Starting materials used are 9H-tribenzo[a,c,e]cyclohepten-9-one (CAS Na: 68089-73-6) and 2-bromobiphenyl derivatives. It is possible here to obtain different substitution patterns on the base skeleton through the use of correspondingly substituted biphenylenes (Scheme 1). The synthesis of 9H-tribenzo[a,c,e]cyclohepten-9-one is described in Chem. Sci., 2011, 2, 2029.

Scheme 1

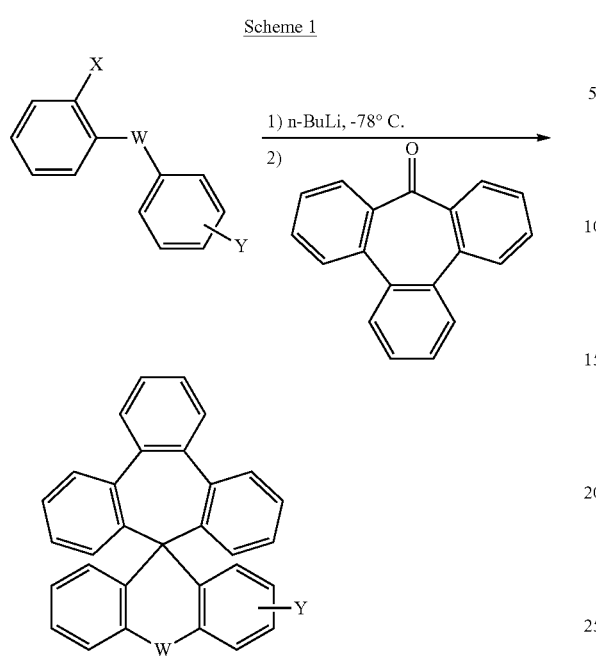

In this scheme, W represents a bridge between the phenyl groups and X is a halide such as chlorine, bromine or iodine and Y is a reactive leaving group or a substituent. It is then possible to introduce further groups via Y.

The synthesis of the inventive compounds can be conducted by the methods and reaction types known in the prior art. In particular, it is possible to synthesize the compounds from a correspondingly halogen-substituted base skeleton by introduction of the amino group, as shown in Scheme 2. It is possible here either first to introduce a primary amine having an Ar$^1$ substituent and to introduce the further Ar$^1$ group in a further coupling reaction, as shown in Scheme 2 a). It is likewise possible to introduce the secondary amine Ar$^1$Ar$^1$NH directly in one step, as shown in Scheme 2 b). Suitable Y groups in the base skeleton are reactive leaving groups, for example Cl, Br, I, triflate or tosylate. Suitable coupling reactions are, for example, coupling reactions according to Hartwig-Buchwald or according to Ullmann. The reaction conditions which can be used for these coupling reactions are known to those skilled in the art of organic synthesis.

Scheme 2:

a)

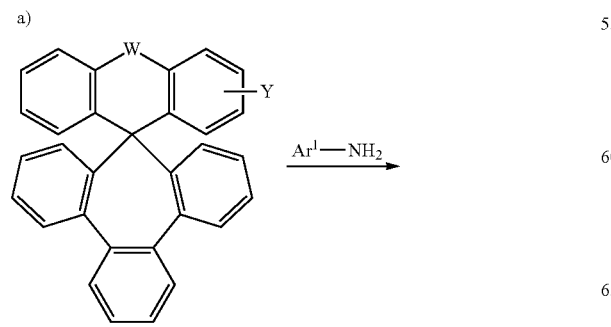

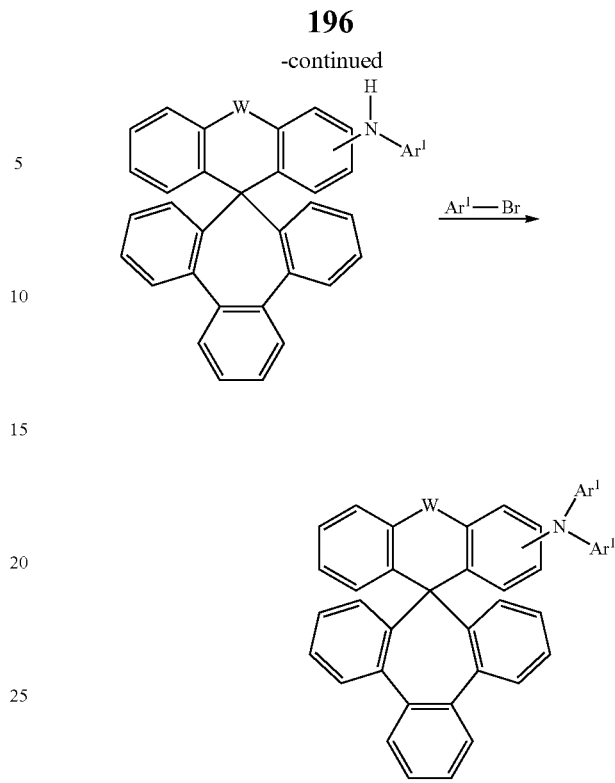

b)

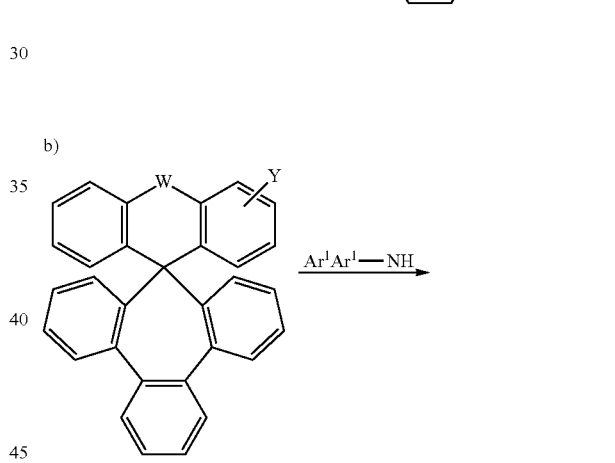

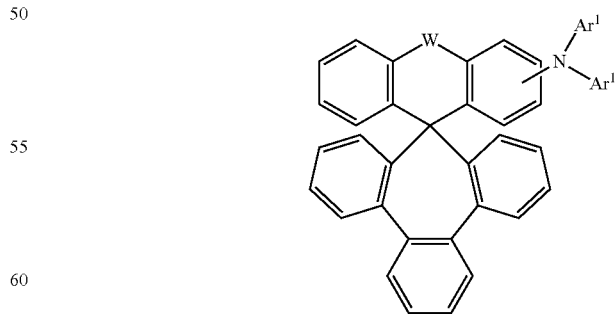

For compounds having a linker, the Ar$^2$—NAr$^1$Ar$^1$ group can likewise be introduced via a metal-catalysed coupling reaction, for example via a Suzuki coupling or a Stille coupling (Scheme 3).

Scheme 3

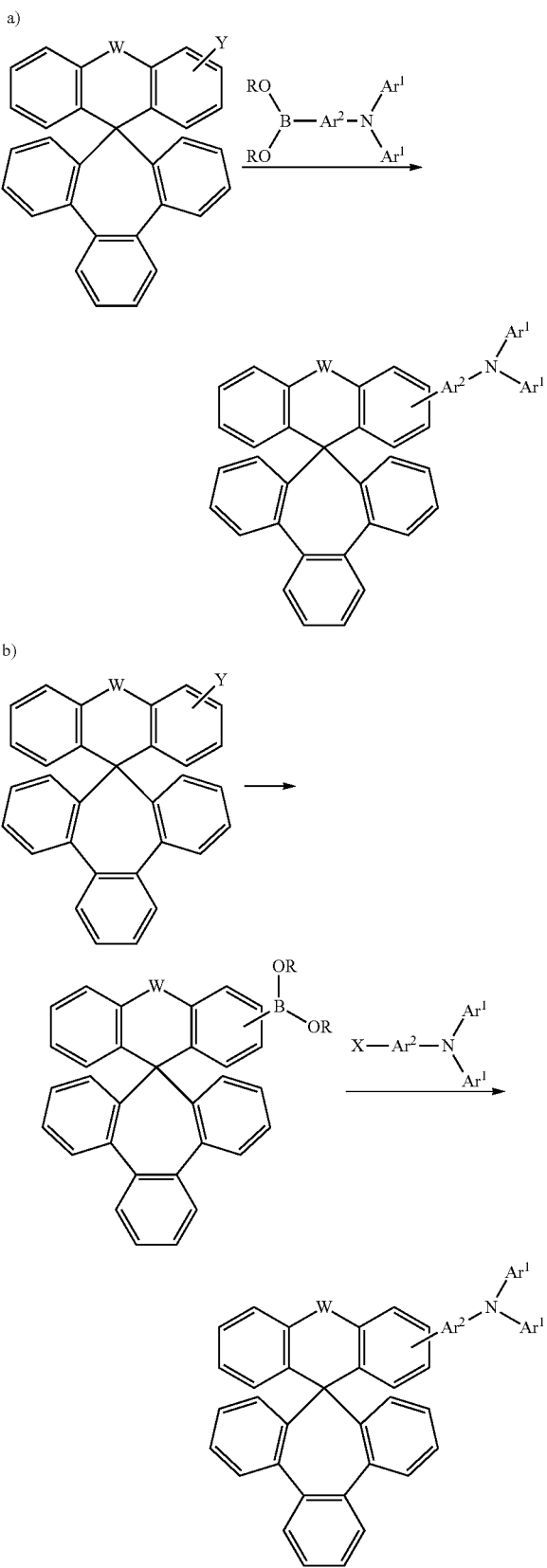

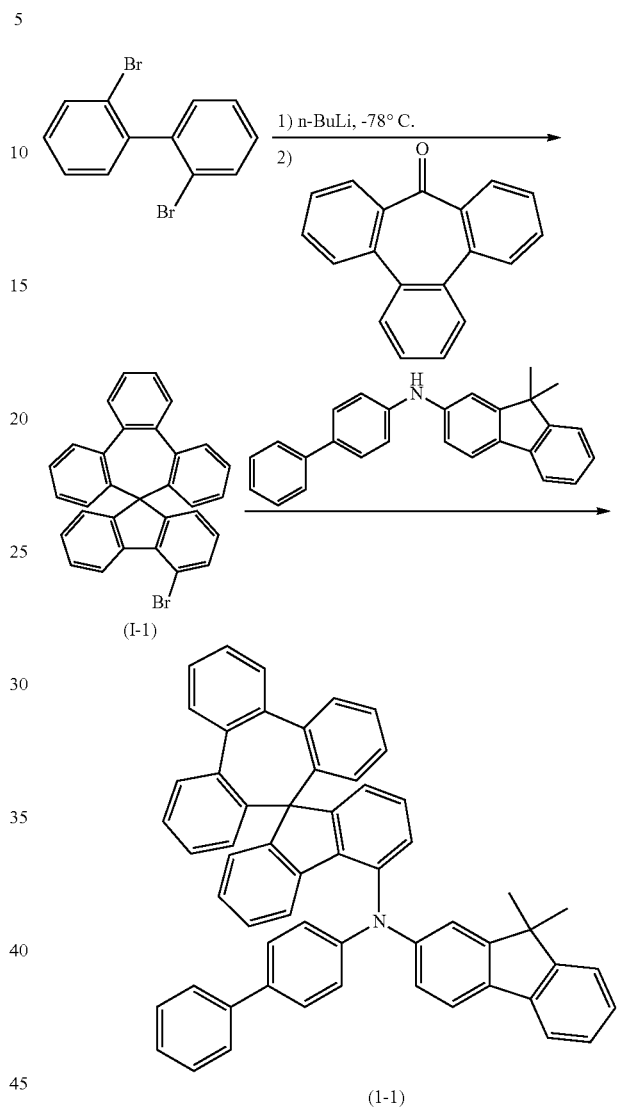

Y and X here are reactive leaving groups. Scheme 3 a) and Scheme 3 b) show two different routes for coupling of a triarylamine to the base skeleton.

Synthesis of Compound (I-1)

Synthesis of Compound (I-1)

26.7 g (85.8 mmol) of 2,2'-dibromobiphenyl are dissolved in a baked-out flask in 300 ml of dried THF. The reaction mixture is cooled to −78° C. At this temperature, 34.3 ml of a 2.5 M solution of n-BuLi in hexane (85.8 mmol) are slowly added dropwise. The mixture is stirred at −70° C. for a further 1 h. Subsequently, 20.0 g of tribenzocyclohepten-9-one (CAS No.: 68089-73-6) (78 mmol) are dissolved in 100 ml of THF and added dropwise at −70° C. After the addition has ended, the reaction mixture is warmed gradually to room temperature, quenched with $NH_4Cl$ and then concentrated on a rotary evaporator. 500 ml of acetic acid are added cautiously to the concentrated solution and then 90 ml of fuming HCl are added. The mixture is heated to 75° C. and kept at this temperature for 5 h. During this time, a white solid precipitates out. The mixture is then cooled to room temperature, and the precipitated solid is filtered off with suction and washed with methanol. The residue is dried at 40° C. under reduced pressure. The yield is 29 g (62 mmol), 79% of theory.

Analogously, the following compounds (I-2) to (I-12) are prepared.
| Ex. | Reactant 1 | Reactant 2 | Product | Yield |
|---|---|---|---|---|
| I-2 | 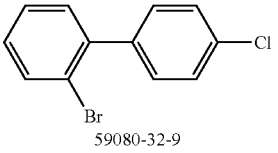 59080-32-9 | 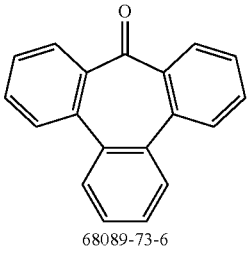 68089-73-6 | 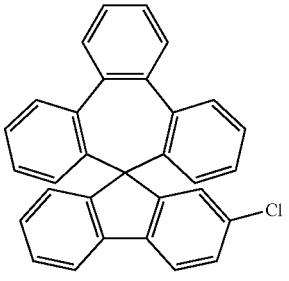 [SMILES: Clc1ccc2c(c1)C1(c3ccccc3-c3ccccc3-c3ccccc31)c1ccccc1-2] | 78% |
| I-3 | 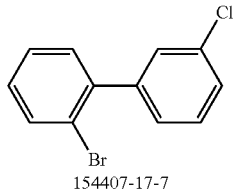 154407-17-7 | 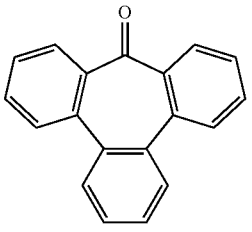 [SMILES: O=c1c2ccccc2c2ccccc2c2ccccc12] | 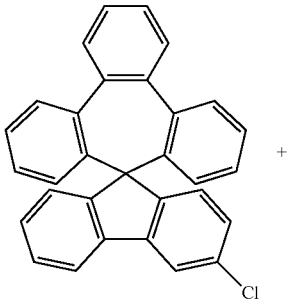 [SMILES: Clc1ccc2c(c1)-c1ccccc1C21c2ccccc2-c2ccccc2-c2ccccc21] + 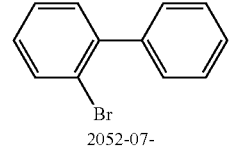 | 63% |
| I-4 | 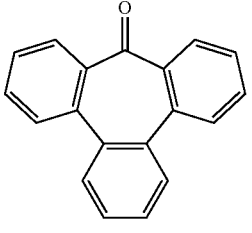 [SMILES: O=c1c2ccccc2c2ccccc2c2ccccc12] 2052-07- | 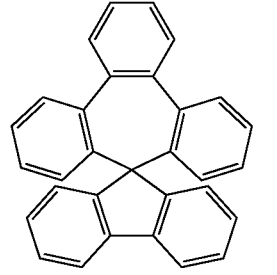 [SMILES: c1ccc2c(c1)-c1ccccc1C1(c3ccccc3-2)c2ccccc2-c2ccccc21] | 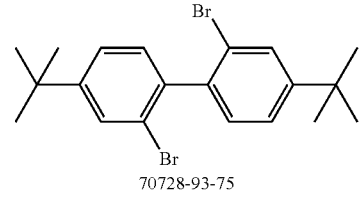 | 87% |
| I-5 | 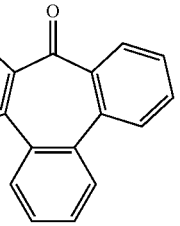 70728-93-75 | 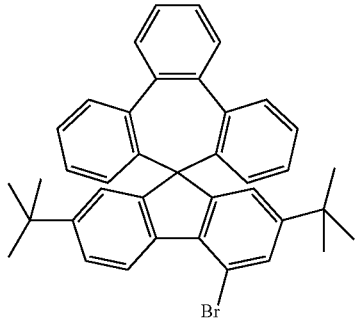 [SMILES: CC(C)(C)c1ccc2c(c1)C1(c3ccccc3-c3ccccc3-c3ccccc31)c1cc(C(C)(C)C)cc(Br)c1-2] | (product shown) | 75% |

-continued
| Ex. | Reactant 1 | Reactant 2 | Product | Yield |
|---|---|---|---|---|
| I-6 | 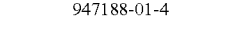 947188-01-4 | 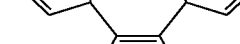 |  | 60% |
| I-7 |  7025-06-1 | 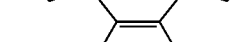 | 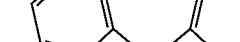 | 63% |
| I-8 | 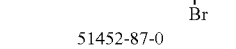 51452-87-0 | 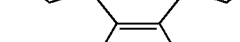 | 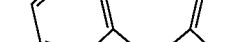 | 45% |
| I-9 | 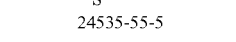 24535-55-5 |  |  | 64% |
| I-10 | 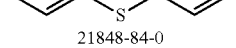 21848-84-0 |  |  | 67% |

-continued

| Ex. | Reactant 1 | Reactant 2 | Product | Yield |
|---|---|---|---|---|
| I-11 | 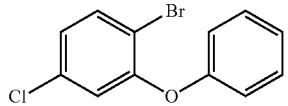 [SMILES: Clc1ccc(Br)c(Oc2ccccc2)c1] | 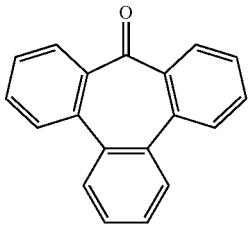 [SMILES: O=c1c2ccccc2c2ccccc2c2ccccc12] | 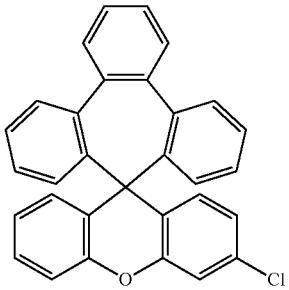 [SMILES: Clc1ccc2c(c1)Oc1ccccc1C21c2ccccc2-c2ccccc2-c2ccccc21] | 71% |
| I-12 | 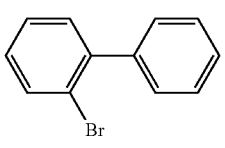 [SMILES: Brc1ccccc1-c1ccccc1] 2052-07-5 | 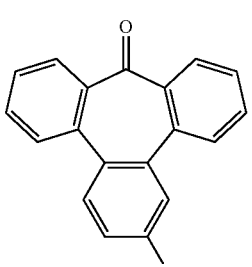 19713-54-3 | 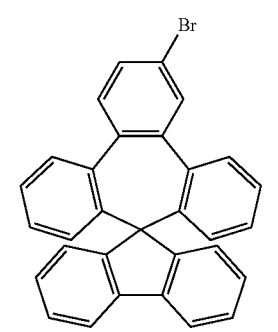 [SMILES: Brc1ccc2c(c1)-c1ccccc1C1(c3ccccc3-2)c2ccccc2-c2ccccc21] | 77% |

Synthesis of Compound (1-1)

7.9 g of biphenyl-4-yl-(9,9-dimethyl-9H-fluoren-2-yl)amine (22 mmol) and 10.6 g of the bromo derivative (I-1) (22 mmol) are dissolved in 200 mL of THF. The solution is degassed and saturated with $N_2$. Thereafter, 1.1 ml (1.1 mmol) of a 1 M tri-tert-butylphosphine solution and 0.12 g (55 mmol) of palladium(II) acetate are added thereto. Subsequently, 5.3 g of sodium tert-butoxide (55 mmol) are added. The reaction mixture is heated to boiling under a protective atmosphere for 3 h. The mixture is subsequently partitioned between toluene and water, and the organic phase is washed three times with water, dried over $Na_2SO_4$ and concentrated by rotary evaporation. After the crude product has been filtered through silica gel with toluene, the remaining residue is recrystallized from heptane/toluene and finally sublimed under high vacuum. The purity is 99.9%. The yield is 13.2 g (80% of theory).

Analogously, the following compounds (1-2) to (1-24) are prepared.

| Ex. | Reactant 1 | Reactant 2 | Product | Yield |
|---|---|---|---|---|
| 1-2 | 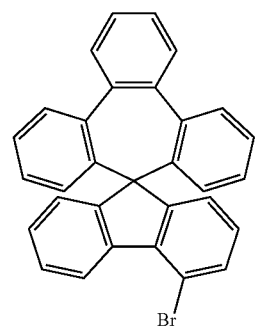 [SMILES: Brc1cccc2c1-c1ccccc1C21c2ccccc2-c2ccccc2-c2ccccc21] | 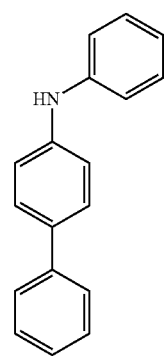 [SMILES: c1ccc(Nc2ccc(-c3ccccc3)cc2)cc1] 32228-99-2 | 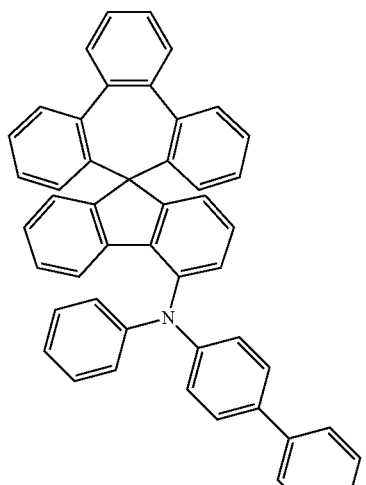 | 79% |

-continued
| Ex. | Reactant 1 | Reactant 2 | Product | Yield |
|---|---|---|---|---|
| 1-3 | 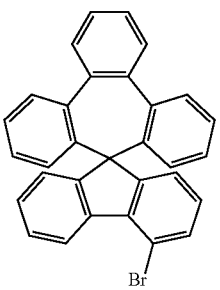 [SMILES: Brc1cccc2c1-c1ccccc1C21c2ccccc2-c2ccccc2-c2ccccc21] | 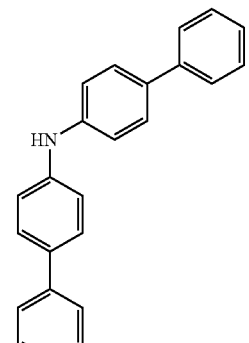
102113-98-4 | 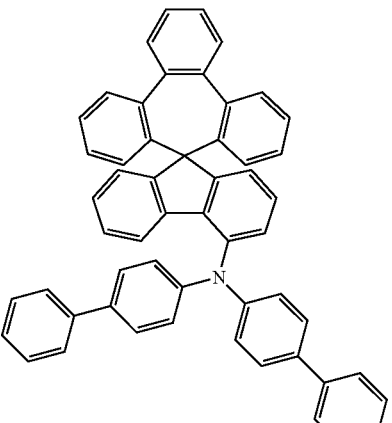 | 84% |
| 1-4 | 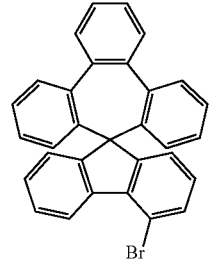 [SMILES: Brc1cccc2c1-c1ccccc1C21c2ccccc2-c2ccccc2-c2ccccc21] | 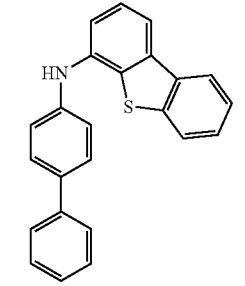 [SMILES: c1ccc(-c2ccc(Nc3cccc4c3sc3ccccc34)cc2)cc1]
1448185-87-2 | 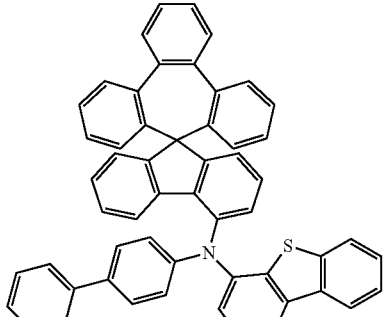 | 92% |
| 1-5 | 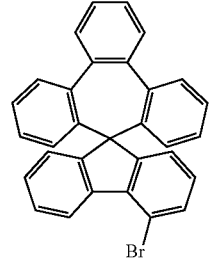 [SMILES: Brc1cccc2c1-c1ccccc1C21c2ccccc2-c2ccccc2-c2ccccc21] | 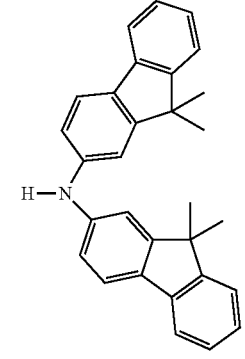 [SMILES: CC1(C)c2ccccc2-c2ccc(Nc3ccc4c(c3)C(C)(C)c3ccccc3-4)cc21]
500717-23-7 | 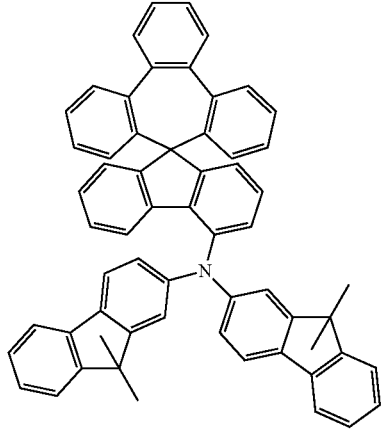 | 77% |

-continued

| Ex. | Reactant 1 | Reactant 2 | Product | Yield |
|---|---|---|---|---|
| 1-6 | | | | 81% |
| 1-7 | | | | 85% |
| 1-8 | | 955959-89-4 | | 81% |
| 1-9 | | 1198395-24-2 | | 77% |

-continued

| Ex. | Reactant 1 | Reactant 2 | Product | Yield |
|---|---|---|---|---|
| 1-10 | | 1300028-94-7 | | 76% |
| 1-11 | | 897921-59-4 | | 69% |
| 1-12 | | | | 74% |
| 1-13 | | | | 80% |

-continued

| Ex. | Reactant 1 | Reactant 2 | Product | Yield |
|---|---|---|---|---|
| 1-14 | | 102113-98-4 | | 61% |
| 1-15 | | 500717-23-7 | | 60% |
| 1-16 | | | | 71% |

-continued
| Ex. | Reactant 1 | Reactant 2 | Product | Yield |
|---|---|---|---|---|
| 1-17 | 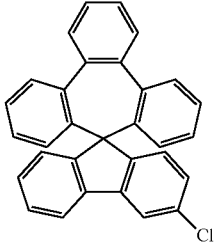 [SMILES: Clc1ccc2c(c1)-c1ccccc1C21c2ccccc2-c2ccccc2-c2ccccc21] | 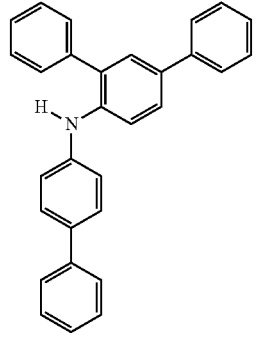 [SMILES: c1ccc(-c2ccc(Nc3ccc(-c4ccccc4)cc3-c3ccccc3)cc2)cc1] | 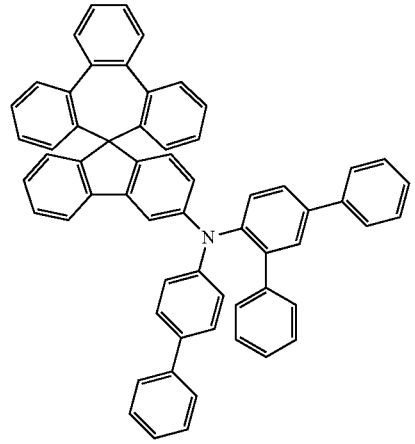 [SMILES: c1ccc(-c2ccc(N(c3ccc4c(c3)-c3ccccc3C43c4ccccc4-c4ccccc4-c4ccccc43)c3ccc(-c4ccccc4)cc3-c3ccccc3)cc2)cc1] | 69% |
| 1-18 | 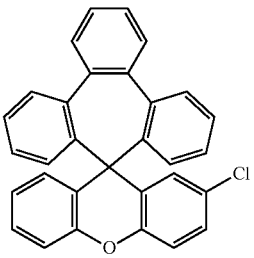 | 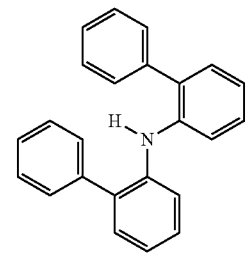 [SMILES: c1ccc(-c2ccccc2Nc2ccccc2-c2ccccc2)cc1] | 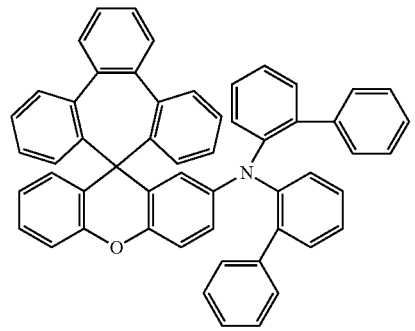 [SMILES: c1ccc(-c2ccccc2N(c2ccc3c(c2)C2(c4ccccc4O3)c3ccccc3-c3ccccc3-c3ccccc32)c2ccccc2-c2ccccc2)cc1] | 40% |
| 1-19 | 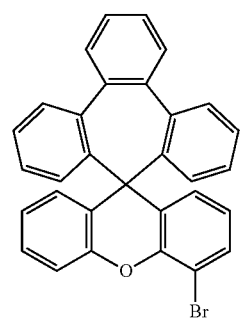 [SMILES: Brc1cccc2c1Oc1ccccc1C21c2ccccc2-c2ccccc2-c2ccccc21] | 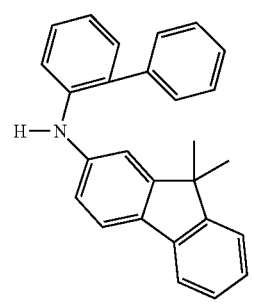 [SMILES: CC1(C)c2ccccc2-c2ccc(Nc3ccccc3-c3ccccc3)cc21] | 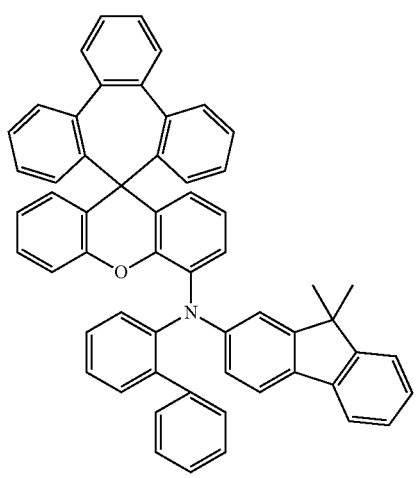 [SMILES: CC1(C)c2ccccc2-c2ccc(N(c3ccccc3-c3ccccc3)c3cccc4c3Oc3ccccc3C43c4ccccc4-c4ccccc4-c4ccccc43)cc21] | 70% |

-continued
| Ex. | Reactant 1 | Reactant 2 | Product | Yield |
|---|---|---|---|---|
| 1-20 | 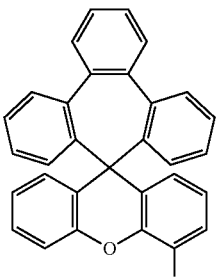 | 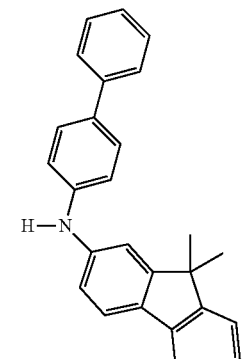 | 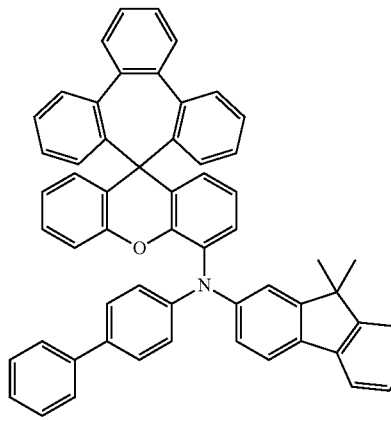 | 78% |
| 1-21 | 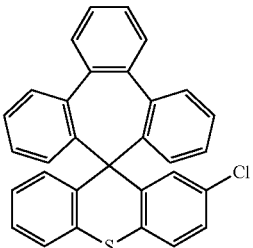 | 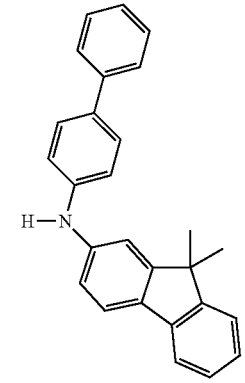 [SMILES: CC1(C)c2ccccc2-c2ccc(Nc3ccc(-c4ccccc4)cc3)cc21] | 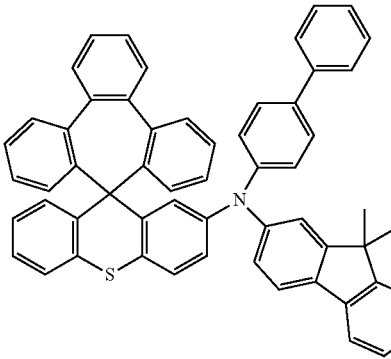 | 81% |
| 1-22 | 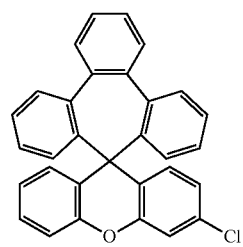 [SMILES: Clc1ccc2c(c1)Oc1ccccc1C21c2ccccc2-c2ccccc2-c2ccccc21] | 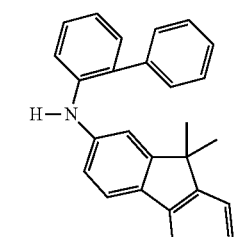 | 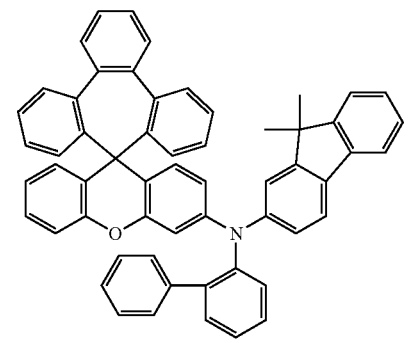 [SMILES: CC1(C)c2ccccc2-c2ccc(N(c3ccc4c(c3)Oc3ccccc3C43c4ccccc4-c4ccccc4-c4ccccc43)c3ccccc3-c3ccccc3)cc21] | 77% |
| 1-23 | 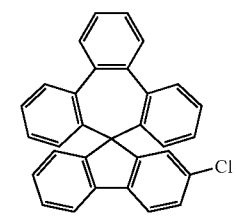 [SMILES: Clc1ccc2c(c1)C1(c3ccccc3-c3ccccc3-c3ccccc31)c1ccccc1-2] | 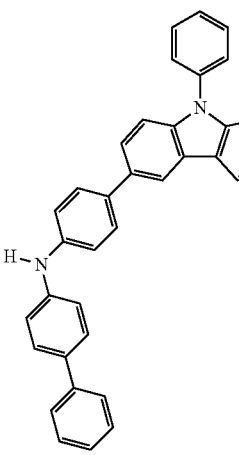 | 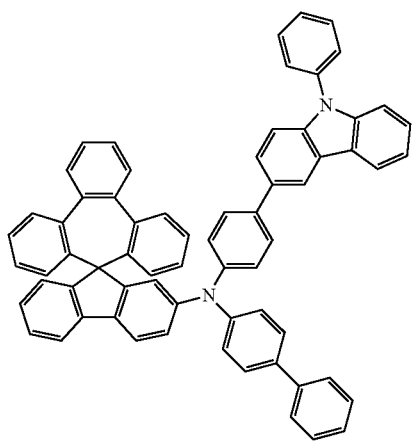 [SMILES: c1ccc(-c2ccc(N(c3ccc(-c4ccc5c(c4)c4ccccc4n5-c4ccccc4)cc3)c3ccc4c(c3)C3(c5ccccc5-c5ccccc5-c5ccccc53)c3ccccc3-4)cc2)cc1] | 67% |

-continued

| Ex. | Reactant 1 | Reactant 2 | Product | Yield |
|---|---|---|---|---|
| 1-24 | 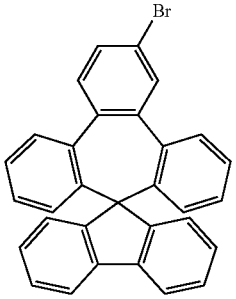 [SMILES: Brc1ccc2c(c1)-c1ccccc1C1(c3ccccc3-2)c2ccccc2-c2ccccc21] | 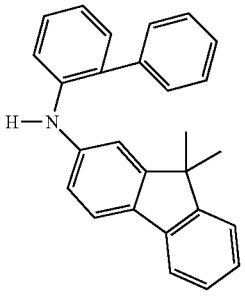 [SMILES: CC1(C)c2ccccc2-c2ccc(Nc3ccccc3-c3ccccc3)cc21] | 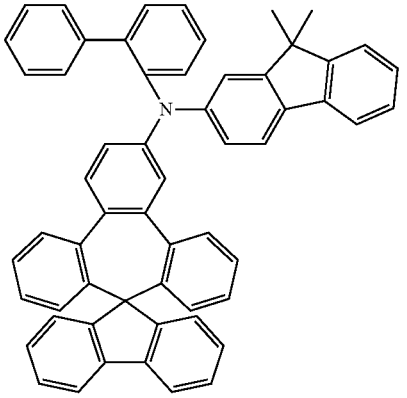 [SMILES: CC1(C)c2ccccc2-c2ccc(N(c3ccc4c(c3)-c3ccccc3C3(c5ccccc5-4)c4ccccc4-c4ccccc43)c3ccccc3-c3ccccc3)cc21] | 81% |

Example 2

Synthesis of Compound (2-1)

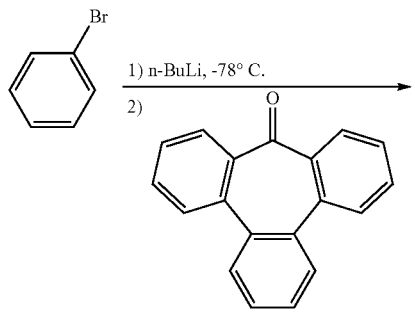

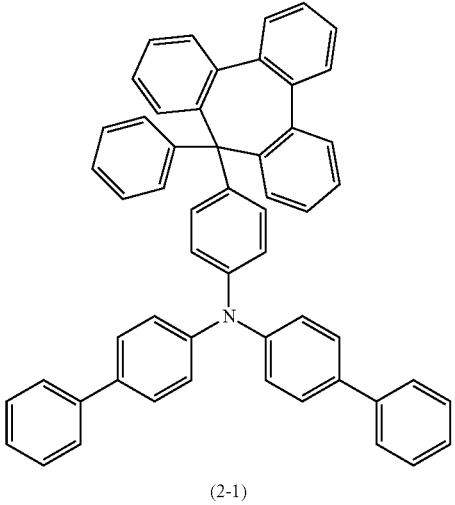

(2-1)

Synthesis of Compound (II-1)

40 g (255 mmol) of bromophenol are dissolved in a baked-out flask in 600 ml of dried THF. The reaction mixture is cooled to −78° C. At this temperature, 102 ml of a 2.5 M solution of n-BuLi in hexane (255 mmol) are slowly added dropwise. The mixture is stirred at −70° C. for a further 0.5 h. Subsequently, 65.3 g of tribenzocyclohepten-9-one (CAS No.: 68089-73-6) (255 mmol) are dissolved in 200 ml of THF and added dropwise at −70° C. After the addition has ended, the reaction mixture is warmed gradually to room temperature, quenched with $NH_4Cl$ and then concentrated on a rotary evaporator. The crude product is stirred with 500 ml of heptane at 80° C. for a further 2 h. After cooling, the precipitated solid is filtered off with suction and washed once with 100 ml of heptane and twice with 100 ml each time of ethanol. Yield: 66.5 g, 78%.

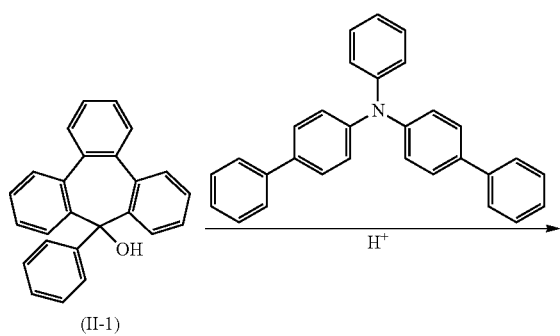

(II-1)

In an analogous manner, the following compounds are obtained:
| Ex. | Reactant 1 | Reactant 2 | Product | Yield |
|---|---|---|---|---|
| II-2 | 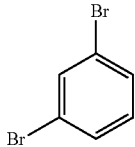 | 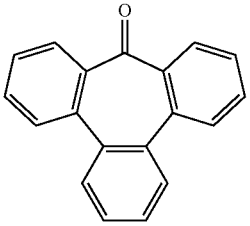 [SMILES: O=c1c2ccccc2c2ccccc2c2ccccc12] | 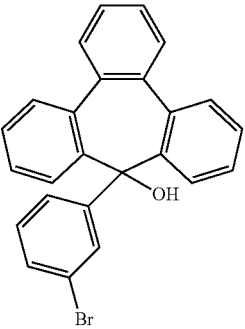 [SMILES: OC1(c2cccc(Br)c2)c2ccccc2-c2ccccc2-c2ccccc21] | 85% |
| II-3 | 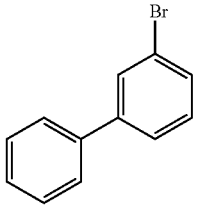 [SMILES: Brc1cccc(-c2ccccc2)c1] | 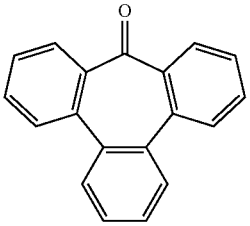 [SMILES: O=c1c2ccccc2c2ccccc2c2ccccc12] | 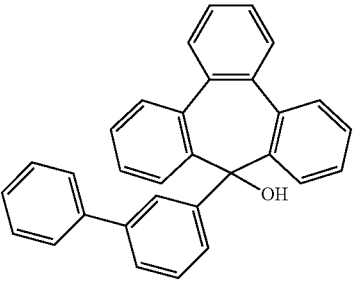 [SMILES: OC1(c2cccc(-c3ccccc3)c2)c2ccccc2-c2ccccc2-c2ccccc21] | 70% |
| II-4 | 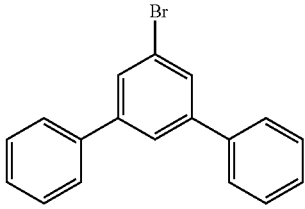 [SMILES: Brc1cc(-c2ccccc2)cc(-c2ccccc2)c1] | 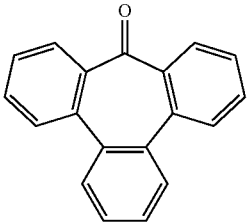 [SMILES: O=c1c2ccccc2c2ccccc2c2ccccc12] | 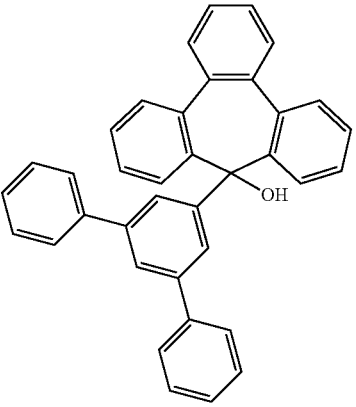 [SMILES: OC1(c2cc(-c3ccccc3)cc(-c3ccccc3)c2)c2ccccc2-c2ccccc2-c2ccccc21] | 67% |
| II-5 | 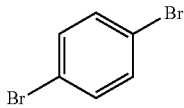 | 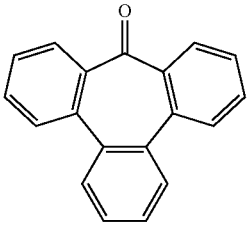 [SMILES: O=c1c2ccccc2c2ccccc2c2ccccc12] | 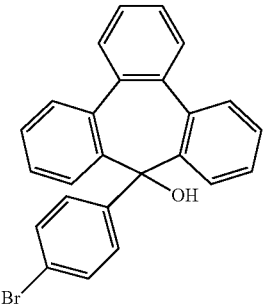 [SMILES: OC1(c2ccc(Br)cc2)c2ccccc2-c2ccccc2-c2ccccc21] | 83% |

| Ex. | Reactant 1 | Reactant 2 | Product | Yield |
|---|---|---|---|---|
| II-6 | 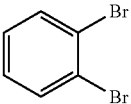 | 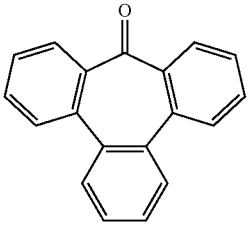 [SMILES: O=c1c2ccccc2c2ccccc2c2ccccc12] | 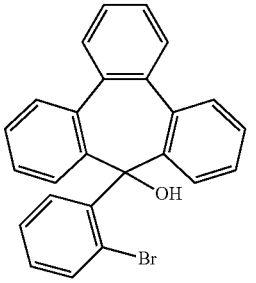 [SMILES: OC1(c2ccccc2Br)c2ccccc2-c2ccccc2-c2ccccc21] | 81% |

Synthesis of Compound (2-1)

A mixture of 20 g (60 mmol) of compound II-1 and 26.17 g (60 mmol) of bis(biphenyl-4-yl)phenylamine [122215-84-3], trifluoromethanesulphonic acid [1493-13-6] 18 g (120 mmol, 10.5 ml) and 400 ml of dioxane is heated under reflux for 24 h. After cooling, 200 ml of water are added, the mixture is stirred for a further 30 min, the organic phase is removed and the latter is filtered through a short Celite bed and then the solvent is removed under reduced pressure. The residue is recrystallized from toluene/heptane and finally sublimed under high vacuum. The purity is 99.9%. The yield is 32.9 g (73% of theory).

Analogously, the following compounds (2-2) to (2-11) are prepared.

| Ex. | Reactant 1 | Reactant 2 | Product: | Yield |
|---|---|---|---|---|
| 2-2 | 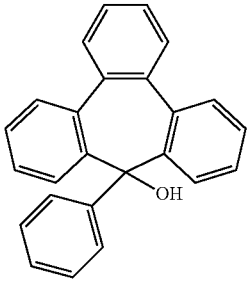 [SMILES: OC1(c2ccccc2)c2ccccc2-c2ccccc2-c2ccccc21] | 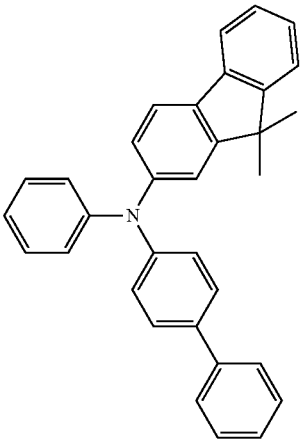\
1391737-67-9 | 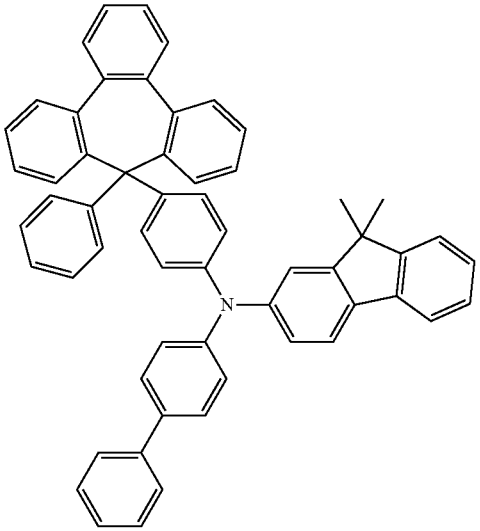 [SMILES: CC1(C)c2ccccc2-c2ccc(N(c3ccc(-c4ccccc4)cc3)c3ccc(C4(c5ccccc5)c5ccccc5-c5ccccc5-c5ccccc54)cc3)cc21] | 85% |
| 2-3 | 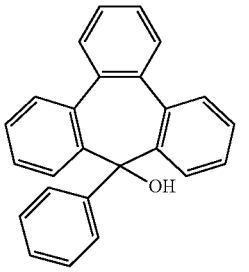 [SMILES: OC1(c2ccccc2)c2ccccc2-c2ccccc2-c2ccccc21] | 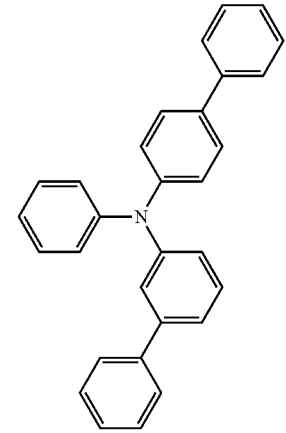 [SMILES: c1ccc(-c2ccc(N(c3ccccc3)c3cccc(-c4ccccc4)c3)cc2)cc1] | 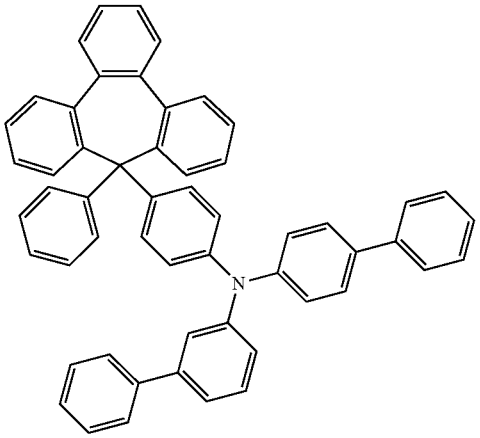 [SMILES: c1ccc(-c2ccc(N(c3ccc(C4(c5ccccc5)c5ccccc5-c5ccccc5-c5ccccc54)cc3)c3cccc(-c4ccccc4)c3)cc2)cc1] | 74% |

| Ex. | Reactant 1 | Reactant 2 | Product: | Yield |
|---|---|---|---|---|
| 2-4 | | | | 70% |
| 2-6 | | | | 58% |
| 2-7 | | | | 64% |

-continued

| Ex. | Reactant 1 | Reactant 2 | Product: | Yield |
|---|---|---|---|---|
| 2-8 | | | | 46% |
| 2-9 | | | | 79% |
| 2-10 | | | | 72% |
| 2-11 | | | | 65% |

Example 3

Synthesis of Compound (3-1)

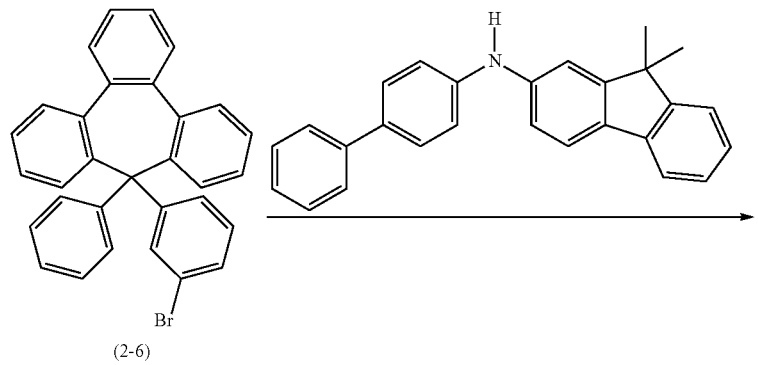

(2-6)

(3-1)

9.16 g of biphenyl-4-yl(9,9-dimethyl-9H-fluoren-2-yl) amine (25 mmol) and 12 g of the bromo derivative (2-6) (25 mmol) are dissolved in 200 mL of toluene. The solution is degassed and saturated with $N_2$. Thereafter, 1.27 ml (1.27 mmol) of a 1 M tri-tert-butylphosphine solution and 0.14 g (0.63 mmol) of palladium(II) acetate are added thereto. Subsequently, 6.1 g of sodium tert-butoxide (63.4 mmol) are added. The reaction mixture is heated to boiling under a protective atmosphere for 8 h. The mixture is subsequently partitioned between toluene and water, and the organic phase is washed three times with water, dried over $Na_2SO_4$ and concentrated by rotary evaporation. After the crude product has been filtered through silica gel with toluene, the remaining residue is recrystallized from heptane/toluene and finally sublimed under high vacuum. The purity is 99.9%. The yield is 15 g (78% of theory).

Synthesis of Compound (3-2) to (3-8)

Analogously, the following compounds (3-2) to (3-8) are prepared,

| Ex. | Reactant 1 | Reactant 2 |
|---|---|---|
| 3-2 | 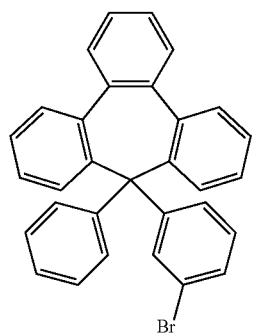 [SMILES: Brc1cccc(C2(c3ccccc3)c3ccccc3-c3ccccc3-c3ccccc32)c1] | 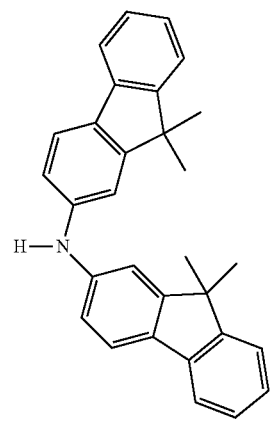500717-23-7 |
| 3-3 | 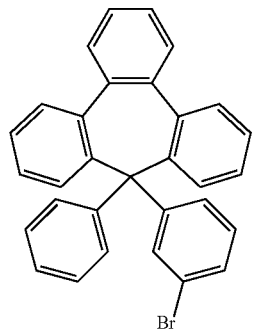 [SMILES: Brc1cccc(C2(c3ccccc3)c3ccccc3-c3ccccc3-c3ccccc32)c1] | 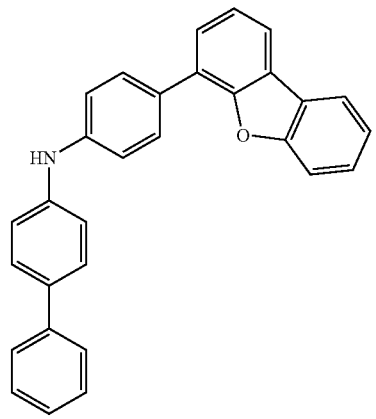955959-89-4 |
| 3-4 | 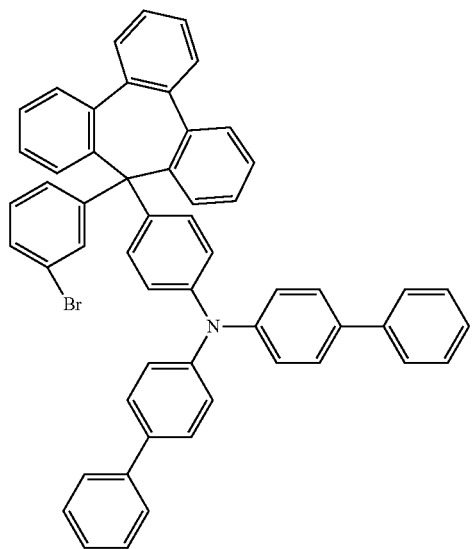 [SMILES: Brc1cccc(C2(c3ccc(N(c4ccc(-c5ccccc5)cc4)c4ccc(-c5ccccc5)cc4)cc3)c3ccccc3-c3ccccc3-c3ccccc32)c1] | 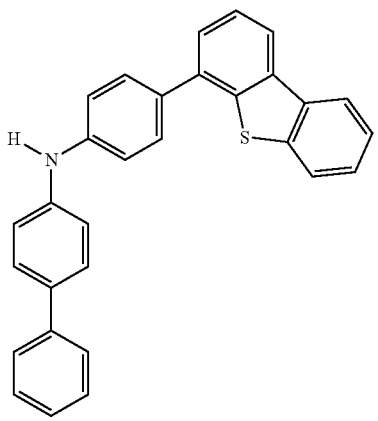 [SMILES: c1ccc(-c2ccc(Nc3ccc(-c4cccc5c4sc4ccccc45)cc3)cc2)cc1] |

3-5 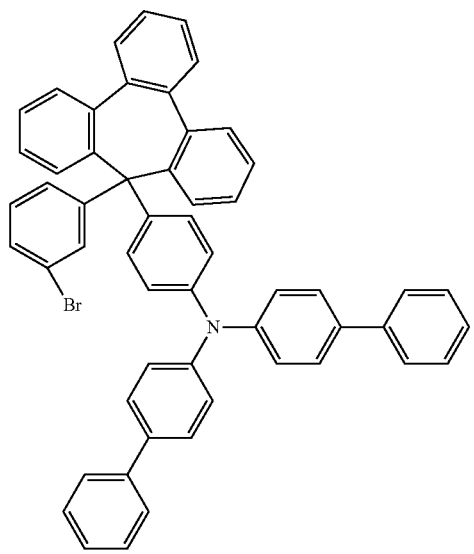 [SMILES: Brc1cccc(C2(c3ccc(N(c4ccc(-c5ccccc5)cc4)c4ccc(-c5ccccc5)cc4)cc3)c3ccccc3-c3ccccc3-c3ccccc32)c1] 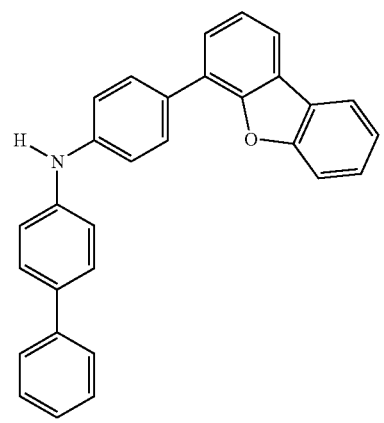 [SMILES: c1ccc(-c2ccc(Nc3ccc(-c4cccc5c4oc4ccccc45)cc3)cc2)cc1]
3-6 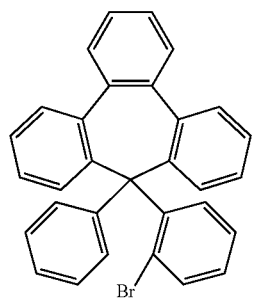 [SMILES: Brc1ccccc1C1(c2ccccc2)c2ccccc2-c2ccccc2-c2ccccc21] 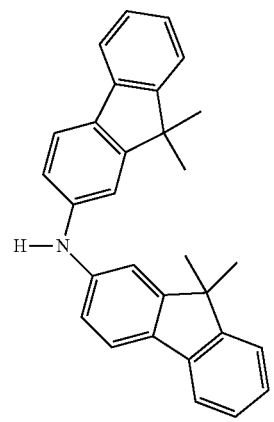
500717-23-7
3-7 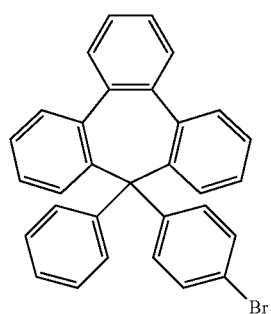 [SMILES: Brc1ccc(C2(c3ccccc3)c3ccccc3-c3ccccc3-c3ccccc32)cc1] 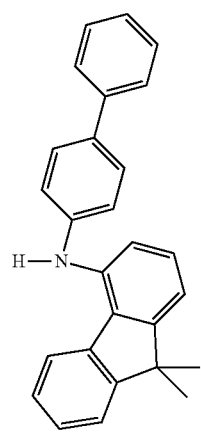 [SMILES: CC1(C)c2ccccc2-c2c(Nc3ccc(-c4ccccc4)cc3)cccc21]

3-8
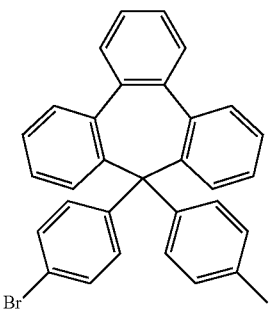 [SMILES: Cc1ccc(C2(c3ccc(Br)cc3)c3ccccc3-c3ccccc3-c3ccccc32)cc1]
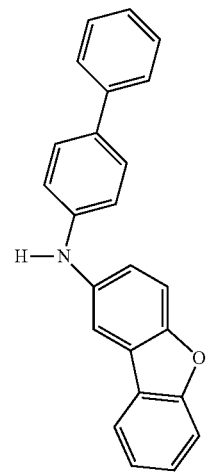 [SMILES: c1ccc(-c2ccc(Nc3ccc4oc5ccccc5c4c3)cc2)cc1]
| Ex. | Product | Yield |
|---|---|---|
| 3-2 | 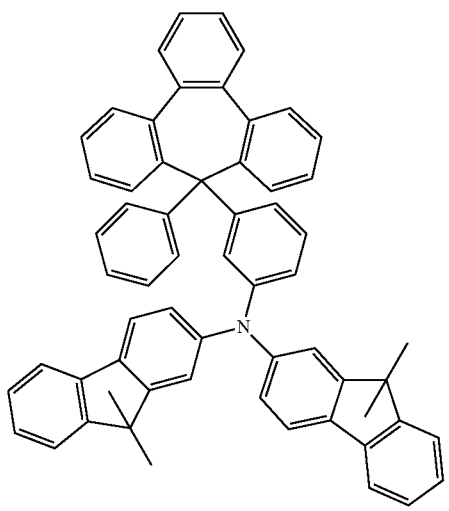 | 79% |
| 3-3 | 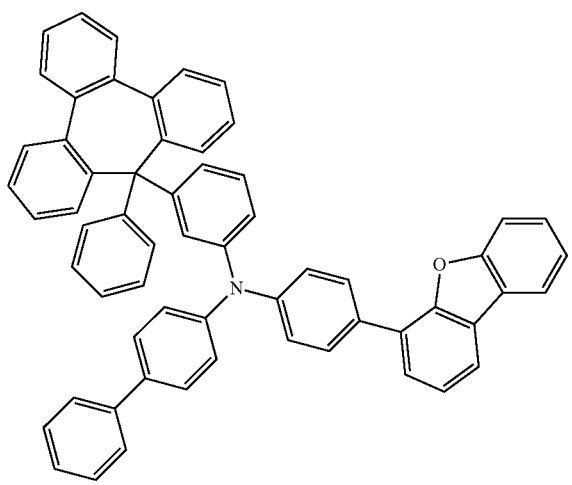 [SMILES: c1ccc(-c2ccc(N(c3ccc(-c4cccc5c4oc4ccccc45)cc3)c3cccc(C4(c5ccccc5)c5ccccc5-c5ccccc5-c5ccccc54)c3)cc2)cc1] | 84% |

| 3-4 | 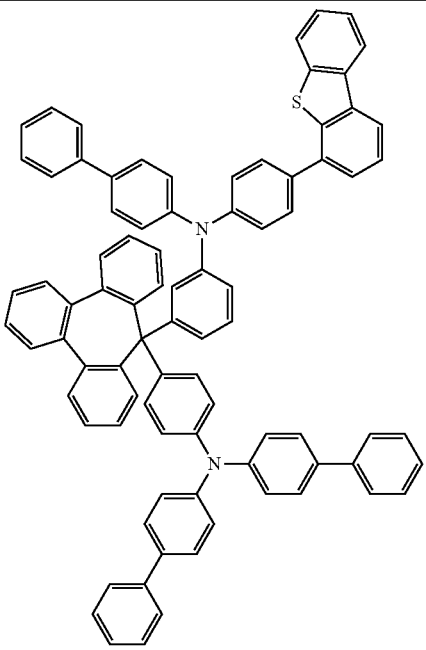 | 85% |
| 3-5 | 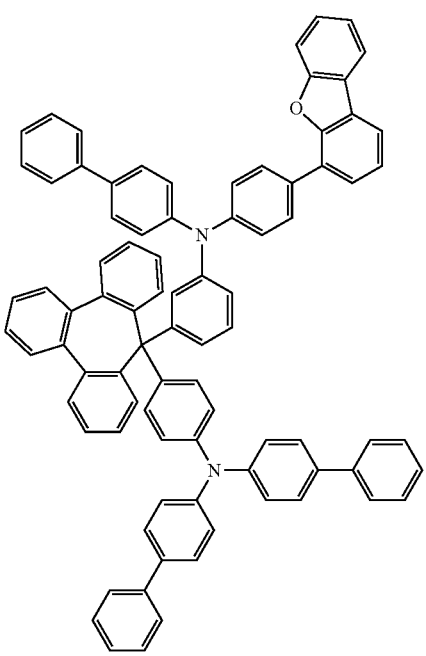 [SMILES: c1ccc(-c2ccc(N(c3ccc(-c4ccccc4)cc3)c3ccc(C4(c5cccc(N(c6ccc(-c7ccccc7)cc6)c6ccc(-c7cccc8c7oc7ccccc78)cc6)c5)c5ccccc5-c5ccccc5-c5ccccc54)cc3)cc2)cc1] | 80% |

| | | |
|---|---|---|
| 3-6 | 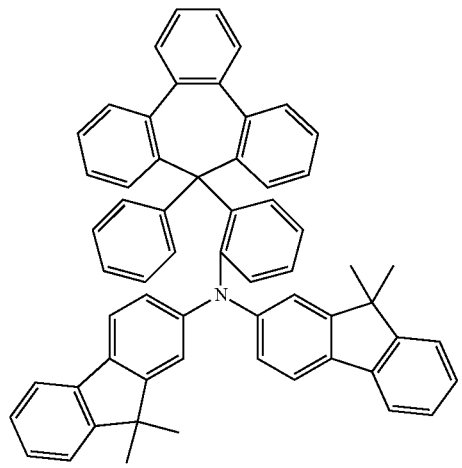 [SMILES: CC1(C)c2ccccc2-c2ccc(N(c3ccc4c(c3)C(C)(C)c3ccccc3-4)c3ccccc3C3(c4ccccc4)c4ccccc4-c4ccccc4-c4ccccc43)cc21] | 71% |
| 3-7 | 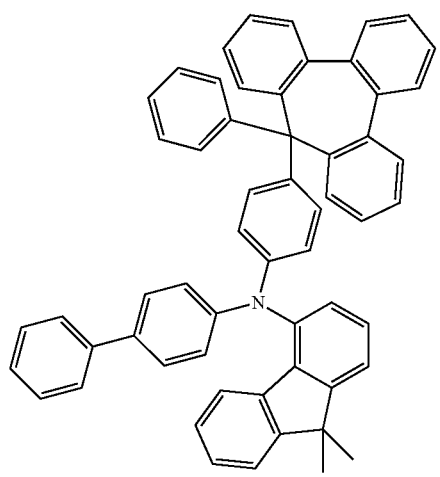 [SMILES: CC1(C)c2ccccc2-c2c(N(c3ccc(-c4ccccc4)cc3)c3ccc(C4(c5ccccc5)c5ccccc5-c5ccccc5-c5ccccc54)cc3)cccc21] | 81% |
| 3-8 | 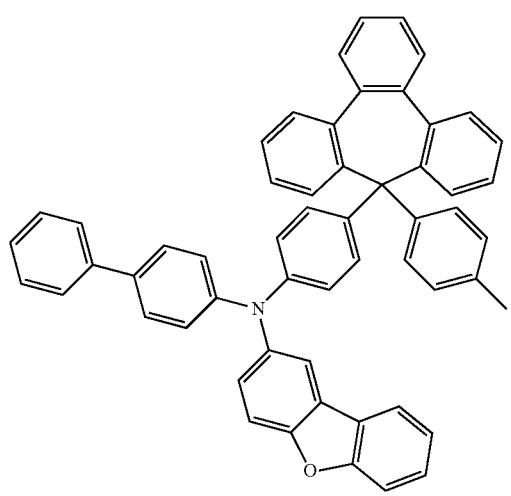 [SMILES: Cc1ccc(C2(c3ccc(N(c4ccc(-c5ccccc5)cc4)c4ccc5oc6ccccc6c5c4)cc3)c3ccccc3-c3ccccc3-c3ccccc32)cc1] | 87% |

Example 4
Synthesis of Compound 4-1
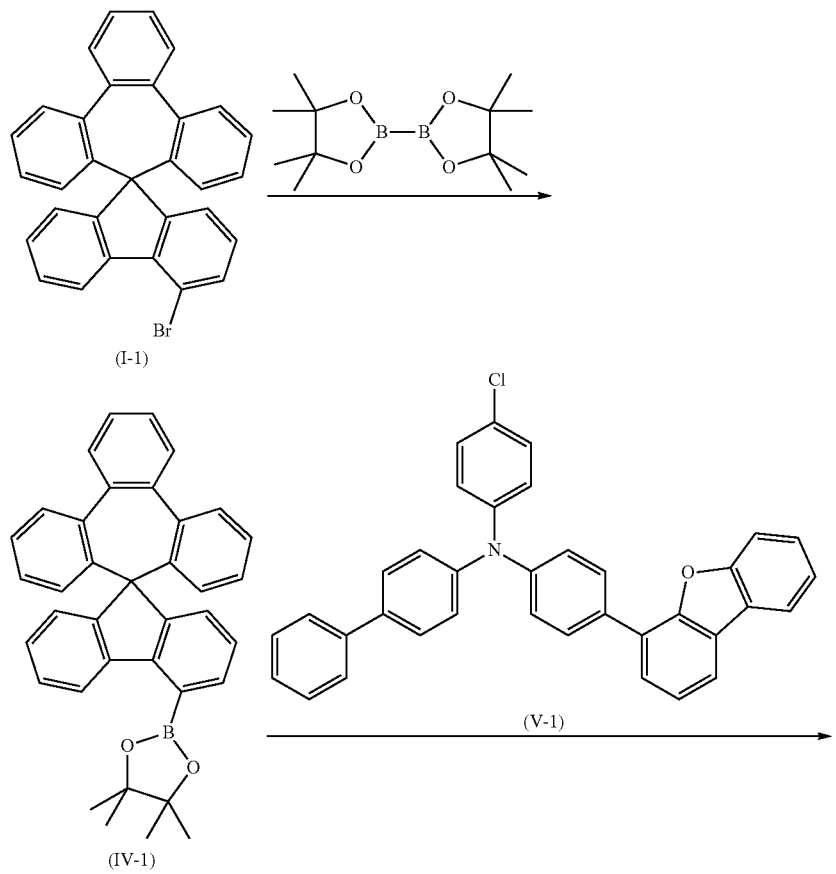

Intermediate: Boronic Ester Derivative (IV-1)

10 g (21.2 mmol) of the bromo derivative, 6.6 g (25.4 mmol) of bis(pinacolato)diborane and 6.3 g (63.6 mmol) of potassium acetate are suspended in 200 ml of DMF. To this suspension is added 0.52 g (0.64 mmol) of 1,1-bis(diphenylphosphino)ferrocenedichloropalladium(II) complex with DCM. The reaction mixture is heated under reflux for 6 h.

After cooling, the organic phase is removed, washed three times with 300 mL of water and then concentrated to dryness. The residue is recrystallized from toluene (10.3 g, 94% yield).

Analogously, the following compounds (IV-2) to (IV-13) are prepared.

| Ex. | Reactant 1 | Product | Yield |
|---|---|---|---|
| IV-2 | | | 90% |
| IV-3 | | | 67% |
| IV-4 | | | 88% |
| IV-5 | | | 88% |

-continued

| Ex. | Reactant 1 | Product | Yield |
|---|---|---|---|
| IV-6 | | | 92% |
| IV-7 | | | 84% |
| IV-8 | | | 87% |
| IV-9 | | | 80% |

-continued

| Ex. | Reactant 1 | Product | Yield |
|---|---|---|---|
| IV-10 | | | 72% |
| IV-11 | | | 92% |
| IV-12 | | | 88% |

| Ex. | Reactant 1 | Product | Yield |
|---|---|---|---|
| IV-13 | | | 90% |

Precursor: Biphenyl-4-yl(4-chlorophenyl)(4-dibenzofuran-4-ylphenyl)amine (V-1)

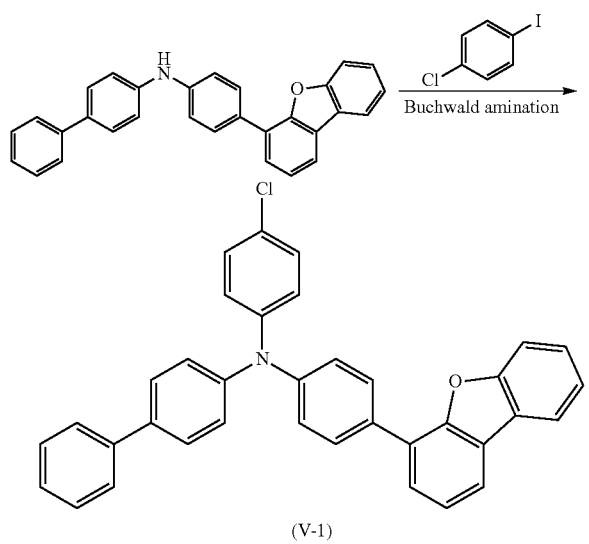

(V-1)

17 g of biphenyl-4-yl(4-dibenzofuran-4-ylphenyl)amine (41 mmol) and 14.8 g of 4-chloroiodobenzene (62 mmol) are dissolved in 260 ml of toluene. The solution is degassed and saturated with $N_2$. Thereafter, 1.6 ml (1.6 mmol) of a 1 M tri-tert-butylphosphine solution and 0.19 g (0.83 mmol) of palladium(II) acetate are added thereto, and then 6.0 g of sodium tert-butoxide (62 mmol) are added. The reaction mixture is heated to boiling under a protective atmosphere for 5 h. The mixture is subsequently partitioned between toluene and water, and the organic phase is washed three times with water and dried over $Na_2SO_4$ and concentrated by rotary evaporation. After the crude product has been filtered through silica gel with toluene, the remaining residue is recrystallized from heptane/toluene. The yield is 16 g (75% of theory).

Analogously, the following compounds (V-2) to (V-8) are prepared.

| Ex. | Reactant 1 | Reactant 2 | Product | Yield |
|---|---|---|---|---|
| V-2 | | | | 78% |

-continued

| Ex. | Reactant 1 | Reactant 2 | Product | Yield |
|---|---|---|---|---|
| V-3 | | | | 83% |
| V-4 | | | | 81% |
| V-5 | | | | 91% |

| Ex. | Reactant 1 | Reactant 2 | Product | Yield |
|---|---|---|---|---|
| V-6 | | | | 85% |
| V-7 | | | | 75% |
| V-8 | | | | 88% |

Synthesis of Compound 4-1

12 g (23.1 mmol) of pinacolboronic ester derivative (IV-1) and 12.1 g (23.1 mmol) of chloro derivative (V-1) are suspended in 1750 ml of dioxane and 7.0 g of caesium fluoride (46.3 mmol). 2.05 g (2.8 mmol) of bis(tricyclohexylphosphine)palladium dichloride are added to this suspension, and the reaction mixture is heated under reflux for 20 h. After cooling, the organic phase is removed, filtered through silica gel, washed three times with 100 mL of water and then concentrated to dryness. After the crude product has been filtered through silica gel with toluene, the remaining residue is recrystallized from heptane/toluene and finally sublimed under high vacuum; purity is 99.9%. The yield is 16.2 g (80% of theory).

Synthesis of Compounds (4-2) to (4-10)

Analogously to the synthesis of compound (2-1) described in Example 1, the following compounds (4-2) to (4-10) are also prepared.

| Ex. | Reactant 1 | Reactant 2 |
|---|---|---|
| 4-2 | 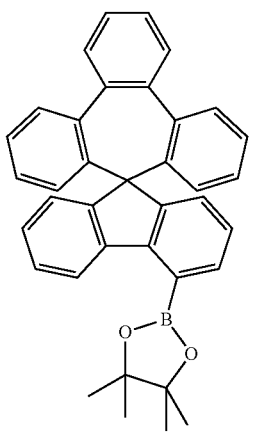 [SMILES: CC1(C)OB(c2cccc3c2-c2ccccc2C32c3ccccc3-c3ccccc3-c3ccccc32)OC1(C)C] | 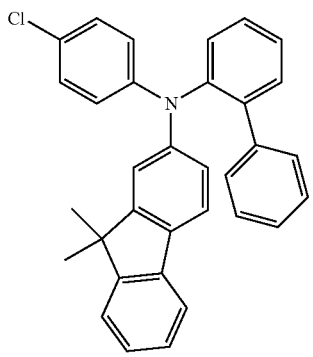 [SMILES: CC1(C)c2ccccc2-c2ccc(N(c3ccc(Cl)cc3)c3ccccc3-c3ccccc3)cc21] |
| 4-3 | 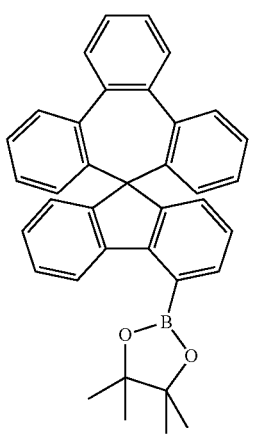 [SMILES: CC1(C)OB(c2cccc3c2-c2ccccc2C32c3ccccc3-c3ccccc3-c3ccccc32)OC1(C)C] | 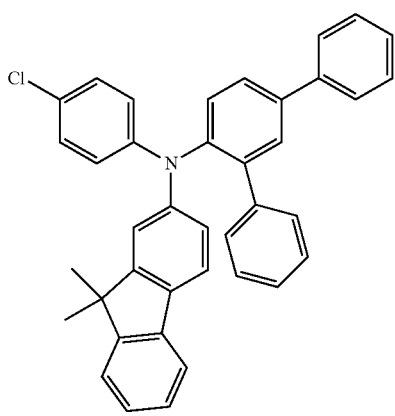 [SMILES: CC1(C)c2ccccc2-c2ccc(N(c3ccc(Cl)cc3)c3ccc(-c4ccccc4)cc3-c3ccccc3)cc21] |
| 4-4 | 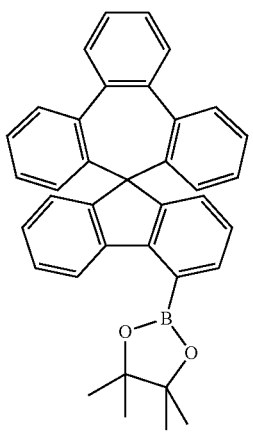 [SMILES: CC1(C)OB(c2cccc3c2-c2ccccc2C32c3ccccc3-c3ccccc3-c3ccccc32)OC1(C)C] | 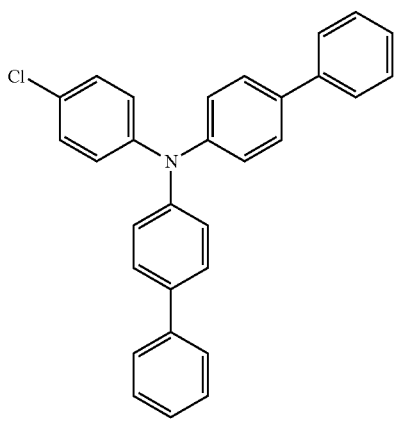 [SMILES: Clc1ccc(N(c2ccc(-c3ccccc3)cc2)c2ccc(-c3ccccc3)cc2)cc1] |

| | | | |
|---|---|---|---|
| 4-5 | 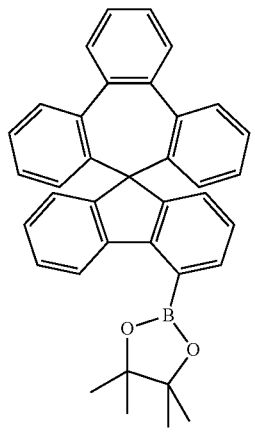 [SMILES: CC1(C)OB(c2cccc3c2-c2ccccc2C32c3ccccc3-c3ccccc3-c3ccccc32)OC1(C)C] | | 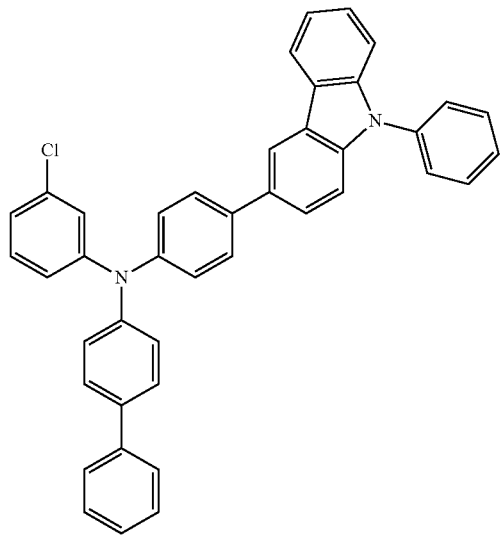 [SMILES: Clc1cccc(N(c2ccc(-c3ccccc3)cc2)c2ccc(-c3ccc4c(c3)c3ccccc3n4-c3ccccc3)cc2)c1] |
| 4-6 | 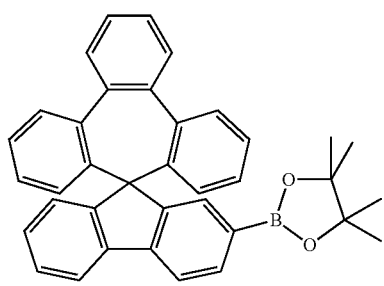 [SMILES: CC1(C)OB(c2ccc3c(c2)C2(c4ccccc4-c4ccccc4-c4ccccc42)c2ccccc2-3)OC1(C)C] | | 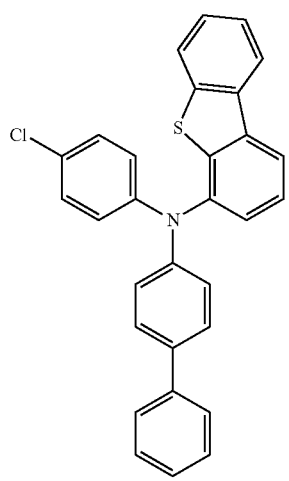 [SMILES: Clc1ccc(N(c2ccc(-c3ccccc3)cc2)c2cccc3c2sc2ccccc23)cc1] |
| 4-7 | 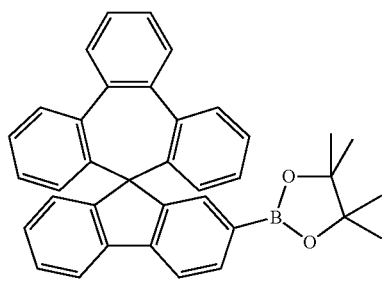 [SMILES: CC1(C)OB(c2ccc3c(c2)C2(c4ccccc4-c4ccccc4-c4ccccc42)c2ccccc2-3)OC1(C)C] | | 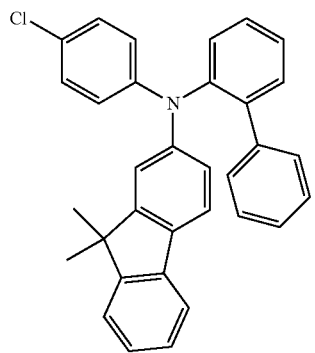 [SMILES: CC1(C)c2ccccc2-c2ccc(N(c3ccc(Cl)cc3)c3ccccc3-c3ccccc3)cc21] |

4-8 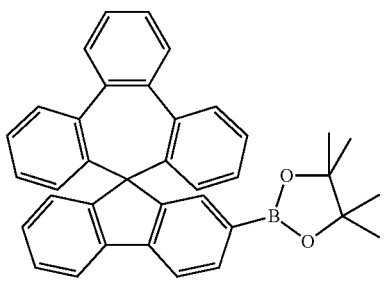 [SMILES: CC1(C)OB(c2ccc3c(c2)C2(c4ccccc4-c4ccccc4-c4ccccc42)c2ccccc2-3)OC1(C)C] 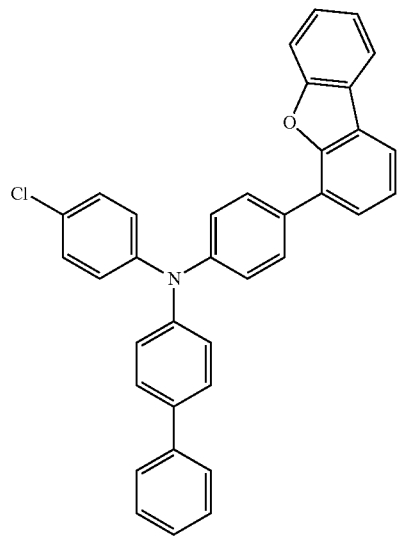 [SMILES: Clc1ccc(N(c2ccc(-c3ccccc3)cc2)c2ccc(-c3cccc4c3oc3ccccc34)cc2)cc1]
4-9 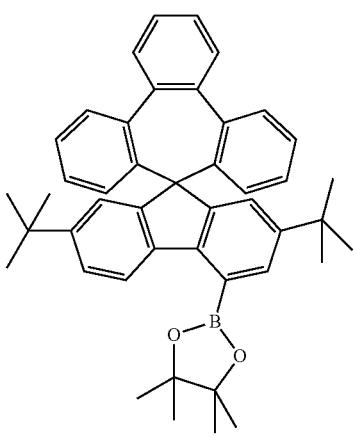 [SMILES: CC(C)(C)c1ccc2c(c1)C1(c3ccccc3-c3ccccc3-c3ccccc31)c1cc(C(C)(C)C)cc(B3OC(C)(C)C(C)(C)O3)c1-2] 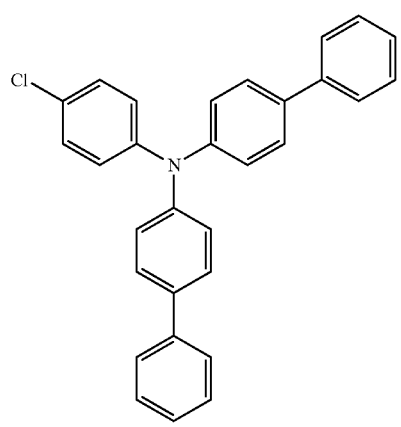 [SMILES: Clc1ccc(N(c2ccc(-c3ccccc3)cc2)c2ccc(-c3ccccc3)cc2)cc1]
410 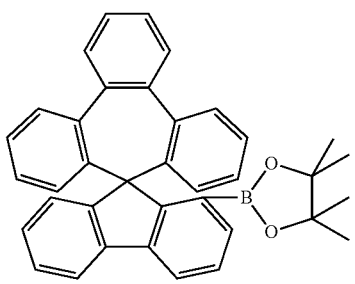 [SMILES: CC1(C)OB(c2cccc3c2C2(c4ccccc4-c4ccccc4-c4ccccc42)c2ccccc2-3)OC1(C)C] 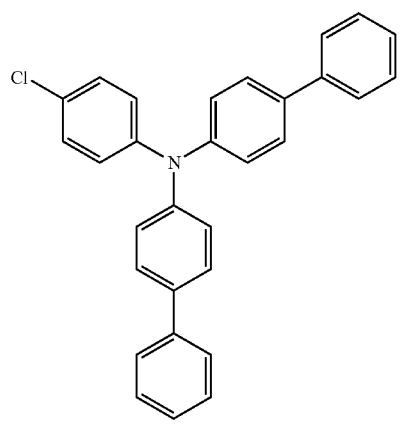 [SMILES: Clc1ccc(N(c2ccc(-c3ccccc3)cc2)c2ccc(-c3ccccc3)cc2)cc1]

4-11 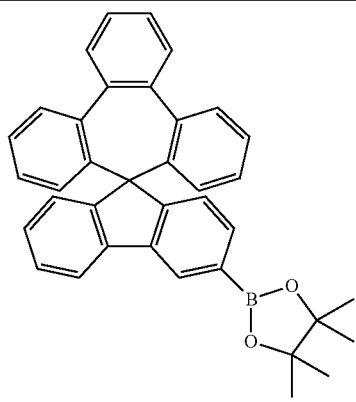 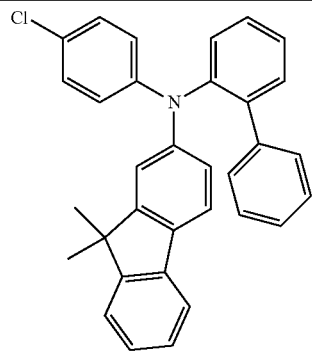
4-12 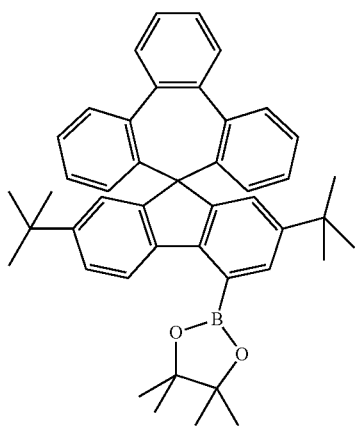 [SMILES: CC(C)(C)c1ccc2c(c1)C1(c3ccccc3-c3ccccc3-c3ccccc31)c1cc(C(C)(C)C)cc(B3OC(C)(C)C(C)(C)O3)c1-2] 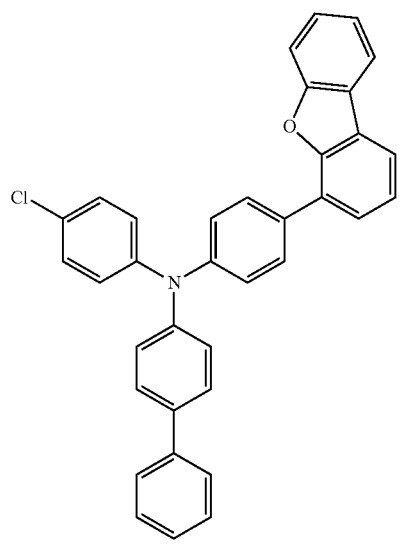 [SMILES: Clc1ccc(N(c2ccc(-c3ccccc3)cc2)c2ccc(-c3cccc4c3oc3ccccc34)cc2)cc1]
4-13 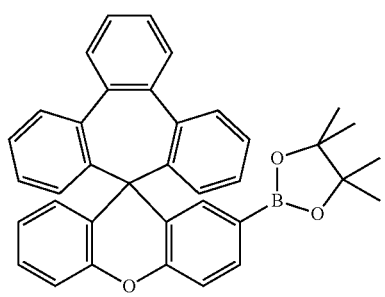 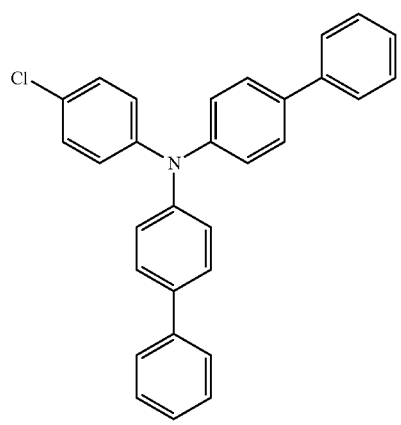 [SMILES: Clc1ccc(N(c2ccc(-c3ccccc3)cc2)c2ccc(-c3ccccc3)cc2)cc1]

| | |
|---|---|
| 4-14 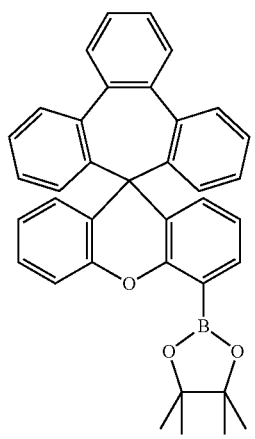 [SMILES: CC1(C)OB(c2cccc3c2Oc2ccccc2C32c3ccccc3-c3ccccc3-c3ccccc32)OC1(C)C] | 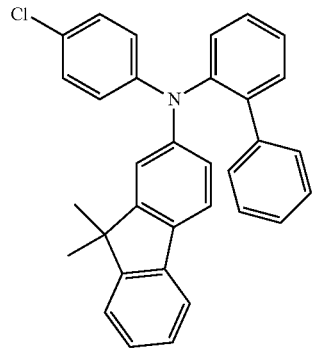 [SMILES: CC1(C)c2ccccc2-c2ccc(N(c3ccc(Cl)cc3)c3ccccc3-c3ccccc3)cc21] |
| 4-15 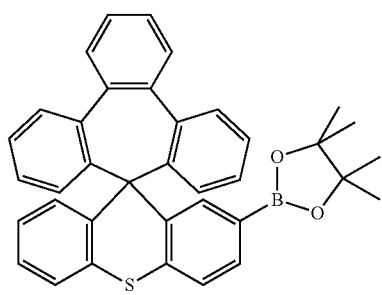 [SMILES: CC1(C)OB(c2ccc3c(c2)C2(c4ccccc4S3)c3ccccc3-c3ccccc3-c3ccccc32)OC1(C)C] | 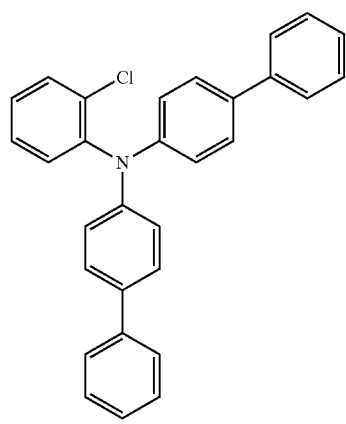 [SMILES: Clc1ccccc1N(c1ccc(-c2ccccc2)cc1)c1ccc(-c2ccccc2)cc1] |
| 4-16 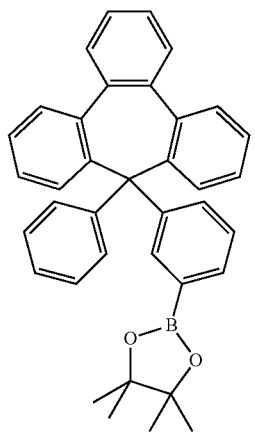 [SMILES: CC1(C)OB(c2cccc(C3(c4ccccc4)c4ccccc4-c4ccccc4-c4ccccc43)c2)OC1(C)C] | 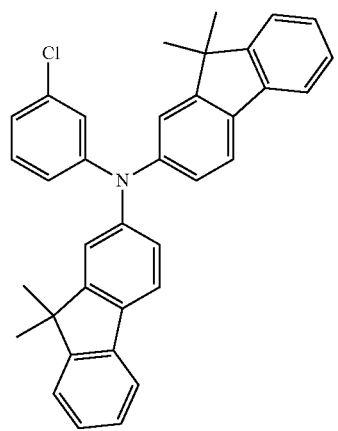 [SMILES: CC1(C)c2ccccc2-c2ccc(N(c3cccc(Cl)c3)c3ccc4c(c3)C(C)(C)c3ccccc3-4)cc21] |

4-17 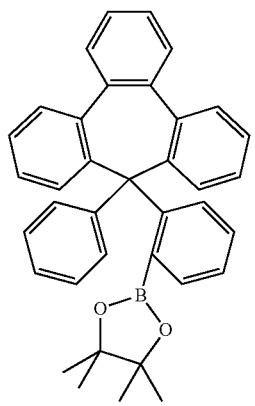 [SMILES: CC1(C)OB(c2ccccc2C2(c3ccccc3)c3ccccc3-c3ccccc3-c3ccccc32)OC1(C)C] 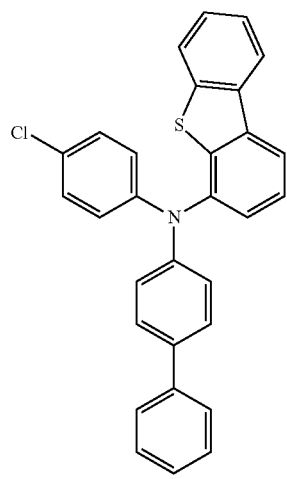 [SMILES: Clc1ccc(N(c2ccc(-c3ccccc3)cc2)c2cccc3c2sc2ccccc23)cc1]
4-18 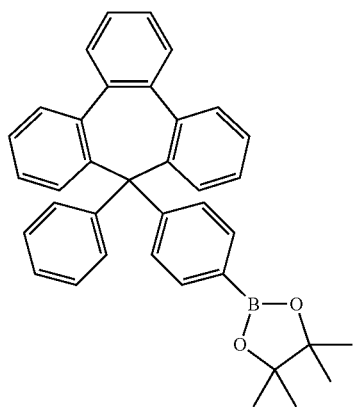 [SMILES: CC1(C)OB(c2ccc(C3(c4ccccc4)c4ccccc4-c4ccccc4-c4ccccc43)cc2)OC1(C)C] 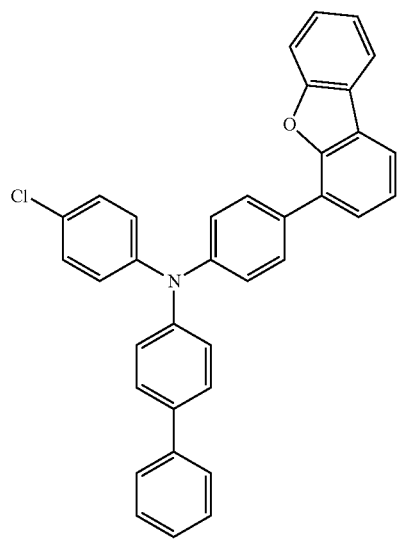 [SMILES: Clc1ccc(N(c2ccc(-c3ccccc3)cc2)c2ccc(-c3cccc4c3oc3ccccc34)cc2)cc1]
4-19 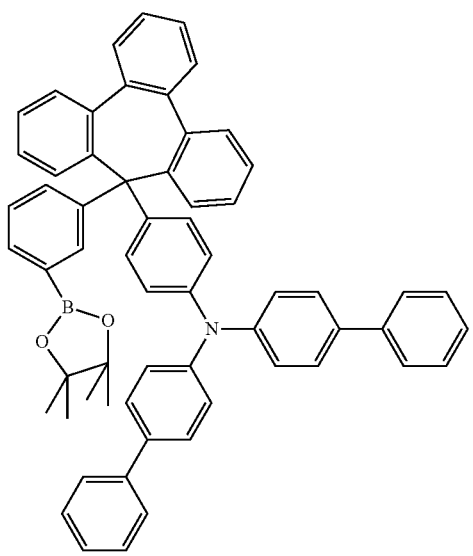 [SMILES: CC1(C)OB(c2cccc(C3(c4ccc(N(c5ccc(-c6ccccc6)cc5)c5ccc(-c6ccccc6)cc5)cc4)c4ccccc4-c4ccccc4-c4ccccc43)c2)OC1(C)C] 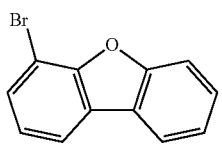 [SMILES: Brc1cccc2c1oc1ccccc12]

| | | |
|---|---|---|
| 4-20 | 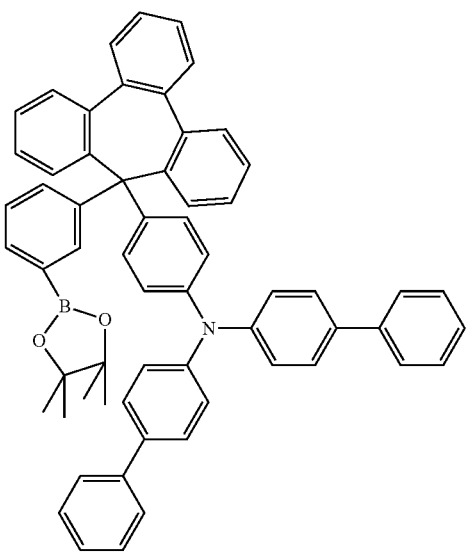 [SMILES: CC1(C)OB(c2cccc(C3(c4ccc(N(c5ccc(-c6ccccc6)cc5)c5ccc(-c6ccccc6)cc5)cc4)c4ccccc4-c4ccccc4-c4ccccc43)c2)OC1(C)C] | 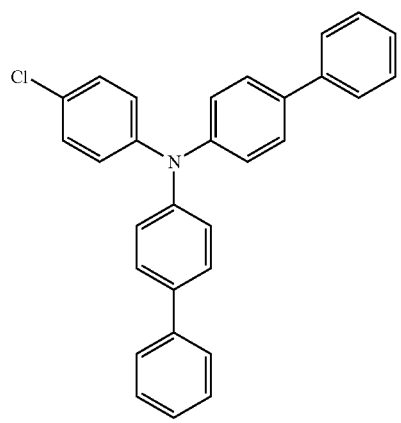 [SMILES: Clc1ccc(N(c2ccc(-c3ccccc3)cc2)c2ccc(-c3ccccc3)cc2)cc1] |
| 4-21 | 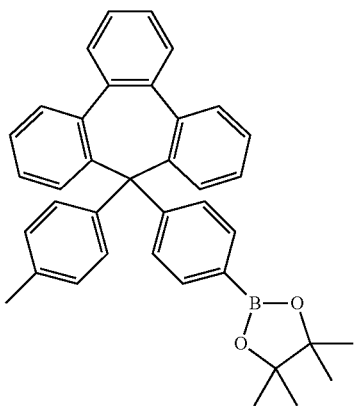 | 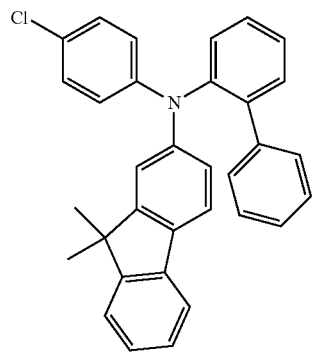 [SMILES: CC1(C)c2ccccc2-c2ccc(N(c3ccc(Cl)cc3)c3ccccc3-c3ccccc3)cc21] |
| Ex. | Product | Yield |
|---|---|---|
| 4-2 | 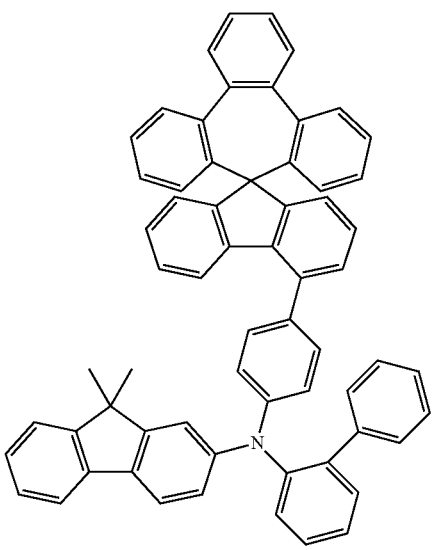 [SMILES: CC1(C)c2ccccc2-c2ccc(N(c3ccc(-c4cccc5c4-c4ccccc4C54c5ccccc5-c5ccccc5-c5ccccc54)cc3)c3ccccc3-c3ccccc3)cc21] | 78% |

| 4-3 | 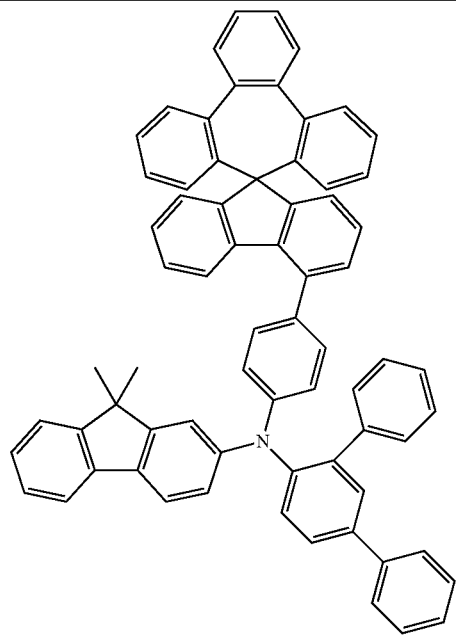 | 71% |
| 4-4 | 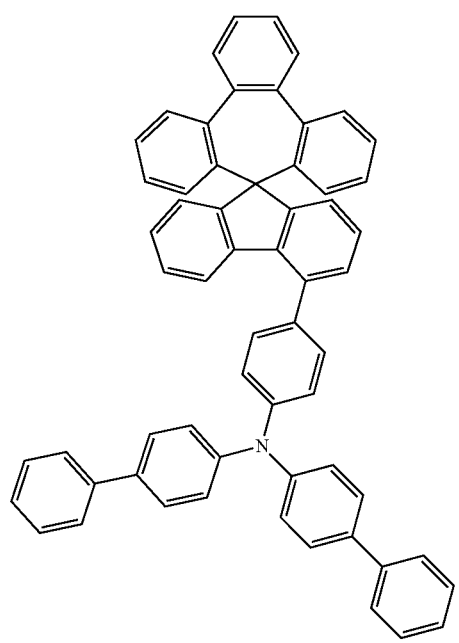 [SMILES: c1ccc(-c2ccc(N(c3ccc(-c4ccccc4)cc3)c3ccc(-c4cccc5c4-c4ccccc4C54c5ccccc5-c5ccccc5-c5ccccc54)cc3)cc2)cc1] | 82% |

| | | |
|---|---|---|
| 4-5 | 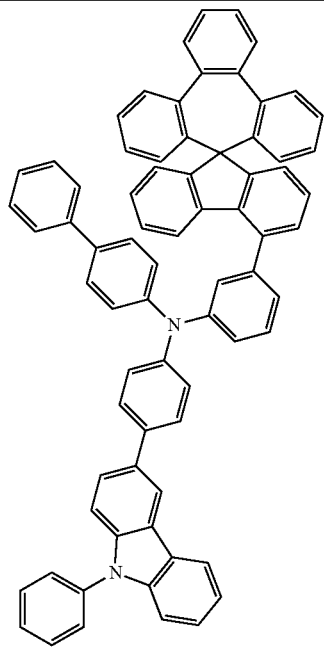 | 89% |
| 4-6 | 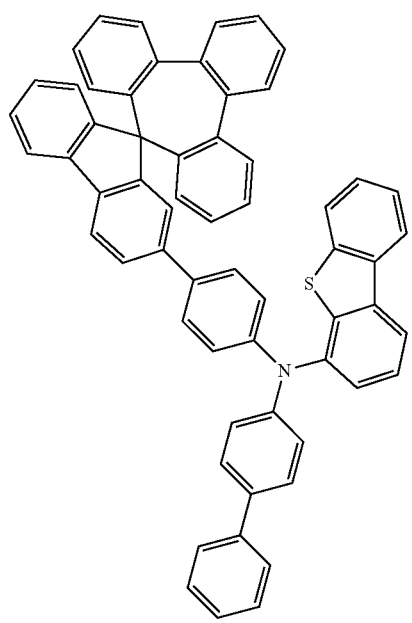 [SMILES: c1ccc(-c2ccc(N(c3ccc(-c4ccc5c(c4)C4(c6ccccc6-c6ccccc6-c6ccccc64)c4ccccc4-5)cc3)c3cccc4c3sc3ccccc34)cc2)cc1] | 69% |

4-7 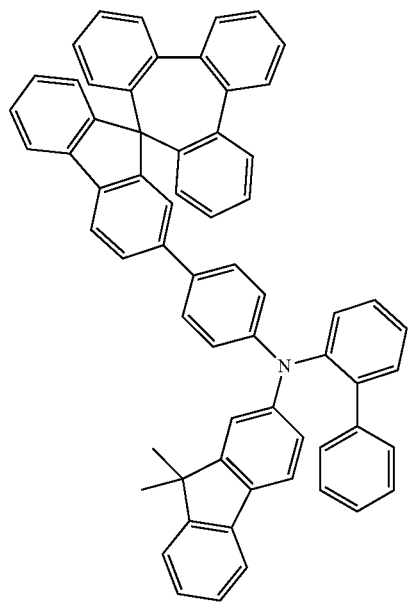 [SMILES: CC1(C)c2ccccc2-c2ccc(N(c3ccc(-c4ccc5c(c4)C4(c6ccccc6-c6ccccc6-c6ccccc64)c4ccccc4-5)cc3)c3ccccc3-c3ccccc3)cc21] 80%
4-8 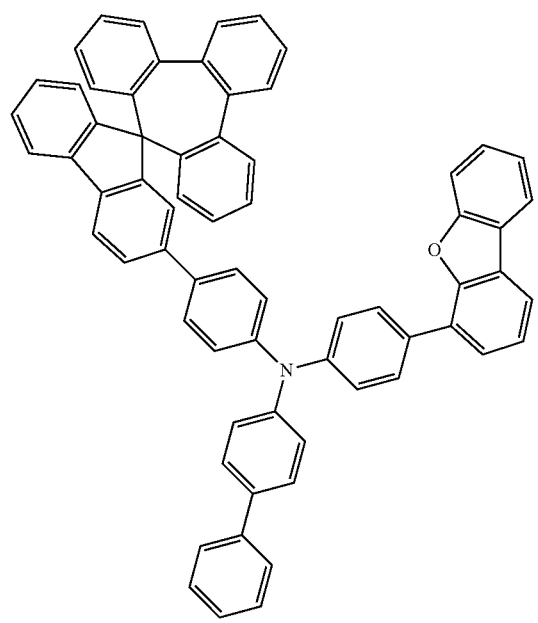 [SMILES: c1ccc(-c2ccc(N(c3ccc(-c4ccc5c(c4)C4(c6ccccc6-c6ccccc6-c6ccccc64)c4ccccc4-5)cc3)c3ccc(-c4cccc5c4oc4ccccc45)cc3)cc2)cc1] 77%

| | | |
|---|---|---|
| 4-9 | 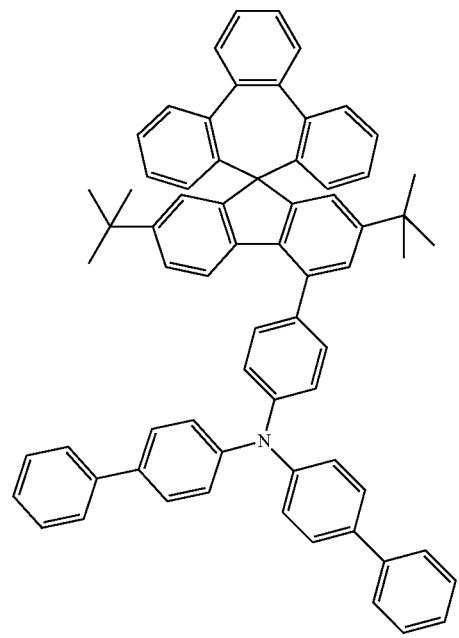 [SMILES: CC(C)(C)c1ccc2c(c1)C1(c3ccccc3-c3ccccc3-c3ccccc31)c1cc(C(C)(C)C)cc(-c3ccc(N(c4ccc(-c5ccccc5)cc4)c4ccc(-c5ccccc5)cc4)cc3)c1-2] | 71% |
| 4-10 | 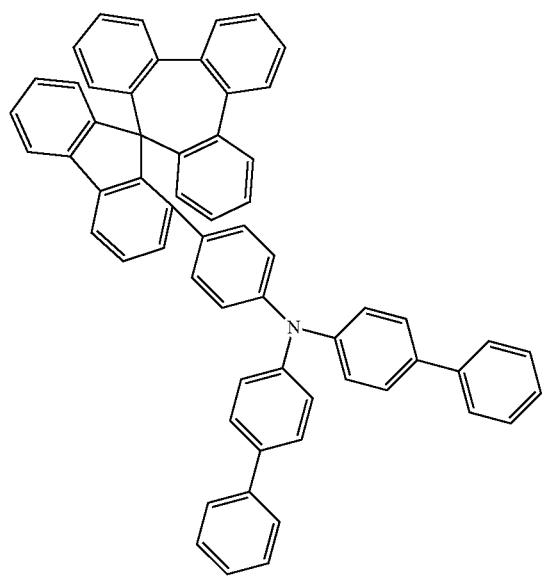 [SMILES: c1ccc(-c2ccc(N(c3ccc(-c4ccccc4)cc3)c3ccc(-c4cccc5c4C4(c6ccccc6-c6ccccc6-c6ccccc64)c4ccccc4-5)cc3)cc2)cc1] | 60% |

| | | |
|---|---|---|
| 4-11 | 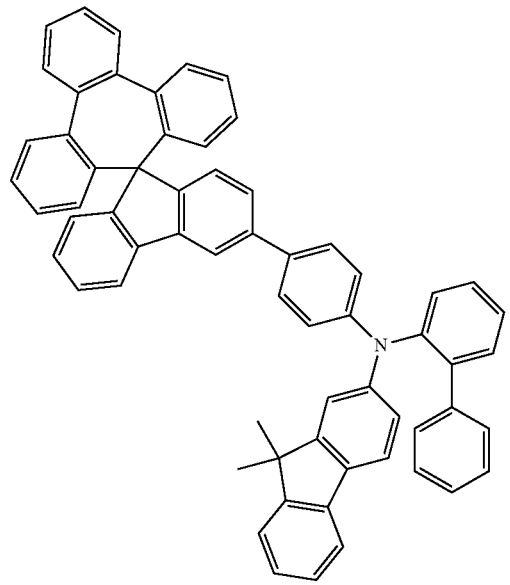 [SMILES: CC1(C)c2ccccc2-c2ccc(N(c3ccc(-c4ccc5c(c4)-c4ccccc4C54c5ccccc5-c5ccccc5-c5ccccc54)cc3)c3ccccc3-c3ccccc3)cc21] | 77% |
| 4-12 | 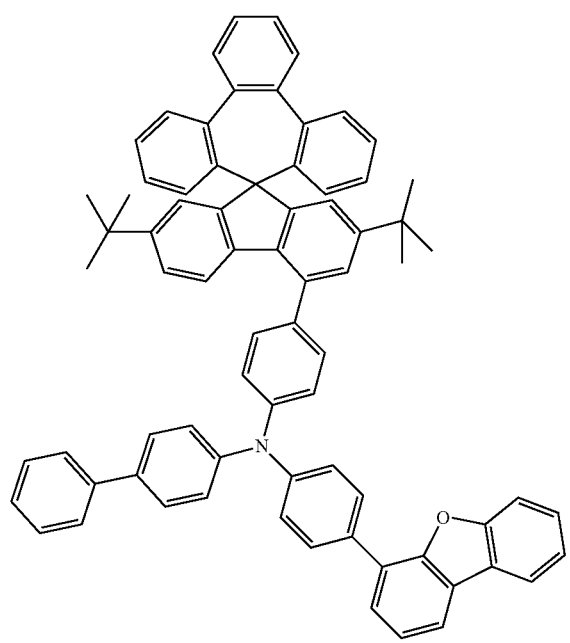 [SMILES: CC(C)(C)c1ccc2c(c1)C1(c3ccccc3-c3ccccc3-c3ccccc31)c1cc(C(C)(C)C)cc(-c3ccc(N(c4ccc(-c5ccccc5)cc4)c4ccc(-c5cccc6c5oc5ccccc56)cc4)cc3)c1-2] | 70% |

4-13 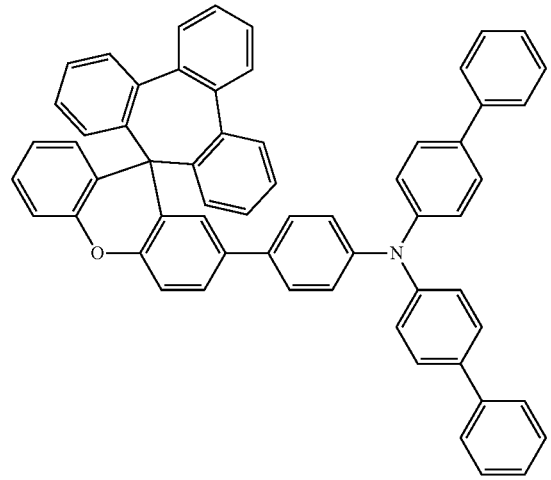 [SMILES: c1ccc(-c2ccc(N(c3ccc(-c4ccccc4)cc3)c3ccc(-c4ccc5c(c4)C4(c6ccccc6O5)c5ccccc5-c5ccccc5-c5ccccc54)cc3)cc2)cc1] 79%
4-14 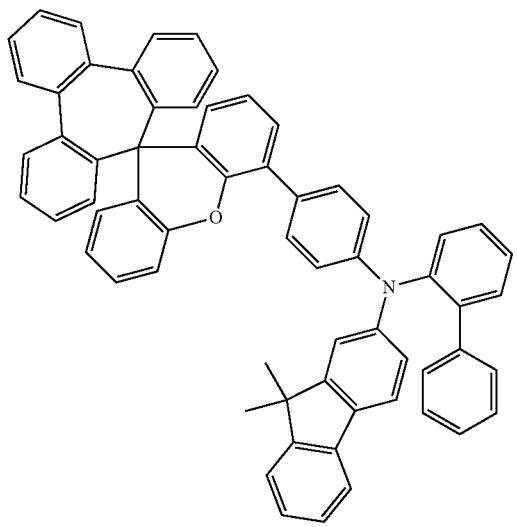 [SMILES: CC1(C)c2ccccc2-c2ccc(N(c3ccc(-c4cccc5c4Oc4ccccc4C54c5ccccc5-c5ccccc5-c5ccccc54)cc3)c3ccccc3-c3ccccc3)cc21] 66%
4-15 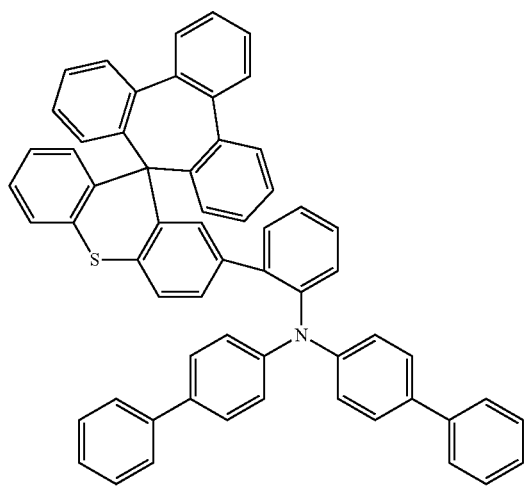 [SMILES: c1ccc(-c2ccc(N(c3ccc(-c4ccccc4)cc3)c3ccccc3-c3ccc4c(c3)C3(c5ccccc5S4)c4ccccc4-c4ccccc4-c4ccccc43)cc2)cc1] 65%

4-16 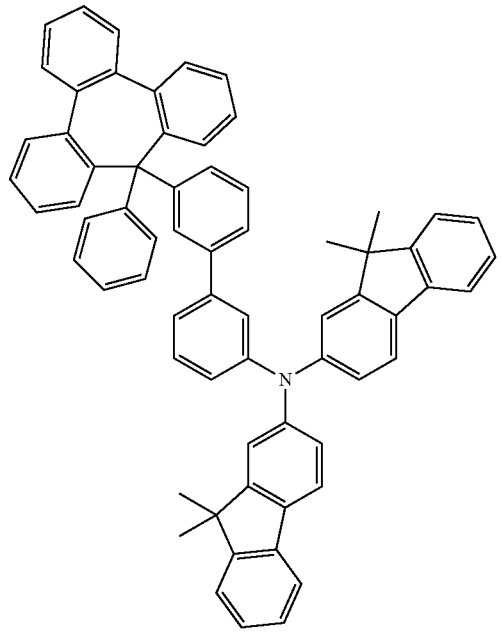 [SMILES: CC1(C)c2ccccc2-c2ccc(N(c3cccc(-c4cccc(C5(c6ccccc6)c6ccccc6-c6ccccc6-c6ccccc65)c4)c3)c3ccc4c(c3)C(C)(C)c3ccccc3-4)cc21] 76%
4-17 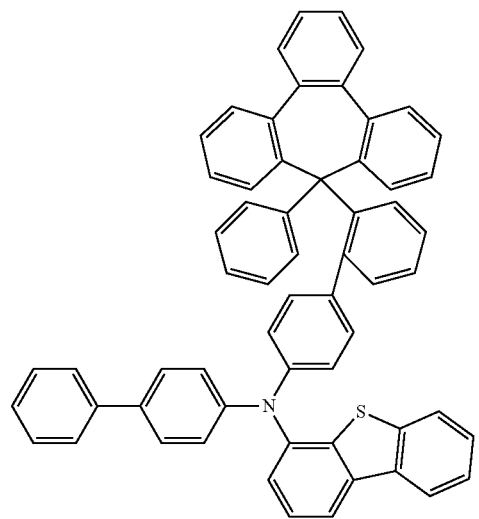 [SMILES: c1ccc(-c2ccc(N(c3ccc(-c4ccccc4C4(c5ccccc5)c5ccccc5-c5ccccc5-c5ccccc54)cc3)c3cccc4c3sc3ccccc34)cc2)cc1] 82%

| 4-18 | 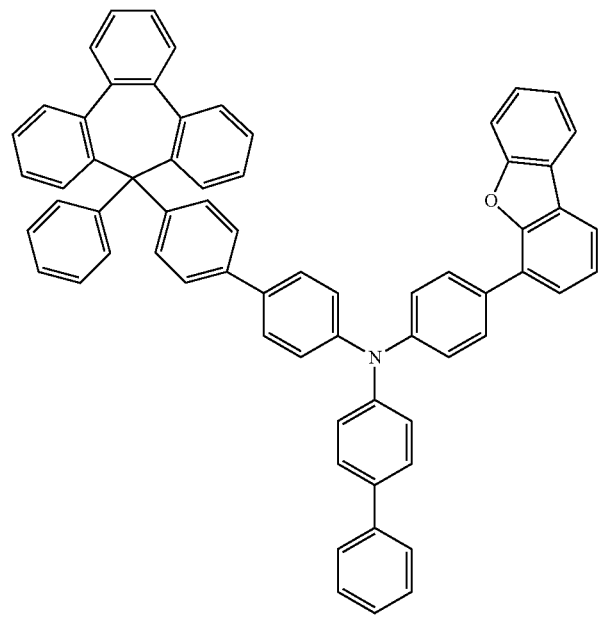 [SMILES: c1ccc(-c2ccc(N(c3ccc(-c4ccc(C5(c6ccccc6)c6ccccc6-c6ccccc6-c6ccccc65)cc4)cc3)c3ccc(-c4cccc5c4oc4ccccc45)cc3)cc2)cc1] | 83% |
|---|---|---|
| 4-19 | 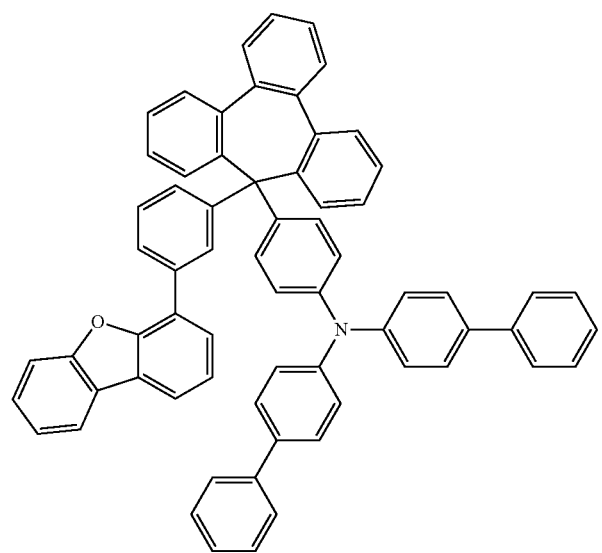 [SMILES: c1ccc(-c2ccc(N(c3ccc(-c4ccccc4)cc3)c3ccc(C4(c5cccc(-c6cccc7c6oc6ccccc67)c5)c5ccccc5-c5ccccc5-c5ccccc54)cc3)cc2)cc1] | 90% |

-continued 4-20 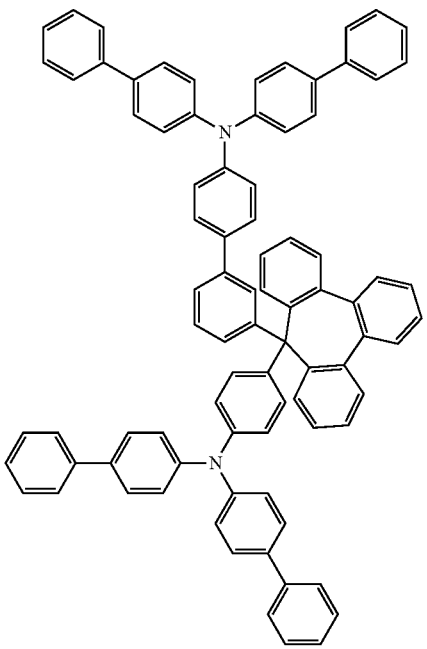 [SMILES: c1ccc(-c2ccc(N(c3ccc(-c4ccccc4)cc3)c3ccc(-c4cccc(C5(c6ccc(N(c7ccc(-c8ccccc8)cc7)c7ccc(-c8ccccc8)cc7)cc6)c6ccccc6-c6ccccc6-c6ccccc65)c4)cc3)cc2)cc1] 61%

4-21 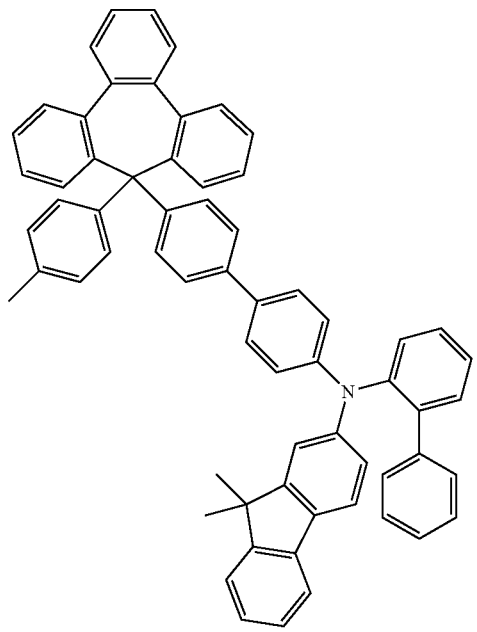 [SMILES: Cc1ccc(C2(c3ccc(-c4ccc(N(c5ccc6c(c5)C(C)(C)c5ccccc5-6)c5ccccc5-c5ccccc5)cc4)cc3)c3ccccc3-c3ccccc3-c3ccccc32)cc1] 77%

B) Device Examples

OLEDs of the invention and OLEDs according to the prior art are produced by a general method according to WO 04/058911, which is adapted to the circumstances described here (e.g. materials).

In the inventive examples which follow, the data for various OLEDs are presented. Substrates used are glass plates coated with structured ITO (indium tin oxide) of thickness 50 nm. The OLEDs have the following layer structure: substrate/p-doped hole transport layer (HIL1)/hole transport layer (HTL)/p-doped hole transport layer (HTL2)/electron blocker layer (EBL)/emission layer (EML)/electron transport layer (ETL)/electron injection layer (EIL) and finally a cathode. The cathode is formed by an aluminum layer of thickness 100 nm. The materials required for production of the OLEDs are shown in Table 1.

All materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as H1:SEB(5%) mean here that the material H1 is present in the layer in a proportion by volume of 95% and SEB in a proportion by volume of 5%. Analogously, the electron transport layers or the hole injection layers may also consist of a mixture of two or more materials.

The OLEDs are characterized in a standard manner. For this purpose, the external quantum efficiency (EQE, measured in percent) is determined as a function of luminance, calculated from current-voltage-luminance characteristics (IUL characteristics) assuming Lambertian radiation characteristics, and the lifetime. The parameter EQE @ 10 mA/cm² refers to the external quantum efficiency at a current density of 10 mA/cm². LD80 @ 60 mA/cm² is the lifetime before the OLED, given a starting brightness at constant current of 60 mA/cm², has fallen to 80% of the starting intensity.

TABLE 1

Structures of the materials used

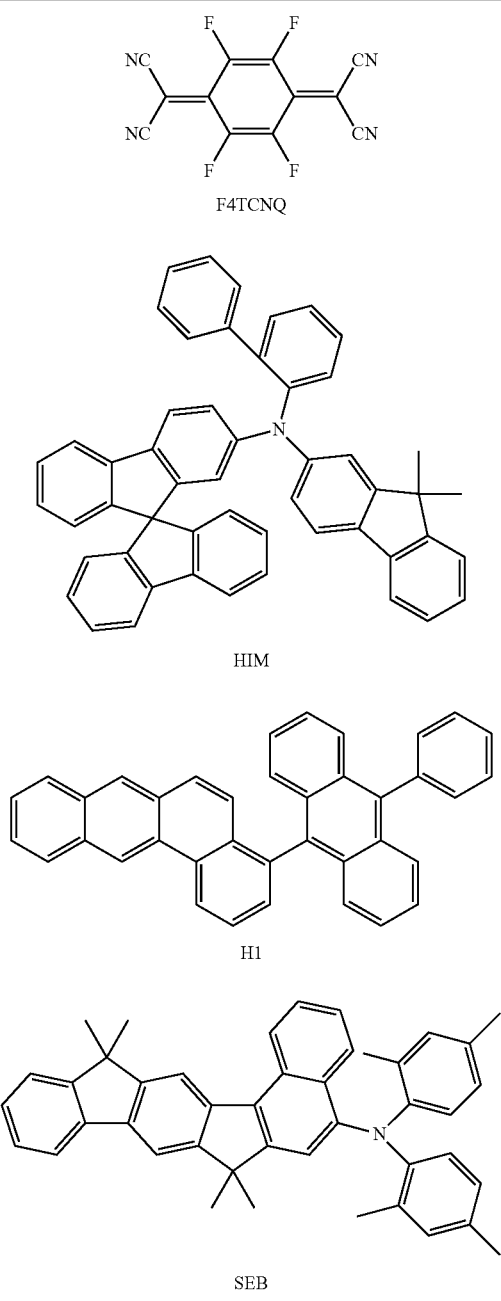

TABLE 1-continued

Structures of the materials used

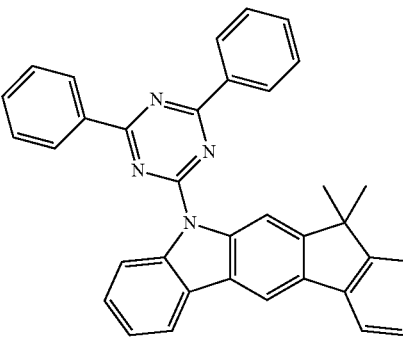

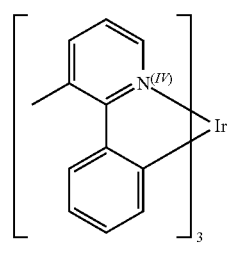

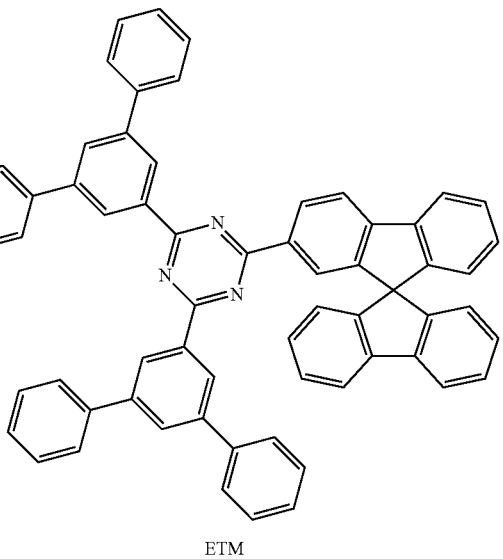

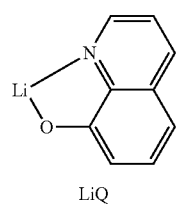

TABLE 1-continued

Structures of the materials used

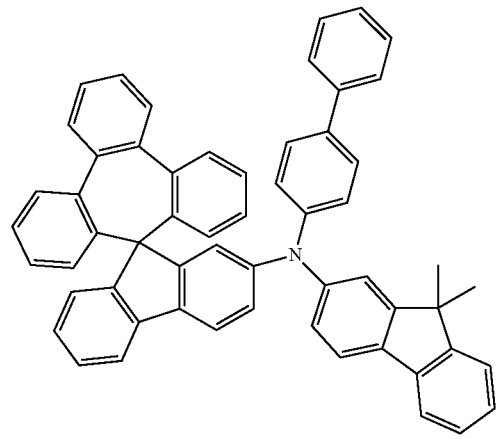

HTM1

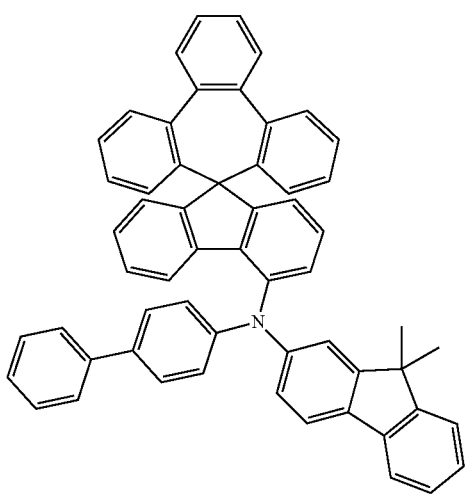

HTM2

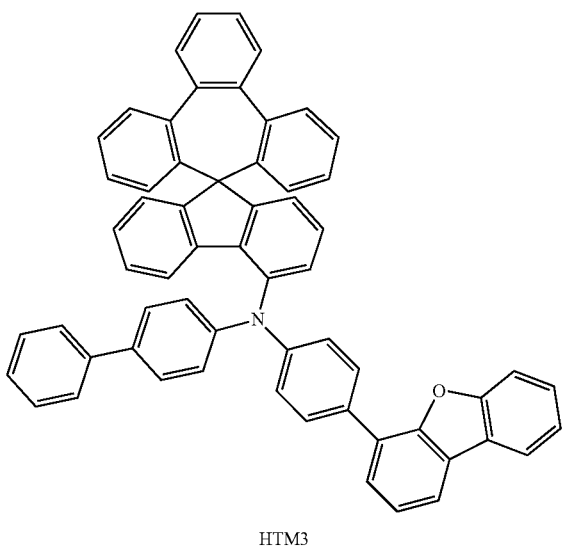

HTM3

TABLE 1-continued

Structures of the materials used

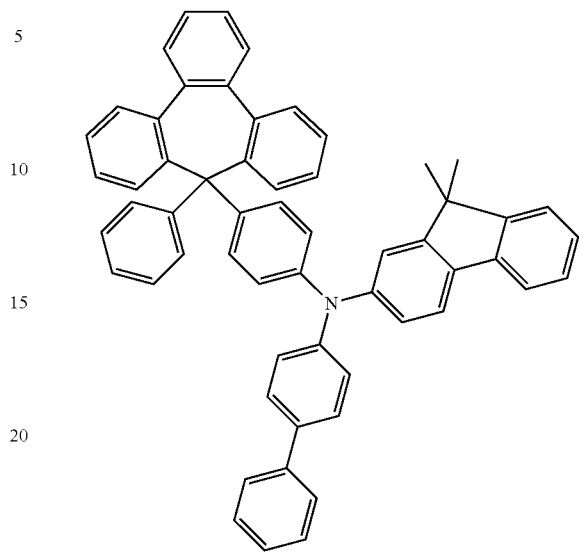

HTM4

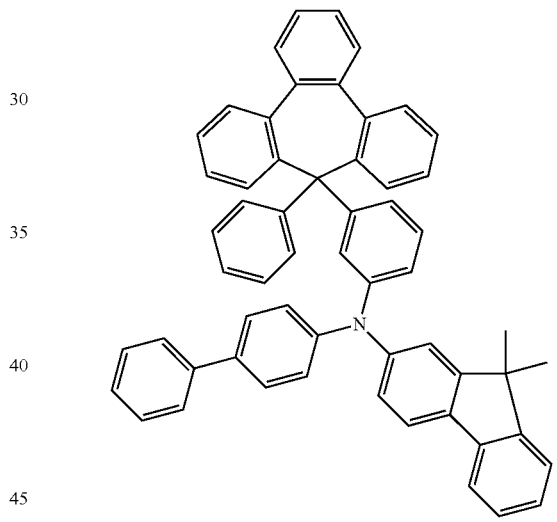

HTM5

Samples HTM1, HTM2, HTM3, HTM4 and HTM5 were compared with one another in a blue-fluorescing OLED. The structure of the stack is as follows: HIM:F4TCNQ(5%)(20 nm)/HIM(155 nm)/HTM_x: F4TCNQ(5%)(20 nm)/HTM_x (20 nm)/H1:SEB(5%)(20 nm)/ETM:LiQ(50%)(30 nm)/ LiQ(1 nm). HTM_x in each case is the inventive material HTM1, HTM2, HTM3, HTM4 or HTM5. If, in the third layer, for example, the doped HTM1 is used in place of HTM_x, it is necessary to use HTM1 in the subsequent layer as well. A cross-combination of doped HTM1 and undoped HTM2 is not considered here.

The evaluation of the external quantum efficiencies at 10 mA/cm² for the experiments conducted shows the following results: HTM1 achieves 8.6% EQE, whereas HTM2 achieves 8.2%, HTM3 8.1%, HTM4 7.8% and HTM5 8.0%. The lifetimes of the devices produced before a decline to 80% of the starting intensity at a constant current of 60 mA/cm² are 310 hours for HTM1, 400 hours for HTM2, 420 hours for HTM3, 350 hours for HTM4 and 410 hours for HTM5.

The same two materials are used to produce a triplet green component having the following structure: HIM:F4TCNQ (5%)(20 nm)/HIM(210 nm)/HTM_x:F4TCNQ(5%)(20 nm)/ HTM_x(20 nm)/H2:TEG(10%)(30 nm)/ETM:LiQ(50%)(40 nm)/LiQ(1 nm). HTM_x in each case is the inventive material HTM1, HTM2, HTM3, HTM4 or HTM5. If, in the third layer, for example, the doped HTM1 is used in place of HTM_x, it is necessary to use HTM1 in the subsequent layer as well. A cross-combination of, for example, doped HTM1 and undoped HTM2 is not considered here.

The external quantum efficiencies show a similar trend to the above-described blue-fluorescing OLED. The external quantum efficiency for HTM1 at 2 mA/cm$^2$ in this experiment is 18.3%. The components containing HTM2 achieve 18.2%, HTM3 17.2%, HTM4 17.5% and HTM5 18.0%. The lifetimes are similarly high to the blue-fluorescing OLED: HTM1 at 20 mA/cm$^2$ has a lifetime before a decline to 80% of the starting intensity of 155 hours. HTM2 has an LD80 of 210 hours, HTM3 of 220 hours, HTM4 of 190 hours and HTM5 of 210 hours.

The invention claimed is:
1. A compound of formula (1)

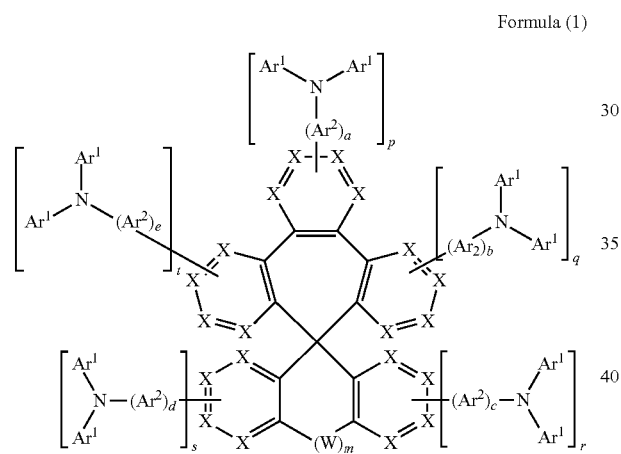

Formula (1)

where the symbols and indices used are as follows:
X is the same or different at each instance and is $CR^1$ or N;
$Ar^2$ is the same or different at each instance and is a bivalent aromatic or heteroaromatic ring system which has 5 to 60 aromatic ring atoms and may be substituted by one or more $R^2$ radicals;
$Ar^1$ is the same or different at each instance and is an aromatic or heteroaromatic ring system which has 5 to 60 aromatic ring atoms and may in each case also be substituted by one or more $R^2$ radicals; where $Ar^1$ and/or $Ar^2$ radicals bonded to the same nitrogen atom may be joined via at least one K group;
K is the same or different at each instance and is a single bond or a bivalent bridge selected from $N(R^2)$, $B(R^2)$, O, C=O, $C(R^2)_2$, $Si(R^2)_2$, $C=C(R^2)_2$, S=O, $P(R^2)$, $P(=O)R^2$ and S;
W is the same or different at each instance and is a single bond or a bivalent bridge selected from $N(R^2)$, $B(R^2)$, O, C=O, $C(R^2)_2$, $Si(R^2)_2$, S and $R^2C$=$CR^2$;
Ar is the same or different at each instance and is an aromatic or heteroaromatic ring system, which may be substituted by one or more $R^3$ radicals;

$R^1$ is the same or different at each instance and is H, D, F, Cl, Br, I, C(=O)Ar, P(=O)Ar$_2$, S(=O)Ar, S(=O)$_2$Ar, $CR^2$=$CR^2$Ar, CN, NO$_2$, Si(R$^2$)$_3$, B(OR$^2$)$_2$, OSO$_2$R$^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent CH$_2$ groups may be replaced by $R^2C$≡$CR^2$, C≡C, Si(R$^2$)$_2$, C=O, C=NR$^2$, P(=O)(R$^2$), SO, SO$_2$, NR$^2$, O, S or CONR$^2$ and where one or more hydrogen atoms may be replaced by D, F, Cl, Br, I, CN or NO$_2$, or an aromatic or heteroaromatic ring system which has 5 to 60 aromatic ring atoms, each of which may be substituted by one or more $R^2$ radicals, or an aryloxy or heteroaryloxy group which has 5 to 40 aromatic ring atoms and may be substituted by one or more $R^2$ radicals, or an aralkyl or heteroalkyl group which has 5 to 40 aromatic ring atoms and may be substituted by one or more $R^2$ radicals, or a combination of these groups; at the same time, two or more $R^2$ substituents together with the atoms to which they are bonded and also with one another, or two $R^1$ substituents, may form a mono- or polycyclic, aliphatic or aromatic ring system;

$R^2$ is the same or different at each instance and is H, D, F, Cl, Br, I, N(R$^3$)$_2$, N(Ar)$_2$, C(=O)Ar, P(=O)Ar$_2$, S(=O)Ar, S(=O)$_2$Ar, $CR^3$=$CR^3$Ar, CN, NO$_2$, Si(R$^3$)$_3$, B(OR$^3$)$_2$, OSO$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent CH$_2$ groups may be replaced by $R^3C$=$CR^3$, C≡C, Si(R$^3$)$_2$, C=O, C=NR$^3$, P(=O)(R$^3$), SO, SO$_2$, NR$^3$, O, S or CONR$^3$ and where one or more hydrogen atoms may be replaced by D, F, Cl, Br, I, CN or NO$_2$, or an aromatic or heteroaromatic ring system which has 5 to 60 aromatic ring atoms, each of which may be substituted by one or more $R^3$ radicals, or an aryloxy or heteroaryloxy group which has 5 to 40 aromatic ring atoms and may be substituted by one or more $R^3$ radicals, or an aralkyl or heteroalkyl group which has 5 to 40 aromatic ring atoms and may be substituted by one or more $R^3$ radicals, or a combination of these groups; at the same time, two or more $R^3$ substituents together with the atoms to which they are bonded and also with one another, or two $R^2$ substituents, may form a mono- or polycyclic, aliphatic or aromatic ring system;

$R^3$ is the same or different at each instance and is H, D, F, Cl, Br, I, C(=O)Ar, P(=O)Ar$_2$, S(=O)Ar, S(=O)$_2$Ar, $CR^4$=$CR^4$Ar, CN, NO$_2$, Si(R$^4$)$_3$, B(OR$^4$)$_2$, OSO$_2$R$^4$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^4$ radicals, where one or more nonadjacent CH$_2$ groups may be replaced by $R^4C$=$CR^4$, C≡C, Si(R$^4$)$_2$, C=O, C=NR$^4$, P(=O)(R$^4$), SO, SO$_2$, NR$^4$, O, S or CONR$^4$ and where one or more hydrogen atoms may be replaced by D, F, Cl, Br, I, CN or NO$_2$, or an aromatic or heteroaromatic ring system which has 5 to 60 aromatic ring atoms, each of which may be substituted by one or more $R^4$ radicals, or an aryloxy or heteroaryloxy group which has 5 to 40 aromatic ring atoms and may be substituted by one or more $R^4$ radicals, or an aralkyl or heteroaralkyl group which has 5 to 40 aromatic ring atoms and may be substituted by one or more $R^4$ radicals, or a combination of these groups; at the same time, two or more $R^4$ substituents together with the atoms to which they are bonded and also with one another, or two $R^3$ substituents, may form a mono- or polycyclic, aliphatic or aromatic ring system;

$R^4$ is the same or different at each instance and is H, D, F or an aliphatic hydrocarbyl radical having 1 to 20 carbon atoms or an aryl or heteroaryl group which has 5 to 40 ring atoms and may be substituted by one or more $R^5$ radicals, or a combination of these groups;

$R^5$ is the same or different at each instance and is H, D, F or an aliphatic hydrocarbyl radical having 1 to 20 carbon atoms;

m is 0 or 1, where m=0 means that no W group is bonded at this position, and the carbon atoms in question that bind to W are each replaced by an X group; and p, q, r, s, t are the same or different at each instance and are 0, 1 or 2;

a, b, c, d, e are the same or different at each instance and are 0, 1 or 2;

where p+q+r+s+t is 1.

2. The compound according to claim 1, wherein W is a single bond.

3. The compound according to claim 1, wherein the index r is 1, and the indices p, q, s and t are each 0, or characterized in that the index s is 1 and the indices p, q, r and t are each 0.

4. The compound according to claim 1, wherein the compound corresponds to formula (2)

Formula (2)

wherein the further symbols and indices used have the definitions given in claim 1.

5. The compound according to claim 1, wherein the compound is a compound of one of the formulae (4) and (5):

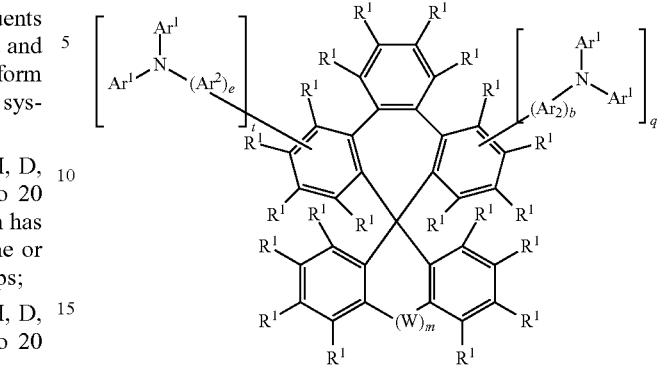

Formula (4)

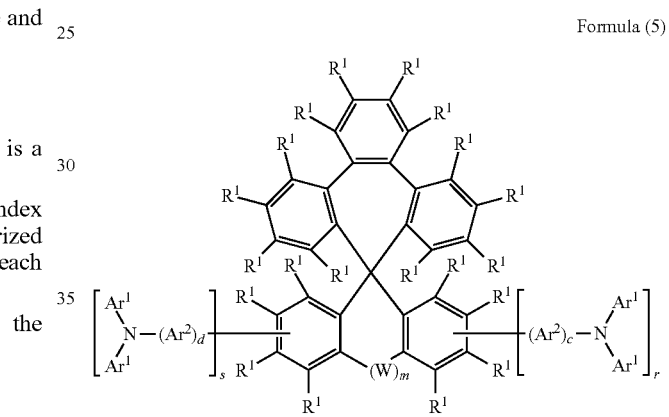

Formula (5)

where the symbols and indices used have the definitions given in claim 1 and t+q=1 or s+r=1.

6. The compound according to claim 1, wherein the compound is a compound of one of the formulae (6) to (11):

Formula (6)

Formula (7)

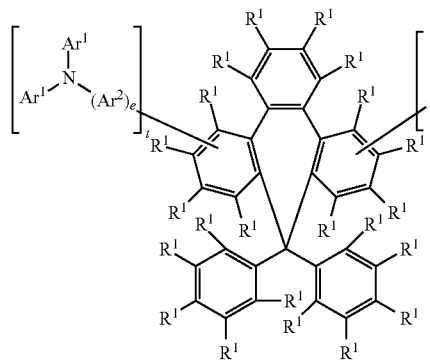

Formula (8)

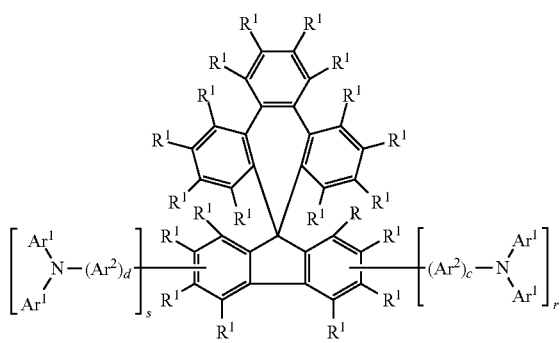

Formula (9)

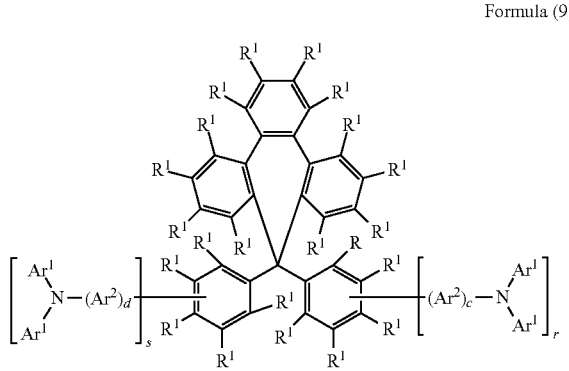

Formula (10)

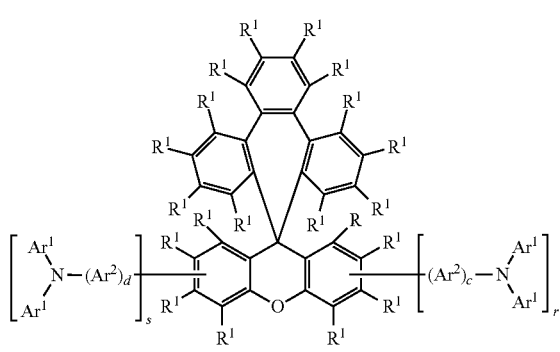

Formula (11)

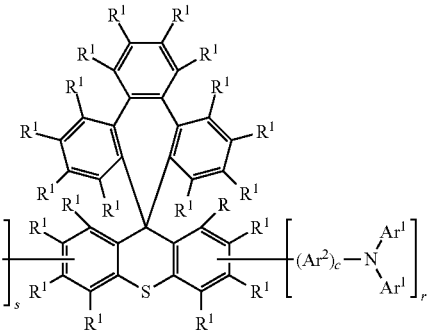

where the symbols and indices used have the definitions given in claim 1 and t+q=1 or s+r=1.

7. A process for preparing a compound according to claim 1, wherein the compound of the formula (1) is formed by one or more coupling reactions and/or cyclizations.

8. A mixture comprising at least one compound according to claim 1 and at least one fluorescent or phosphorescent dopant.

9. A formulation comprising at least one compound according to claim 1 and one or more solvents.

10. A formulation comprising the mixture according to claim 8 and one or more solvents.

11. The formulation as claimed in claim 9, wherein the formulation is a solution, a suspension or a miniemulsion.

12. An electronic device comprising the compound according to claim 1.

13. An electronic device comprising the mixture according to claim 8.

14. An electronic device selected from the group consisting of organic electroluminescent devices, organic integrated circuits, organic field-effect transistors, organic thin-film transistors, organic light-emitting transistors, organic solar cells, organic dye-sensitized solar cells, organic optical detectors, organic photoreceptors, organic field-quench devices, light-emitting electrochemical cells, organic laser diodes and organic plasmon emitting devices, comprising at least one compound according to claim 1.

15. An organic electroluminescent device comprising the compound according to claim 1 wherein said compound is used as matrix material for a fluorescent or phosphorescent compound in an emitting layer and/or in a hole transport layer and/or in a hole injection layer and/or in an electron blocker layer.

16. A compound of formula (2)

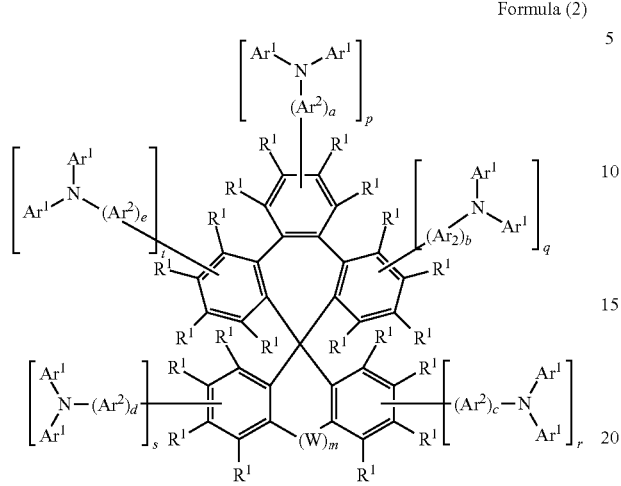

Formula (2)

where the symbols and indices used are as follows:
Ar$^2$ is the same or different at each instance and is a bivalent aromatic or heteroaromatic ring system which has 5 to 60 aromatic ring atoms and may be substituted by one or more R$^2$ radicals;
Ar$^1$ is the same or different at each instance and is an aromatic or heteroaromatic ring system which has 5 to 60 aromatic ring atoms and may in each case also be substituted by one or more R$^2$ radicals; where Ar$^1$ and/or Ar$^2$ radicals bonded to the same nitrogen atom may be joined via at least one K group;
K is the same or different at each instance and is a single bond or a bivalent bridge selected from N(R$^2$), B(R$^2$), O, C=O, C(R$^2$)$_2$, Si(R$^2$)$_2$, C=C(R$^2$)$_2$, S=O, P(R$^2$), P(=O)R$^2$ and S;
W is the same or different at each instance and is a single bond or a bivalent bridge selected from N(R$^2$), B(R$^2$), O, C=O, C(R$^2$)$_2$, Si(R$^2$)$_2$, S and R$^2$C=CR$^2$;
Ar is the same or different at each instance and is an aromatic or heteroaromatic ring system, which may be substituted by one or more R$^3$ radicals;
R$^1$ is the same or different at each instance and is H, D, F, Cl, Br, I, C(=O)Ar, P(=O)Ar$_2$, S(=O)Ar, S(=O)$_2$Ar, CR$^2$=CR$^2$Ar, CN, NO$_2$, Si(R$^2$)$_3$, B(OR$^2$)$_2$, OSO$_2$R$^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^2$ radicals, where one or more nonadjacent CH$_2$ groups may be replaced by R$^2$C=CR$^2$, Si(R$^2$)$_2$, C=O, C=NR, P(=O)(R$^2$), SO, SO$_2$, NR$^2$, O, S or CONR$^2$ and where one or more hydrogen atoms may be replaced by D, F, Cl, Br, I, CN or NO$_2$, or an aromatic or heteroaromatic ring system which has 5 to 60 aromatic ring atoms, each of which may be substituted by one or more R$^2$ radicals, or an aryloxy or heteroaryloxy group which has 5 to 40 aromatic ring atoms and may be substituted by one or more R$^2$ radicals, or an aralkyl or heteroaralkyl group which has 5 to 40 aromatic ring atoms and may be substituted by one or more R$^2$ radicals, or a combination of these groups; at the same time, two or more R$^2$ substituents together with the atoms to which they are bonded and also with one another, or two R$^1$ substituents, may form a mono- or polycyclic, aliphatic or aromatic ring system;
R$^2$ is the same or different at each instance and is H, D, F, Cl, Br, I, N(R$^3$)$_2$, N(Ar)$_2$, C(=O)Ar, P(=O)Ar$_2$, S(=O)Ar, S(=O)$_2$Ar, CR$^3$=CR$^3$Ar, CN, NO$_2$, Si(R$^3$)$_3$, B(OR$^3$)$_2$, OSO$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^3$ radicals, where one or more nonadjacent CH$_2$ groups may be replaced by R$^3$C=CR$^3$, C≡C, Si(R$^3$)$_2$, C=O, C=NR$^3$, P(=O)(R$^3$), SO, SO$_2$, NR$^3$, O, S or CONR$^3$ and where one or more hydrogen atoms may be replaced by D, F, Cl, Br, I, CN or NO$_2$, or an aromatic or heteroaromatic ring system which has 5 to 60 aromatic ring atoms, each of which may be substituted by one or more R$^3$ radicals, or an aryloxy or heteroaryloxy group which has 5 to 40 aromatic ring atoms and may be substituted by one or more R$^3$ radicals, or an aralkyl or heteroaralkyl group which has 5 to 40 aromatic ring atoms and may be substituted by one or more R$^3$ radicals, or a combination of these groups; at the same time, two or more R$^3$ substituents together with the atoms to which they are bonded and also with one another, or two R$^2$ substituents, may form a mono- or polycyclic, aliphatic or aromatic ring system;
R$^3$ is the same or different at each instance and is H, D, F, Cl, Br, I, C(=O)Ar, P(=O)Ar$_2$, S(=O)Ar, S(=O)$_2$Ar, CR$^4$=CR$^4$Ar, CN, NO$_2$, Si(R$^4$)$_3$, B(OR$^4$)$_2$, OSO$_2$R$^4$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^4$ radicals, where one or more nonadjacent CH$_2$ groups may be replaced by R$^4$C=CR$^4$, C≡C, Si(R$^4$)$_2$, C=O, C=NR$^4$, P(=O)(R$^4$), SO, SO$_2$, NR$^4$, O, S or CONR$^4$ and where one or more hydrogen atoms may be replaced by D, F, Cl, Br, I, CN or NO$_2$, or an aromatic or heteroaromatic ring system which has 5 to 60 aromatic ring atoms, each of which may be substituted by one or more R$^4$ radicals, or an aryloxy or heteroaryloxy group which has 5 to 40 aromatic ring atoms and may be substituted by one or more R$^4$ radicals, or an aralkyl or heteroaralkyl group which has 5 to 40 aromatic ring atoms and may be substituted by one or more R$^4$ radicals, or a combination of these groups; at the same time, two or more R$^4$ substituents together with the atoms to which they are bonded and also with one another, or two R$^3$ substituents, may form a mono- or polycyclic, aliphatic or aromatic ring system;
R$^4$ is the same or different at each instance and is H, D, F or an aliphatic hydrocarbyl radical having 1 to 20 carbon atoms or an aryl or heteroaryl group which has 5 to 40 ring atoms and may be substituted by one or more R$^5$ radicals, or a combination of these groups;
R$^5$ is the same or different at each instance and is H, D, F or an aliphatic hydrocarbyl radical having 1 to 20 carbon atoms;
m is 0 or 1, where m=0 means that no W group is bonded at this position, and the carbon atoms in question that bind to W are each replaced by an X group; and
p, q, r, s, t are the same or different at each instance and are 0, 1 or 2;
a, b, c, d, e are the same or different at each instance and are 0, 1 or 2;

where p+q+r+s+t is greater than or equal to 1;

if r is greater than or equal to 1 and s is greater than or equal to 1 and m is equal to 0, and c and d for at least one $(Ar^2)_cN(Ar^1)_2$ group and at least one $(Ar^2)_dN(Ar^1)_2$ group are 0, these two $N(Ar^1)_2$ groups are not arranged in the respective para positions to the quaternary carbon atom of the base skeleton.

17. The compound according to claim 16, wherein W is a single bond.

18. The compound according to claim 16, wherein the sum total of the values of the indices p, q, r, s and t is 1.

19. The compound according to claim 16, wherein the index r is 1, and the indices p, q, s and t are each 0, or characterized in that the index s is 1 and the indices p, q, r and t are each 0.

20. The compound according to claim 16, wherein the compound is a compound of one of the formulae (4) and (5):

Formula (4)

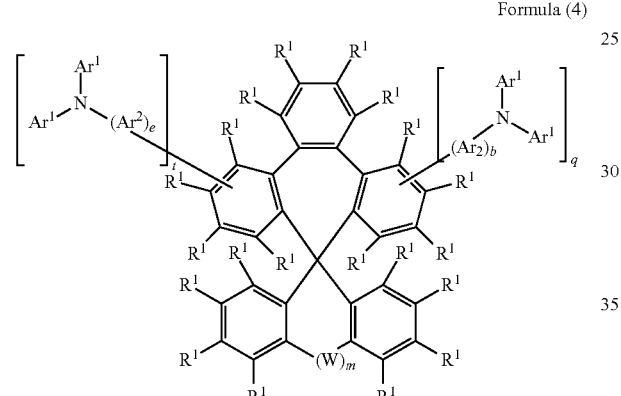

Formula (5)

where the symbols and indices used have the definitions given in claim 16.

21. The compound according to claim 16, wherein the compound is a compound of one of the formulae (6) to (11):

Formula (6)

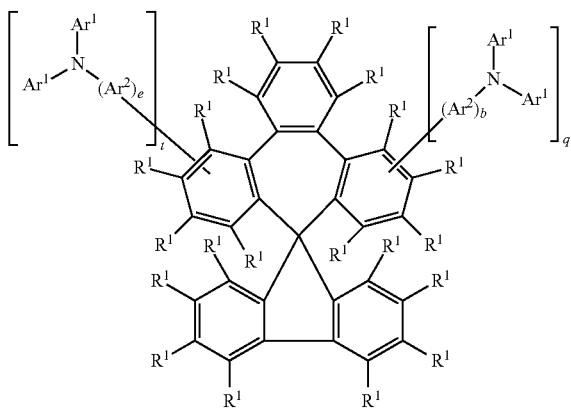

Formula (7)

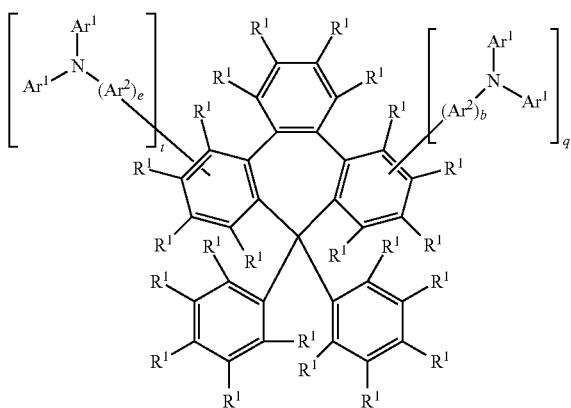

Formula (8)

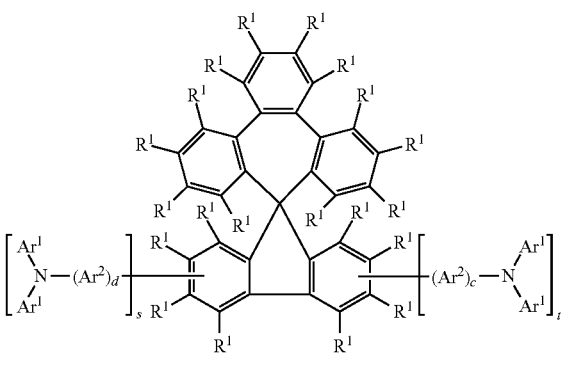

Formula (9)

-continued

Formula (10)

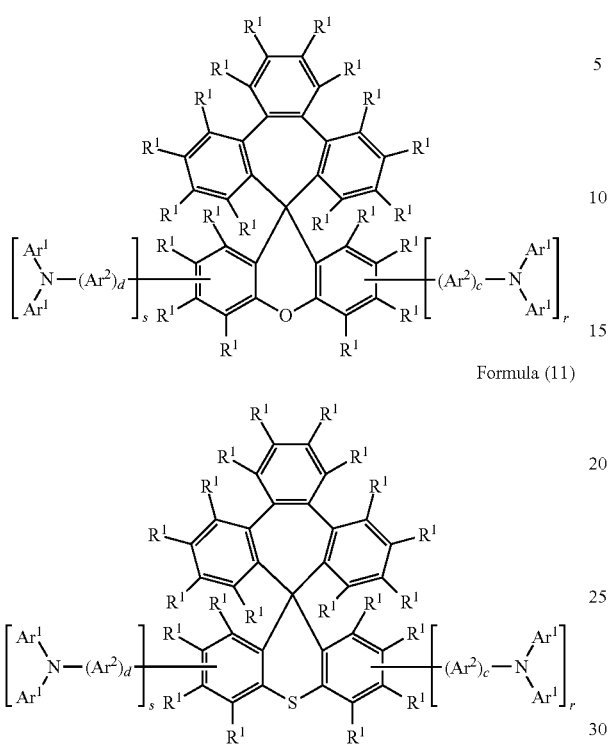

Formula (11)

where the symbols and indices used have the definitions given in claim 16.

22. A process for preparing the compound according to claim 16, wherein the compound of the formula (2) is formed by one or more coupling reactions and/or cyclizations.

23. A mixture comprising at least one compound according to claim 16 and at least one fluorescent or phosphorescent dopant.

24. A formulation comprising at least one compound according to claim 16 and one or more solvents.

25. A formulation comprising the mixture according to claim 23 and one or more solvents.

26. The formulation as claimed in claim 25, wherein the formulation is a solution, a suspension or a miniemulsion.

27. An electronic device comprising the compound according to claim 16.

28. An electronic device comprising the mixture according to claim 23.

29. An electronic device selected from the group consisting of organic electroluminescent devices, organic integrated circuits, organic field-effect transistors, organic thin-film transistors, organic light-emitting transistors, organic solar cells, organic dye-sensitized solar cells, organic optical detectors, organic photoreceptors, organic field-quench devices, light-emitting electrochemical cells, organic laser diodes and organic plasmon emitting devices, comprising at least one compound according to claim 16.

30. An organic electroluminescent device comprising the compound according to claim 16 wherein said compound is used as matrix material for a fluorescent or phosphorescent compound in an emitting layer and/or in a hole transport layer and/or in a hole injection layer and/or in an electron blocker layer.

31. A formulation comprising a mixture and one or more solvents wherein the mixture comprises at least one compound and at least one fluorescent or phosphorescent dopant, wherein the at least one compound is a compound of Formula (1)

Formula (1)

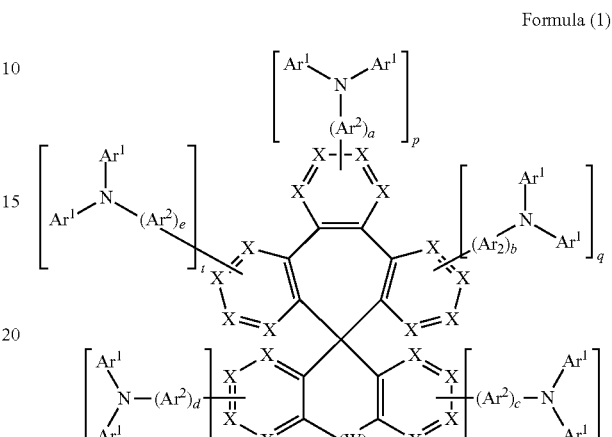

where the symbols and indices used are as follows:

X is the same or different at each instance and is $CR^1$ or N;

$Ar^2$ is the same or different at each instance and is a bivalent aromatic or heteroaromatic ring system which has 5 to 60 aromatic ring atoms and may be substituted by one or more $R^2$ radicals;

$Ar^1$ is the same or different at each instance and is an aromatic or heteroaromatic ring system which has 5 to 60 aromatic ring atoms and may in each case also be substituted by one or more $R^2$ radicals; where $Ar^1$ and/or AP radicals bonded to the same nitrogen atom may be joined via at least one K group;

K is the same or different at each instance and is a single bond or a bivalent bridge selected from $N(R^2)$, $B(R^2)$, O, C=O, $C(R^2)_2$, $Si(R^2)_2$, $C=C(R^2)_2$, S=O, $P(R^2)$, $P(=O)R^2$ and S;

W is the same or different at each instance and is a single bond or a bivalent bridge selected from $N(R^2)$, $B(R^2)$, O, C=O, $C(R^2)_2$, $Si(R^2)_2$, S and $R^2C=CR^2$;

Ar is the same or different at each instance and is an aromatic or heteroaromatic ring system, which may be substituted by one or more $R^3$ radicals;

$R^1$ is the same or different at each instance and is H, D, F, Cl, Br, I, C(=O)Ar, $P(=O)Ar_2$, S(=O)Ar, $S(=O)_2$Ar, $CR^2=CR^2Ar$, CN, $NO_2$, $Si(R^2)_3$, $B(OR^2)_2$, $OSO_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by $R^2C=CR^2$, $Si(R^2)_2$, C=O, $C=NR^2$, $P(=O)(R^2)$, SO, $SO_2$, $NR^2$, O, S or $CONR^2$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^2$ radicals, or an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals, or a combination of these groups; at the same time, two or more $R^2$ substituents together with the atoms to which they are bonded and also with one another, or two $R^1$ substituents, may form a mono- or polycyclic, aliphatic or aromatic ring system;

$R^2$ is the same or different at each instance and is H, D, F, Cl, Br, I, $N(R^3)_2$, $N(Ar)_2$, $C(=O)Ar$, $P(=O)Ar_2$, $S(=O)Ar$, $S(=O)_2Ar$, $CR^3=CR^3Ar$, CN, $NO_2$, $Si(R^3)_3$, $B(OR^3)_2$, $OSO_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by $R^3C=CR^3$, $C\equiv C$, $Si(R^3)_2$, $C=O$, $C=NR^3$, $P(=O)(R^3)$, SO, $SO_2$, $NR^3$, O, S or $CONR^3$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^3$ radicals, or an aryloxy or heteroaryloxy group which has 5 to 40 aromatic ring atoms and may be substituted by one or more $R^3$ radicals, or an aralkyl or heteroaralkyl group which has 5 to 40 aromatic ring atoms and may be substituted by one or more $R^3$ radicals, or a combination of these groups; at the same time, two or more $R^3$ substituents together with the atoms to which they are bonded and also with one another, or two $R^2$ substituents, may form a mono- or polycyclic, aliphatic or aromatic ring system;

$R^3$ is the same or different at each instance and is H, D, F, Cl, Br, I, $C(=O)Ar$, $P(=O)Ar_2$, $S(=O)Ar$, $S(=O)_2Ar$, $CR^4=CR^4Ar$, CN, $NO_2$, $Si(R^4)_3$, $B(OR^4)_2$, $OSO_2R^4$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^4$ radicals, where one or more nonadjacent $CH_2$ groups may be replaced by $R^4C=CR^4$, $C\equiv C$, $Si(R^4)_2$, $C=O$, $C=NR$, $P(=O)(R^4)$, $SO_2$, $NR^4$, O, S or $CONR^4$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^4$ radicals, or an aryloxy or heteroaryloxy group which has 5 to 40 aromatic ring atoms and may be substituted by one or more $R^4$ radicals, or an aralkyl or heteroaralkyl group which has 5 to 40 aromatic ring atoms and may be substituted by one or more $R^4$ radicals, or a combination of these groups; at the same time, two or more $R^4$ substituents together with the atoms to which they are bonded and also with one another, or two $R^3$ substituents, may form a mono- or polycyclic, aliphatic or aromatic ring system;

$R^4$ is the same or different at each instance and is H, D, F or an aliphatic hydrocarbyl radical having 1 to 20 carbon atoms or an aryl or heteroaryl group which has 5 to 40 ring atoms and may be substituted by one or more $R^5$ radicals, or a combination of these groups;

$R^5$ is the same or different at each instance and is H, D, F or an aliphatic hydrocarbyl radical having 1 to 20 carbon atoms;

m is 0 or 1, where m=0 means that no W group is bonded at this position, and the carbon atoms in question that bind to W are each replaced by an X group; and p, q, r, s, t are the same or different at each instance and are 0, 1 or 2;

a, b, c, d, e are the same or different at each instance and are 0, 1 or 2;

where p+q+r+s+t is greater than or equal to 1; and, if r is greater than or equal to 1 and s is greater than or equal to 1 and m is equal to 0, and c and d for at least one $(Ar^2)_cN(Ar^1)_2$ group and at least one $(Ar^2)_dN(Ar^1)_2$ group are 0, these two $N(Ar^1)_2$ groups are not arranged in the respective para positions to the quaternary carbon atom of the base skeleton.

32. The formulation as claimed in claim 31, wherein the formulation is a solution, a suspension or a microemulsion.

33. An electronic device comprising the formulation according to claim 31.

34. An organic electroluminescent device comprising the formulation according to claim 31.

35. A process of making one or more layers of an organic electroluminescent device, which comprises utilizing the solution as claimed in claim 32 to make at least one layer of the organic electroluminescent device.

36. The process as claimed in claim 35, wherein the solution is spin-coated or applied by a printing method.

37. The compound according to claim 1, wherein Ar is the same or different at each instance and is an aryl or heteroaryl group having 5 to 40 aromatic ring atoms and may be substituted by one or more $R^3$ radicals.

38. The compound according to claim 16, wherein Ar is the same or different at each instance and is an aryl or heteroaryl group having 5 to 40 aromatic ring atoms and may be substituted by one or more $R^3$ radicals.

39. The formulation according to claim 31, wherein Ar is the same or different at each instance and is an aryl or heteroaryl group having 5 to 40 aromatic ring atoms and may be substituted by one or more $R^3$ radicals.

* * * * *